(12) United States Patent
Kettschau et al.

(10) Patent No.: US 9,540,392 B2
(45) Date of Patent: Jan. 10, 2017

(54) THIENOPYRIMIDINES

(71) Applicant: BAYER PHARMA AKTIENGESELLSCHAFT, Berlin (DE)

(72) Inventors: Georg Kettschau, Berlin (DE); Florian Puehler, Wellesley, MA (US); Knut Eis, Berlin (DE); Ulrich Klar, Berlin (DE); Dirk Kosemund, Berlin (DE); Detlev Sülzle, Berlin (DE); Philip Lienau, Berlin (DE); Andrea Hägebarth, Berlin (DE); Ulf Bömer, Berlin (DE); Lars Wortmann, Berlin (DE); Keith Graham, Berlin (DE); Antje Margret Wengner, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/403,151

(22) PCT Filed: May 17, 2013

(86) PCT No.: PCT/EP2013/060233
§ 371 (c)(1),
(2) Date: Nov. 21, 2014

(87) PCT Pub. No.: WO2013/174744
PCT Pub. Date: Nov. 28, 2013

(65) Prior Publication Data
US 2015/0133425 A1 May 14, 2015

(30) Foreign Application Priority Data

May 21, 2012 (EP) .................................. 12168670
Feb. 1, 2013 (EP) .................................. 13153607

(51) Int. Cl.
| | | |
|---|---|---|
| C07D 495/04 | (2006.01) |
| C07D 519/00 | (2006.01) |
| A61K 31/519 | (2006.01) |
| A61P 19/02 | (2006.01) |
| A61K 31/5377 | (2006.01) |
| A61K 31/541 | (2006.01) |
| A61K 31/5513 | (2006.01) |
| A61K 45/06 | (2006.01) |

(52) U.S. Cl.
CPC .......... *C07D 495/04* (2013.01); *A61K 31/519* (2013.01); *A61K 31/5377* (2013.01); *A61K 31/541* (2013.01); *A61K 31/5513* (2013.01); *A61K 45/06* (2013.01); *C07D 519/00* (2013.01)

(58) Field of Classification Search
CPC ...... C07D 495/04; A61K 31/53; A61K 31/519
USPC ........................................ 544/278; 514/258.1
See application file for complete search history.

(56) References Cited

U.S. PATENT DOCUMENTS

| | | | |
|---|---|---|---|
| 5,011,472 A | 4/1991 | Aebischer et al. |
| 5,023,252 A | 6/1991 | Hseih |
| 5,444,038 A | 8/1995 | James et al. |
| 2008/0269238 A1 | 10/2008 | Sugihara et al. |
| 2009/0156599 A1 | 6/2009 | Branstetter et al. |
| 2011/0212103 A1 | 9/2011 | Heckel et al. |
| 2015/0152121 A1 | 6/2015 | Klar et al. |
| 2015/0218173 A1 | 8/2015 | Wortmann et al. |
| 2015/0239891 A1 | 8/2015 | Klar et al. |

(Continued)

FOREIGN PATENT DOCUMENTS

| | | |
|---|---|---|
| JP | 200784494 A | 4/2007 |
| WO | 02088138 A1 | 11/2002 |

(Continued)

OTHER PUBLICATIONS

Hou et al., Oncotarget 2012, 3: 118-131.*
(Continued)

*Primary Examiner* — Venkataraman Balasubramanian
(74) *Attorney, Agent, or Firm* — Resek Liang & Frank LLP; Stanley D. Liang

(57) ABSTRACT

The present invention relates to substituted thienopyrimidine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

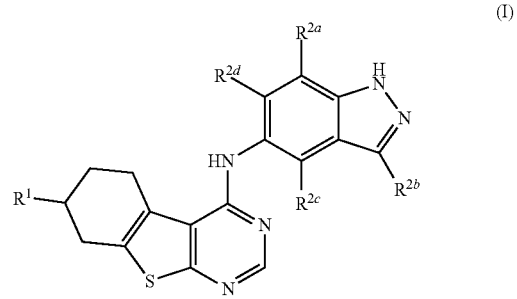

10 Claims, No Drawings

(56) References Cited

U.S. PATENT DOCUMENTS

| | | |
|---|---|---|
| 2015/0252047 A1 | 9/2015 | Klar et al. |
| 2016/0002245 A1 | 1/2016 | Klar et al. |
| 2016/0009734 A1 | 1/2016 | Klar et al. |

FOREIGN PATENT DOCUMENTS

| | | |
|---|---|---|
| WO | 2005010008 A1 | 2/2005 |
| WO | WO 2005/010008 A1 * | 2/2005 |
| WO | 2006136402 A1 | 12/2006 |
| WO | 2007059905 A2 | 5/2007 |
| WO | 2009134658 A2 | 11/2009 |
| WO | 2010006032 A1 | 1/2010 |
| WO | 2010023181 A1 | 3/2010 |
| WO | 2011104334 A1 | 9/2011 |
| WO | 2011104337 A1 | 9/2011 |
| WO | 2011104338 A1 | 9/2011 |
| WO | 2011104340 A1 | 9/2011 |

OTHER PUBLICATIONS

Cecil Textbook of Medicine, edited by Bennet, J.C., and Plum F., 20th edition, vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006,.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Pyne et al. Cancer Res 2011 ;71:6576-6582.*
Cargnello et al. Microbiology and Molecular Biology Reviews, Mar. 2011 ,vol. 75, p. 50-83.*
Jauch, Ralf, et al., Crystal Structures of the Mnk2 Kinase Domain Reveal an Inhibitory Conformation and a Zinc Binding Site, Structure, vol. 13, pp. 1559-1568 (2005).
Jauch, Ralf, et al., Mitogen-activated protein kinases interacting kinases are autoinhibited by a reprogrammed activation segment, EMBO Journal, vol. 25, pp. 4020-4032 (2006).
Buxade, Maria, et al., The Mnks: MAP kinase-interacting kinases (MAP kinase signal-integrating kinases), Frontiers in Bioscience, vol. 13, pp. 5359-5374 (2008).
Konicek, Bruce W, et al., Targeting the eIF4F translation initiation complex for cancer therapy, Cell Cycle, vol. 7, No. 16, pp. 2466-2471 (2008).
Ueda, Takeshi, et al., Mnk2 and Mnk1 are Essential for Constitutive and Inducible Phosphorylation of Eukaryotic Initiation Factor 4E but Not for Cell Growth or Development, Molecular and Cellular Biology, vol. 24, No. 15, pp. 6539-6549 (2004).
Blagden, Sarah P., et al., The biological and therapeutic relevance of mRNA translation in cancer, Nat. Rev. Clin. Oncol., vol. 8, No. 5, pp. 280-291 (2011).
Yoshizawa, Akihiko, et al., Overexpression of Phospho-eIF4E Is Associated with Survival through AKT Pathway in Non-Small Cell Lung Cancer, Clin Cancer Res, vol. 16, No. 1, pp. 240-248 (2009).
Chrestensen, Carol A., et al., Loss of MNK function sensitizes fibroblasts to serum-withdrawal induced apoptosis, Genes to Cells, vol. 12, pp. 1133-1140 (2007).
Chrestensen, Carol A., et al., MNK1 and MNK2 Regulation in HER2-overexpressing Breast Cancer Lines*, Journal of Biological Chemistry, vol. 282, No. 7, pp. 4243-4252 (2007).

Wendel, Hans-Guido, et al., Dissecting eIF4E action in tumorigenesis, Genes and Development, vol. 21, No. 24, pp. 3232-3237 (2007).
Konicek, Bruce W., et al., Therapeutic Inhibition of MAP Kinase Interacting Kinase Blocks Eukaryotic Initiation Factor 4E Phosphorylation and Suppresses Outgrowth of Experimental Lung Metastases, Cancer Res, vol. 71, No. 5, pp. 1849-1857 (2011).
Park, Song-Eun, et al., Efficient Palladium-Catalyzed Amination of Aryl Chlorides Using Dicyclo-hexylamino[(2,6-dimethyl)morpholino]phenylphosphine as a PN2 Ligand, Synthesis, No. 5, pp. 815-823 (2009).
Gewald, Karl, et al., 2-Amino-thiophene aus methylenaktiven Nitrilen, Carbonylverbindungen und Schwefel, Chem. Ber, vol. 99, pp. 94-100 (1966).
Greene, Theodora W., et al., Protective Groups in Organic Sythesis, Third Edition, Wiley (1999).
Berge, Stephen M., et al., Pharmaceutical Salts, Journal of Pharmaceutical Sciences, vol. 66, No. 1, pp. 1-19 (1977).
Wheeler, Rob C., et al., A General, One-Step Synthesis of Substituted Indazoles using a Flow Reactor, Org. Process Res. Dev., vol. 15, pp. 565-569 (2011).
Lukin, Kirill, et al., New Practical Synthesis of Indazoles via Condensation of o-Fluorobenzaldehydes and Their O-Methyloximes with Hydrazine, J. Org. Chem., vol. 71, pp. 8166-8172 (2006).
Li, Xiaoming, et al., Structure-Based Design, Synthesis, and Antimicrobial Activity of Indazole-Derived SAH/MTA Nucleosidase Inhibitors, J. Med. Chem., vol. 46, pp. 5663-5673 (2003).
Strickley, Robert G., Parenteral Formulations of Small Molecules Therapeutics Marketed in the United States (1999)—Part I, PDA Journal of Pharmaceutical Science and Technology, vol. 53, No. 6, 324-349 (1999).
Nema, Sandeep, et al., Excipients and Their Use in Injectable Products, PDA Journal of Pharmaceutical Science and Technology, vol. 51, No. 4, pp. 166-171 (1997).
Cunningham, Barbara, A Growing Issue: Cell Proliferation Assays, The Scientist, vol. 15, No. 13, pp. 1-6 (2001).
Crouch, S.P.M., et al., The use of ATP bioluminescence as a measure of cell proliferation and cytotoxicity, Journal of Immonological Methods, vol. 160, pp. 81-88 (1993).
Powell, M.F., et al., Compendium of Excipients for Parenteral Formulations, PDA Journal of Pharmaceutical Science and Technology, vol. 52, No. 5, pp. 238-239 (1998).
Aiello, Lloyd Paul ,et al., Vascular Endothelial Growth Factor in Ocular Fluid of Patients with Diabetic Retinopathy and Other Retinal Disorders, The New England Journal of Medicine, vol. 331, No. 22, pp. 1480-1487 (1994).
Lopez, Pedro F., et al., Transdifferentiated Retinal Pigment Epithelial Cells are Immunoreactive for Vascular Endothelial Growth Factor in Surgically Excised Age-Related Macular Degeneration-Related Choroidal Neovascular Membranes, Invest Ophthalmol Vis. Sci., vol. 37, No. 5, pp. 855-868 (1996).
Sleebs, Brad E., et al., Identification of 5,6-substituted 4-aminothieno[2,3-dlpyrimidines as LIMKI inhibitors, Bioorganic & Medical Chemistry Letters, vol. 21, pp. 5992-5994 (2011).
Porter, H.D., et al., 5-Nitroindazole, Organic Sythesis, Coll., vol. 3, pp. 660 (1955), vol. 20, pp. 73 (1940).
Pe'Er, Jacob, et al., Hypoxia-Induced Expression of Vascular Endothelial Growth Factor by Retinal Cells is a Common Factor in Neovascularizing Ocular Diseases, Laboratory Investigation, vol. 72, No. 6, pp. 638-645 (1995).
Mass, Robert D., The HER Receptor Family: A Rich Target for Therapeutic Development, Int. J. Radiation Oncology Biol. Phys., vol. 58, No. 3, pp. 932-940 (2004).
Mountzios, Giannis, et al., Aurora Kinases as Targets for Cancer Therapy, Cancer Treatment Reviews, vol. 34, pp. 175-182 (2008).
Pyne, Susan, et al., Sphingosine Kinase Inhibitors and Cancer: Seeking the Golden Sword of Hercules, Cancer Res., vol. 71, pp. 6576-6582 (2011).
Ferrara, Napoleione, VEGF as a Therapeutic Target in Cancer, Oncology, vol. 69 (Supp 3), pp. 11-16 (2005).
Freshney, Ian R., Culture of Animal Cells, A Manual of Basic Technique, Alan R. Liss, Inc., 7 pgs. (1983).

(56) References Cited

OTHER PUBLICATIONS

Gautschi, Oliver, et al., Aurora Kinases as Anticancer Drug Targets, Clin. Cancer Res., vol. 14, No. 6, pp. 1639-1648 (2008).
Golub, T.R., et al., Molecular Classification of Cancer: Class Discovery and Class Prediction by Gene Expression Monitoring, Science, vol. 286, pp. 531-537 (1999).
Cecil Textbook of Medicine, Edited by Bennet, J.C. and Plum, F., 20th Edition, vol. 1, 1004-1010 (1996).
Cohen, Philip, The Development and Therapeutic Potential of Protein Kinase Inhibitors, Current Opinion in Chemical Biology, vol. 3, pp. 459-465 (1999).
Cargnello, Marie, et al., Activation and Function of the MAPKs and their Substrates, the MAPK-Activated Protein Kinases, Microbiology and Molecular Biology Reviews, vol. 75, No. 1, pp. 50-83 (2011).
Qiu, Yun, et al., Signaling Network of the Btk Family Kinases, Oncogene, vol. 19, pp. 5651-5661 (2000).
Fabbro, Doriano, et al., Protein Kinases as Targets for Anticancer Agents: From Inhibitors to Useful Drugs, Pharmacology & Therapeutics, vol. 93, pp. 79-98 (2002).
Jain, Rakesh K., et al., Lessons from Phase III Clinical Trials on Anti-VEGF Therapy for Cancer, Nature Clinical Practice Oncology, vol. 3, No. 1, pp. 24-40 (2006).
Hou, Jidiang, et al., Targeting Mnks for Cancer Therapy, Oncotarget, vol. 3, No. 2, pp. 118-131 (2012).
Dermer, Gerald B., Bio/Technology, vol. 12, pp. 320 (1994).
Adesso, L., et al. Gemcitable Triggers a Pro-Survival Response in Pancreatic Cancer Cells through Activation of the MNK2/eIF4E Pathway, Oncogene, vol. 32, pp. 2848-2857 (2013).
Shi, Y., et al. MNK Kinases Facilitate c-myc IRES Activity in Rapamycin-Treated Multiple Myeloma Cells, Oncogene, vol. 32, pp. 190-197 (2013).

* cited by examiner

THIENOPYRIMIDINES

The present invention relates to substituted thienopyrimidine compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2). Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK2a binds to and is activated only by ERK. MKNK1b has low activity under all conditions and MKNK2b has a basal activity independent of ERK or p38 MAP Kinase. [Buxade M et al., Frontiers in Bioscience 5359-5374, May 1, 2008]

MKNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methyl-guanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually less efficiently translated due to their long and complex 5'UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as over-expression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eµ-Myc transgenic hematopoietic stem cells to produce tumors in mice. Comparable results were achieved when an eIF4E carrying a S209D mutation was analyzed. The S209D mutation mimicks a phosphorylation at the MKNK1 phosphorylation site. In contrast, a non-phosphorylatable form of eIF4E attenuated tumor growth [Wendel H G, et al., Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. In summary, eIF4E phosphorylation through MKNK protein activity can promote cellular proliferation and survival and is critical for malignant transformation. Inhibition of MKNK activity may provide a tractable cancer therapeutic approach.

Substituted thienopyrimidine compounds have been disclosed in prior art for the treatment or prophylaxis of different diseases:

WO 2010/006032 A1 (Duquesne University of the Holy Spirit) addresses tricyclic compounds as antimitotic agents. According to the general formula of claim 1, the tricycles inter alia comprise 5,6,7,8-tetrahydrobenzo[1]thieno[2,3-d]pyrimidines that may carry substituents at the carbocycle and one aromatic or heteroaromatic moiety at an optional 4-amino group. Furthermore, they may be unsubstituted at position 2 in the pyrimidine ring. However, the examples provided clearly differ from the compounds of the present invention. While the vast majority contains the C6 carbocycle completely unsaturated as aromatic ring, only two examples show a tetrahydrobenzo substructure in combination with a 4-amino group and in both cases the latter is bisubstituted by a phenyl and a methyl group. Furthermore, the specified compounds are with no exception pyrimidin-2-amines or 2-methyl-pyrimidines.

JP2007084494 (Oncorex Inc.) relates to PIM-1 inhibitors. One claim comprises 5,6,7,8-tetrahydrobenzo[1]thieno[2,3-d]pyrimidin-4-amines that can be monosubstituted at the amino group by optionally substituted phenyl. However, the optional substituents of phenyl are restricted to hydroxy, alkoxy or alkenyloxy. The tricyclic core does not show further substitutions. The only example of a direct substitution at the 4-amino group by phenyl is compound VII-2 with meta-methoxyphenyl.

WO 2002/088138 A1 (Bayer Pharmaceuticals Corporation) relates to PDE7b inhibitors and comprises 5,6,7,8-tetrahydrobenzo[1]thieno[2,3-d]pyrimidin-4-amines where the carbocycle and the 4-amino group may be optionally substituted by a wide range of substituents. The respective oxa, thia or aza analoga at position 7 with no further substituents at that ring are also claimed, the sulphur may be oxidized to sulphone and the nitrogen can be substituted. However, pyrid-4-yl in the 5,6,7,8-tetrahydrobenzo series and 3,4-dichlorophenyl and indazol-5-yl in the 6,9-dihydro-7H-pyrano series are the only examples with direct aromatic substitution at the 4-amino group.

WO 2005/010008 A1 (Bayer Pharmaceuticals Corporation) discloses 5,6,7,8-tetrahydrobenzo[1]thieno[2,3-d]pyrimidin-4-amines as proliferation inhibitors of A431 and BT474 cells which are model cell lines used in biomedical research. More specifically, A431 and BT474 cells are used in studies of the cell cycle and cancer-associated cell signalling pathways since they express abnormally high levels of the epidermal growth factor receptor (EGFR) and HER2, respectively. Substitution at the 4-amino group is limited to monosubstitution by either optionally substituted phenyl or optionally substituted indazolyl. The carbocycle may be substituted one or two times at position 7 by optionally substituted alkyl or alkenyl, by substituted carbonyl, hydroxy, optionally substituted amino or may be linked to the nitrogen of one or two saturated six membered rings optionally bearing a second heteroatom. Regarding the aromatic substituents at the 4-amino group, disclosed examples cover phenyl with a broad range of substituents and some indazol-5-yls but all are substituted at the nitrogen at position 1. Furthermore, all examples show an alkyl group in position 7 that is terminally further substituted by an amino group or hydroxyl group or in case of synthetic intermediates also by an ester function. Furthermore, as shown hereinafter, the compounds disclosed in WO 2005/010008 A1 are potent EGFR inhibitors but less effective MKNK inhibitors whereas the compounds of the present invention are potent MKNK inhibitors and less effective EGFR inhibitors. WO 2009/134658 (National Health Research Institutes) relates to inhibitors of Aurora kinase. The patent application generically covers tricyclic thieno[2,3-d]pyrimidin-4-amines with the third ring fused to the thiophene subunit. However, an optional aryl or heteroaryl substituent at the 4-amino group must carry a side chain involving a carbonyl, thiocarbonyl or iminomethylene group. The vast majority of more than 250 examples is formed by bicyclic 6,7-dihydrofuro[3,2-d]pyrimidin-4-amines that show in 4 cases a direct aromatic substitution at the 4-amino group but additionally substitution by two phenyl groups at the dihydrofuro subunit. None of the very few examples for tricyclic compounds shows direct substitution by an aromatic moiety at the 4-amino group.

WO 2006/136402 A1 and WO 2007/059905 A2 (Develogen AG) disclose thienopyrimidin-4-amines and their use for the prophylaxis and/or treatment of diseases which can be influenced by the inhibition of the kinase activity of Mnk1 and/or Mnk2. The 4-amino-group is substituted by a substituted phenyl group. The WO publications do not disclose any biological data.

WO 2010/023181 A1, WO 2011/104334 A1, WO 2011/104337 A1, WO 2011/104338 A1 and WO 2011/104340 A1 (Boehringer Ingelheim) relate to thienopyrimidin-4-amines for the prophylaxis and/or treatment of diseases which can be influenced by the inhibition of the kinase activity of Mnk1 and/or Mnk2. In case of the disclosed thienopyrimidin-4-amines there is no tetrahydrobenzo ring fused to the thienopyrimidine core. Additionally, the 4-amino group does not carry an indazol-5-yl substituent. In case of the compounds disclosed in WO 2010/023181 A1 the $IC_{50}$ values vary between 0.035 µM and 0.68 µM with respect Mnk1, and between 0.006 µM and 0.56 µM with respect to Mnk2. In case of the compounds disclosed in WO 2011/104334 A1 the $IC_{50}$ values vary between 1 nM and 9700 nM with respect to Mnk2. In case of the compounds disclosed in WO 2011/104337 A1 the $IC_{50}$ values vary between 2 nM and 8417 nM with respect to Mnk2. In case of the compounds disclosed in WO 2011/104338 A1 the $IC_{50}$ values vary between 8 nM and 58 nM with respect to Mnk2. In case of the compounds disclosed in WO 2011/104340 A1 the $IC_{50}$ values vary between 3 nM and 5403 nM with respect to Mnk2. ALL WO publications contain the statement that the compounds described therein show improved solubility, are highly selective and show improved metabolic stability when compared to the compounds disclosed in WO 2006/136402 A1 and WO 2007/059905 A2 (Develogen AG, see above). However, besides the $IC_{50}$ values discussed in this paragraph, there are no more data proving this statement.

The state of the art described above does not describe the specific substituted thienopyrimidine compounds of general formula (I) of the present invention as defined herein or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit MKNK1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1 kinase, such as, for example, haematological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Additionally, the compounds of the present invention show higher kinase inhibition selectivity and/or better performance in cellular assays than the MKNK inhibitors disclosed in prior art.

SUMMARY OF THE INVENTION

The present invention covers compounds of general formula (I):

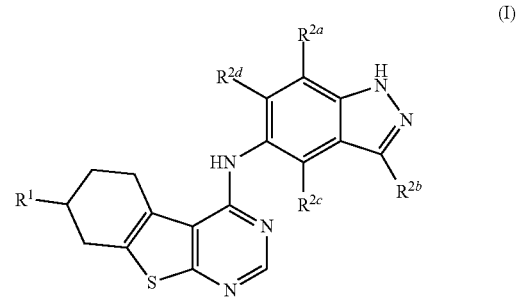

in which:

$R^1$ represents a group selected from:
—C(=O)O—$R^3$, —C(=O)N(H)$R^3$, —C(=O)N$R^3R^4$;

$R^{2a}$, $R^{2b}$, $R^{2c}$, $R^{2d}$
represent, independently from each other, a hydrogen atom or a group selected from $C_1$-$C_3$-alkyl-, $C_1$-$C_3$-alkoxy-, halo-, hydroxy-, halo-$C_1$-$C_3$-alkyl-, halo-$C_1$-$C_3$-alkoxy-, cyano-, —N(H)$R^5$, —N$R^5R^4$;

$R^3$ represents a hydrogen atom or an optionally substituted group selected from:
$C_1$-$C_6$-alkyl-, $C_2$-$C_6$-alkenyl-, $C_2$-$C_6$-alkynyl-, —(CH$_2$)$_q$—(C$_3$-C$_7$-cycloalkyl), —(CH$_2$)$_q$—O—(C$_3$-C$_7$-cycloalkyl), —(CH$_2$)$_q$—(C$_4$-C$_7$-cycloalkenyl), —(CH$_2$)$_q$—O—(C$_4$-C$_7$-cycloalkenyl), —(CH$_2$)$_q$-(3- to 10-membered heterocycloalkyl), —(CH$_2$)$_q$—O-(3- to 10-membered heterocycoalkyl), —(CH$_2$)$_q$-(4- to 10-membered heterocycloalkenyl), —(CH$_2$)$_q$—O-(4- to 10-membered heterocycloalkenyl),
—(CH$_2$)$_q$-aryl, —(CH$_2$)$_q$—O-aryl, —(CH$_2$)$_q$-heteroaryl, —(CH$_2$)$_q$—O-heteroaryl, $R^4$ represents an optionally substituted group selected from:
$C_1$-$C_6$-alkyl-, $C_2$-$C_6$-alkenyl-, $C_2$-$C_6$-alkynyl-, halo-$C_1$-$C_6$-alkyl-, hydroxy-$C_1$-$C_6$-alkyl-, $C_1$-$C_6$-alkoxy-$C_1$-$C_6$-alkyl-;

or

N$R^3R^4$ together
represent an optionally substituted 3- to 10-membered heterocycloalkyl or an optionally substituted 4- to 10-membered heterocycloalkenyl group;

$R^5$ represents a hydrogen atom, a $C_1$-$C_6$-alkyl- or a $C_3$-$C_7$-cycloalkyl-group;

q represents an integer of 0, 1, 2 or 3;

or a tautomer, an N-oxide, a hydrate, a solvate, or a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine or a chlorine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —CF$_3$, —CHF$_2$, —CH$_2$F, —CF$_2$CF$_3$, or —CH$_2$CF$_3$.

The term "$C_1$-$C_6$-alkoxy" is to be understood as preferably meaning a linear or branched, saturated, monovalent, hydrocarbon group of formula —O—(C$_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —OCF$_3$, —OCHF$_2$, —OCH$_2$F, —OCF$_2$CF$_3$, or —OCH$_2$CF$_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —CH$_2$CH$_2$OCF$_3$, —CH$_2$CH$_2$OCHF$_2$, —CH$_2$CH$_2$OCH$_2$F, —CH$_2$CH$_2$OCF$_2$CF$_3$, or —CH$_2$CH$_2$OCH$_2$CF$_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3- enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethyl-but-1-ynyl group. Particularly, said alkynyl group is ethynyl, prop-1-ynyl, or prop-2-ynyl.

The term "$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Particularly, said ring contains 3, 4, 5 or 6 carbon atoms ("$C_3$-$C_6$-cycloalkyl").

The term "$C_4$-$C_7$-cycloalkenyl" is to be understood as preferably meaning a monovalent, monocyclic hydrocarbon ring which contains 4, 5, 6 or 7 carbon atoms and one or two double bonds, in conjugation or not, as the size of said cycloalkenyl ring allows. Said $C_4$-$C_7$-cycloalkenyl group is for example a cyclobutenyl, cyclopentenyl, or cyclohexenyl group.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl-group or a $C_3$-$C_7$-cycloalkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a biphenyl group (a "$C_{12}$-aryl" group), or a ring having 13 carbon atoms, (a "$C_{13}$-aryl" group), e.g. a fluorenyl group, or a ring having 14 carbon atoms, (a "$C_{14}$-aryl" group), e.g. an anthracenyl group. Preferably, the aryl group is a phenyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridinyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridyl includes pyridin-2-yl, pyridin-3-yl, and pyridin-4-yl; or the term thienyl includes thien-2-yl and thien-3-yl. Preferably, the heteroaryl group is a pyridinyl group.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

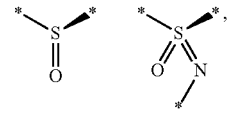

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, or (E)- or (Z)-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

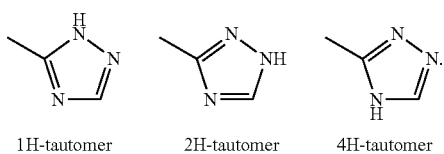

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

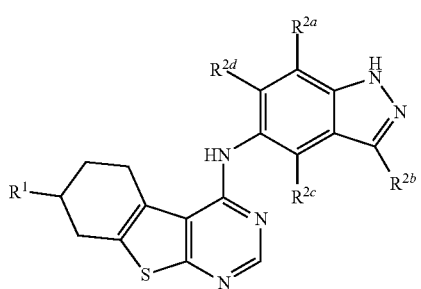

(I)

in which:
$R^1$ represents a group selected from:
—C(=O)O—$R^3$, —C(=O)N(H)$R^3$, —C(=O)N$R^3$$R^4$;
$R^{2a}$, $R^{2b}$, $R^{2c}$, $R^{2d}$
represent, independently from each other, a hydrogen atom or a group selected from: $C_1$-$C_3$-alkyl-, $C_1$-$C_3$-alkoxy-, halo-, hydroxy-, halo-$C_1$-$C_3$-alkyl-, halo-$C_1$-$C_3$-alkoxy-, cyano-, —N(H)$R^5$, —N$R^5$$R^4$;
$R^3$ represents a hydrogen atom or a group selected from:
$C_1$-$C_6$-alkyl-, $C_2$-$C_6$-alkenyl-, $C_2$-$C_6$-alkynyl-, —(CH$_2$)$_q$—($C_3$-$C_7$-cycloalkyl), —(CH$_2$)$_q$—O—($C_3$-$C_7$-cycloalkyl), —(CH$_2$)$_q$—($C_4$-$C_7$-cycloalkenyl), —(CH$_2$)$_q$—O—($C_4$-$C_7$-cycloalkenyl), —(CH$_2$)$_q$-(3- to 10-membered heterocycloalkyl), —(CH$_2$)$_q$—O-(3- to 10-membered heterocyoalkyl), —(CH$_2$)$_q$-(4- to 10-membered heterocycloalkenyl), —(CH$_2$)$_q$—O-(4- to 10-membered heterocycloalkenyl),
—(CH$_2$)$_q$-aryl, —(CH$_2$)$_q$—O-aryl, —(CH$_2$)$_q$-heteroaryl, —(CH$_2$)$_q$—O-heteroaryl;
wherein said selected group is optionally substituted;

$R^4$ represents a group selected from:
$C_1$-$C_6$-alkyl-, $C_2$-$C_6$-alkenyl-, $C_2$-$C_6$-alkynyl-, halo-$C_1$-$C_6$-alkyl-, hydroxy-$C_1$-$C_6$-alkyl-, $C_1$-$C_6$-alkoxy-$C_1$-$C_6$-alkyl-;
wherein said selected group is optionally substituted;
or
N$R^3$$R^4$ together
represent an optionally substituted 3- to 10-membered heterocycloalkyl or an optionally substituted 4- to 10-membered heterocycloalkenyl group;
$R^5$ represents a hydrogen atom, a $C_1$-$C_6$-alkyl- or $C_3$-$C_7$-cycloalkyl-group;
q represents an integer of 0, 1, 2 or 3;
or a tautomer, an N-oxide, a hydrate, a solvate, or a salt thereof, or a mixture of same.

In a preferred embodiment, the invention relates to compounds of formula (I), supra, wherein $R^1$ represents —C(=O)O—$R^3$.

In another preferred embodiment, the invention relates to compounds of formula (I), supra, wherein $R^1$ represents —C(=O)N(H)$R^3$.

In another preferred embodiment, the invention relates to compounds of formula (I), supra, wherein $R^1$ represents —C(=O)N$R^3$$R^4$.

In another preferred embodiment, the invention relates to compounds of formula (I), supra, wherein $R^{2a}$ represents a hydrogen atom.

In another preferred embodiment, the invention relates to compounds of formula (I), supra, wherein $R^{2b}$ represents a hydrogen atom or a group selected from: $C_1$-$C_3$-alkyl-, halo-$C_1$-$C_3$-alkyl-, cyano-.

In another preferred embodiment, the invention relates to compounds of formula (I), supra, wherein $R^{2b}$ represents a hydrogen atom or a $C_1$-$C_3$-alkyl-group.

In another preferred embodiment, the invention relates to compounds of formula (I), supra, wherein $R^{2b}$ represents a hydrogen atom.

In another preferred embodiment, the invention relates to compounds of formula (I), supra, wherein $R^{2c}$ represents a hydrogen atom or a group selected from: $C_1$-$C_3$-alkyl-, $C_1$-$C_3$-alkoxy-, halo-, —N(H)$R^5$, —N$R^5$$R^4$.

In another preferred embodiment, the invention relates to compounds of formula (I), supra, wherein $R^{2c}$ represents a hydrogen atom or a $C_1$-$C_3$-alkyl-group.

In another preferred embodiment, the invention relates to compounds of formula (I), supra, wherein $R^{2c}$ represents a hydrogen atom.

In another preferred embodiment, the invention relates to compounds of formula (I), supra, wherein $R^{2d}$ represents a hydrogen atom or a group selected from: $C_1$-$C_3$-alkyl-, $C_1$-$C_3$-alkoxy-, halo-, —N(H)$R^5$, —N$R^5$$R^4$.

In another preferred embodiment, the invention relates to compounds of formula (I), supra, wherein $R^{2d}$ represents a hydrogen atom or a group selected from: $C_1$-$C_3$-alkyl-, $C_1$-$C_3$-alkoxy-, halo-.

In another preferred embodiment, the invention relates to compounds of formula (I), supra, wherein $R^{2d}$ represents a $C_1$-$C_3$-alkoxy-group, preferably a methoxy-, ethoxy- or iso-propoxy-group.

In another preferred embodiment, the invention relates to compounds of formula (I), supra, wherein $R^{2d}$ represents a hydrogen atom or a $C_1$-$C_3$-alkoxy-group, preferably a methoxy-, ethoxy- or iso-propoxy-group.

In another preferred embodiment, the invention relates to compounds of formula (I), supra, wherein each of $R^{2a}$, $R^{2b}$ represents a hydrogen atom.

In another preferred embodiment, the invention relates to compounds of formula (I), supra, wherein each of $R^{2a}$, $R^{2b}$, and $R^{2c}$ represents a hydrogen atom.

In another preferred embodiment, the invention relates to compounds of formula (I), supra, wherein each of $R^{2a}$, $R^{2b}$ represents a hydrogen atom, $R^{2c}$ represents a hydrogen atom or a $C_1$-$C_3$-alkyl-group, and $R^{2d}$ does not represent a hydrogen atom.

In another preferred embodiment, the invention relates to compounds of formula (I), supra, wherein each of $R^{2a}$, $R^{2b}$, and $R^{2c}$ represents a hydrogen atom, and $R^{2d}$ represents a hydrogen atom or a group selected from: $C_1$-$C_3$-alkoxy-, halo-.

In another preferred embodiment, the invention relates to compounds of formula (I), supra, wherein each of $R^{2a}$, $R^{2b}$, and $R^{2c}$ represents a hydrogen atom, and $R^{2d}$ represents a group selected from: $C_1$-$C_3$-alkoxy-, halo-.

In another preferred embodiment, the invention relates to compounds of formula (I), supra, wherein each of $R^{2a}$, $R^{2b}$, and $R^{2c}$ represents a hydrogen atom, and $R^{2d}$ represents a $C_1$-$C_3$-alkoxy-group, preferably a methoxy-, ethoxy- or iso-propoxy-group.

In another preferred embodiment, the invention relates to compounds of formula (I), supra, wherein each of $R^{2a}$, $R^{2b}$, and $R^{2c}$ represents a hydrogen atom, and $R^{2d}$ represents a halogen atom, preferably a fluorine atom.

In another preferred embodiment, the invention relates to compounds of formula (I), supra, wherein each of $R^{2a}$, $R^{2b}$, $R^{2c}$ and $R^{2d}$ represents a hydrogen atom.

In another preferred embodiment, the invention relates to compounds of formula (Ia):

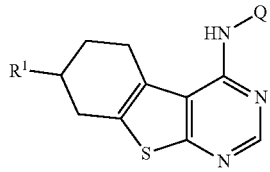

(Ia)

in which Q is selected from:

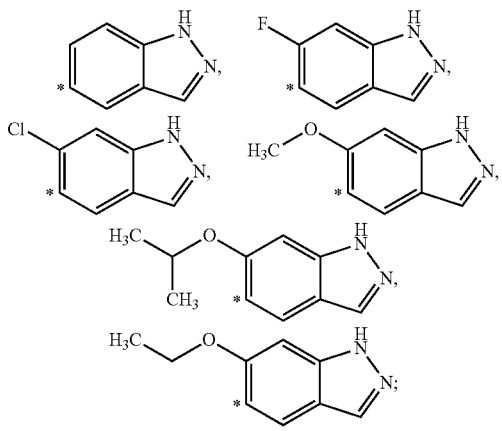

wherein * indicates the point of attachment of said groups with the rest of the molecule.

In another preferred embodiment, the invention relates to compounds of formula (Ia):

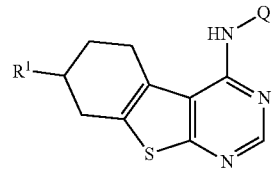

(Ia)

in which:
Q is selected from:

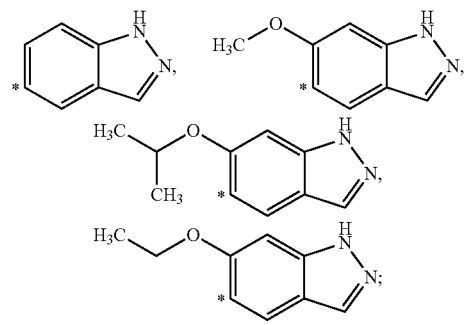

wherein * indicates the point of attachment of said groups with the rest of the molecule.

In another preferred embodiment, the invention relates to compounds of formula (I), supra, wherein $R^3$ represents a hydrogen atom or a group selected from:
$C_1$-$C_6$-alkyl-, $C_2$-$C_6$-alkynyl-, $C_3$-$C_7$-cycloalkyl-, —$(CH_2)_q$—($C_3$-$C_7$-cycloalkyl), —$(CH_2)_q$—O—($C_3$-$C_7$-cycloalkyl),
3- to 10-membered heterocycloalkyl,
—$(CH_2)_q$-(3- to 10-membered heterocycloalkyl),
—$(CH_2)_q$—O-(3- to 10-membered heterocycoalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;
said group being optionally substituted, one or more times, identically or differently, with a substituent selected from:
halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl, $C_1$-$C_6$-alkoxy-$C_1$-$C_6$-alkyl, halo-$C_1$-$C_6$-alkoxy-$C_1$-$C_6$-alkyl-, —$(CH_2)_q$-aryl, —$(CH_2)_q$-heteroaryl, —$(CH_2)_q$—($C_3$-$C_7$-cycloalkyl), —$(CH_2)_q$-(3- to 10-membered heterocycloalkyl),
$R^5$—O—, —C(=O)$R^5$, —C(=O)O—$R^5$, —OC(=O)—$R^5$, —N(H)C(=O)$R^5$, —N($R^4$)C(=O)$R^5$, —N(H)C(=O)N$R^5R^4$, —N($R^4$)C(=O)N$R^5R^4$, —N(H)$R^5$, —N$R^5R^4$, —C(=O)N(H)$R^5$, —C(=O)N$R^5R^4$,
$R^4$—S—, $R^4$—S(=O)—, $R^4$—S(=O)$_2$—, —N(H)S(=O)$R^4$, —N($R^4$)S(=O)$R^4$, —S(=O)N(H)$R^5$, —S(=O)N$R^5R^4$, —N(H)S(=O)$_2R^4$, —N($R^4$)S(=O)$_2R^4$, —S(=O)$_2$N(H)$R^5$, —S(=O)$_2$N$R^5R^4$,
—S(=O)(=N$R^5$)$R^4$, —S(=O)(=N$R^4$)$R^5$, —N=S(=O)($R^5$)$R^4$;
or
when two substituents are present ortho to each other on an aryl- or heteroaryl-ring, said two substituents together form a bridge:
*O$(CH_2)_p$O*, *NH(C(=O))NH*, wherein * represent the point of attachment to said aryl- or heteroaryl-ring, wherein p is 1 or 2.

In another preferred embodiment, the invention relates to compounds of formula (I), supra, wherein $R^3$ represents a hydrogen atom or a group selected from:
$C_1$-$C_6$-alkyl-, $C_2$-$C_6$-alkenyl-, $C_2$-$C_6$-alkynyl-, $C_3$-$C_7$-cycloalkyl-,
—$(CH_2)_q$—($C_3$-$C_7$-cycloalkyl), —$(CH_2)_q$—O—($C_3$-$C_7$-cycloalkyl), $C_4$-$C_7$-cycloalkenyl-,
—$(CH_2)_q$—($C_4$-$C_7$-cycloalkenyl), —$(CH_2)_q$—O—($C_4$-$C_7$-cycloalkenyl),
3- to 10-membered heterocycloalkyl, —$(CH_2)_q$-(3- to 10-membered heterocycloalkyl), —$(CH_2)_q$—O-(3- to 10-membered heterocycoalkyl),
4- to 10-membered heterocycloalkenyl, —$(CH_2)_q$-(4- to 10-membered heterocycloalkenyl), —$(CH_2)_q$—O-(4- to 10-membered heterocycloalkenyl),
aryl, —$(CH_2)_q$-aryl, —$(CH_2)_q$—O-aryl, heteroaryl, —$(CH_2)_q$-heteroaryl,
—$(CH_2)_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —$(CH_2)_q$-aryl, —N(H)$R^5$, —$NR^5R^4$, $R^4$—S(=O)$_2$—, —S(=O)$_2$N(H)$R^5$;
or
when two substituents are present ortho to each other on an aryl- or heteroaryl-ring, said two substituents together form a bridge:
*O($CH_2)_p$O*, *NH(C(=O))NH*, wherein * represent the point of attachment to said aryl- or heteroaryl-ring, wherein p is 1 or 2.

In another preferred embodiment, the invention relates to compounds of formula (I), supra, wherein $R^3$ represents a hydrogen atom or a group selected from:
$C_1$-$C_6$-alkyl-, $C_2$-$C_6$-alkynyl-, $C_3$-$C_7$-cycloalkyl-, —$(CH_2)_q$—($C_3$-$C_7$-cycloalkyl),
—$(CH_2)_q$—O—($C_3$-$C_7$-cycloalkyl), 3- to 10-membered heterocycloalkyl, —$(CH_2)_q$-(3- to 10-membered heterocycloalkyl), —$(CH_2)_q$—O-(3- to 10-membered heterocycoalkyl), aryl, —$(CH_2)_q$-aryl, —$(CH_2)_q$—O-aryl, heteroaryl, —$(CH_2)_q$-heteroaryl,
—$(CH_2)_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —$(CH_2)_q$-aryl, —N(H)$R^5$, —$NR^5R^4$, $R^4$—S(=O)$_2$—, —S(=O)$_2$N(H)$R^5$;
or
when two substituents are present ortho to each other on an aryl- or heteroaryl-ring, said two substituents together form a bridge:
*O($CH_2)_p$O*, *NH(C(=O))NH*, wherein * represent the point of attachment to said aryl- or heteroaryl-ring, wherein p is 1 or 2.

In another preferred embodiment, the invention relates to compounds of formula (I), supra, wherein $R^3$ represents a hydrogen atom or a group selected from:
$C_1$-$C_6$-alkyl-, $C_3$-$C_7$-cycloalkyl-, —$(CH_2)_q$—($C_3$-$C_7$-cycloalkyl), —$(CH_2)_q$-(3- to 10-membered heterocycloalkyl), —$(CH_2)_q$-aryl, —$(CH_2)_q$-heteroaryl;
said group being optionally substituted, one or more times, identically or differently, with a substituent selected from:
halo-, hydroxy-, cyano-, $C_1$-$C_6$-alkyl-, $C_1$-$C_6$-alkoxy-, —$(CH_2)_q$-aryl,
—N(H)$R^5$, —$NR^5R^4$, —C(=O)$NR^5R^4$, $R^4$—S(=O)$_2$—, —S(=O)$_2$N(H)$R^5$.

In another preferred embodiment, the invention relates to compounds of formula (I), supra, wherein $R^3$ represents a group selected from: aryl, —$(CH_2)_q$-aryl; said group being optionally substituted, one or more times, identically or differently, with a substituent selected from:
halo-, hydroxy-, cyano-, $C_1$-$C_6$-alkyl-, halo-$C_1$-$C_6$-alkyl-, $C_1$-$C_6$-alkoxy-, —N(H)$R^5$, —$NR^5R^4$.

In another preferred embodiment, the invention relates to compounds of formula (I), supra, wherein $R^3$ represents a hydrogen atom or a group selected from:
$C_1$-$C_6$-alkyl-, —$(CH_2)_q$—($C_3$-$C_7$-cycloalkyl), —$(CH_2)_q$-aryl, —$(CH_2)_q$—O-aryl,
—$(CH_2)_q$-heteroaryl;
said group being optionally substituted, one or more times, identically or differently, with a substituent selected from:
halo-, hydroxy-, $C_1$-$C_6$-alkyl-,
halo-$C_1$-$C_6$-alkyl-, $C_1$-$C_6$-alkoxy-, —$NR^5R^4$, —S(=O)$_2$N(H)$R^5$;
or
when two substituents are present ortho to each other on an aryl- or heteroaryl-ring, said two substituents together form a bridge:
*O($CH_2)_p$O*, wherein * represent the point of attachment to said aryl- or heteroaryl-ring, wherein p is 1 or 2.

In another preferred embodiment, the invention relates to compounds of formula (I), supra, wherein $R^3$ represents a hydrogen atom or a $C_1$-$C_6$-alkyl-group.

In another preferred embodiment, the invention relates to compounds of formula (I), supra, wherein $NR^3R^4$ together represent a 3- to 10-membered heterocycloalkyl group; which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, $R^6R^7N$—$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —$(CH_2)_q$—$C_3$-$C_7$-cycloalkyl-, —$(CH_2)_q$-aryl, —$(CH_2)_q$-heteroaryl, —C(=O)$R^5$, —C(=O)O—$R^5$, —N(H)C(=O)$R^5$, $R^5$—S(=O)$_2$— or —C(=O)$NR^6R^7$;
wherein said $C_1$-$C_6$-alkyl-, —$(CH_2)_q$—$C_3$-$C_7$-cycloalkyl, —$(CH_2)_q$-aryl, or —$(CH_2)_q$-heteroaryl group is optionally substituted, one or more times, identically or differently, with a group selected from: cyano-, $C_1$-$C_6$-alkyl-, —$NR^6R^7$, —C(=O)N(H)$R^5$, —C(=O)$NR^6R^7$.
$R^6$ represents a hydrogen atom, a $C_1$-$C_6$-alkyl- or a $C_3$-$C_7$-cycloalkyl-group, and $R^7$ represents a hydrogen atom, a $C_1$-$C_6$-alkyl- or a $C_3$-$C_7$-cycloalkyl-group; or $NR^6R^7$ together represent a 3- to 10-membered heterocycloalkyl or a 4- to 10-membered heterocycloalkenyl group.

In another preferred embodiment, the invention relates to compounds of formula (I), supra, wherein $NR^3R^4$ together represent a 3- to 10-membered heterocycloalkyl group; which is optionally substituted, one or more times, identically or differently, with hydroxyl, $C_1$-$C_6$-alkyl-, $C_1$-$C_6$-alkoxy-, hydroxy-$C_1$-$C_6$-alkyl-, $C_1$-$C_6$-alkoxy-$C_1$-$C_6$-alkyl-, —$(CH_2)_q$—$C_3$-$C_7$-cycloalkyl, —$(CH_2)_q$-aryl, —$(CH_2)_q$-heteroaryl, —C(=O)$R^5$, —C(=O)O—$R^5$, —N(H)C(=O)$R^5$, $R^5$—S(=O)$_2$—, $R^6R^7N$—$C_1$-$C_6$-alkyl- or —C(=O)$NR^6R^7$; wherein said $C_1$-$C_6$-alkyl-, —$(CH_2)_q$—$C_3$-$C_7$-cycloalkyl, —$(CH_2)_q$-aryl, or —$(CH_2)_q$-heteroaryl group is optionally substituted, one or more times, identically or differently, with a group selected from: cyano-, $C_1$-$C_6$-alkyl-, —$NR^6R^7$, —C(=O)N(H)$R^5$, —C(=O)$NR^6R^7$.

In another preferred embodiment, the invention relates to compounds of formula (I), supra, wherein $NR^3R^4$ together represent a 3- to 10-membered heterocycloalkyl group; which is optionally substituted, one or more times, identically or differently, with —CN, —OH, $C_1$-$C_6$-alkyl-, $R^6R^7N$—$C_1$-$C_6$-alkyl- or —C(=O)$NR^6R^7$.

In another preferred embodiment, the invention relates to compounds of formula (I), supra, wherein $NR^3R^4$ together represent a 3- to 10-membered heterocycloalkyl-group; which is optionally substituted, one or more times, identically or differently, with halo-, hydroxy-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-.

In another preferred embodiment, the invention relates to compounds of formula (I), supra, wherein $NR^3R^4$ together represent a 3- to 10-membered heterocycloalkyl-group; said group being optionally substituted with $C_1$-$C_3$-alkyl-.

In another preferred embodiment, the invention relates to compounds of formula (I), supra, wherein $R^4$ represents a group selected from: $C_1$-$C_6$-alkyl-, halo-$C_1$-$C_6$-alkyl-, hydroxy-$C_1$-$C_6$-alkyl-.

In another preferred embodiment, the invention relates to compounds of formula (I), supra, wherein $R^4$ represents a group selected from: $C_1$-$C_6$-alkyl-, $C_2$-$C_6$-alkynyl-.

In another preferred embodiment, the invention relates to compounds of formula (I), supra, wherein $R^4$ represents a $C_1$-$C_6$-alkyl-group.

In another preferred embodiment, the invention relates to compounds of formula (I), supra, wherein $R^5$ represents a hydrogen atom, a $C_1$-$C_6$-alkyl- or $C_3$-$C_7$-cycloalkyl-group.

In another preferred embodiment, the invention relates to compounds of formula (I), supra, wherein $R^5$ represents a hydrogen atom or a $C_1$-$C_6$-alkyl-group.

In another preferred embodiment, the invention relates to compounds of formula (I), supra, wherein $R^5$ represents a $C_1$-$C_6$-alkyl-group.

In another preferred embodiment, the invention relates to compounds of formula (I), supra, wherein $R^5$ represents a hydrogen atom.

In another preferred embodiment, the invention relates to compounds of formula (I), supra, wherein $R^6$ represents a $C_1$-$C_6$-alkyl-group.

In another preferred embodiment, the invention relates to compounds of formula (I), supra, wherein $R^7$ represents a $C_1$-$C_6$-alkyl-group.

In another preferred embodiment, the invention relates to compounds of formula (I), supra, wherein $NR^6R^7$ together represent a 3- to 10-membered heterocycloalkyl group.

In another preferred embodiment, the invention relates to compounds of formula (I), supra, wherein $R^5$, $R^6$ and $R^7$ represent a $C_1$-$C_6$-alkyl-group.

In another preferred embodiment, the invention relates to compounds of formula (I), supra, wherein p represents 1.

In another preferred embodiment, the invention relates to compounds of formula (I), supra, wherein q represents 0.

In another preferred embodiment, the invention relates to compounds of formula (I), supra, wherein q represents 1.

In another preferred embodiment, the invention relates to compounds of formula (I), supra, wherein q represents 2.

In another preferred embodiment, the invention relates to compounds of formula (I), supra, wherein $R^1$ is selected from:

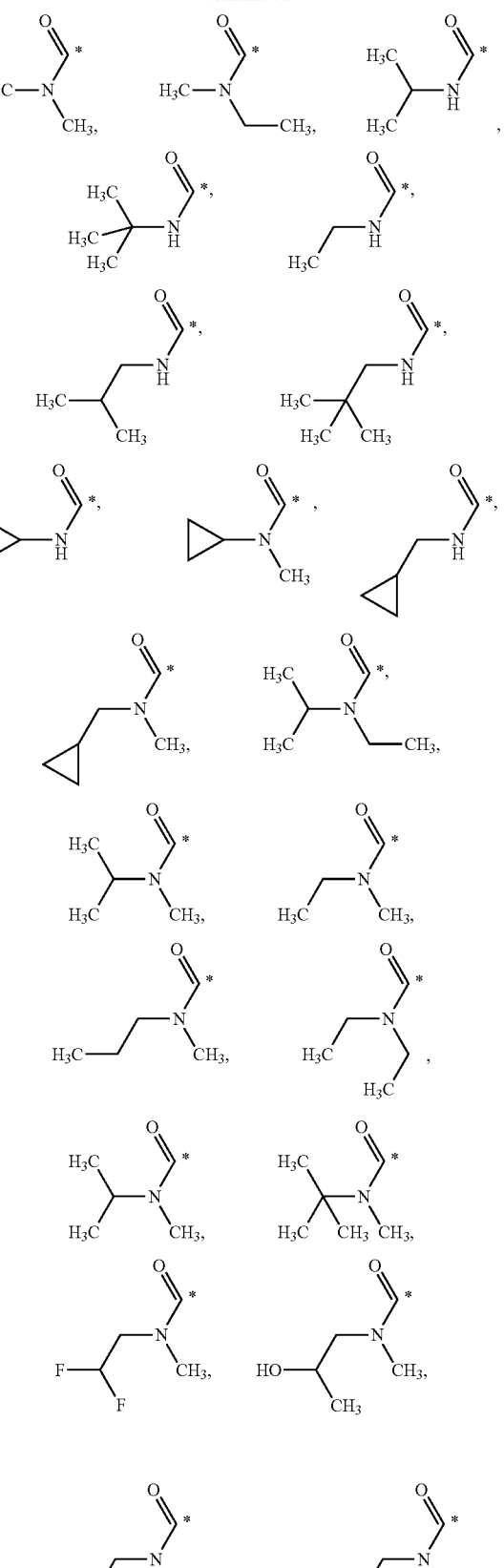

-continued
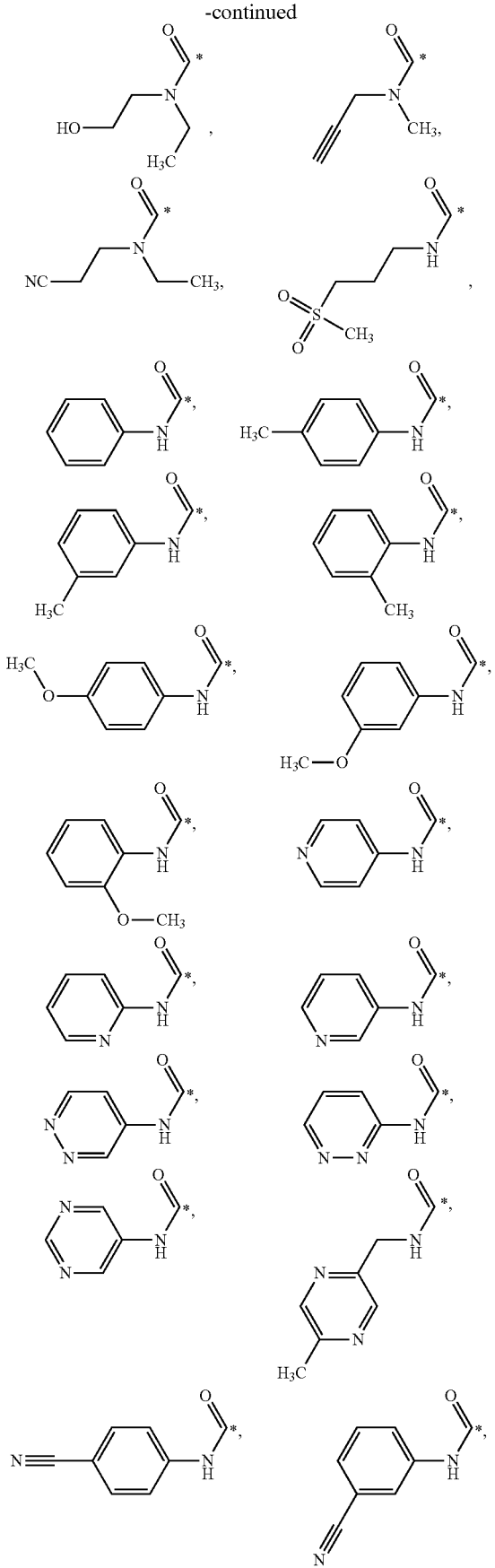
-continued
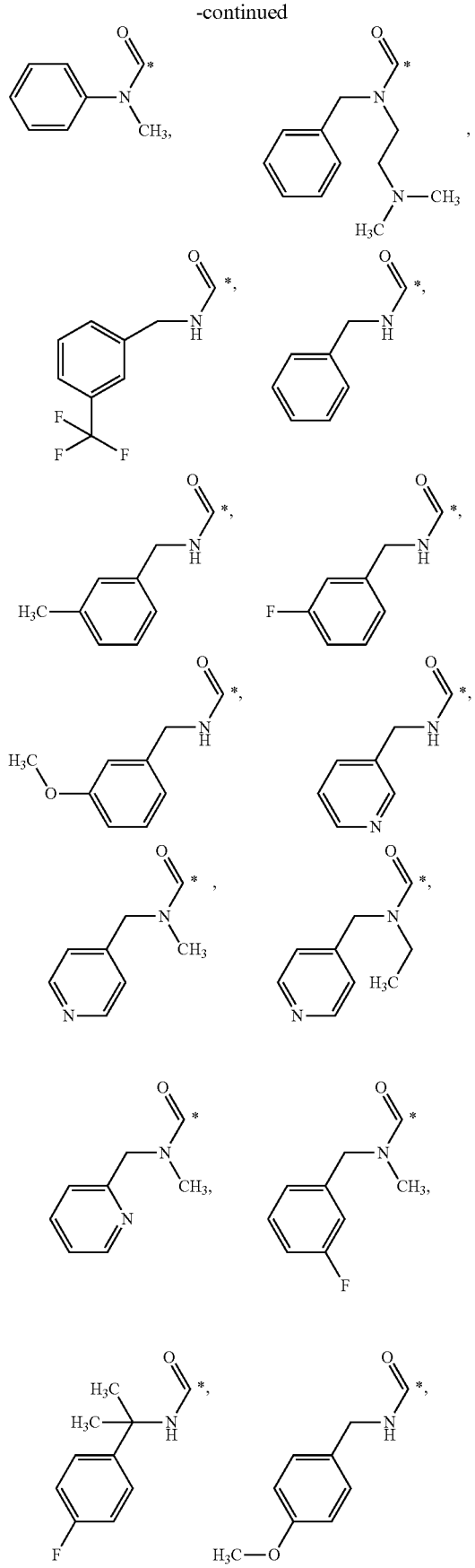

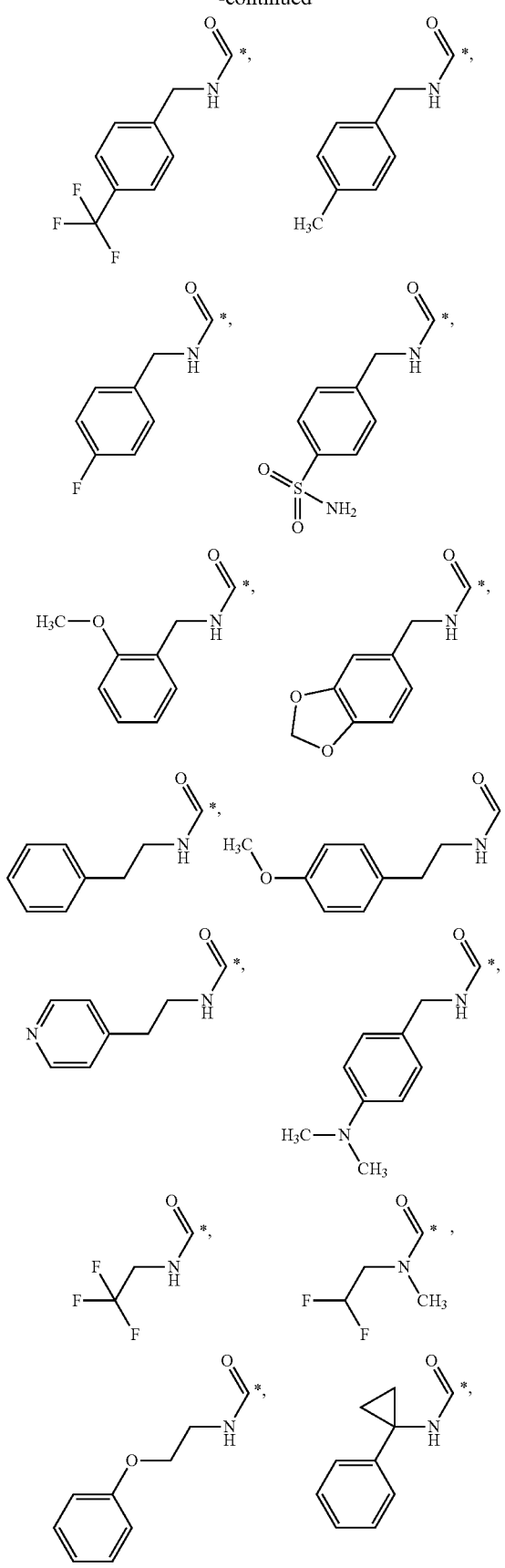
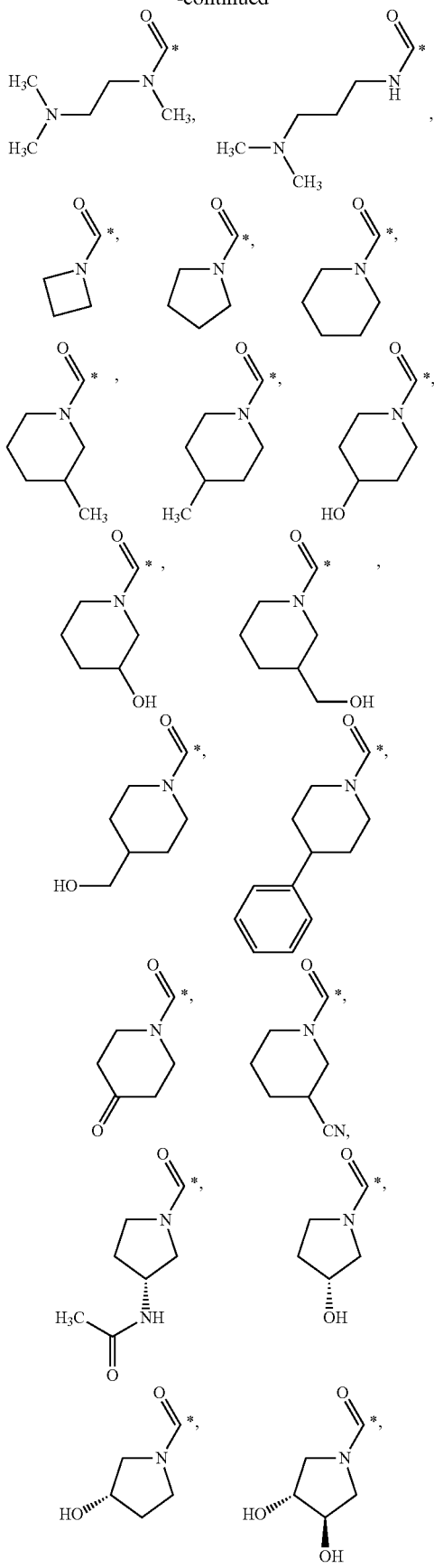

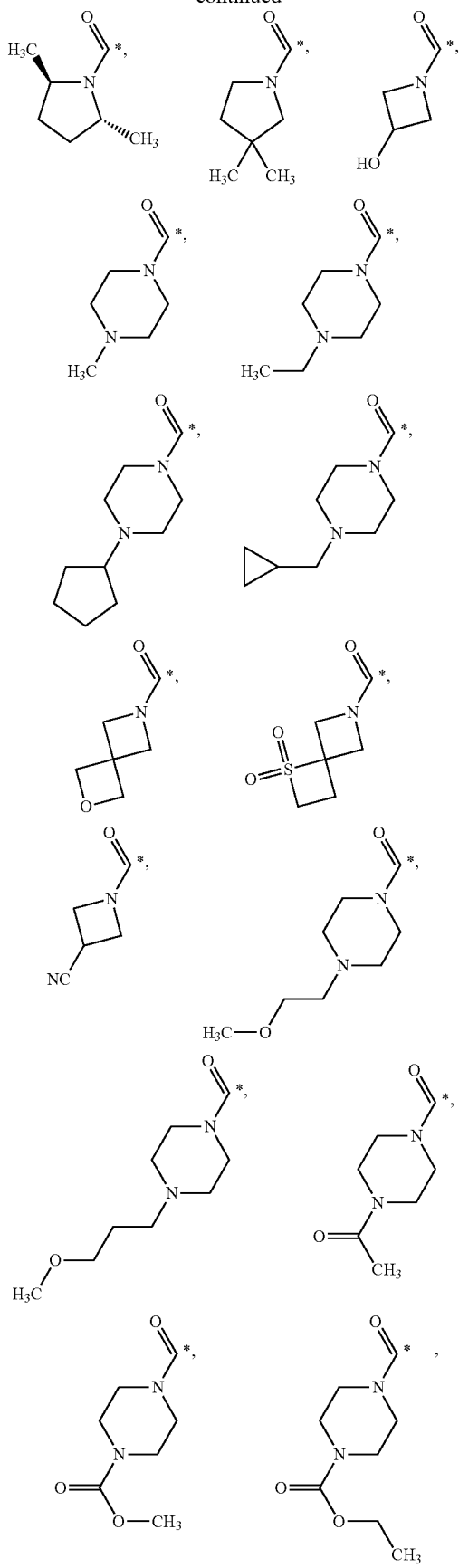
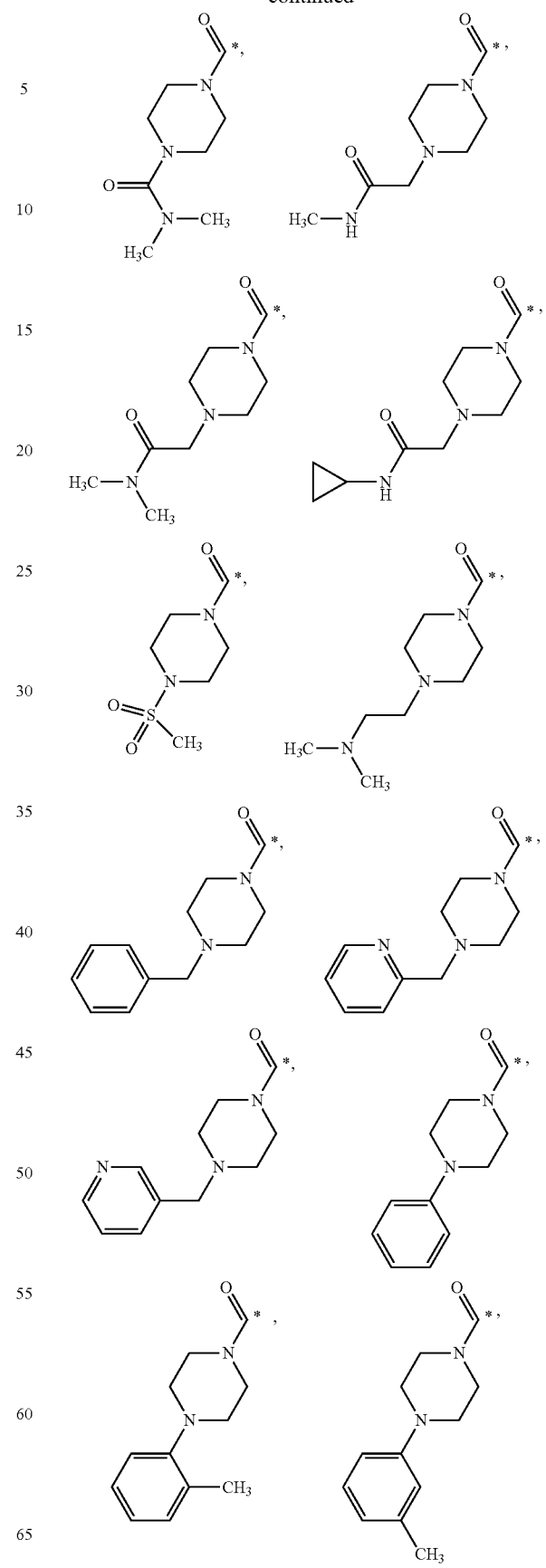

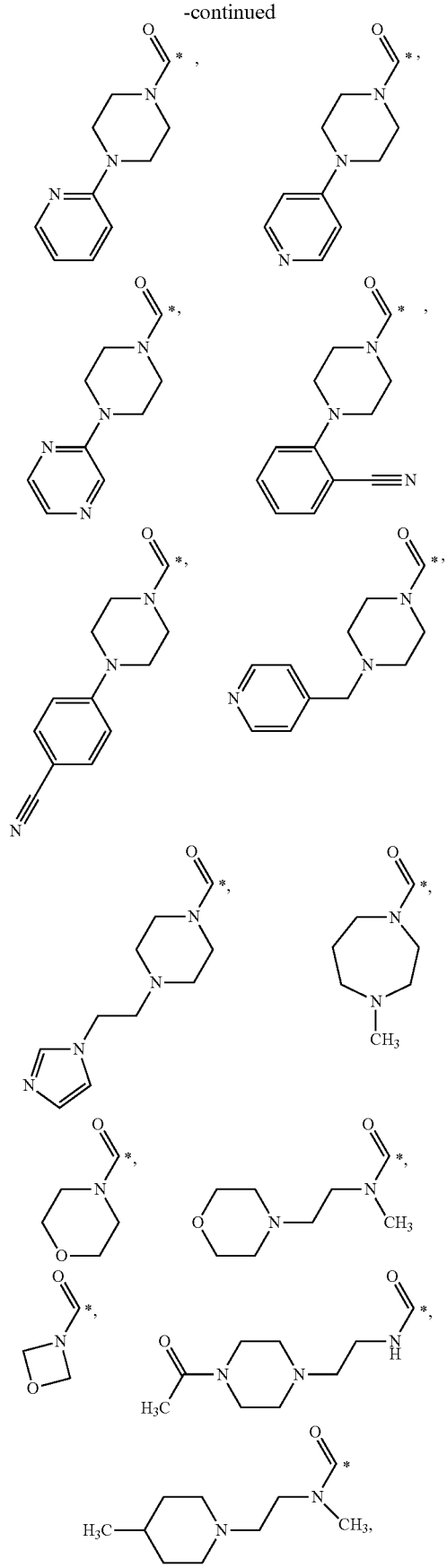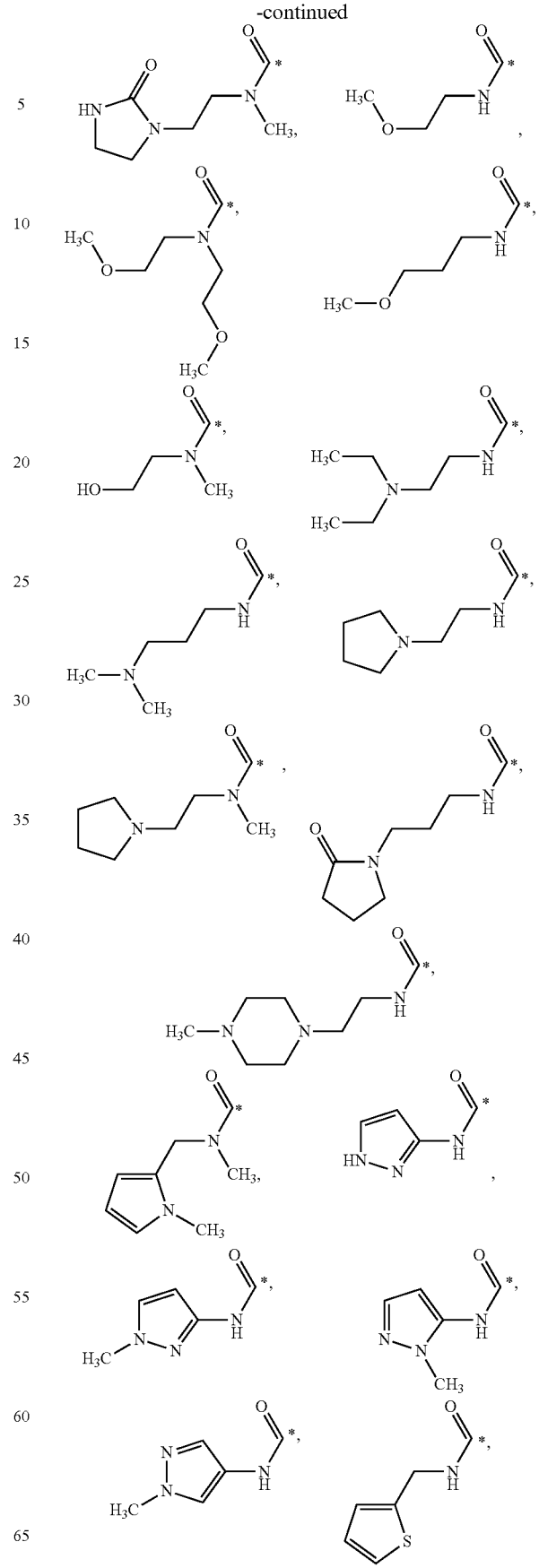

-continued

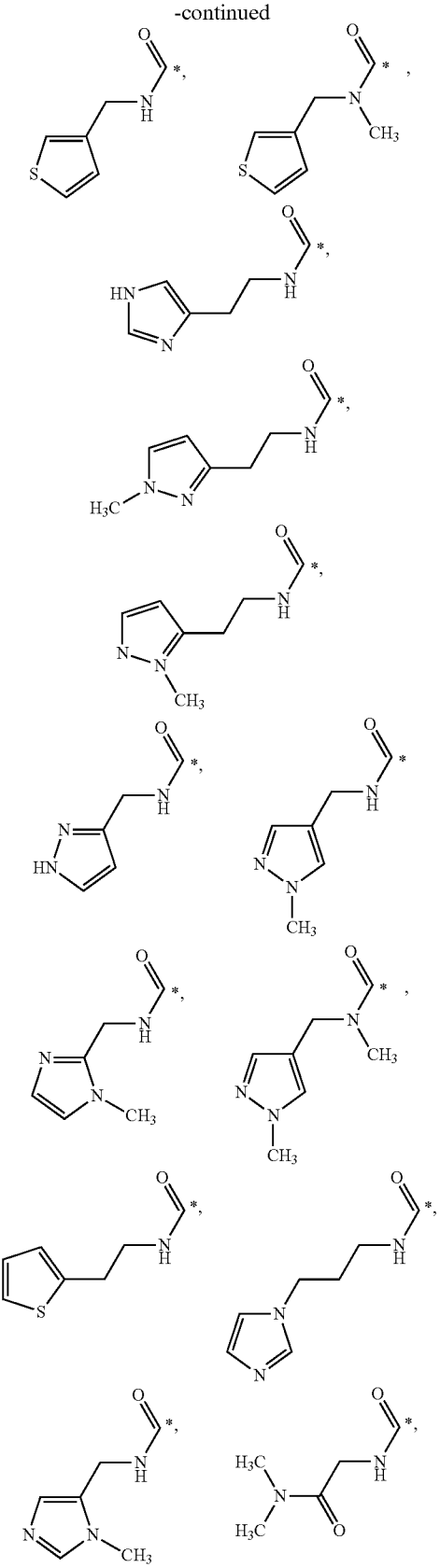

wherein * indicates the point of attachment of said groups with the rest of the molecule.

In a further embodiment of the above-mentioned aspect, the invention relates to compounds of formula (I), according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of formula (I):

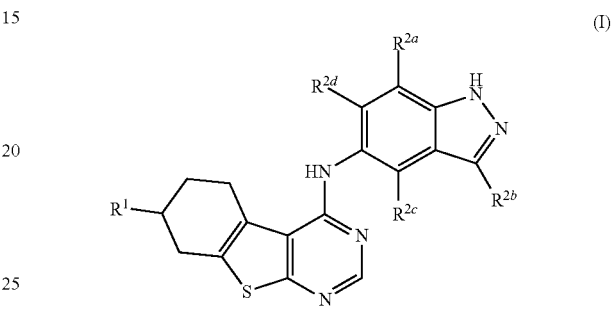

(I)

in which:

$R^1$ represents a group selected from:
—C(=O)O—$R^3$, —C(=O)N(H)$R^3$, —C(=O)N$R^3R^4$;

$R^{2a}$ represents a hydrogen atom or a group selected from:
$C_1$-$C_3$-alkyl-, $C_1$-$C_3$-alkoxy-, halo-, hydroxy-, halo-$C_1$-$C_3$-alkyl-,
halo-$C_1$-$C_3$-alkoxy-, cyano-, —N(H)$R^5$, —N$R^5R^4$;

$R^{2b}$ represents a hydrogen atom or a group selected from:
$C_1$-$C_3$-alkyl-, $C_1$-$C_3$-alkoxy-, halo-, hydroxy-, halo-$C_1$-$C_3$-alkyl-,
halo-$C_1$-$C_3$-alkoxy-, cyano-, —N(H)$R^5$, —N$R^5R^4$;

$R^{2c}$ represents a hydrogen atom or a group selected from:
$C_1$-$C_3$-alkyl-, $C_1$-$C_3$-alkoxy-, halo-, hydroxy-, halo-$C_1$-$C_3$-alkyl-,
halo-$C_1$-$C_3$-alkoxy-, cyano-, —N(H)$R^5$, —N$R^5R^4$;

$R^{2d}$ represents a hydrogen atom or a group selected from:
$C_1$-$C_3$-alkyl-, $C_1$-$C_3$-alkoxy-, halo-, hydroxy-, halo-$C_1$-$C_3$-alkyl-, halo-$C_1$-$C_3$-alkoxy-, cyano-, —N(H)$R^5$, —N$R^5R^4$;

$R^3$ represents a hydrogen atom or a group selected from:
$C_1$-$C_6$-alkyl-, $C_2$-$C_6$-alkenyl-, $C_2$-$C_6$-alkynyl-, —(CH$_2$)$_q$—($C_3$-$C_7$-cycloalkyl), —(CH$_2$)$_q$—O—($C_3$-$C_7$-cycloalkyl), —(CH$_2$)$_q$—($C_4$-$C_7$-cycloalkenyl), —(CH$_2$)$_q$—O—($C_4$-$C_7$-cycloalkenyl), —(CH$_2$)$_q$-(3- to 10-membered heterocycloalkyl), —(CH$_2$)$_q$—O-(3- to 10-membered heterocycloalkyl), —(CH$_2$)$_q$-(4- to 10-membered heterocycloalkenyl), —(CH$_2$)$_q$—O-(4- to 10-membered heterocycloalkenyl),
—(CH$_2$)$_q$-aryl, —(CH$_2$)$_q$—O-aryl, —(CH$_2$)$_q$-heteroaryl, —(CH$_2$)$_q$—O-heteroaryl;

said group being optionally substituted, one or more times, identically or differently, with a substituent selected from:
halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-,
—(CH$_2$)$_q$-aryl, —(CH$_2$)$_q$-heteroaryl, —(CH$_2$)$_q$—($C_3$-$C_7$-cycloalkyl), —(CH$_2$)$_q$-(3- to 10-membered heterocycloalkyl), halo-$C_1$-$C_6$-alkoxy-$C_1$-$C_6$-alkyl-, $R^5$—O—, —C(=O)$R^5$, —C(=O)O—$R^5$, —OC(=O)—$R^5$, —N(H)C(=O)$R^5$, —N($R^4$)C(=O)$R^5$, —N(H)C(=O)N$R^5R^4$, —N($R^4$)C(=O)N$R^5R^4$, —N(H)$R^5$, —N$R^5R^4$, —C(=O)N(H)$R^5$, —C(=O)N$R^5R^4$, $R^4$—S—, $R^4$—S(=O)—, $R^4$—S(=O)$_2$—, —N(H)S(=O)$R^4$, —N($R^4$)S(=O)$R^4$, —S(=O)N(H)$R^5$, —S(=O)N$R^5R^4$, —N(H)S(=O)$_2R^4$, —N($R^4$)S(=O)$_2R^4$, —S(=O)$_2$N(H)$R^5$, —S(=O)$_2$N$R^5R^4$, —S(=O)(=N$R^5$)$R^4$, —S(=O)(=N$R^4$)$R^5$, —N=S(=O)($R^5$)$R^4$;

or when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;

$R^4$ represents a group selected from:
$C_1$-$C_6$-alkyl-, $C_2$-$C_6$-alkenyl-, $C_2$-$C_6$-alkynyl-, halo-$C_1$-$C_6$-alkyl-, hydroxy-$C_1$-$C_6$-alkyl-, $C_1$-$C_6$-alkoxy-$C_1$-$C_6$-alkyl-;

or

N$R^3R^4$ together
represent a 3- to 10-membered heterocycloalkyl or 4- to 10-membered heterocycloalkenyl group;
which is optionally substituted, one or more times, identically or differently, with halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, $R^6R^7$N—$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —(CH$_2$)$_q$—$C_3$-$C_7$-cycloalkyl, —(CH$_2$)$_q$-aryl, —(CH$_2$)$_q$-heteroaryl, $R^5$—O—, —C(=O)$R^5$, —C(=O)O—$R^5$, —OC(=O)—$R^5$, —N(H)C(=O)$R^5$, —N($R^4$)C(=O)$R^5$, —N(H)C(=O)N$R^6R^7$, —N($R^5$)C(=O)N$R^6R^7$, —N(H)$R^5$, —N$R^6R^7$, —C(=O)N(H)$R^5$, —C(=O)N$R^6R^7$, $R^5$—S—, $R^5$—S(=O)—, $R^5$—S(=O)$_2$—, —N(H)S(=O)$R^5$, —N($R^5$)S(=O)$R^6$, —S(=O)N(H)$R^5$, —S(=O)N$R^6R^7$, —N(H)S(=O)$_2R^5$, —N($R^5$)S(=O)$_2R^6$, —S(=O)$_2$N(H)$R^6$, —S(=O)$_2$N$R^6R^7$, —S(=O)(=N$R^5$)$R^6$, —S(=O)(=N$R^5$)$R^6$, —N=S(=O)($R^5$)$R^6$;
wherein said $C_1$-$C_6$-alkyl-, —(CH$_2$)$_q$—$C_3$-$C_7$-cycloalkyl, —(CH$_2$)$_q$-aryl, or —(CH$_2$)$_q$-heteroaryl group is optionally substituted, one or more times, identically or differently, with a group selected from: halo-, hydroxy-, oxo-(O=), cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, $R^6R^7$N—$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $R^5$—O—, —C(=O)$R^5$, —C(=O)O—$R^5$, —OC(=O)—$R^5$, —N(H)C(=O)$R^5$, —N($R^4$)C(=O)$R^5$, —N(H)C(=O)N$R^6R^7$, —N($R^5$)C(=O)N$R^6R^7$, —N(H)$R^5$, —N$R^6R^7$, —C(=O)N(H)$R^5$, —C(=O)N$R^6R^7$, $R^5$—S—, $R^5$—S(=O)—, $R^5$—S(=O)$_2$—, —N(H)S(=O)$R^5$, —N($R^5$)S(=O)$R^6$, —S(=O)N(H)$R^5$, —S(=O)N$R^5R^6$, —N(H)S(=O)$_2R^5$, —N($R^5$)S(=O)$_2R^6$, —S(=O)$_2$N(H)$R^6$, —S(=O)$_2$N$R^5R^6$, —S(=O)(=N$R^5$)$R^6$, —S(=O)(=N$R^5$)$R^6$, —N=S(=O)($R^5$)$R^6$;

$R^5$ represents a hydrogen atom, a $C_1$-$C_6$-alkyl- or a $C_3$-$C_7$-cycloalkyl-group;

$R^6$ represents a hydrogen atom, a $C_1$-$C_6$-alkyl- or a $C_3$-$C_7$-cycloalkyl-group;

$R^7$ represents a hydrogen atom, a $C_1$-$C_6$-alkyl- or a $C_3$-$C_7$-cycloalkyl-group;

or

N$R^6R^7$ together represent a 3- to 10-membered heterocycloalkyl or a 4- to 10-membered heterocycloalkenyl group;

p represents an integer of 1 or 2;
q represents an integer of 0, 1, 2 or 3;
or a tautomer, an N-oxide, a hydrate, a solvate, or a salt thereof, or a mixture of same.

In a preferred embodiment, the invention relates to compounds of formula (I):

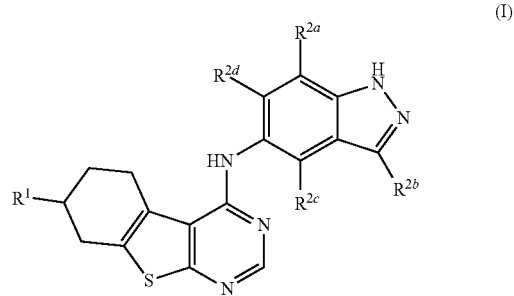

in which:

$R^1$ represents a group selected from:
—C(=O)O—$R^3$, —C(=O)N(H)$R^3$, —C(=O)N$R^3R^4$;

$R^{2a}$ represents a hydrogen atom or a $C_1$-$C_3$-alkyl-group;

$R^{2b}$ represents a hydrogen atom or a group selected from:
$C_1$-$C_3$-alkyl-, halo-$C_1$-$C_3$-alkyl-, cyano-;

$R^{2c}$ represents a hydrogen atom or a group selected from:
$C_1$-$C_3$-alkyl-, $C_1$-$C_3$-alkoxy-, halo-, —N(H)$R^5$, —N$R^5R^4$;

$R^{2d}$ represents a hydrogen atom or a group selected from:
$C_1$-$C_3$-alkyl-, $C_1$-$C_3$-alkoxy-, halo-, —N(H)$R^5$, —N$R^5R^4$;

$R^3$ represents a hydrogen atom or a group selected from:
$C_1$-$C_6$-alkyl-, $C_2$-$C_6$-alkenyl-, $C_2$-$C_6$-alkynyl-, $C_3$-$C_7$-cycloalkyl-, —(CH$_2$)$_q$—($C_3$-$C_7$-cycloalkyl), —(CH$_2$)$_q$—O—($C_3$-$C_7$-cycloalkyl), $C_4$-$C_7$-cycloalkenyl-, —(CH$_2$)$_q$—($C_4$-$C_7$-cycloalkenyl), —(CH$_2$)$_q$—O—($C_4$-$C_7$-cycloalkenyl),
3- to 10-membered heterocycloalkyl, —(CH$_2$)$_q$-(3- to 10-membered heterocycloalkyl),
—(CH$_2$)$_q$—O-(3- to 10-membered heterocycoalkyl),
4- to 10-membered heterocycloalkenyl,
—(CH$_2$)$_q$-(4- to 10-membered heterocycloalkenyl),
—(CH$_2$)$_q$—O-(4- to 10-membered heterocycloalkenyl),
aryl, —(CH$_2$)$_q$-aryl, —(CH$_2$)$_q$—O-aryl, heteroaryl, —(CH$_2$)$_q$-heteroaryl, —(CH$_2$)$_q$—O-heteroaryl;
said group being optionally substituted, one or more times, identically or differently, with a substituent selected from:
halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-,
halo-$C_1$-$C_6$-alkoxy-$C_1$-$C_6$-alkyl-, $R^5$—O—, —C(=O)$R^5$, —C(=O)O—$R^5$, —OC(=O)—$R^5$, —N(H)C(=O)$R^5$, —N($R^4$)C(=O)$R^5$, —N(H)C(=O)N$R^5R^4$, —N($R^4$)C(=O)N$R^5R^4$, —N(H)$R^5$, —NR$^5$R$^4$, —C(=O)N(H)R$^5$, —C(=O)NR$^5$R$^4$, R$^4$—S—, R$^4$—S(=O)—, R$^4$—S(=O)$_2$—,
—N(H)S(=O)R$^4$, —N(R$^4$)S(=O)R$^4$, —S(=O)N(H)R$^5$, —S(=O)NR$^5$R$^4$,
—N(H)S(=O)$_2$R$^4$, —N(R$^4$)S(=O)$_2$R$^4$, —S(=O)$_2$N(H)R$^5$, —S(=O)$_2$NR$^5$R$^4$,
—S(=O)(=NR$^5$)R$^4$, —S(=O)(=NR$^4$)R$^5$, —N=S(=O)(R$^5$)R$^4$;
or
when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;
R$^4$ represents a C$_1$-C$_6$-alkyl- or hydroxy-C$_1$-C$_6$-alkyl-group;
or
NR$^3$R$^4$ together
represent a 3- to 10-membered heterocycloalkyl or a 4- to 10-membered heterocycloalkenyl group;
which is optionally substituted, one or more times, identically or differently, with halo-, hydroxyl-, cyano-, nitro-, C$_1$-C$_6$-alkyl-, halo-C$_1$-C$_6$-alkyl-,
C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, —NR$^6$R$^7$, R$^6$R$^7$N—C$_1$-C$_6$-alkyl-,
halo-C$_1$-C$_6$-alkoxy-C$_1$-C$_6$-alkyl-, C$_2$-C$_6$-alkenyl-, C$_2$-C$_6$-alkynyl-,
C$_3$-C$_7$-cycloalkyl- or —C(=O)NR$^6$R$^7$;
R$^5$ represents a hydrogen atom, a C$_1$-C$_6$-alkyl- or a C$_3$-C$_7$-cycloalkyl-group;
R$^6$ represents a hydrogen atom, a C$_1$-C$_6$-alkyl- or a C$_3$-C$_7$-cycloalkyl-group;
R$^7$ represents a hydrogen atom, a C$_1$-C$_6$-alkyl- or a C$_3$-C$_7$-cycloalkyl-group;
or
NR$^6$R$^7$ together represent a 3- to 10-membered heterocycloalkyl or 4- to 10-membered heterocycloalkenyl group;
p represents an integer of 1 or 2;
q represents an integer of 1, 2 or 3;
or a tautomer, an N-oxide, a hydrate, a solvate, or a salt thereof, or a mixture of same.

In another preferred embodiment, the invention relates to compounds of formula (I):

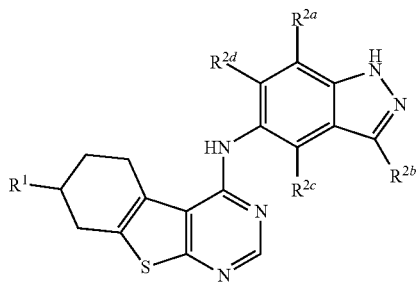

in which:
R$^1$ represents a group selected from:
—C(=O)O—R$^3$, —C(=O)N(H)R$^3$, —C(=O)NR$^3$R$^4$;
R$^{2a}$ represents a hydrogen atom;
R$^{2b}$ represents a hydrogen atom or a group selected from: C$_1$-C$_3$-alkyl-, halo-C$_1$-C$_3$-alkyl-, cyano-;
R$^{2c}$ represents a hydrogen atom or a group selected from: C$_1$-C$_3$-alkyl-, C$_1$-C$_3$-alkoxy-, halo-, —N(H)R$^5$, —NR$^5$R$^4$;

R$^{2d}$ represents a hydrogen atom or a group selected from: C$_1$-C$_3$-alkyl-, C$_1$-C$_3$-alkoxy-, halo-, —N(H)R$^5$, —NR$^5$R$^4$;
R$^3$ represents a hydrogen atom or a group selected from:
C$_1$-C$_6$-alkyl-, C$_2$-C$_6$-alkynyl-, C$_3$-C$_7$-cycloalkyl-,
—(CH$_2$)$_q$—(C$_3$-C$_7$-cycloalkyl),
—(CH$_2$)$_q$—O—(C$_3$-C$_7$-cycloalkyl),
3- to 10-membered heterocycloalkyl,
—(CH$_2$)$_q$-(3- to 10-membered heterocycloalkyl),
—(CH$_2$)$_q$—O-(3- to 10-membered heterocycoalkyl),
aryl, —(CH$_2$)$_q$-aryl, —(CH$_2$)$_q$—O-aryl, heteroaryl,
—(CH$_2$)$_q$-heteroaryl, —(CH$_2$)$_q$—O-heteroaryl;
said group being optionally substituted, one or more times, identically or differently, with a substituent selected from:
halo-, hydroxy-, oxo-(O=), cyano-, nitro-, C$_1$-C$_6$-alkyl-, C$_2$-C$_6$-alkenyl-, C$_2$-C$_6$-alkynyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-,
halo-C$_1$-C$_6$-alkoxy-C$_1$-C$_6$-alkyl-, R$^5$—O—, —C(=O)R$^5$, —C(=O)O—R$^5$, —OC(=O)—R$^5$,
—N(H)C(=O)R$^5$, —N(R$^4$)C(=O)R$^5$, —N(H)C(=O)NR$^5$R$^4$, —N(R$^4$)C(=O)NR$^5$R$^4$, —N(H)R$^5$,
—NR$^5$R$^4$, —C(=O)N(H)R$^5$, —C(=O)NR$^5$R$^4$, R$^4$—S—, R$^4$—S(=O)—, R$^4$—S(=O)$_2$—,
—N(H)S(=O)R$^4$, —N(R$^4$)S(=O)R$^4$, —S(=O)N(H)R$^5$, —S(=O)NR$^5$R$^4$,
—N(H)S(=O)$_2$R$^4$, —N(R$^4$)S(=O)$_2$R$^4$, —S(=O)$_2$N(H)R$^5$, —S(=O)$_2$NR$^5$R$^4$,
—S(=O)(=NR$^5$)R$^4$, —S(=O)(=NR$^4$)R$^5$, —N=S(=O)(R$^5$)R$^4$;
or
when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;
R$^4$ represents a C$_1$-C$_6$-alkyl- or a hydroxy-C$_1$-C$_6$-alkyl-group;
or
NR$^3$R$^4$ together
represent a 3- to 10-membered heterocycloalkyl or a 4- to 10-membered heterocycloalkenyl group;
which is optionally substituted, one or more times, identically or differently, with halo-, hydroxyl-, cyano-, nitro-, C$_1$-C$_6$-alkyl-, halo-C$_1$-C$_6$-alkyl-, C$_1$-C$_6$-alkoxy-,
halo-C$_1$-C$_6$-alkoxy-, hydroxy-C$_1$-C$_6$-alkyl-, C$_1$-C$_6$-alkoxy-C$_1$-C$_6$-alkyl-, —NR$^6$R$^7$, R$^6$R$^7$N—C$_1$-C$_6$-alkyl-,
halo-C$_1$-C$_6$-alkoxy-C$_1$-C$_6$-alkyl-, C$_2$-C$_6$-alkenyl-, C$_2$-C$_6$-alkynyl-, C$_3$-C$_7$-cycloalkyl- or —C(=O)NR$^6$R$^7$;
R$^5$ represents a hydrogen atom or a C$_1$-C$_6$-alkyl-group;
R$^6$ represents a hydrogen atom or a C$_1$-C$_6$-alkyl-group;
R$^7$ represents a hydrogen atom or a C$_1$-C$_6$-alkyl-group;
or
NR$^6$R$^7$ together represent a 3- to 10-membered heterocycloalkyl group;
p represents an integer of 1 or 2;
q represents an integer of 1, 2 or 3;
or a tautomer, an N-oxide, a hydrate, a solvate, or a salt thereof, or a mixture of same.

In another preferred embodiment, the invention relates to compounds of formula (I):

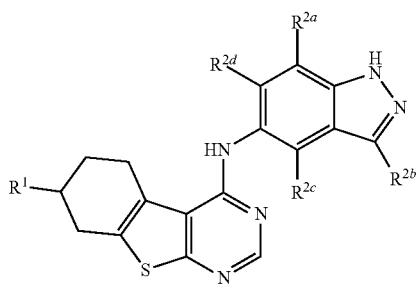

(I)

in which:
R¹ represents a group selected from:
—C(=O)O—R³, —C(=O)N(H)R³, —C(=O)NR³R⁴;
$R^{2a}$ represents a hydrogen atom;
$R^{2b}$ represents a hydrogen atom or a $C_1$-$C_3$-alkyl-group;
$R^{2c}$ represents a hydrogen atom or a group selected from:
  $C_1$-$C_3$-alkyl-,  $C_1$-$C_3$-alkoxy-,  halo-,  —N(H)R⁵, —NR⁵R⁴;
$R^{2d}$ represents a hydrogen atom or a group selected from:
  $C_1$-$C_3$-alkyl-,  $C_1$-$C_3$-alkoxy-,  halo-,  —N(H)R⁵, —NR⁵R⁴;
R³ represents a hydrogen atom or a group selected from:
  $C_1$-$C_6$-alkyl-,  $C_2$-$C_6$-alkynyl-,  $C_3$-$C_7$-cycloalkyl-,
  —(CH₂)$_q$—($C_3$-$C_7$-cycloalkyl),
  —(CH₂)$_q$—O—($C_3$-$C_7$-cycloalkyl),
  3- to 10-membered heterocycloalkyl,
  —(CH₂)$_q$-(3- to 10-membered heterocycloalkyl),
  —(CH₂)$_q$—O-(3- to 10-membered heterocycoalkyl),
  aryl, —(CH₂)$_q$-aryl, —(CH₂)$_q$—O-aryl, heteroaryl,
  —(CH₂)$_q$-heteroaryl,
  —(CH₂)$_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —N(H)R⁵, —NR⁵R⁴, —R⁴—S(=O)₂—;
or
when two substituents are present ortho to each other on an aryl- or heteroaryl-ring, said two substituents together form a bridge:
*O(CH₂)$_p$O*, *NH(C(=O))NH*, wherein * represent the point of attachment to said aryl- or heteroaryl-ring;
R⁴ represents a $C_1$-$C_6$-alkyl-group;
or
NR³R⁴ together
  represent a 3- to 10-membered heterocycloalkyl group;
  which is optionally substituted, one or more times, identically or differently, with —CN, —OH, $C_1$-$C_6$-alkyl-, R⁶R⁷N—, R⁶R⁷N—$C_1$-$C_6$-alkyl- or —C(=O)NR⁶R⁷;
R⁵ represents a hydrogen atom or a $C_1$-$C_6$-alkyl-group;
R⁶ represents a hydrogen atom or a $C_1$-$C_6$-alkyl-group;
R⁷ represents a hydrogen atom or a $C_1$-$C_6$-alkyl-group;
or
NR⁶R⁷ together represent a 3- to 10-membered heterocloalkyl group;
p represents 1;
q represents an integer of 1, 2 or 3;
or a tautomer, an N-oxide, a hydrate, a solvate, or a salt thereof, or a mixture of same.
In another preferred embodiment, the invention relates to compounds of formula (I):

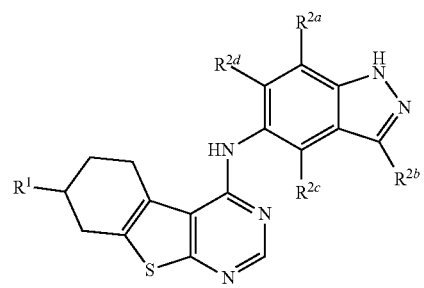

(I)

in which:
R¹ represents a group selected from:
—C(=O)O—R³, —C(=O)N(H)R³, —C(=O)NR³R⁴;
$R^{2a}$ represents a hydrogen atom;
$R^{2b}$ represents a hydrogen atom or a $C_1$-$C_3$-alkyl-group;
$R^{2c}$ represents a hydrogen atom or a group selected from:
  $C_1$-$C_3$-alkyl-,  $C_1$-$C_3$-alkoxy-,  halo-,  —N(H)R⁵, —NR⁵R⁴;
$R^{2d}$ represents a hydrogen atom or a group selected from:
  $C_1$-$C_3$-alkyl-,  $C_1$-$C_3$-alkoxy-,  halo-,  —N(H)R⁵, —NR⁵R⁴;
R³ represents a hydrogen atom or a group selected from:
  $C_1$-$C_6$-alkyl-,  $C_2$-$C_6$-alkynyl-,  $C_3$-$C_7$-cycloalkyl-,
  —(CH₂)$_q$—($C_3$-$C_7$-cycloalkyl), 3- to 10-membered heterocycloalkyl, —(CH₂)$_q$-(3- to 10-membered heterocycloalkyl), aryl, —(CH₂)$_q$-aryl,
  —(CH₂)$_q$—O-aryl, heteroaryl, —(CH₂)$_q$-heteroaryl,
  —(CH₂)$_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —N(H)R⁵, —NR⁵R⁴, —R⁴—S(=O)₂—;
or
when two substituents are present ortho to each other on an aryl- or heteroaryl-ring, said two substituents together form a bridge:
*O(CH₂)$_p$O*, *NH(C(=O))NH*, wherein * represent the point of attachment to said aryl- or heteroaryl-ring;
R⁴ represents a $C_1$-$C_6$-alkyl-group;
or
NR³R⁴ together
  represent a 3- to 10-membered heterocycloalkyl group;
  which is optionally substituted, one or more times, identically or differently, with —CN, —OH, $C_1$-$C_6$-alkyl-, R⁶R⁷N—, R⁶R⁷N—$C_1$-$C_6$-alkyl- or —C(=O)NR⁶R⁷;
R⁵ represents a hydrogen atom or a $C_1$-$C_6$-alkyl-group;
R⁶ represents a hydrogen atom or a $C_1$-$C_6$-alkyl-group;
R⁷ represents a hydrogen atom or a $C_1$-$C_6$-alkyl-group;
or
NR⁶R⁷ together represent a 3- to 10-membered heterocycloalkyl group;
p represents 1;
q represents an integer of 1, 2 or 3;
or a tautomer, an N-oxide, a hydrate, a solvate, or a salt thereof, or a mixture of same.
In another preferred embodiment, the invention relates to compounds of formula (I):

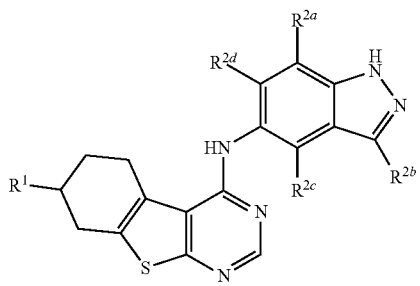 (I)

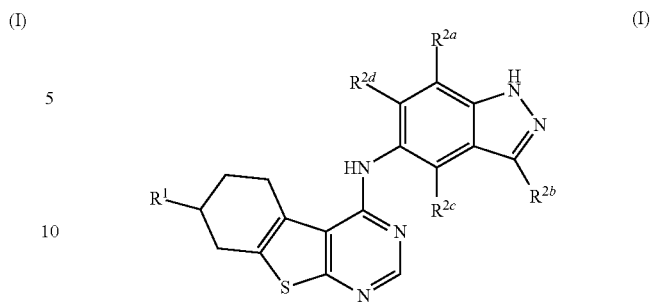 (I)

in which:

$R^1$ represents a group selected from:
—C(=O)O—$R^3$, —C(=O)N(H)$R^3$, —C(=O)N$R^3R^4$;

$R^{2a}$ represents a hydrogen atom;

$R^{2b}$ represents a hydrogen atom;

$R^{2c}$ represents a hydrogen atom;

$R^{2d}$ represents a hydrogen atom or a group selected from:
$C_1$-$C_3$-alkoxy-, halo-;

$R^3$ represents a hydrogen atom or a group selected from:
$C_1$-$C_6$-alkyl-, $C_2$-$C_6$-alkynyl-, $C_3$-$C_7$-cycloalkyl-, —(CH$_2$)$_q$—(C$_3$-C$_7$-cycloalkyl), 3- to 10-membered heterocycloalkyl, —(CH$_2$)$_q$-(3- to 10-membered heterocycloalkyl), aryl, —(CH$_2$)$_q$-aryl, —(CH$_2$)$_q$—O-aryl, heteroaryl, —(CH$_2$)$_q$-heteroaryl, —(CH$_2$)$_q$—O-heteroaryl;

said group being optionally substituted, one or more times, identically or differently, with a substituent selected from:

halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —N(H)$R^5$, —NR$^5$R$^4$, —R$^4$—S(=O)$_2$—;

or when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;

$R^4$ represents a $C_1$-$C_6$-alkyl-group;

or

NR$^3$R$^4$ together represent a 3- to 10-membered heterocycloalkyl group;
which is optionally substituted, one or more times, identically or differently, with —CN, —OH, $C_1$-$C_6$-alkyl-, R$^6$R$^7$N—$C_1$-$C_6$-alkyl- or —C(=O)NR$^6$R$^7$;

$R^5$ represents a hydrogen atom or a $C_1$-$C_6$-alkyl-group;

$R^6$ represents a hydrogen atom or a $C_1$-$C_6$-alkyl-group;

$R^7$ represents a hydrogen atom or a $C_1$-$C_6$-alkyl-group;

or

NR$^6$R$^7$ together represent a 3- to 10-membered heterocycloalkyl group;

p represents 1;

q represents an integer of 1, 2 or 3;

or a tautomer, an N-oxide, a hydrate, a solvate, or a salt thereof, or a mixture of same.

In another preferred embodiment, the invention relates to compounds of formula (I):

in which:

$R^1$ represents a group selected from:
—C(=O)O—$R^3$, —C(=O)N(H)$R^3$, —C(=O)N$R^3R^4$;

$R^{2a}$ represents a hydrogen atom;

$R^{2b}$ represents a hydrogen atom or a group selected from:
$C_1$-$C_3$-alkyl-, halo-$C_1$-$C_3$-alkyl-cyano-;

$R^{2c}$ represents a hydrogen atom or a group selected from:
$C_1$-$C_3$-alkyl-, $C_1$-$C_3$-alkoxy-, halo-, —N(H)$R^5$, —NR$^5$R$^4$;

$R^{2d}$ represents a hydrogen atom or a group selected from:
$C_1$-$C_3$-alkyl-, $C_1$-$C_3$-alkoxy-, halo-, —N(H)$R^5$, —NR$^5$R$^4$;

$R^3$ represents a hydrogen atom or a group selected from:
$C_1$-$C_6$-alkyl-, $C_2$-$C_6$-alkynyl-, $C_3$-$C_7$-cycloalkyl-, —(CH$_2$)$_q$—(C$_3$-C$_7$-cycloalkyl), —(CH$_2$)$_q$—O—(C$_3$-C$_7$-cycloalkyl), 3- to 10-membered heterocycloalkyl, —(CH$_2$)$_q$-(3- to 10-membered heterocycloalkyl), —(CH$_2$)$_q$—O-(3- to 10-membered heterocycoalkyl), aryl, —(CH$_2$)$_q$-aryl, —(CH$_2$)$_q$—O-aryl, heteroaryl, —(CH$_2$)$_q$-heteroaryl, —(CH$_2$)$_q$—O-heteroaryl;

said group being optionally substituted, one or more times, identically or differently, with a substituent selected from:

halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —N(H)$R^5$, —NR$^5$R$^4$, R$^4$—S(=O)$_2$—;

or when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;

$R^4$ represents a $C_1$-$C_6$-alkyl-group;

or

NR$^3$R$^4$ together represent a 3- to 10-membered heterocycloalkyl group;
which is optionally substituted, one or more times, identically or differently, with —CN, —OH, $C_1$-$C_6$-alkyl-, R$^6$R$^7$N—$C_1$-$C_6$-alkyl- or —C(=O)NR$^6$R$^7$;

$R^5$ represents a hydrogen atom or a $C_1$-$C_6$-alkyl-group;

$R^6$ represents a hydrogen atom or a $C_1$-$C_6$-alkyl-group;

$R^7$ represents a hydrogen atom or a $C_1$-$C_6$-alkyl-group;

or

NR$^6$R$^7$ together represent a 3- to 10-membered heterocycloalkyl group;

p represents 1;

q represents an integer of 1, 2 or 3;

or a tautomer, an N-oxide, a hydrate, a solvate, or a salt thereof, or a mixture of same.

In another preferred embodiment, the invention relates to compounds of formula (I):

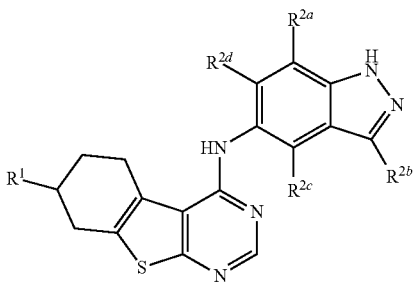

(I)

in which:
R¹ represents a group selected from:
—C(=O)O—R³, —C(=O)N(H)R³, —C(=O)NR³R⁴;
$R^{2a}$ represents a hydrogen atom;
$R^{2b}$ represents a hydrogen atom;
$R^{2c}$ represents a hydrogen atom;
$R^{2d}$ represents a group selected from:
$C_1$-$C_3$-alkoxy-, halo-;
R³ represents a hydrogen atom or a group selected from:
$C_1$-$C_6$-alkyl-, $C_2$-$C_6$-alkynyl-, $C_3$-$C_7$-cycloalkyl-, —(CH₂)$_q$—($C_3$-$C_7$-cycloalkyl), —(CH₂)$_q$—O—($C_3$-$C_7$-cycloalkyl), 3- to 10-membered heterocycloalkyl, —(CH₂)$_q$-(3- to 10-membered heterocycloalkyl), —(CH₂)$_q$—O-(3- to 10-membered heterocycoalkyl), aryl, —(CH₂)$_q$-aryl, —(CH₂)$_q$—O-aryl, heteroaryl, —(CH₂)$_q$-heteroaryl, —(CH₂)$_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-, $C_1$-$C_6$-alkoxy-, —N(H)R⁵, —NR⁵R⁴, R⁴—S(=O)₂—;
or
when two substituents are present ortho to each other on an aryl- or heteroaryl-ring, said two substituents together form a bridge:
*O(CH₂)$_p$O*, *NH(C(=O))NH*, wherein * represent the point of attachment to said aryl- or heteroaryl-ring;
R⁴ represents a $C_1$-$C_6$-alkyl-group;
or
NR³R⁴ together
represent a 3- to 10-membered heterocycloalkyl group;
which is optionally substituted, one or more times, identically or differently, with —CN, —OH, $C_1$-$C_6$-alkyl-, R⁶R⁷N—$C_1$-$C_6$-alkyl- or —C(=O)NR⁶R⁷;
R⁵ represents a hydrogen atom or a $C_1$-$C_6$-alkyl-group;
R⁶ represents a hydrogen atom or a $C_1$-$C_6$-alkyl-group;
R⁷ represents a hydrogen atom or a $C_1$-$C_6$-alkyl-group;
or
NR⁶R⁷ together represent a 3- to 10-membered heterocycloalkyl group;
p represents 1;
q represents an integer of 1, 2 or 3;
or a tautomer, an N-oxide, a hydrate, a solvate, or a salt thereof, or a mixture of same.
In another preferred embodiment, the invention relates to compounds of formula (I):

(I)

in which:
R¹ represents a group selected from —C(=O)N(H)R³, —C(=O)NR³R⁴;
$R^{2a}$ represents a hydrogen atom;
$R^{2b}$ represents a hydrogen atom;
$R^{2c}$ represents a hydrogen atom;
$R^{2d}$ represents a hydrogen atom or a $C_1$-$C_3$-alkoxy-group;
R³ represents a hydrogen atom or a group selected from $C_1$-$C_6$-alkyl-, —(CH₂)$_q$—($C_3$-$C_7$-cycloalkyl), —(CH₂)$_q$-aryl, —(CH₂)$_q$—O-aryl, —(CH₂)$_q$-heteroaryl;
said group being optionally substituted, one or more times, identically or differently, with a substituent selected from:
halo-, hydroxy-, $C_1$-$C_6$-alkyl-, halo-$C_1$-$C_6$-alkyl-, $C_1$-$C_6$-alkoxy-, —NR⁵R⁴, —S(=O)₂N(H)R⁵;
or
when two substituents are present ortho to each other on an aryl- or heteroaryl-ring, said two substituents together form a bridge:
*O(CH₂)$_p$O*, wherein * represent the point of attachment to said aryl- or heteroaryl-ring;
R⁴ represents a group selected from: $C_1$-$C_6$-alkyl-, $C_2$-$C_6$-alkynyl-;
or
NR³R⁴ together
represent a 3- to 10-membered heterocycloalkyl-group;
which is optionally substituted, one or more times, identically or differently, with —CN, halo-, hydroxy-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-;
R⁵ represents a hydrogen atom, a $C_1$-$C_6$-alkyl- or $C_3$-$C_7$-cycloalkyl-group;
p represents an integer of 1;
q represents an integer of 0, 1 or 2;
or a tautomer, an N-oxide, a hydrate, a solvate, or a salt thereof, or a mixture of same.
In another preferred embodiment, the invention relates to compounds of formula (I):

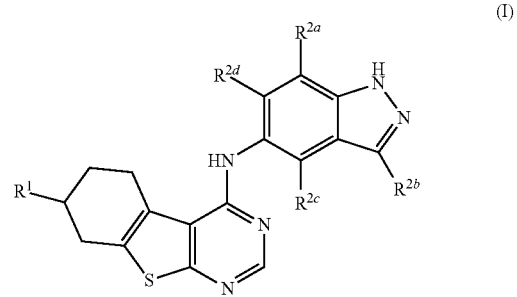

(I)

in which:
R$^1$ represents a —C(=O)O—R$^3$ group;
R$^{2a}$ represents a hydrogen atom;
R$^{2b}$ represents a hydrogen atom;
R$^{2c}$ represents a hydrogen atom;
R$^{2d}$ represents a hydrogen atom or a group selected from C$_1$-C$_3$-alkoxy-, halo-;
R$^3$ represents a hydrogen atom or a C$_1$-C$_6$-alkyl-group
or a tautomer, an N-oxide, a hydrate, a solvate, or a salt thereof, or a mixture of same.

In another preferred embodiment, the invention relates to compounds of formula (I):

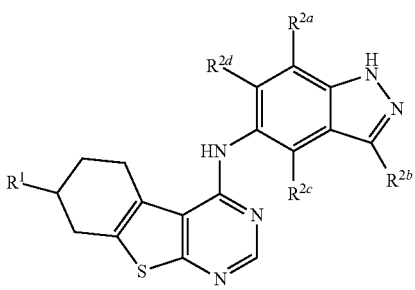

(I)

in which:
R$^1$ represents a —C(=O)NR$^3$R$^4$ group;
R$^{2a}$, R$^{2b}$, R$^{2c}$
represent a hydrogen atom;
R$^{2d}$ represents a C$_1$-C$_3$-alkoxy-group, preferably a methoxy-, ethoxy- or iso-propoxy-group;
R$^3$ represents a hydrogen atom or a C$_1$-C$_6$-alkyl-group;
R$^4$ represents a group selected from: C$_1$-C$_6$-alkyl-, halo-C$_1$-C$_6$-alkyl-, hydroxy-C$_1$-C$_6$-alkyl-;
or
NR$^3$R$^4$ together
represents a 3- to 10-membered heterocycloalkyl-group; said group being optionally substituted with C$_1$-C$_3$-alkyl-, —CN or —OH;
or a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula (I), supra, in which method an intermediate compound of general formula (II):

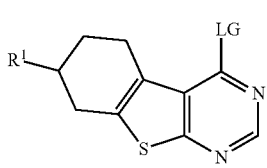

(II)

in which R$^1$ is as defined for the compounds of general formula (I), supra, and LG represents a leaving group (as defined hereinafter),
is allowed to react with a compound of general formula (III):

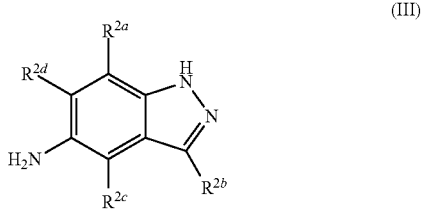

(III)

in which R$^{2a}$, R$^{2b}$, R$^{2c}$, and R$^{2d}$ are as defined for the compounds of general formula (I), supra,
thus providing a compound of general formula (I):

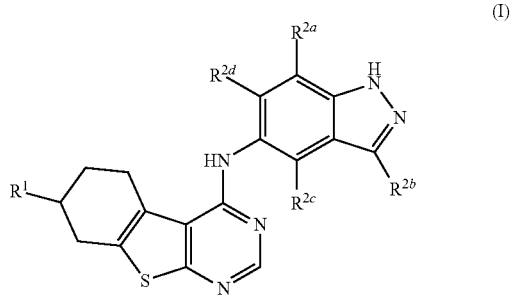

(I)

in which R$^1$, R$^{2a}$, R$^{2b}$, R$^{2c}$, and R$^{2d}$ are as defined for the compounds of general formula (I), supra.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, and (4-methoxy-benzene)sulfonyloxy.

In accordance with a further aspect, the present invention covers intermediate compounds which are useful in the preparation of compounds of the present invention of general formula (I), particularly in the method described herein.

In particular, the present invention covers compounds of general formula (II):

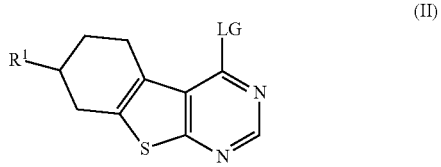

(II)

in which R$^1$ is as defined for the compounds of general formula (I), supra, and LG represents a leaving group.

In accordance with yet another aspect, the present invention covers the use of the intermediate compounds of general formula (II):

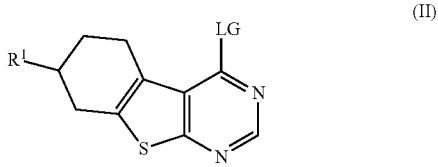

in which R[1] is as defined for the compounds of general formula (I), supra, and LG represents a leaving group;
for the preparation of a compound of general formula (I) as defined supra.

Synthesis of Compounds of General Formula (I) of the Present Invention

Compounds of general formula (I), wherein $R^1$, $R^{2a}$, $R^{2b}$, $R^{2c}$, and $R^{2d}$ have the meaning as given for general formula (I), supra, can be synthesized according to the general procedure depicted in Scheme 1, wherein LG stands for a leaving group.

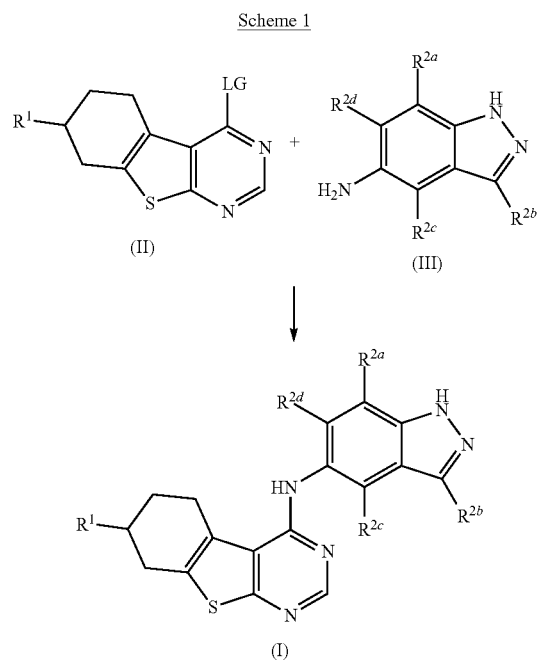

Scheme 1

Scheme 1 exemplifies the main route that allows variations in $R^1$, $R^{2a}$, $R^{2b}$, $R^{2c}$, and $R^{2d}$. The coupling of pyrimidine-derived synthons such as (II) with aromatic amines such as (III) can be accomplished by reacting the two reactants in a suitable solvent, such as ethanol or a related lower aliphatic alcohol, in the presence of an acid such as hydrogen chloride. Alternatively, such amination reactions can be performed using catalysis by metals, such as palladium (see e.g. J. Y. Yoon et al., *Synthesis* 2009, (5), 815, and literature cited therein).

Modification of any of the substituents, $R^1$, $R^{2a}$, $R^{2b}$, $R^{2c}$, and $R^{2d}$ can be achieved before and/or after the exemplified transformation. However, also other routes may be used to synthesise the target compounds, in accordance with common general knowledge of a person skilled in the art of organic synthesis.

Said modifications can be such as the introduction of protecting groups, cleavage of protecting groups, reduction or oxidation of functional groups, formation or cleavage of esters or carboxamides, halogenation, metallation, substitution or other reactions known to a person skilled in the art. These transformations include those which introduce a functionality which allows for further interconversion of substituents. Appropriate protecting groups and their introduction and cleavage are well-known to a person skilled in the art (see for example T. W. Greene and P. G. M. Wuts in Protective Groups in Organic Synthesis, 3$^{rd}$ edition, Wiley 1999). Further, it possible that two or more successive steps may be performed without work-up being performed between said steps, e.g. a "one-pot" reaction, as it is well-known to a person skilled in the art.

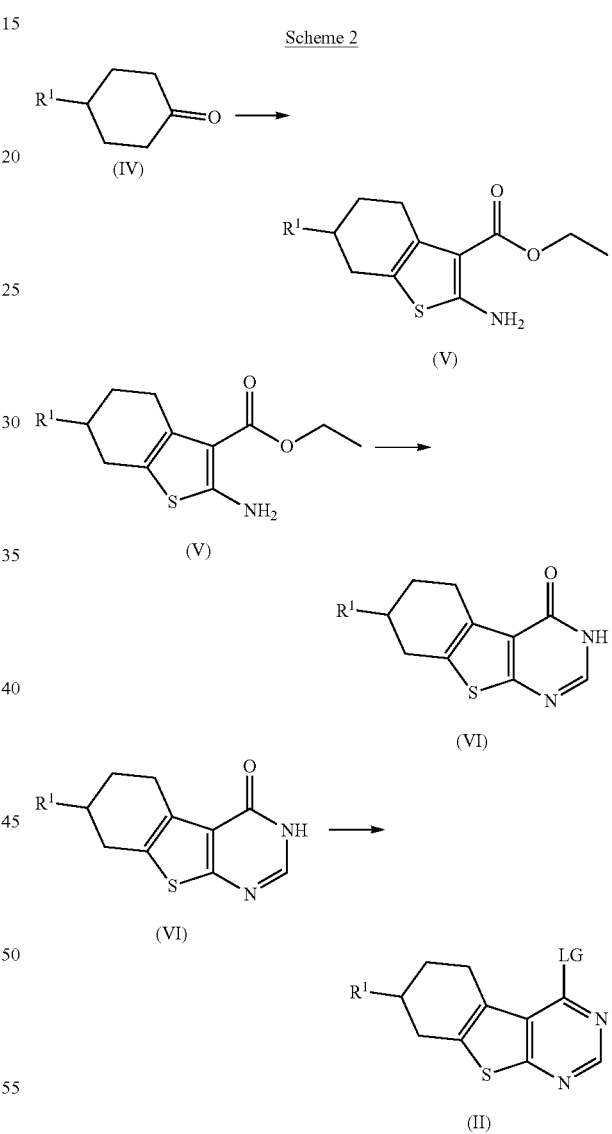

Scheme 2

Compounds of the general formula (II), wherein $R^1$ has the meaning as given for general formula (I), and wherein LG stands for a leaving group, are known to the person skilled in the art and can be readily prepared as shown in Scheme 2 by a so-called Gewald thiophene synthesis (for a seminal publication see e.g. K. Gewald et al., *Chem. Ber.* 1966, 94, 99), starting from ketones of the general formula (IV), to give the intermediate thiophene derivatives (V). Said intermediates are then cyclised to the thienopyrimidones (VI) employing a suitable $C_1$ synthon such as formamide. The resulting pyrimidones (VI) are then transferred into compounds of the general formula (II) by suitable procedures known to the person skilled in the art, such as treatment with a chlorinating agent. An instructive exemplary protocol for the sequence outlined in Scheme 2 can be found in WO 2005/010008, example 14, steps 1 to 3.

If $R^1$ in compounds of the formula (II) represents a carboxylic ester, e.g. an ethyl ester, it is well possible to convert said ester into a carboxamide in the presence of LG e.g. representing a chloride, by mild ester hydrolysis using e.g. lithium hydroxide, followed by carboxamide coupling by procedures well known to the person skilled in the art.

Compounds of the formula (III) are known to the person skilled in the art, and are commercially available with a wide range of substituents. Their synthesis has been described inter alia by means of diazotation of the corresponding ortho-toluidines, followed by cyclisation to the indazole (see e.g. H. D. Porter and W. D. Peterson, *Org. Syn., Coll. Vol.* 3 (1955), 660, or U.S. Pat. No. 5,444,038). Recently, the synthesis of substituted indazoles suitable as intermediates via reaction of ortho-fluorobenzaldehydes with hydrazine hydrate has been described (see e.g. R. C. Wheeler et al., *Org. Process Res. Dev* 2011, 15, 565, for a related publication see also K. Lukin et al., *J. Org. Chem.* 2006, 71, 8166). Both processes typically yield indazoles featuring an amine precursor, such as a nitro group, which can be readily converted into the desired indazole-5-amine by reduction (see e.g. J. Med. Chem. 2003, 46, 5663).

Multiple interconversions of $R^1$, $R^{2a}$, $R^{2b}$, $R^{2c}$, and $R^{2d}$ within compounds of the general formula (I) are possible which may be exemplified by but are not limited to the conversion of compounds in which $R^1$ stands for a carboxylic ester, into carboxamides, in which $R^1$ stands for —C(=O)N(H)$R^3$ or —C(=O)N$R^3R^4$, by cleavage of said ester to the corresponding carboxylic acid, followed by carboxamide coupling by procedures well known to the person skilled in the art.

Experimental Section

The following table lists the abbreviations used in this paragraph, and in the examples section.

| Abbreviation | Meaning |
| --- | --- |
| HPLC | high performance liquid chromatography |
| LC-MS | liquid chromatography - mass spectrometry |
| NMR | nuclear magnetic resonance |
| DMSO | dimethylsulfoxide |
| ppm | parts per million |
| ESI | Electrospray ionisation |
| s | singlet |
| d | doublet |
| t | triplet |
| q | quadruplet |
| sept | septet |
| br | broad |
| m | multiplet |

Chemical names were generated using ACD/Name Batch Version 12.01.

HPLC & LC-MS Methods

Analytical Methods

LC-MS Method A1

Instrument MS: Waters ZQ; Instrument HPLC: Waters UPLC Acquity

Column: Acquity BEH C18 (Waters), 50 mm×2.1 mm, 1.7 µm

Solvent: Eluent A: Water+0.1% formic acid, eluent B: acetonitrile (Lichrosolv Merck);

Gradient: 0.0 min 99% A—1.6 min 1% A—1.8 min 1% A—1.81 min 99% A—2.0 min 99% A;

Temperature: 60° C.

Flow: 0.800 mL/min

UV detection PDA 210-400 nm

Preparative Methods

Method P1:

System: Labomatic HD-3000 HPLC gradient pump, Labomatic Labocol Vario-2000 fraction collector, standard UV detector Column: Chromatorex C-18 125×30 mm Eluents: A: 0.1% formic acid in water, B: acetonitrile Gradient: A85%/B 15%→A45%/B 55%

Method P2:

System: Labomatic HD-3000 HPLC gradient pump, Labomatic Labocol Vario-2000 fraction collector, standard UV detector Column: Chromatorex C-18 125×30 mm Eluents: A: 0.1% formic acid in water, B: acetonitrile Gradient: A90%/B 10%→A50%/B 50%

Method P3:

System: Labomatic HD-3000 HPLC gradient pump, Labomatic Labocol Vario-2000 fraction collector, standard UV detector Column: Chromatorex C-18 125×30 mm Eluents: A: 0.1% formic acid in water, B: acetonitrile Gradient: A70%/B 30%→A30%/B 70%

Method P4:

System: Labomatic HD-3000 HPLC gradient pump, Labomatic Labocol Vario-2000 fraction collector, standard UV detector Column: Chromatorex C-18 125×30 mm Eluents: A: 0.1% formic acid in water, B: acetonitrile Gradient: A70%/B 30%→A30%/B 70%

INTERMEDIATES

Intermediate Compound 1A

4-Chloro-5,6,7,8-tetrahydro[1]benzothieno[2,3-d]pyrimidine-7-carboxylic acid

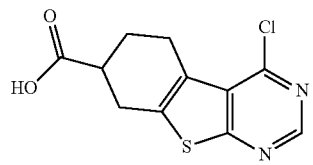 [SMILES: O=C(O)C1CCc2c(sc3ncnc(Cl)c23)C1]

A mixture of ethyl 4-chloro-5,6,7,8-tetrahydro[1]benzothieno[2,3-d]pyrimidine-7-carboxylate (15.0 g), 1 N aqueous lithium hydroxide (303 mL, 6 eq), and tetrahydrofuran (875 mL) was stirred for 3 h at room temperature. The mixture was then acidified (approx. pH 3) by addition of 4 N aqueous hydrochloric acid (76 mL), and the organic solvents were then removed in vacuo. The remaining aqueous suspension was filtered, and the residue was washed with water, isopropanol and diethyl ether to give the target compound (13.2 g).

¹H-NMR (300 MHz, DMSO-d₆): δ [ppm]=1.81-1.98 (m, 1H), 2.13-2.31 (m, 1H), 2.81-3.24 (m, 5H), 8.83 (s, 1H), 12.54 (br. s, 1H).
MS (ESIpos) m/z=269 (³⁵Cl), 271 (³⁷Cl) [M+H]⁺.

Intermediate Compound 2A

4-Chloro-N-isopropyl-5,6,7,8-tetrahydro[1]benzothieno[2,3-d]pyrimidine-7-carboxamide

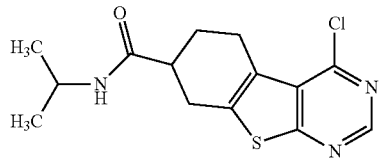 [SMILES: CC(C)NC(=O)C1CCc2c(sc3ncnc(Cl)c23)C1]

To a solution of 4-chloro-5,6,7,8-tetrahydro[1]benzothieno[2,3-d]pyrimidine-7-carboxylic acid (13.2 g) in N,N-dimethylformamide (0.55 L) was added N,N-diisopropylamine (25.6 mL), followed by isopropylamine (12.5 mL) and T3P (propylphosphinic anhydride; 29.2 mL of a 50% solution in ethyl acetate). The mixture was stirred for 20 h at room temperature. Water (2.5 L) was added, followed by solid sodium chloride, and the mixture was stirred for 30 min under ice cooling. The precipitate was isolated by filtration, washed with water, and dried to give the target compound which was sufficiently pure for further processing.
¹H-NMR (400 MHz, DMSO-d₆): δ [ppm]=1.06 (d, 6H), 1.72-1.89 (m, 1H), 2.02-2.14 (m, 1H), 2.58-2.70 (m, 1H), 2.83-3.05 (m, 3H), 3.17-3.27 (m, 1H), 3.80-3.94 (m, 1H), 7.84 (d, 1H), 8.81 (s, 1H).
MS (ESIpos) m/z=310 (³⁵Cl), 312 (³⁷Cl) [M+H]⁺.

EXAMPLES

Example 1

Ethyl 4-(1H-indazol-5-ylamino)-5,6,7,8-tetrahydro[1]benzothieno[2,3-d]pyrimidine-7-carboxylate

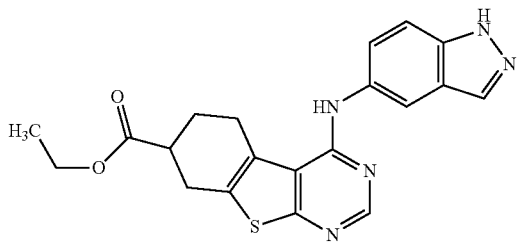 [SMILES: CCOC(=O)C1CCc2c(sc3ncnc(Nc4ccc5[nH]ncc5c4)c23)C1]

To a mixture of ethyl 4-chloro-5,6,7,8-tetrahydro[1]benzothieno[2,3-d]pyrimidine-7-carboxylate (14.4 g, for a preparation see e.g. WO 2005/010008, example 14, steps 1 to 3) and 5-aminoindazole (9.69 g, 1.5 eq) in ethanol (138 mL) was added a 4 N solution of hydrogen chloride in dioxane (2.6 mL, 0.2 eq.). The mixture was heated to reflux with stirring for 2 h. The mixture was concentrated in vacuo, and dissolved in a 9:1 mixture of dichloromethane and methanol. The mixture was then extracted with 5% aqueous sodium hydroxide, water, and brine, and the organic layer was dried with sodium sulfate and evaporated. Trituration of the residue with diethyl ether in an ultrasound bath gave 17.9 g of the target compound.
¹H-NMR (300 MHz, DMSO-d₆): δ [ppm]=1.23 (t, 3H), 1.87-2.02 (m, 1H), 2.15-2.30 (m, 1H), 2.89-3.29 (m, 5H), 4.14 (q, 2H), 7.44-7.57 (m, 2H), 7.98 (s, 1H), 8.06 (s, 1H), 8.24 (br. s., 1H), 8.31 (s, 1H), 13.05 (br. s., 1H).
MS (ESIpos) m/z=394 [M+H]⁺.

Example 2

4-(1H-Indazol-5-ylamino)-5,6,7,8-tetrahydro[1]benzothieno[2,3-d]pyrimidine-7-carboxylic acid

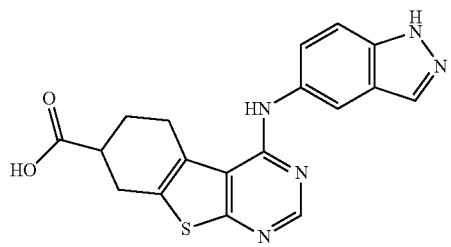 [SMILES: O=C(O)C1CCc2c(sc3ncnc(Nc4ccc5[nH]ncc5c4)c23)C1]

To a mixture of ethyl 4-(1H-indazol-5-ylamino)-5,6,7,8-tetrahydro[1]benzothieno[2,3-d]pyrimidine-7-carboxylate (6.6 g) and ethanol (85 mL) was added an aqueous 10 N solution of sodium hydroxide (32 mL) under ice cooling. The cooling bath was removed, and the mixture was stirred at room temperature for 30 min. Ethanol (53 mL) was added (to maintain stirrability) and stirring at room temperature was continued for another 30 min. The mixture was added to water, acidified to pH4 with aqueous hydrochloric acid, and the target compound was isolated by filtration to give 5.5 g of a light brown solid.
¹H-NMR (300 MHz, DMSO-d₆): δ [ppm]=1.83-2.01 (m, 1H), 2.12-2.29 (m, 1H), 2.77-3.28 (m, 5H), 7.42-7.60 (m, 2H), 7.98 (s, 1H), 8.06 (s, 1H), 8.22 (s, 1H), 8.31 (s, 1H), 12.90 (br. s., 2H).
MS (ESIpos) m/z=366 [M+H]⁺.

Example 3

4-(1H-Indazol-5-ylamino)-5,6,7,8-tetrahydro[1]benzothieno[2,3-d]pyrimidine-7-carboxamide

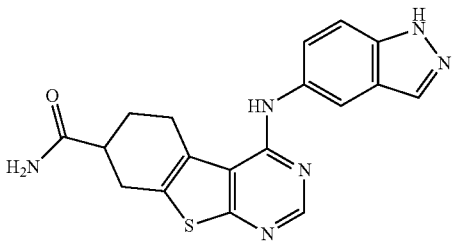 [SMILES: NC(=O)C1CCc2c(sc3ncnc(Nc4ccc5[nH]ncc5c4)c23)C1]

To a solution of 4-(1H-indazol-5-ylamino)-5,6,7,8-tetrahydro[1]benzothieno[2,3-d]pyrimidine-7-carboxylic acid (300 mg) in N,N-dimethylformamide (24 mL) was added formamide (0.59 mL, 20 eq) and sodium ethoxide (0.20 g, 4.0 eq) at room temperature. The mixture was stirred 3 hours, was then concentrated and the residue was purified per preparative HPLC (Method P2) to give the target compound as a solid (57 mg).

¹H-NMR (400 MHz, DMSO-d₆): δ [ppm]=1.73-1.91 (m, 1H), 2.06-2.19 (m, 1H), 2.59-2.72 (m, 1H), 2.86-3.01 (m, 2H), 3.06-3.20 (m, 1H), 3.23-3.28 (m, 1H), 6.94 (br. s., 1H), 7.41-7.56 (m, 3H), 7.99 (s, 1H), 8.05 (s, 1H), 8.20 (s, 1H), 8.30 (s, 1H), 13.01 (br. s., 1H).

MS (ESIpos) m/z=365 [M+H]⁺.

Example 4

4-(1H-Indazol-5-ylamino)-N-[3-(methylsulfonyl)propyl]-5,6,7,8-tetrahydro[1]benzothieno[2,3-d]pyrimidine-7-carboxamide

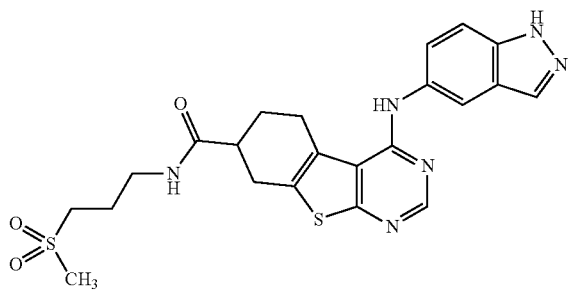 [SMILES: CS(=O)(=O)CCCNC(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (300 mg) and 3-(methylsulfonyl)propyl-1-amine hydrochloride (137 mg) in N,N-dimethylformamide (20 mL) was added N,N-diisopropylethylamine (170 mg), followed by COMU ((1-Cyano-2-ethoxy-2-oxoethylidenaminooxy)dimethylamino-morpholino-carbenium hexafluorophosphate; 422 mg), and the mixture was stirred overnight at room temperature. The mixture was partitioned between water and dichloromethane, and the organic layer was dried over magnesium sulfate and evaporated. To remove undesired impurities, the residue was partitioned between 1 N aqueous hydrochloric acid and dichloromethane, and the aqueous layer was then neutralized by addition of aqueous sodium bicarbonate, followed by dichloromethane, whereupon the target compound precipitated and was isolated by filtration (60 mg).

¹H-NMR (400 MHz, DMSO-d₆): δ [ppm]=1.80-1.92 (m, 3H), 2.05-2.16 (m, 1H), 2.60-2.72 (m, 1H), 2.91-3.01 (m, 5H), 3.07-3.29 (m, 6H), 7.45-7.56 (m, 2H), 7.99 (s, 1H), 8.05 (s, 1H), 8.11 (t, 1H), 8.20 (s, 1H), 8.31 (s, 1H), 13.01 (s, 1H).

MS (ESIpos) m/z=485 [M+H]⁺.

Example 5

4-(1H-Indazol-5-ylamino)-N-phenyl-5,6,7,8-tetrahydro[1]benzothieno[2,3-d]pyrimidine-7-carboxamide

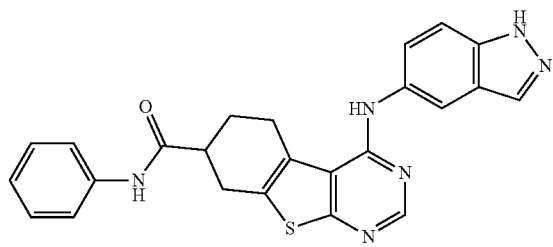 [SMILES: O=C(Nc1ccccc1)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (400 mg) and aniline (399 μL) in N,N-dimethylformamide (12 mL) was added N,N-diisopropylethylamine (915 μL), followed by T3P (propylphosphinic anhydride; 3.13 mL of a 50% solution in ethyl acetate), and the mixture was stirred for 4 h at 60° C. To drive the reaction to completion, aniline (199 μL) was added, followed by N,N-diisopropylamine (458 μL), and T3P (0.78 mL of a 50% solution in ethyl acetate), and the mixture was stirred for another 4 h at 40° C. The mixture was concentrated in vacuo and the residue was purified by preparative HPLC (Method P1) to give 255 mg of the target compound.

¹H-NMR (300 MHz, DMSO-d₆): δ [ppm]=1.85-1.98 (m, 1H), 2.16-2.30 (m, 1H), 2.84-3.42 (m, 5H, partly overlapped with water signal), 7.05 (t, 1H), 7.32 (t, 2H), 7.46-7.57 (m, 2H), 7.65 (d, 2H), 8.00 (s, 1H), 8.06 (s, 1H), 8.25 (s, 1H), 8.32 (s, 1H), 10.10 (s, 1H), 13.03 (br. s., 1H).

MS (ESIpos) m/z=441 [M+H]⁺.

Example 6

4-(1H-Indazol-5-ylamino)-N-isopropyl-5,6,7,8-tetrahydro[1]benzothieno[2,3-d]pyrimidine-7-carboxamide

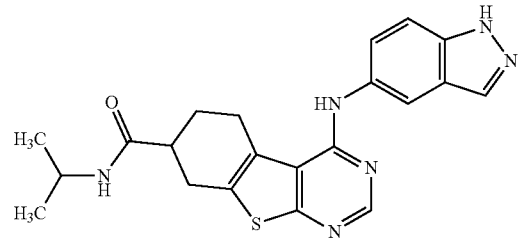 [SMILES: CC(C)NC(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (500 mg) and isopropylamine (443 μL) in N,N-dimethylformamide (14 mL) was added N,N-diisopropylethylamine (1.09 mL), followed by T3P (propylphosphinic anhydride; 3.71 mL of a 50% solution in ethyl acetate), and the mixture was stirred overnight at RT. Water was added, and the supernatant was decanted. The residue was purified by preparative HPLC (Method P1) to give 226 mg of the target compound.

¹H-NMR (300 MHz, DMSO-d₆): δ [ppm]=1.09 (d, 6H), 1.75-1.90 (m, 1H), 2.00-2.14 (m, 1H), 2.56-2.68 (m, 1H), 2.86-2.98 (m, 2H), 3.05-3.28 (m, 1H), 3.80-3.96 (m, 1H), 7.45-7.57 (m, 2H), 7.83 (d, 1H), 7.98 (s, 1H), 8.06 (s, 1H), 8.20 (s, 1H), 8.31 (s, 1H), 13.01 (br. s., 1H).

MS (ESIpos) m/z=407 [M+H]⁺.

Example 7

N-(Cyclopropylmethyl)-4-(1H-indazol-5-ylamino)-5,6,7,8-tetrahydro[1]benzothieno[2,3-d]pyrimidine-7-carboxamide

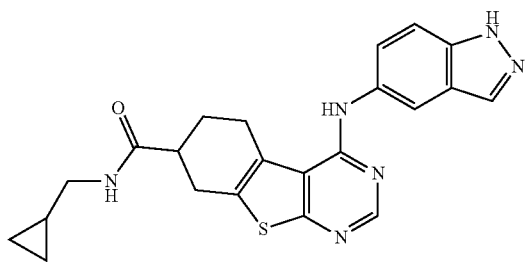 [SMILES: O=C(NCC1CC1)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (500 mg) and cyclopropylmethylamine (451 µL) in N,N-dimethylformamide (14 mL) was added N,N-diisopropylethylamine (1.09 mL), followed by T3P (propylphosphinic anhydride; 3.71 mL of a 50% solution in ethyl acetate), and the mixture was stirred overnight at RT. To drive the reaction to completion, additional portions of cyclopropylmethylamine (451 µL), N,N-diisopropylamine (1.09 mL), and T3P (3.71 mL of a 50% solution in ethyl acetate) were added, and stirring at 60° C. was continued for 4 h. The mixture was added to water, and the precipitated crude product was isolated by filtration to give the target compound (510 mg) in sufficient purity for further processing.

$^1$H-NMR (300 MHz, DMSO-$d_6$): δ [ppm]=0.09-0.24 (m, 2H), 0.35-0.49 (m, 2H), 0.81-1.01 (m, 1H), 1.74-1.93 (m, 1H), 2.02-2.16 (m, 1H), 2.61-2.75 (m, 1H), 2.88-3.05 (m, 4H), 3.08-3.28 (m, 2H), 7.44-7.58 (m, 2H), 7.94-8.12 (m, 3H), 8.20 (s, 1H), 8.31 (s, 1H), 13.00 (br. s., 1H).

MS (ESIpos) m/z=419 [M+H]$^+$.

Example 8

25 [4-(1H-Indazol-5-ylamino)-5,6,7,8-tetrahydro[1]benzothieno[2,3-d]pyrimidin-7-yl](4-methylpiperazin-1-yl)methanone

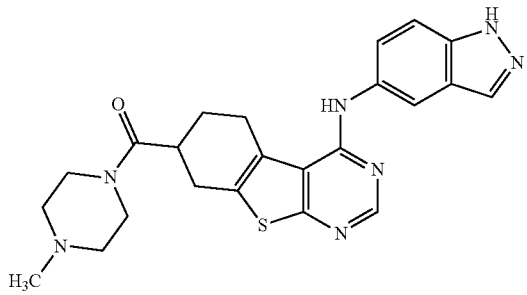 [SMILES: CN1CCN(C(=O)C2CCc3c(sc4ncnc(Nc5ccc6[nH]ncc6c5)c34)C2)CC1]

To a mixture of 4-(1H-indazol-5-ylamino)-5,6,7,8-tetrahydro[1]benzothieno[2,3-d]pyrimidine-7-carboxylic acid (500 mg) and 1-methylpiperazine (755 mg) in N,N-dimethylformamide (14 mL) was added N,N-diisopropylethylamine (1.36 mL), followed by T3P (propylphosphinic anhydride; 4.64 mL of a 50% solution in ethyl acetate), and the mixture was stirred at 60° C. for 2 hrs. Since addition of water did not lead to product precipitation, the crude product was partitioned between 0.75 M aqueous sodium carbonate and dichloromethane, extracted with dichloromethane again, and the combined organic layers were dried over sodium sulfate and evaporated. After concentration in vacuo, the residue was purified by preparative HPLC (Method P2) to give 436 mg of the target compound.

$^1$H-NMR (300 MHz, DMSO-$d_6$): δ [ppm]=1.71-1.89 (m, 1H), 1.96-2.11 (m, 1H), 2.25-2.42 (m, 4H), 2.82-3.05 (m, 2H), 3.11-3.35 (m, 6H), 3.46-3.63 (m, 4H), 7.45-7.55 (m, 2H), 7.99 (s, 1H), 8.05 (s, 1H), 8.14 (s, 1H), 8.18 (s, 1H), 8.31 (s, 1H), 12.99 (br. s., 1H).

MS (ESIpos) m/z=448 [M+H]$^+$.

Example 9

4-(1H-indazol-5-ylamino)-N-[3-(trifluoromethyl)benzyl]-5,6,7,8-tetrahydro[1]benzothieno[2,3-d]pyrimidine-7-carboxamide

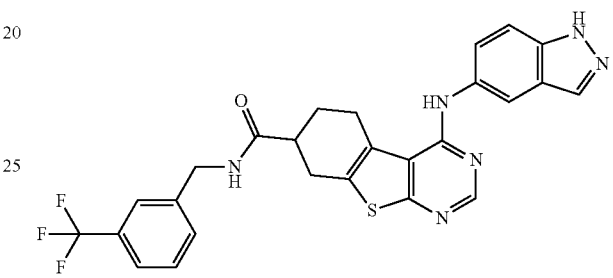

To a mixture of 4-(1H-indazol-5-ylamino)-5,6,7,8-tetrahydro[1]benzothieno[2,3-d]pyrimidine-7-carboxylic acid (500 mg) and 3-(trifluoromethyl)benzylamine (1.14 g) in N,N-dimethylformamide (14 mL) was added N,N-diisopropylethylamine (1.36 mL), followed by T3P (propylphosphinic anhydride; 4.64 mL of a 50% solution in ethyl acetate), and the mixture was stirred at 60° C. for 2 h. After slight concentration in vacuo, the product was stirred with water overnight and the crude product was isolated by filtration. Preparative HPLC (Method P3) gave 510 mg of the target compound.

$^1$H-NMR (300 MHz, DMSO-$d_6$): δ [ppm]=1.78-1.96 (m, 1H), 2.08-2.21 (m, 1H), 2.70-2.84 (m, 1H), 2.95-3.04 (m, 2H), 3.09-3.36 (m, 2H, overlaps with water signal), 4.42 (d, 2H), 7.45-7.68 (m, 6H), 7.99 (s, 1H), 8.06 (s, 1H), 8.18-8.26 (m, 1H), 8.31 (s, 1H), 8.67 (t, 1H), 12.98 (br. s, 1H).

MS (ESIpos) m/z=523 [M+H]$^+$.

Example 10

4-(1H-indazol-5-ylamino)-N,N-dimethyl-5,6,7,8-tetrahydro[1]benzothieno[2,3-d]pyrimidine-7-carboxamide

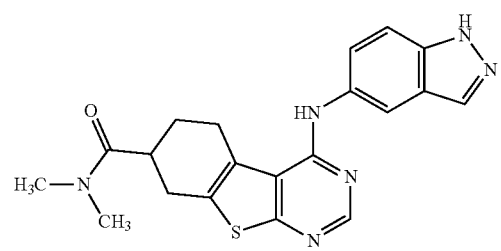 [SMILES: CN(C)C(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (200 mg) and dimethyl ammonium chloride (223 mg, 5 eq.) in N,N-dimethylformamide (12 mL) was added N,N-diisopropylethylamine (0.95 mL), followed by T3P (propylphosphinic anhydride; 1.63 mL of a 50% solution in ethyl acetate), and the mixture was stirred at 40° C. for 3 h. After cooling to room temperature, the mixture was concentrated and the residue was purified by preparative HPLC (Method P2) to give 77 mg of the target compound.

$^1$H-NMR (300 MHz, DMSO-d$_6$): δ [ppm]=1.67-1.86 (m, 1H), 2.00-2.13 (m, 1H), 2.88 (s, 3H), 2.88-2.98 (m, 2H), 3.10 (s, 3H), 3.14-3.35 (m, 3H, overlaps with water signal), 7.45-7.56 (m, 2H), 7.99 (s, 1H), 8.06 (s, 1H), 8.21 (s, 1H), 8.31 (s, 1H), 13.03 (br. s, 1H).

MS (ESIpos) m/z=393 [M+H]$^+$.

Example 11

4-(1H-indazol-5-ylamino)-N-methyl-5,6,7,8-tetrahydro[1]benzothieno[2,3-d]pyrimidine-7-carboxamide

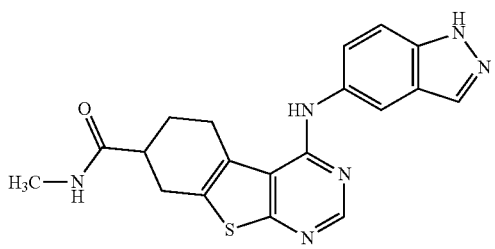 [SMILES: CNC(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (150 mg) and N,N-diisopropylethylamine (0.29 mL) in N,N-dimethylformamide (6 mL) was added methyl ammonium chloride (83 mg, 3 eq.), followed by T3P (propylphosphinic anhydride; 0.29 mL of a 50% solution in ethyl acetate), and the mixture was stirred at RT for 18 h. To drive the reaction to completion, additional portions of N,N-diisopropylethylamine (0.29 mL), methyl ammonium chloride (83 mg), and T3P (propylphosphinic anhydride; 0.29 mL of a 50% solution in ethyl acetate) were added and the mixture was stirred at 60° C. for 6 h. After cooling to room temperature, water (0.5 mL) was added, and the mixture was concentrated in vacuo. The residue was purified by preparative HPLC (Method P1) to give 41 mg of the target compound.

$^1$H NMR (400 MHz, DMSO-d$_6$) δ ppm 1.76-1.89 (m, 1H), 2.04-2.14 (m, 1H), 2.63 (d, 3H), 2.61-2.69 (m, 1H), 2.90-2.98 (m, 2H), 3.08-3.33 (m, 2H, overlaps with water signal), 7.46-7.55 (m, 2H), 7.94 (q, 1H), 7.99 (s, 1H), 8.05 (s, 1H), 8.20 (s, 1H), 8.31 (s, 1H), 12.99 (br. s, 1H).

MS (ESIpos) m/z=379 [M+H]$^+$.

Example 12

4-(1H-indazol-5-ylamino)-N-(2-methoxyphenyl)-5,6,7,8-tetrahydro[1]benzothieno[2,3-d]pyrimidine-7-carboxamide

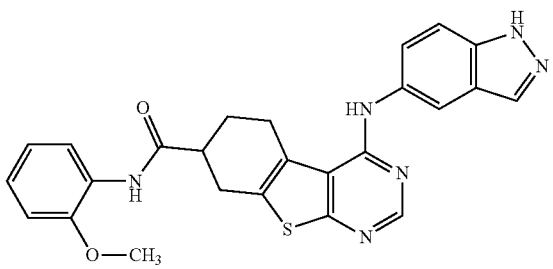 [SMILES: COc1ccccc1NC(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (150 mg) and ortho-methoxyaniline (56 mg, 1.1 eq.) in N,N-dimethylformamide (6 mL) was added N,N-diisopropylethylamine (0.11 mL), followed by T3P (propylphosphinic anhydride; 0.29 mL of a 50% solution in ethyl acetate), and the mixture was stirred at RT for 48 h. To drive the reaction to completion, additional portions of ortho-methoxyaniline (167 mg, 3.3 eq.), N,N-diisopropylethylamine (0.32 mL), and T3P (propylphosphinic anhydride; 0.88 mL of a 50% solution in ethyl acetate) were added and the mixture was stirred at 80° C. for 5 h. The crude product mixture was purified by preparative HPLC (Method P1) to give 58 mg of the target compound.

$^1$H-NMR (300 MHz, DMSO-d$_6$): δ [ppm]=1.81-2.01 (m, 1H), 2.13-2.29 (m, 1H), 2.83-3.35 (m, 5H, partly overlapped with water signal), 3.84 (s, 3H), 6.86-6.96 (m, 1H), 7.01-7.14 (m, 2H), 7.45-7.57 (m, 2H), 7.92-8.02 (m, 2H), 8.06 (s, 1H), 8.25 (s, 1H), 8.32 (s, 1H), 9.33 (s, 1H), 13.04 (br. s, 1H).

MS (ESIpos) m/z=471 [M+H]$^+$.

Example 13

4-(1H-indazol-5-ylamino)-N-(3-methoxyphenyl)-5,6,7,8-tetrahydro[1]benzothieno[2,3-d]pyrimidine-7-carboxamide

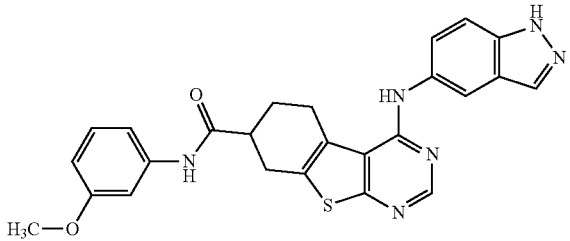 [SMILES: COc1cccc(NC(=O)C2CCc3c(sc4ncnc(Nc5ccc6[nH]ncc6c5)c34)C2)c1]

To a mixture of 4-(1H-indazol-5-ylamino)-5,6,7,8-tetrahydro[1]benzothieno[2,3-d]pyrimidine-7-carboxylic acid (150 mg) and meta-methoxyaniline (56 mg, 1.1 eq.) in N,N-dimethylformamide (6 mL) was added N,N-diisopropylethylamine (0.11 mL), followed by T3P (propylphosphinic anhydride; 0.29 mL of a 50% solution in ethyl acetate), and the mixture was stirred at 80° C. for 3 h. To drive the reaction to completion, additional portions of meta-methoxyaniline (176 mg, 3.5 eq.), N,N-diisopropylethylamine (0.25 mL), and T3P (propylphosphinic anhydride; 0.86 mL of a 50% solution in ethyl acetate) were added and the mixture was stirred at RT for 48 h. The crude product mixture was purified by preparative HPLC (Method P1) to give 70 mg of the target compound.

$^1$H-NMR (300 MHz, DMSO-d$_6$): δ [ppm]=1.82-2.03 (m, 1H), 2.14-2.31 (m, 1H), 2.83-3.37 (m, 5H, partly overlapped with water signal), 3.73 (s, 3H), 6.58-6.68 (m, 1H), 7.19 (s, 2H), 7.33-7.42 (m, 1H), 7.46-7.58 (m, 2H), 7.99 (s, 1H), 8.06 (s, 1H), 8.26 (s, 1H), 8.32 (s, 1H), 10.10 (s, 1H), 13.05 (br. s, 1H).

MS (ESIpos) m/z=471 [M+H]$^+$.

Example 14

4-(1H-indazol-5-ylamino)-N-(4-methoxyphenyl)-5,6,7,8-tetrahydro[1]benzothieno[2,3-d]pyrimidine-7-carboxamide

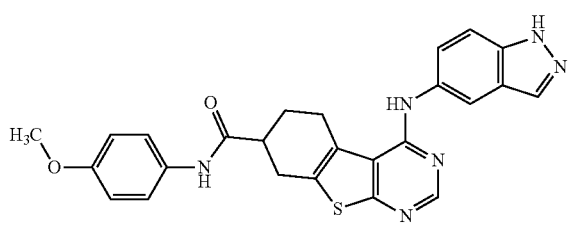 [SMILES: COc1ccc(NC(=O)C2CCc3c(sc4ncnc(Nc5ccc6[nH]ncc6c5)c34)C2)cc1]

To a mixture of 4-(1H-indazol-5-ylamino)-5,6,7,8-tetrahydro[1]benzothieno[2,3-d]pyrimidine-7-carboxylic acid (150 mg) and para-methoxyaniline (56 mg, 1.1 eq.) in N,N-dimethylformamide (6 mL) was added N,N-diisopropylethylamine (0.11 mL), followed by T3P (propylphosphinic anhydride; 0.29 mL of a 50% solution in ethyl acetate), and the mixture was stirred at RT for 45 min, followed by 7 h at 80° C. To drive the reaction to completion, additional portions of para-methoxyaniline (167 mg, 3.3 eq.), N,N-diisopropylethylamine (0.32 mL), and T3P (propylphosphinic anhydride; 0.88 mL of a 50% solution in ethyl acetate) were added and the mixture was stirred at 70° C. for 3 h. After cooling to room temperature, the mixture was concentrated in vacuo. The residue was purified by preparative HPLC (Method P1) to give 48 mg of the target compound.

$^1$H-NMR (300 MHz, DMSO-d$_6$): δ [ppm]=1.83-2.02 (m, 1H), 2.14-2.29 (m, 1H), 2.80-3.40 (m, 5H, partly overlapped with water signal), 3.72 (s, 3H), 6.89 (d, 2H), 7.46-7.59 (m, 4H), 7.99 (s, 1H), 8.06 (s, 1H), 8.25 (s, 1H), 8.32 (s, 1H), 9.96 (s, 1H), 13.04 (br. s, 1H).

MS (ESIpos) m/z=471 [M+H]$^+$.

Example 15

4-(1H-indazol-5-ylamino)-N-(2-methylphenyl)-5,6,7,8-tetrahydro[1]benzothieno[2,3-d]pyrimidine-7-carboxamide

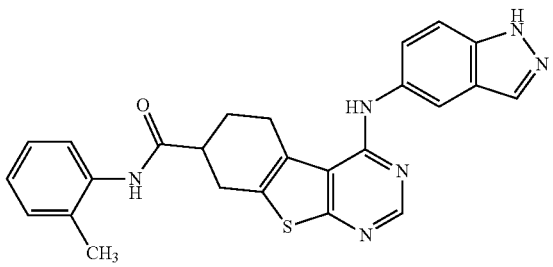 [SMILES: Cc1ccccc1NC(=O)C1CCc2c(sc3ncnc(Nc4ccc5[nH]ncc5c4)c23)C1]

To a mixture of 4-(1H-indazol-5-ylamino)-5,6,7,8-tetrahydro[1]benzothieno[2,3-d]pyrimidine-7-carboxylic acid (150 mg) and ortho-toluidine (176 mg, 4 eq.) in N,N-dimethylformamide (6 mL) was added N,N-diisopropylethylamine (0.34 mL), followed by T3P (propylphosphinic anhydride; 1.17 mL of a 50% solution in ethyl acetate), and the mixture was stirred at 80° C. for 24 h. To drive the reaction to completion, additional portions of ortho-toluidine (176 mg, 4 eq.), N,N-diisopropylethylamine (0.34 mL), and T3P (propylphosphinic anhydride; 1.17 mL of a 50% solution in ethyl acetate) were added and the mixture was stirred at 80° C. for 6 h. After cooling to room temperature, the mixture was concentrated in vacuo. The residue was purified by preparative HPLC (Method P1) to give 81 mg of the target compound.

$^1$H-NMR (300 MHz, DMSO-d$_6$): δ [ppm]=1.86-2.04 (m, 1H), 2.18-2.32 (m, 1H), 2.23 (s, 3H), 2.91-3.42 (m, 5H, partly overlapped with water signal), 7.06-7.27 (m, 3H), 7.40 (br. d, 1H), 7.47-7.58 (m, 2H), 8.00 (s, 1H), 8.07 (s, 1H), 8.26 (s, 1H), 8.32 (s, 1H), 9.48 (s, 1H), 13.04 (br. s., 1H).

MS (ESIpos) m/z=455 [M+H]$^+$.

Example 16

4-(1H-indazol-5-ylamino)-N-(3-methylphenyl)-5,6,7,8-tetrahydro[1]benzothieno[2,3-d]pyrimidine-7-carboxamide

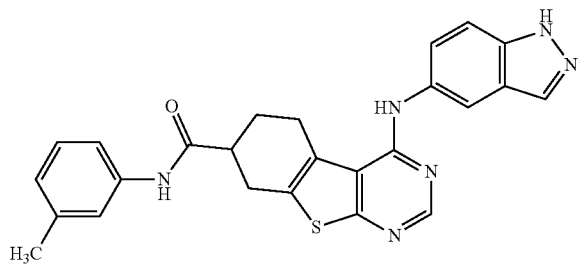 [SMILES: Cc1cccc(NC(=O)C2CCc3c(sc4ncnc(Nc5ccc6[nH]ncc6c5)c34)C2)c1]

To a mixture of 4-(1H-indazol-5-ylamino)-5,6,7,8-tetrahydro[1]benzothieno[2,3-d]pyrimidine-7-carboxylic acid (680 mg) and meta-toluidine (1.04 g, 6 eq.) in N,N-dimethylformamide (24 mL) was added N,N-diisopropylethylamine (1.7 mL), followed by T3P (propylphosphinic anhydride; 5.8 mL of a 50% solution in ethyl acetate), and the mixture was stirred at 50° C. for 4 h. The mixture was then added to water, the precipitated crude product was isolated by filtration and purified by preparative HPLC (Method P3) to give 525 mg of the target compound.

$^1$H-NMR (300 MHz, DMSO-d$_6$): δ [ppm]=1.81-2.01 (m, 1H), 2.14-2.33 (m, 1H), 2.28 (s, 3H), 2.83-3.40 (m, 5H, partly overlapped with water signal), 6.87 (br. d, 1H), 7.19 (t, 1H), 7.42 (br. d, 1H), 7.47-7.58 (m, 3H), 8.00 (s, 1H), 8.06 (s, 1H), 8.25 (s, 1H), 8.32 (s, 1H), 10.03 (s, 1H), 13.04 (s, 1H).
MS (ESIpos) m/z=455 [M+H]+.

Example 17

4-(1H-indazol-5-ylamino)-N-(4-methylphenyl)-5,6,7,8-tetrahydro[1]benzothieno[2,3-d]pyrimidine-7-carboxamide

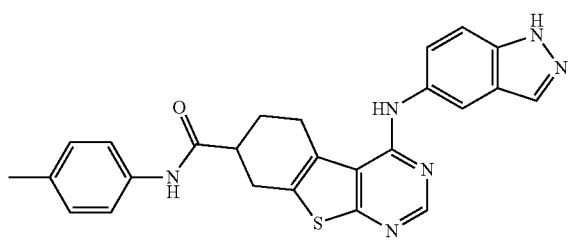 [SMILES: Cc1ccc(NC(=O)C2CCc3c(sc4ncnc(Nc5ccc6[nH]ncc6c5)c34)C2)cc1]

To a mixture of 4-(1H-indazol-5-ylamino)-5,6,7,8-tetrahydro[1]benzothieno[2,3-d]pyrimidine-7-carboxylic acid (150 mg) and para-toluidine (176 mg, 4 eq.) in N,N-dimethylformamide (6 mL) was added N,N-diisopropylethylamine (0.34 mL), followed by T3P (propylphosphinic anhydride; 1.17 mL of a 50% solution in ethyl acetate), and the mixture was stirred at 80° C. for 18 h. To drive the reaction to completion, additional portions of para-toluidine (176 mg, 4 eq.), N,N-diisopropylethylamine (0.34 mL), and T3P (propylphosphinic anhydride; 1.17 mL of a 50% solution in ethyl acetate) were added and the mixture was stirred at 80° C. for 2 h. After cooling to room temperature, the mixture was added to water, the precipitated crude product was isolated by filtration and then purified by preparative HPLC (Method P3) to give 41 mg of the target compound.

$^1$H-NMR (300 MHz, DMSO-d$_6$): δ [ppm]=1.83-2.01 (m, 1H), 2.15-2.31 (m, 1H), 2.26 (s, 3H), 2.82-3.41 (m, 5H), partly overlapped with water signal), 7.12 (d, 2H), 7.44-7.59 (m, 4H), 8.00 (s, 1H), 8.06 (s, 1H), 8.23 (s, 1H), 8.32 (s, 1H), 9.98 (s, 1H), 13.01 (br. s., 1H).
MS (ESIpos) m/z=455 [M+H]+.

Example 18

N-(3-Fluorobenzyl)-4-(1H-indazol-5-ylamino)-5,6,7,8-tetrahydro[1]benzothieno-[2,3-d]pyrimidine-7-carboxamide

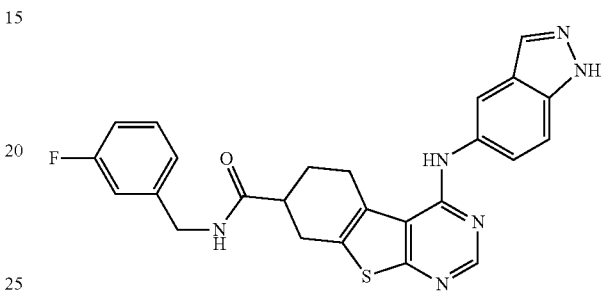

To a mixture of 4-(1H-indazol-5-ylamino)-5,6,7,8-tetrahydro[1]benzothieno[2,3-d]-pyrimidine-7-carboxylic acid (55 mg) and N,N-diisopropylamine (0.08 mL) in N,N-dimethylformamide (1 mL) was added 1-(3-fluorophenyl)methanamine (24 mg), followed by T3P (propylphosphinic anhydride; 0.07 mL of a 50% solution in N,N-dimethylformamide). The mixture was shaken over night at RT.
The obtained mixture was subjected to HPLC purification to yield 10 mg of the title compound solid material.
LC-MS (Method A1): R$_t$=1.0 min; MS (ESIpos) m/z=473 [M+H]+.

The compounds in Table 1 were prepared, purified and analysed in analogy to example 18.

TABLE 1

| Example | Structure | IUPAC Name | retention time [min] | MW found [M + H]+ |
|---|---|---|---|---|
| 19 | 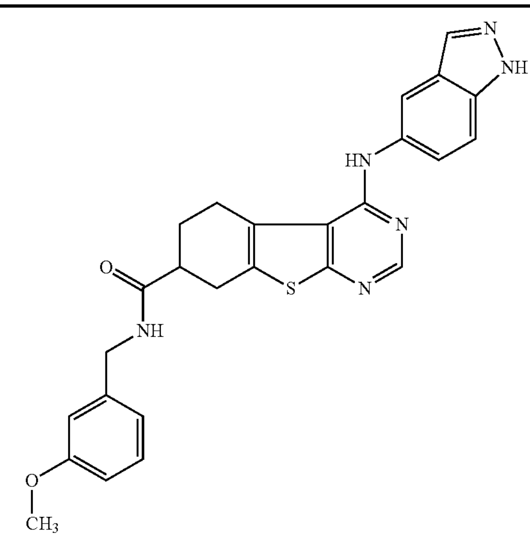 | 4-(1H-indazol-5-ylamino)-N-(3-methoxybenzyl)-5,6,7,8-tetrahydro[1]benzothieno[2,3-d]pyrimidine-7-carboxamide | 0.98 | 485 |

TABLE 1-continued

| Example | Structure | IUPAC Name | retention time [min] | MW found [M + H]+ |
|---|---|---|---|---|
| 20 | 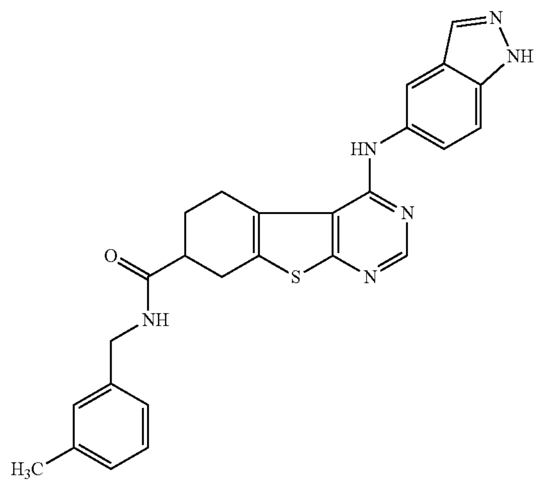 [SMILES: Cc1cccc(CNC(=O)C2CCc3c(sc4ncnc(Nc5ccc6[nH]ncc6c5)c34)C2)c1] | 4-(1H-indazol-5-ylamino)-N-(3-methylbenzyl)-5,6,7,8-tetrahydro[1]benzothieno[2,3-d]pyrimidine-7-carboxamide | 1.0 | 469 |
| 21 | 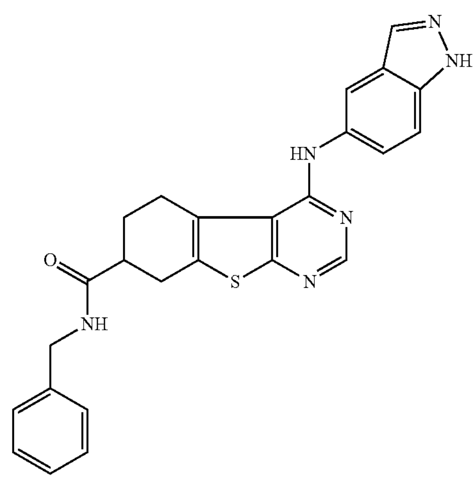 [SMILES: O=C(NCc1ccccc1)C1CCc2c(sc3ncnc(Nc4ccc5[nH]ncc5c4)c23)C1] | N-Benzyl-4-(1H-indazol-5-ylamino)-5,6,7,8-tetrahydro[1]benzothieno[2,3-d]pyrimidine-7-carboxamide | 0.98 | 455 |
| 22 | 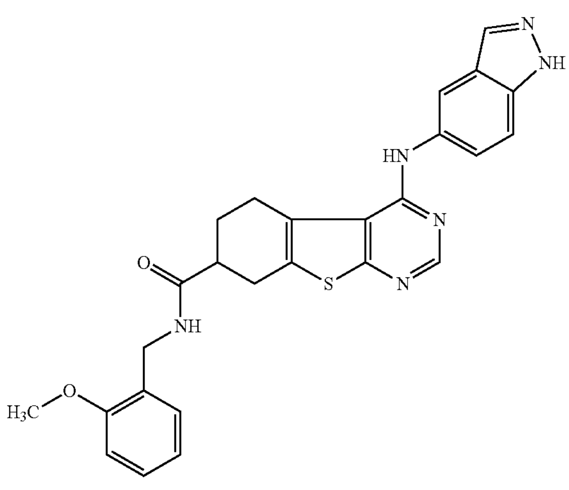 [SMILES: COc1ccccc1CNC(=O)C1CCc2c(sc3ncnc(Nc4ccc5[nH]ncc5c4)c23)C1] | 4-(1H-Indazol-5-ylamino)-N-(2-methoxybenzyl)-5,6,7,8-tetrahydro[1]benzothieno[2,3-d]pyrimidine-7-carboxamide | 1.0 | 485 |

TABLE 1-continued
| Example | Structure | IUPAC Name | retention time [min] | MW found [M + H]+ |
|---|---|---|---|---|
| 23 | 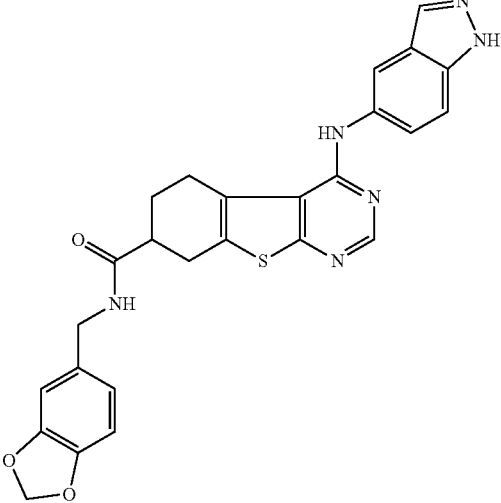 | N-(1,3-Benzodioxol-5-ylmethyl)-4-(1H-indazol-5-ylamino)-5,6,7,8-tetrahydro[1]benzothieno[2,3-d]pyrimidine-7-carboxamide | 0.96 | 499 |
| 24 | 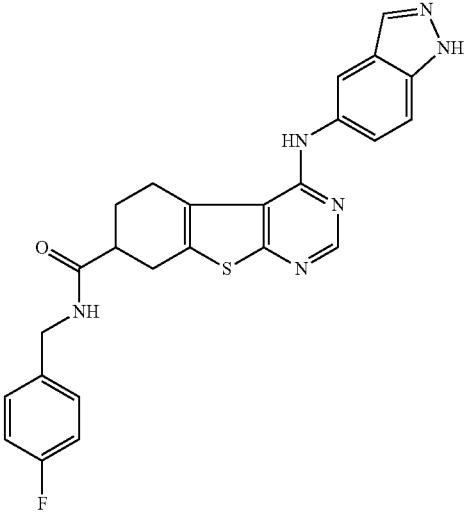 [SMILES: O=C(NCc1ccc(F)cc1)C1CCc2c(sc3ncnc(Nc4ccc5[nH]ncc5c4)c23)C1] | N-(4-Fluorobenzyl)-4-(1H-indazol-5-ylamino)-5,6,7,8-tetrahydro[1]benzothieno[2,3-d]pyrimidine-7-carboxamide | 1.0 | 473 |
| 25 | 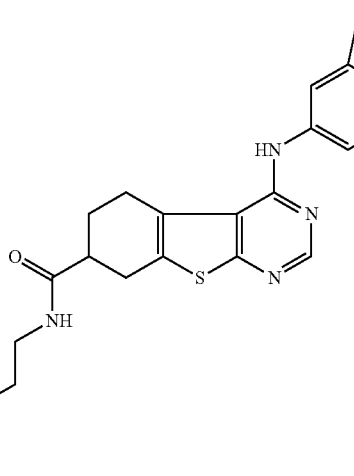 | 4-(1H-Indazol-5-ylamino)-N-[2-(4-methoxyphenyl)ethyl]-5,6,7,8-tetrahydro[1]benzothieno[2,3-d]pyrimidine-7-carboxamide | 1.0 | 499 |

TABLE 1-continued

| Example | Structure | IUPAC Name | retention time [min] | MW found [M + H]+ |
|---|---|---|---|---|
| 26 | 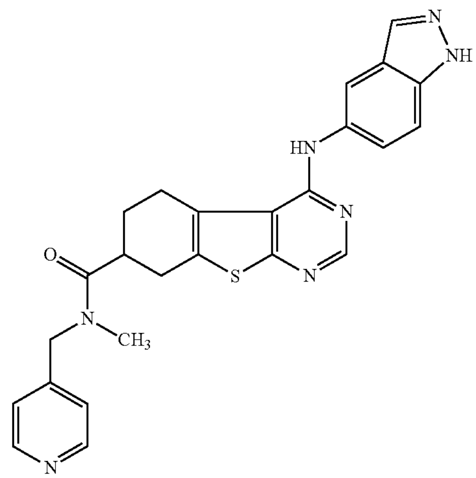 [SMILES: CN(Cc1ccncc1)C(=O)C1CCc2c(sc3ncnc(Nc4ccc5[nH]ncc5c4)c23)C1] | 4-(1H-Indazol-5-ylamino)-N-methyl-N-(pyridin-4-ylmethyl)-5,6,7,8-tetrahydro[1]benzothieno[2,3-d]pyrimidine-7-carboxamide | 0.65 | 470 |
| 27 | 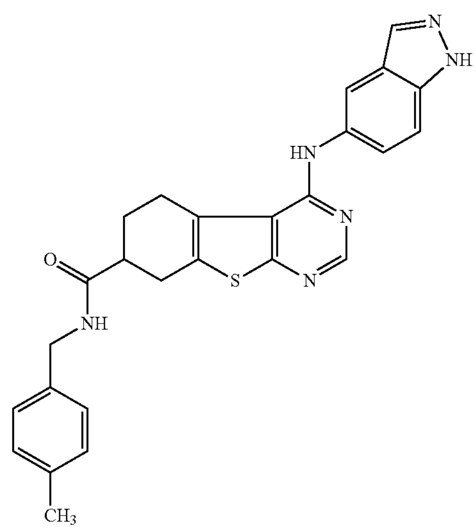 [SMILES: Cc1ccc(CNC(=O)C2CCc3c(sc4ncnc(Nc5ccc6[nH]ncc6c5)c34)C2)cc1] | 4-(1H-Indazol-5-ylamino)-N-(4-methylbenzyl)-5,6,7,8-tetrahydro[1]benzothieno[2,3-d]pyrimidine-7-carboxamide | 1.1 | 469 |
| 28 | 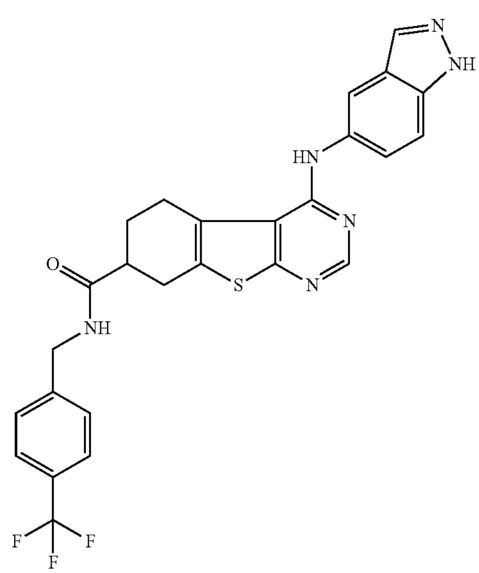 [SMILES: O=C(NCc1ccc(C(F)(F)F)cc1)C1CCc2c(sc3ncnc(Nc4ccc5[nH]ncc5c4)c23)C1] | 4-(1H-Indazol-5-ylamino)-N-[4-(trifluoromethyl)benzyl]-5,6,7,8-tetrahydro[1]benzothieno[2,3-d]pyrimidine-7-carboxamide | 1.1 | 523 |

TABLE 1-continued
| Example | Structure | IUPAC Name | retention time [min] | MW found [M + H]+ |
|---|---|---|---|---|
| 29 | 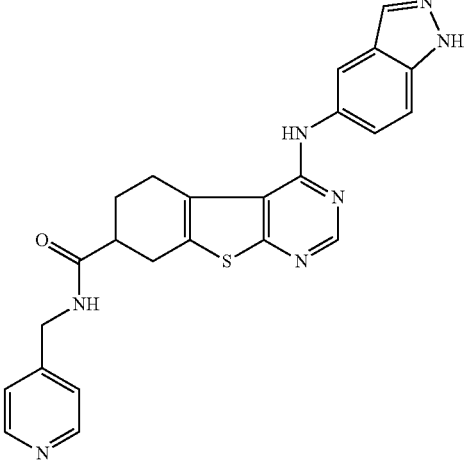 | 4-(1H-Indazol-5-ylamino)-N-(pyridin-4-ylmethyl)-5,6,7,8-tetrahydro[1]benzothieno[2,3-d]pyrimidine-7-carboxamide | 0.61 | 456 |
| 30 | 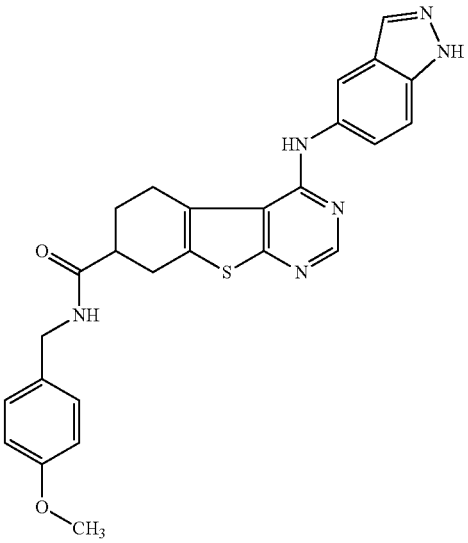 [SMILES: COc1ccc(CNC(=O)C2CCc3c(sc4ncnc(Nc5ccc6[nH]ncc6c5)c34)C2)cc1] | 4-(1H-Indazol-5-ylamino)-N-(4-methoxybenzyl)-5,6,7,8-tetrahydro[1]benzothieno[2,3-d]pyrimidine-7-carboxamide | 0.98 | 485 |
| 31 | 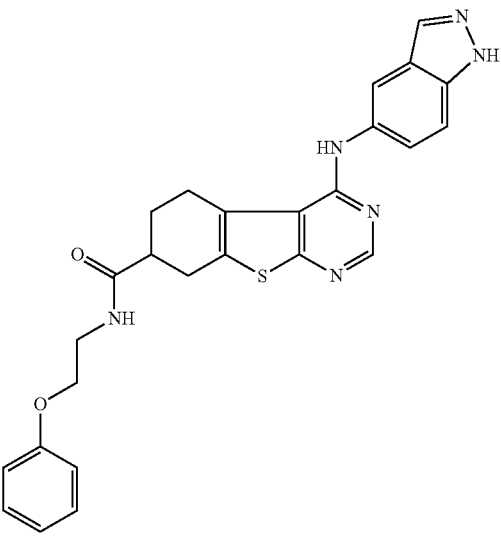 [SMILES: O=C(NCCOc1ccccc1)C1CCc2c(sc3ncnc(Nc4ccc5[nH]ncc5c4)c23)C1] | 4-(1H-Indazol-5-ylamino)-N-(2-phenoxyethyl)-5,6,7,8-tetrahydro[1]benzothieno[2,3-d]pyrimidine-7-carboxamide | 1.0 | 485 |

TABLE 1-continued

| Example | Structure | IUPAC Name | retention time [min] | MW found [M + H]+ |
|---|---|---|---|---|
| 32 | 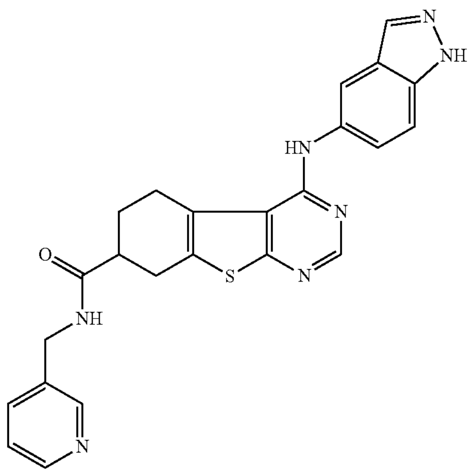 [SMILES: O=C(NCc1cccnc1)C1CCc2c(sc3ncnc(Nc4ccc5[nH]ncc5c4)c23)C1] | 4-(1H-Indazol-5-ylamino)-N-(pyridin-3-ylmethyl)-5,6,7,8-tetrahydro[1]benzothieno[2,3-d]pyrimidine-7-carboxamide | 0.64 | 456 |
| 33 | 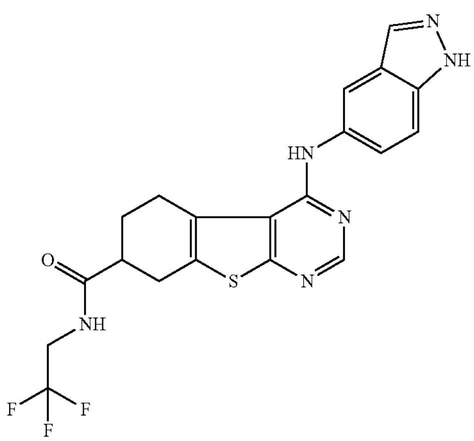 [SMILES: O=C(NCC(F)(F)F)C1CCc2c(sc3ncnc(Nc4ccc5[nH]ncc5c4)c23)C1] | 4-(1H-Indazol-5-ylamino)-N-(2,2,2-trifluoroethyl)-5,6,7,8-tetrahydro[1]benzothieno[2,3-d]pyrimidine-7-carboxamide | 0.91 | 446 |
| 34 | 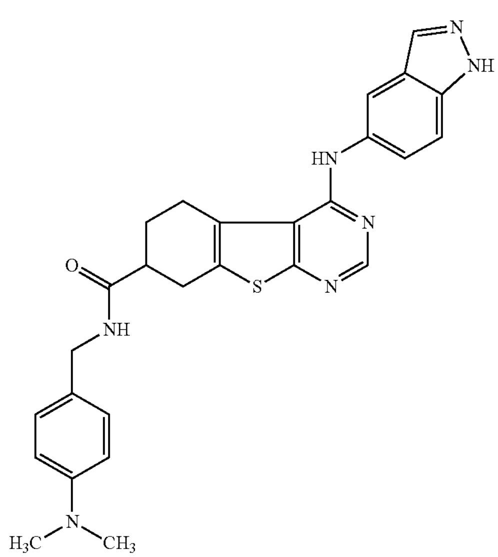 [SMILES: CN(C)c1ccc(CNC(=O)C2CCc3c(sc4ncnc(Nc5ccc6[nH]ncc6c5)c34)C2)cc1] | N-[4-(Dimethylamino)benzyl]-4-(1H-indazol-5-ylamino)-5,6,7,8-tetrahydro[1]benzothieno[2,3-d]pyrimidine-7-carboxamide | 0.79 | 447 |

TABLE 1-continued

| Example | Structure | IUPAC Name | retention time [min] | MW found [M + H]+ |
|---|---|---|---|---|
| 35 | 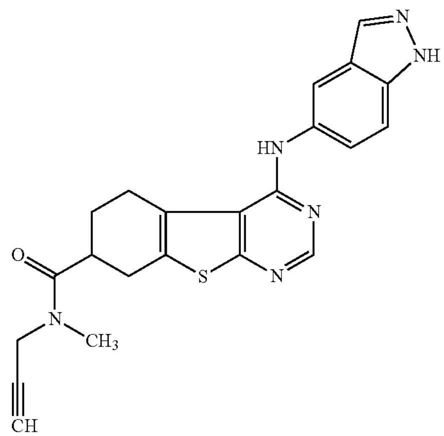 [SMILES: C#CCN(C)C(=O)C1CCc2c(sc3ncnc(Nc4ccc5[nH]ncc5c4)c23)C1] | 4-(1H-Indazol-5-ylamino)-N-methyl-N-(prop-2-yn-1-yl)-5,6,7,8-tetrahydro[1]benzothieno[2,3-d]pyrimidine-7-carboxamide | 0.89 | 417 |
| 36 | 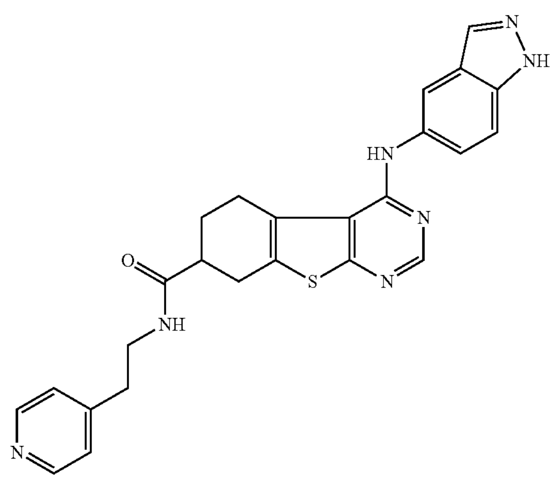 [SMILES: O=C(NCCc1ccncc1)C1CCc2c(sc3ncnc(Nc4ccc5[nH]ncc5c4)c23)C1] | 4-(1H-Indazol-5-ylamino)-N-[2-(pyridin-4-yl)ethyl]-5,6,7,8-tetrahydro[1]benzothieno[2,3-d]pyrimidine-7-carboxamide | 0.62 | 470 |
| 37 | 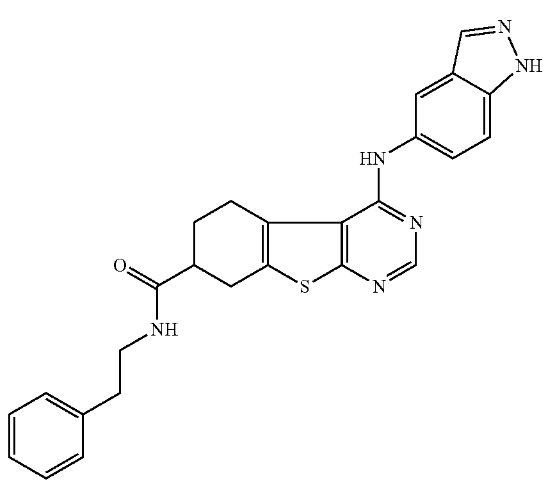 [SMILES: O=C(NCCc1ccccc1)C1CCc2c(sc3ncnc(Nc4ccc5[nH]ncc5c4)c23)C1] | 4-(1H-Indazol-5-ylamino)-N-(2-phenylethyl)-5,6,7,8-tetrahydro[1]benzothieno[2,3-d]pyrimidine-7-carboxamide | 1.0 | 469 |

TABLE 1-continued

| Example | Structure | IUPAC Name | retention time [min] | MW found [M + H]+ |
|---|---|---|---|---|
| 38 | 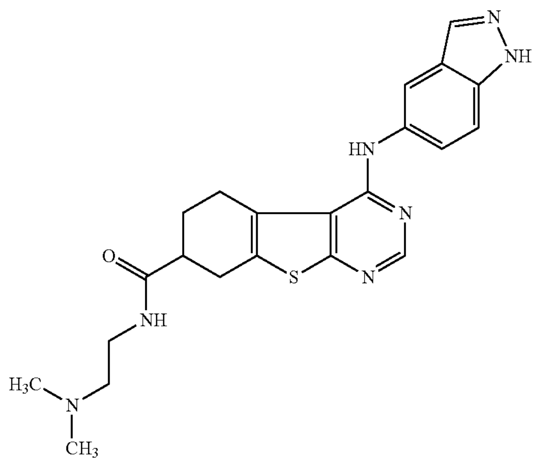 [SMILES: CN(C)CCNC(=O)C1CCc2c(sc3ncnc(Nc4ccc5[nH]ncc5c4)c23)C1] | N-[2-(Dimethylamino)ethyl]-4-(1H-indazol-5-ylamino)-5,6,7,8-tetrahydro[1]benzothieno[2,3-d]pyrimidine-7-carboxamide | 0.58 | 436 |
| 39 | 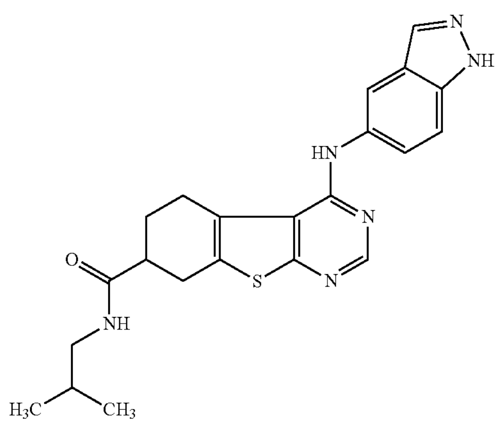 [SMILES: CC(C)CNC(=O)C1CCc2c(sc3ncnc(Nc4ccc5[nH]ncc5c4)c23)C1] | 4-(1H-Indazol-5-ylamino)-N-(2-methylpropyl)-5,6,7,8-tetrahydro[1]benzothieno[2,3-d]pyrimidine-7-carboxamide | 0.95 | 421 |
| 40 | 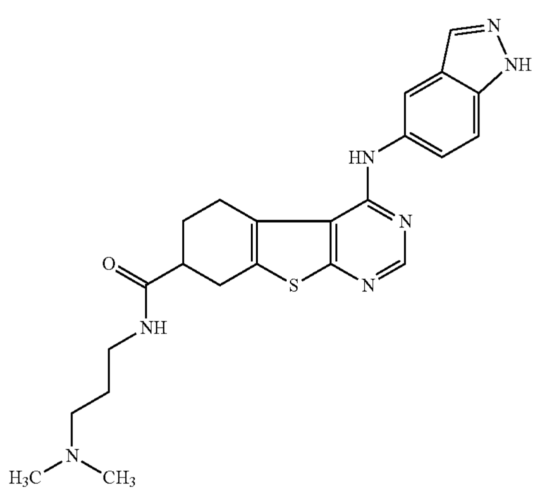 [SMILES: CN(C)CCCNC(=O)C1CCc2c(sc3ncnc(Nc4ccc5[nH]ncc5c4)c23)C1] | N-[3-(Dimethylamino)propyl]-4-(1H-indazol-5-ylamino)-5,6,7,8-tetrahydro[1]benzothieno[2,3-d]pyrimidine-7-carboxamide | 0.59 | 450 |

TABLE 1-continued

| Example | Structure | IUPAC Name | retention time [min] | MW found [M + H]+ |
|---|---|---|---|---|
| 41 | 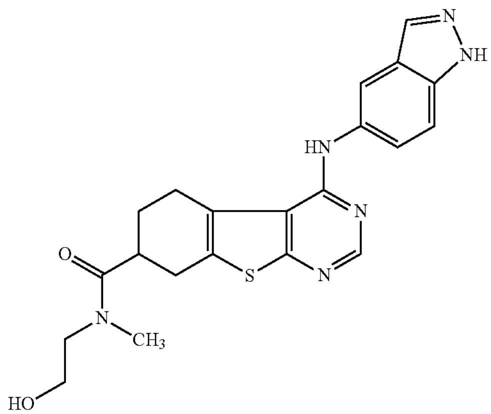 [SMILES: CN(CCO)C(=O)C1CCc2c(sc3ncnc(Nc4ccc5[nH]ncc5c4)c23)C1] | N-(2-Hydroxyethyl)-4-(1H-indazol-5-ylamino)-N-methyl-5,6,7,8-tetrahydro[1]benzothieno[2,3-d]pyrimidine-7-carboxamide | 0.72 | 423 |
| 42 | 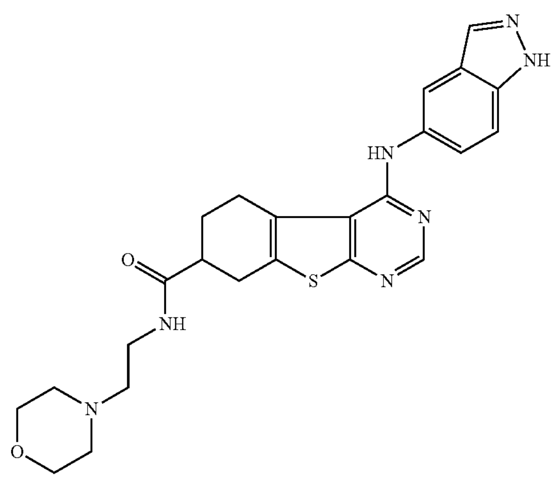 [SMILES: O=C(NCCN1CCOCC1)C1CCc2c(sc3ncnc(Nc4ccc5[nH]ncc5c4)c23)C1] | 4-(1H-Indazol-5-ylamino)-N-[2-(morpholin-4-yl)ethyl]-5,6,7,8-tetrahydro[1]benzothieno[2,3-d]pyrimidine-7-carboxamide | 0.6 | 478 |
| 43 | 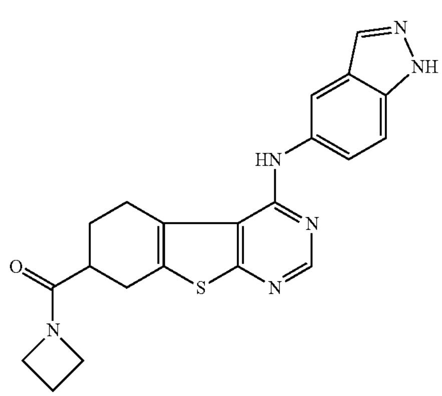 [SMILES: O=C(C1CCc2c(sc3ncnc(Nc4ccc5[nH]ncc5c4)c23)C1)N1CCC1] | Azetidin-1-yl[4-(1H-indazol-5-ylamino)-5,6,7,8-tetrahydro[1]benzothieno[2,3-d]pyrimidin-7-yl]methanone | 0.81 | 405 |

TABLE 1-continued

| Example | Structure | IUPAC Name | retention time [min] | MW found [M + H]+ |
|---|---|---|---|---|
| 44 | 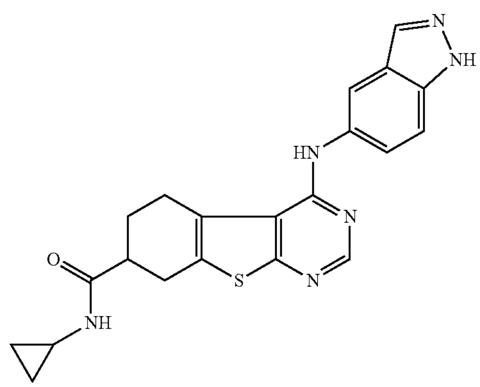 [SMILES: O=C(NC1CC1)C1CCc2c(sc3ncnc(Nc4ccc5[nH]ncc5c4)c23)C1] | N-Cyclopropyl-4-(1H-indazol-5-ylamino)-5,6,7,8-tetrahydro[1]benzothieno[2,3-d]pyrimidine-7-carboxamide | 0.81 | 405 |
| 45 | 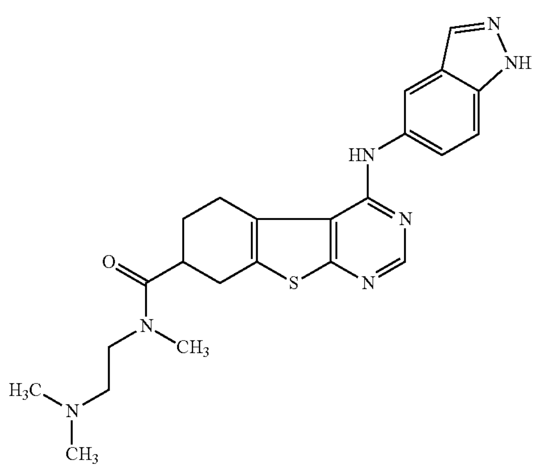 [SMILES: CN(C)CCN(C)C(=O)C1CCc2c(sc3ncnc(Nc4ccc5[nH]ncc5c4)c23)C1] | N-[2-(Dimethylamino)ethyl]-4-(1H-indazol-5-ylamino)-N-methyl-5,6,7,8-tetrahydro[1]benzothieno[2,3-d]pyrimidine-7-carboxamide | 0.6 | 450 |
| 46 | 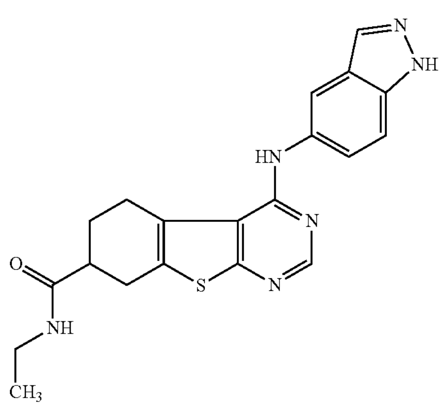 [SMILES: CCNC(=O)C1CCc2c(sc3ncnc(Nc4ccc5[nH]ncc5c4)c23)C1] | N-Ethyl-4-(1H-indazol-5-ylamino)-5,6,7,8-tetrahydro[1]benzothieno[2,3-d]pyrimidine-7-carboxamide | 0.8 | 393 |

TABLE 1-continued

| Example | Structure | IUPAC Name | retention time [min] | MW found [M + H]+ |
|---|---|---|---|---|
| 47 | 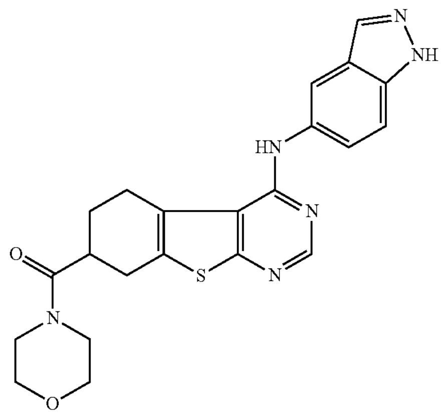 [SMILES: O=C(C1CCc2c(sc3ncnc(Nc4ccc5[nH]ncc5c4)c23)C1)N1CCOCC1] | [4-(1H-Indazol-5-ylamino)-5,6,7,8-tetrahydro[1]benzothieno[2,3-d]pyrimidin-7-yl](morpholin-4-yl)methanone | 0.8 | 435 |
| 48 | 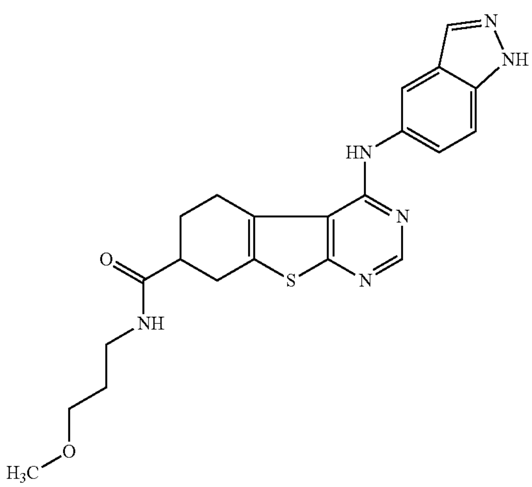 [SMILES: COCCCNC(=O)C1CCc2c(sc3ncnc(Nc4ccc5[nH]ncc5c4)c23)C1] | 4-(1H-Indazol-5-ylamino)-N-(3-methoxypropyl)-5,6,7,8-tetrahydro[1]benzothieno[2,3-d]pyrimidine-7-carboxamide | 0.82 | 437 |
| 49 | 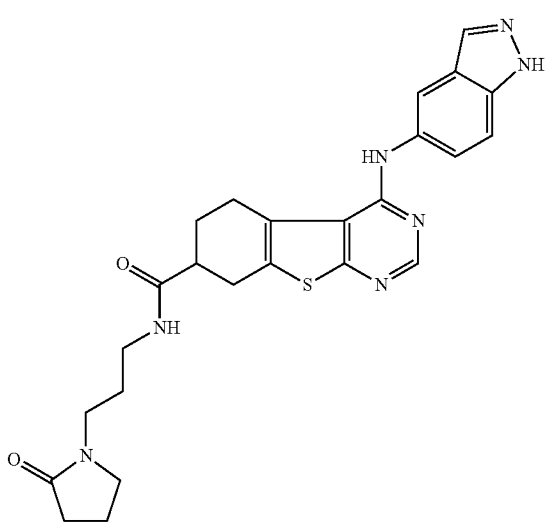 [SMILES: O=C(NCCCN1CCCC1=O)C1CCc2c(sc3ncnc(Nc4ccc5[nH]ncc5c4)c23)C1] | 4-(1H-Indazol-5-ylamino)-N-[3-(2-oxopyrrolidin-1-yl)propyl]-5,6,7,8-tetrahydro[1]benzothieno[2,3-d]pyrimidine-7-carboxamide | 0.78 | 490 |

TABLE 1-continued

| Example | Structure | IUPAC Name | retention time [min] | MW found [M + H]+ |
|---|---|---|---|---|
| 50 | 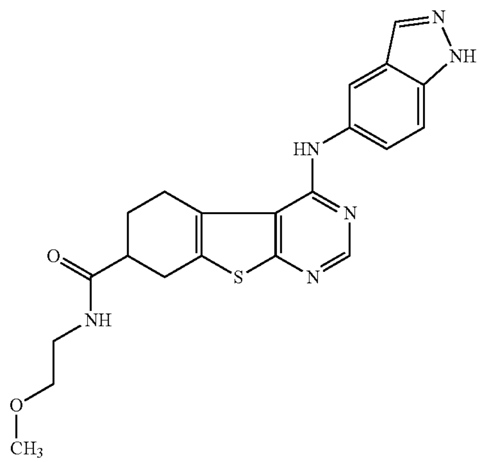 [SMILES: COCCNC(=O)C1CCc2c(sc3ncnc(Nc4ccc5[nH]ncc5c4)c23)C1] | 4-(1H-Indazol-5-ylamino)-N-(2-methoxyethyl)-5,6,7,8-tetrahydro[1]benzothieno[2,3-d]pyrimidine-7-carboxamide | 0.79 | 423 |
| 51 | 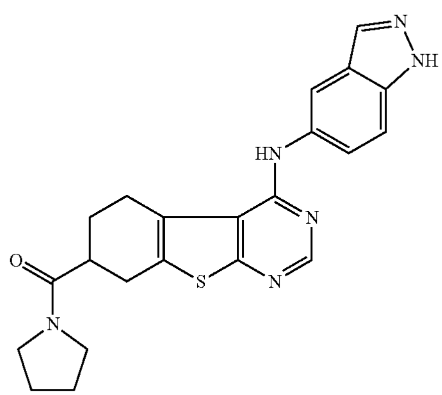 [SMILES: O=C(C1CCc2c(sc3ncnc(Nc4ccc5[nH]ncc5c4)c23)C1)N1CCCC1] | [4-(1H-Indazol-5-ylamino)-5,6,7,8-tetrahydro[1]benzothieno[2,3-d]pyrimidin-7-yl](pyrrolidin-1-yl)methanone | 0.88 | 419 |
| 52 | 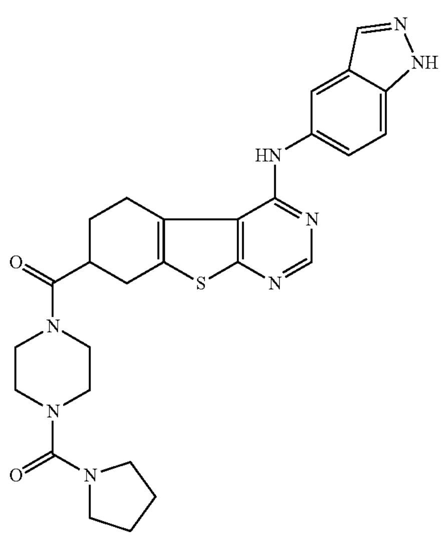 [SMILES: O=C(C1CCc2c(sc3ncnc(Nc4ccc5[nH]ncc5c4)c23)C1)N1CCN(C(=O)N2CCCC2)CC1] | [4-(1H-Indazol-5-ylamino)-5,6,7,8-tetrahydro[1]benzothieno[2,3-d]pyrimidin-7-yl][4-(pyrrolidin-1-ylcarbonyl)piperazin-1-yl]methanone | 0.89 | 531 |

Example 53

Ethyl 4-[(6-chloro-1H-indazol-5-yl)amino]-5,6,7,8-tetrahydro[1]benzothieno[2,3-d]pyrimidine-7-carboxylate

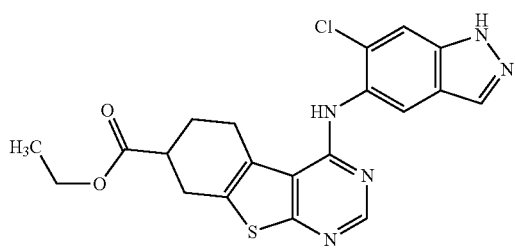 [SMILES: CCOC(=O)C1CCc2c(sc3ncnc(Nc4cc5cn[nH]c5cc4Cl)c23)C1]

To a mixture of ethyl 4-(1H-indazol-5-ylamino)-5,6,7,8-tetrahydro[1]benzothieno[2,3-d]pyrimidine-7-carboxylate (650 mg) and 5-amino-6-chloroindazole (422 mg, 1.15 eq) in ethanol (8.0 mL) were added 4 Å molecular sieves (2 g), followed by a 4 N solution of hydrogen chloride in dioxane (821 μL, 1.5 eq). The mixture was heated to reflux for 16 h and added to water after cooling to room temperature. The precipitate was isolated by filtration and triturated with DMSO. Insolubles were removed by filtration, the filtrate was concentrated in vacuo to give the crude product which was purified by preparative HPLC (Method P4) yielding 35 mg of the target compound.

$^1$H-NMR (300 MHz, DMSO-$d_6$): δ [ppm]=1.22 (t, 3H), 1.89-2.05 (m, 1H), 2.16-2.31 (m, 1H), 2.89-3.30 (m, 5H, partly overlapped with water signal), 4.14 (q, 2H), 7.77 (s, 1H), 8.07-8.16 (m, 2H), 8.25 (s, 1H), 8.29 (s, 1H), 13.21 (br. s., 1H).

MS (ESIpos) m/z=428 ($^{35}$Cl), 430 ($^{37}$Cl) [M+H]$^+$.

Example 54

Ethyl 4-[(6-fluoro-1H-indazol-5-yl)amino]-5,6,7,8-tetrahydro[1]benzothieno[2,3-d]pyrimidine-7-carboxylate

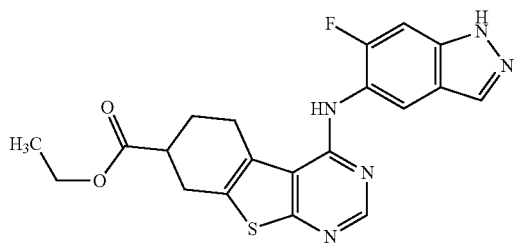 [SMILES: CCOC(=O)C1CCc2c(sc3ncnc(Nc4cc5cn[nH]c5cc4F)c23)C1]

To a mixture of ethyl 4-chloro-5,6,7,8-tetrahydro[1]benzothieno[2,3-d]pyrimidine-7-carboxylate (1.36 g, for a preparation see e.g. WO 2005/010008, example 14, steps 1 to 3) and 5-amino-6-fluoroindazole (0.76 g, 1.1 eq) in ethanol (30 mL) were added molecular sieves (4 Å, 1 g), and a 4 N solution of hydrogen chloride in dioxane (1.7 mL, 1.5 eq.). The mixture heated to reflux with stirring for 18 h. After cooling to room temperature, the mixture was added to water, the precipitate was filtered off and was triturated with methanol. The residue was treated with hot DMSO, all insolubles were filtered off and the filtrate was evaporated to give the crude target compound sufficiently pure for the following step (1.5 g). An analytical sample was obtained by preparative HPLC purification (Method P4).

$^1$H-NMR (400 MHz, DMSO-$d_6$): δ [ppm]=1.23 (t, 3H), 1.88-2.03 (m, 1H), 2.16-2.28 (m, 1H), 2.91-3.26 (m, 5H, partly overlapped with water signal), 4.14 (q, 2H), 7.43 (d, 1H), 8.01 (d, 1H), 8.11 (s, 1H), 8.22 (s, 1H), 8.27 (s, 1H), 13.12 (br. s., 1H).

MS (ESIpos) m/z=412 [M+H]$^+$.

Example 55

4-[(6-Fluoro-1H-indazol-5-yl)amino]-5,6,7,8-tetrahydro[1]benzothieno[2,3-d]pyrimidine-7-carboxylic acid

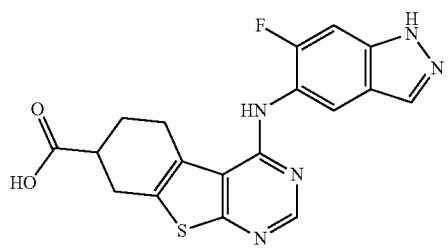 [SMILES: O=C(O)C1CCc2c(sc3ncnc(Nc4cc5cn[nH]c5cc4F)c23)C1]

To ethyl 4-[(6-fluoro-1H-indazol-5-yl)amino]-5,6,7,8-tetrahydro[1]benzothieno[2,3-d]pyrimidine-7-carboxylate (1.35 g) in ethanol (30 mL) was added 10 N aqueous sodium hydroxide (6.6 mL, 20 eq) and the mixture was stirred at RT for 2 h. Water was added, and the mixture was extracted with dichloromethane. The aqueous layer was acidified with 2 N aqueous hydrochloric acid. The crude product precipitated and was then triturated with diethyl ether to give 677 mg of the target compound.

$^1$H-NMR (300 MHz, DMSO-$d_6$): δ [ppm]=1.83-2.05 (m, 1H), 2.13-2.32 (m, 1H), 2.79-3.26 (m, 5H, partly overlapped with water signal), 7.44 (d, 1H), 8.02 (d, 1H), 8.11 (d, 1H), 8.22 (s, 1H), 8.27 (s, 1H), 12.61 (br. s., 1H), 13.02 (br. s., 1H).

MS (ESIpos) m/z=384 [M+H]$^+$.

Example 56

Ethyl 4-[(6-methoxy-1H-indazol-5-yl)amino]-5,6,7,8-tetrahydro[1]benzothieno[2,3-d]pyrimidine-7-carboxylate

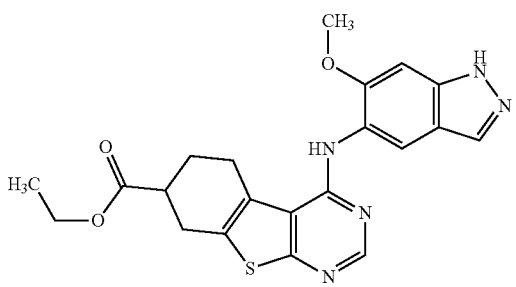 [SMILES: CCOC(=O)C1CCc2c(sc3ncnc(Nc4cc5cn[nH]c5cc4OC)c23)C1]

To a mixture of ethyl 4-chloro-5,6,7,8-tetrahydro[1]benzothieno[2,3-d]pyrimidine-7-carboxylate (473 mg, for a preparation see e.g. WO 2005/010008, example 14, steps 1 to 3) and 5-amino-6-methoxyindazole (300 mg, 1.15 eq) in ethanol (6.0 mL) were added molecular sieves (4 Å, 2 g), and a 4 N solution of hydrogen chloride in dioxane (0.63 mL, 1.6 eq.). The mixture heated to reflux with stirring for 16 h. Molecular sieves were removed by filtration, and the filtrate was concentrated, re-dissolved in DMSO, and filtered again. Concentration in vacuo and purification by preparative HPLC (Method P3, elution impeded by poor solubility) gave 40 mg of the target compound as a brownish solid.

$^1$H-NMR (400 MHz, DMSO-$d_6$): δ [ppm]=1.23 (t, 3H), 1.87-2.04 (m, 1H), 2.26-2.38 (m, 1H), 2.88-3.26 (m, 5H, partly overlapped with water signal), 3.98 (s, 3H), 4.07-4.21 (m, 2H), 7.09 (s, 1H), 8.00 (s, 1H), 8.20 (s, 1H), 8.46 (s, 1H), 8.77 (s, 1H), 12.84 (br. s., 1H).

MS (ESIpos) m/z=424 [M+H]$^+$.

Example 57

4-[(6-Methoxy-1H-indazol-5-yl)amino]-5,6,7,8-tetrahydro[1]benzothieno[2,3-d]pyrimidine-7-carboxylic acid

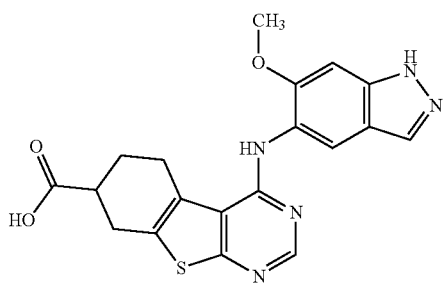 [SMILES: COc1cc2[nH]ncc2cc1Nc1ncnc2sc3c(c12)CCC(C(=O)O)C3]

To a mixture of ethyl 4-chloro-5,6,7,8-tetrahydro[1]benzothieno[2,3-d]pyrimidine-7-carboxylate (1.19 g) and 5-amino-6-methoxyindazole (750 mg, 1.15 eq) in ethanol (25 mL) were added molecular sieves (4 Å, 2 g), and a 4 N solution of hydrogen chloride in dioxane (1.50 mL, 1.5 eq.). The mixture heated to reflux with stirring for 16 h. After cooling to room temperature, the mixture was filtered, and the residue was triturated with ethanol. The residue was discarded, and the filtrate was concentrated in vacuo, re-dissolved in ethanol (30 mL), and treated with 10 N aqueous sodium hydroxide (7.56 mL). The mixture was stirred for 2 h at room temperature and was then diluted with water (100 mL), extracted with dichloromethane, and the aqueous layer was then acidified with aqueous hydrochloric acid. The precipitate was isolated and triturated with diethyl ether and then subjected to preparative HPLC (Method P1). As in the preceding example, product elution was impeded by poor solubility of the target compound, which was isolated in three batches (overall 70 mg) involving repeated rinsing of the column.

$^1$H-NMR (300 MHz, DMSO-$d_6$): δ [ppm]=1.85-2.05 (m, 1H), 2.22-2.30 (m, 1H), 2.80-3.25 (m, 5H, partly overlapped with water signal), 3.98 (s, 3H), 7.08 (s, 1H), 8.00 (s, 1H), 8.23 (s, 1H), 8.46 (s, 1H), 8.75 (s, 1H), 12.78 (br. s., 2H).

MS (ESIpos) m/z=396 [M+H]$^+$.

Example 58

N-Ethyl-4-[(6-methoxy-1H-indazol-5-yl)amino]-5,6,7,8-tetrahydro[1]benzothieno[2,3-d]pyrimidine-7-carboxamide

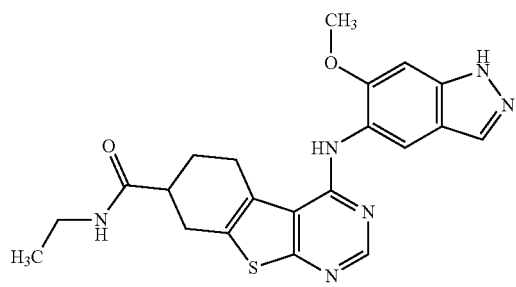 [SMILES: CCNC(=O)C1CCc2c(sc3ncnc(Nc4cc5cn[nH]c5cc4OC)c23)C1]

To a mixture of 4-[(6-methoxy-1H-indazol-5-yl)amino]-5,6,7,8-tetrahydro[1]benzothieno[2,3-d]pyrimidine-7-carboxylic acid (50 mg) and N,N-diisopropylethylamine (88 µL) in N,N-dimethylformamide (2.0 mL) was added ethyl ammonium chloride (31 mg), followed by T3P (propylphosphinic anhydride; 90 µL of a 50% solution in ethyl acetate), and the resulting mixture was stirred for 18 h at RT. Water was added, the mixture was concentrated in vacuo and the residue was purified by preparative HPLC (Method P1) to give 28 mg of the target compound.

$^1$H-NMR (300 MHz, DMSO-$d_6$): δ [ppm]=1.05 (t, 3H), 1.76-1.98 (m, 1H), 2.11-2.29 (m, 1H), 2.57-2.75 (m, 1H), 2.87-3.28 (m, 6H, partly overlapped with water signal), 3.98 (s, 3H), 7.09 (s, 1H), 8.00 (s, 2H), 8.23 (s, 1H), 8.46 (s, 1H), 8.78 (s, 1H), 12.82 (br. s, 1H).

MS (ESIpos) m/z=423 [M+H]$^+$.

Example 59

N-Isopropyl-4-[(6-methyl-1H-indazol-5-yl)amino]-5,6,7,8-tetrahydro[1]benzothieno[2,3-d]pyrimidine-7-carboxamide

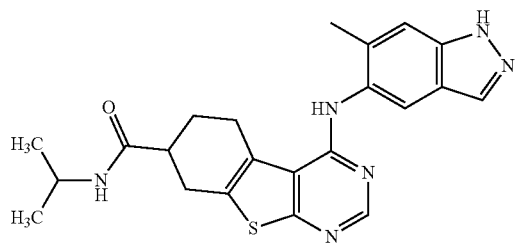 [SMILES: Cc1cc2[nH]ncc2cc1Nc1ncnc2sc3c(c12)CCC(C(=O)NC(C)C)C3]

To a mixture of 4-chloro-N-isopropyl-5,6,7,8-tetrahydro [1]benzothieno[2,3-d]pyrimidine-7-carboxamide (300 mg, see Intermediate 2A) and 6-methyl-1H-indazol-5-amine (225 mg, 1.5 eq) in ethanol (10 mL) was added a 4 N solution of hydrogen chloride in dioxane (48 µL, 0.2 eq), and the mixture was heated subsequently to 80° C. for 2 h (reflux, no turnover detected), followed by 1 h at 130° C. (microwave oven, partial turnover). Additional heating for 4 h at 150° C. in a microwave oven gave complete turnover. After cooling to room temperature, the mixture was concentrated in vacuo and the residue was purified by preparative HPLC (method P1) to give 145 mg of the target compound.

¹H-NMR (300 MHz, DMSO-d₆): δ [ppm]=1.09 (d, 6H), 1.73-1.91 (m, 1H), 2.01-2.14 (m, 1H), 2.29 (s, 3H), 2.55-2.68 (m, 1H), 2.82-3.15 (m, 3H), 3.21-3.29 (m, 1H, partly overlapped with water signal), 3.79-3.97 (m, 1H), 3.85 (sept, 1H), 7.43 (s, 1H), 7.78 (s, 1H), 7.82 (d, 1H), 8.01 (s, 1H), 8.08 (s, 1H), 8.18 (s, 1H), 12.92 (br. s, 1H).

MS (ESIpos) m/z=421 [M+H]⁺.

Example 60

(RS)-Ethyl 4-[(4-methyl-1H-indazol-5-yl)amino]-5,6,7,8-tetrahydro[1]benzothieno[2,3-d]pyrimidine-7-carboxylate

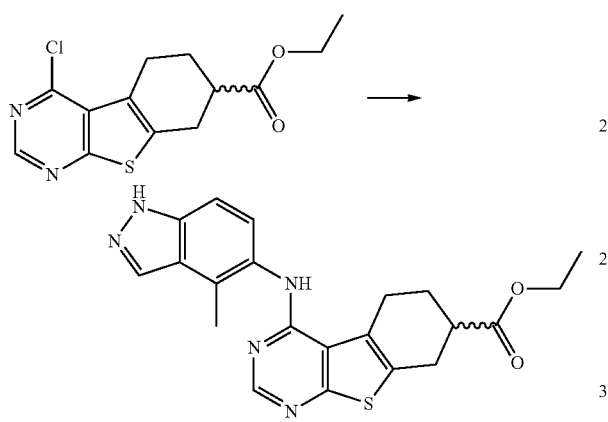

876.7 mg (2.95 mmol) (RS)-ethyl 4-chloro-5,6,7,8-tetrahydro[1]benzothieno[2,3-d]pyrimidine-7-carboxylate (prepared according to WO 2005/010008, example 14, steps 1 to 3) were transformed in analogy to example 1 using 6-methyl-1H-indazol-5-amine to give after working up and purification 92 mg (7%) of the title compound.

¹H-NMR (DMSO-d₆): δ=1.23 (3H), 1.94 (1H), 2.22 (1H), 2.38 (3H), 2.92-3.28 (5H), 4.14 (2H), 7.28 (1H), 7.37 (1H), 8.08 (1H), 8.14 (2H), 13.02 (1H) ppm.

Example 61

(RS)-Ethyl 4-[(3-methyl-1H-indazol-5-yl)amino]-5,6,7,8-tetrahydro[1]benzothieno[2,3-d]pyrimidine-7-carboxylate

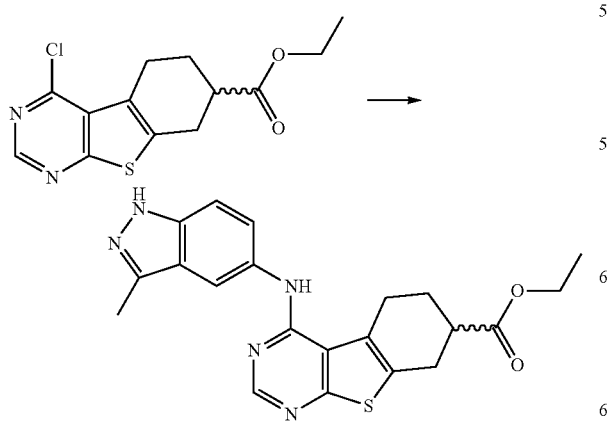

1.00 g (3.37 mmol) (RS)-ethyl 4-chloro-5,6,7,8-tetrahydro[1]benzothieno[2,3-d]pyrimidine-7-carboxylate (prepared according to WO 2005/010008, example 14, steps 1 to 3) were transformed in analogy to example 1 using 3-methyl-1H-indazol-5-amine to give after working up and purification 581 mg (42%) of the title compound.

¹H-NMR (DMSO-d₆): δ=1.19 (3H), 1.90 (1H), 2.18 (1H), 2.43 (3H), 2.85-3.24 (5H), 4.10 (2H), 7.39 (1H), 7.45 (1H), 7.80 (1H), 8.17 (1H), 8.25 (1H), 12.56 (1H) ppm.

Example 62

(RS)-4-[(3-Methyl-1H-indazol-5-yl)amino]-5,6,7,8-tetrahydro[1]benzothieno[2,3-d]pyrimidine-7-carboxylic acid

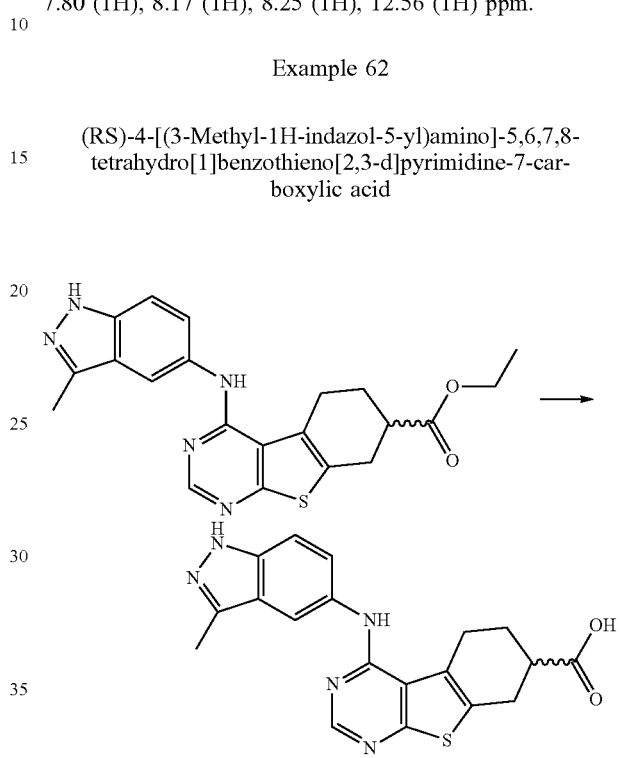

1.50 g (3.68 mmol) (RS)-ethyl 4-[(3-methyl-1H-indazol-5-yl)amino]-5,6,7,8-tetrahydro[1]benzothieno[2,3-d]pyrimidine-7-carboxylate (prepared according to example 61) were transformed in analogy to example 2 to give after working up and purification 85 mg (6%) of the title compound.

¹H-NMR (DMSO-d₆): δ=1.90 (1H), 2.18 (1H), 2.44 (3H), 2.83 (1H), 2.93-3.29 (5H), 7.44 (2H), 7.82 (1H), 8.32 (1H), 8.57 (1H), 12.57 (1H) ppm.

Example 63

(RS)-4-[(6-Fluoro-1H-indazol-5-yl)amino]-N-(propan-2-yl)-5,6,7,8-tetrahydro[1]benzothieno[2,3-d]pyrimidine-7-carboxamide

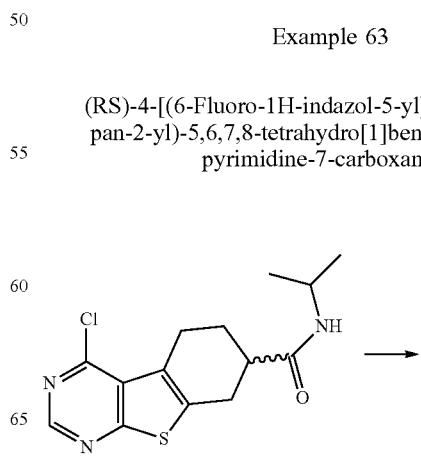

-continued

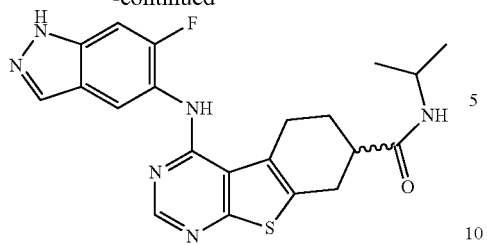

60 mg (194 µmol) (RS)-4-chloro-N-isopropyl-5,6,7,8-tetrahydro[1]benzothieno[2,3-d]pyrimidine-7-carboxamide (prepared according to intermediate example 2a) were transformed in analogy to example 1 using 6-fluoro-1H-indazol-5-amine to give after working up and purification 8.4 mg (9%) of the title compound.

$^1$H-NMR (DMSO-d$_6$): δ=1.08 (6H), 1.87 (1H), 2.17 (1H), 2.62 (1H), 2.93 (2H), 3.10 (1H), 3.25 (1H), 3.87 (1H), 3.97 (3H), 7.09 (1H), 7.83 (1H), 7.99 (1H), 8.22 (1H), 8.46 (1H), 8.78 (1H), 12.83 (1H) ppm.

Example 64

(RS)-4-[(6-Methoxy-1H-indazol-5-yl)amino]-N,N-dimethyl-5,6,7,8-tetrahydro[1]benzothieno[2,3-d]pyrimidine-7-carboxamide

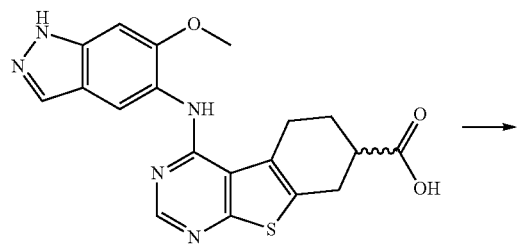

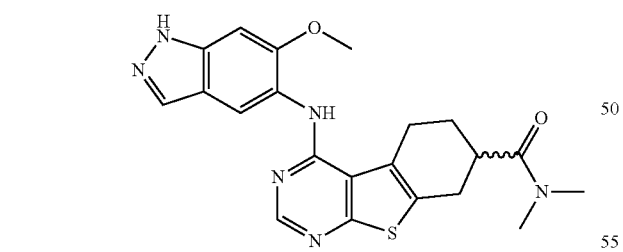

200 mg (506 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-methylmethanamine to give after working up and purification 167 mg (74%) of the title compound.

$^1$H-NMR (DMSO-d$_6$): δ=1.83 (1H), 2.14 (1H), 2.87 (3H), 2.89-2.99 (2H), 3.10 (3H), 3.14-3.25 (3H), 3.98 (3H), 7.09 (1H), 7.99 (1H), 8.21 (1H), 8.45 (1H), 8.77 (1H), 12.83 (1H) ppm.

Example 65

(RS)-{4-[(6-Methoxy-1H-indazol-5-yl)amino]-5,6,7,8-tetrahydro[1]benzothieno[2,3-d]pyrimidin-7-yl}(4-methylpiperazin-1-yl)methanone

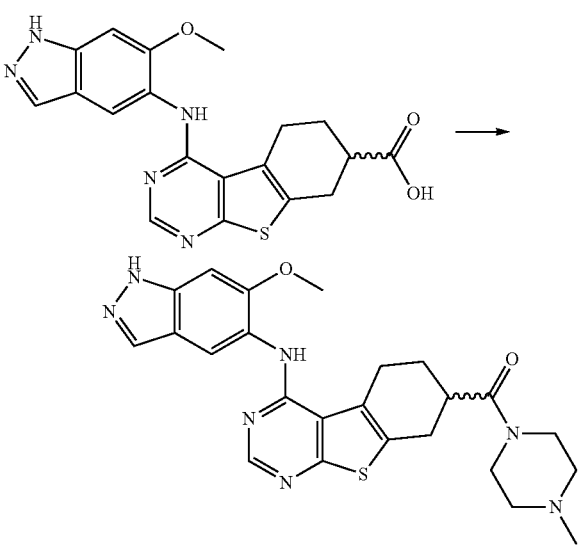

200 mg (506 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 1-methylpiperazine to give after working up and purification 197.6 mg (78%) of the title compound.

$^1$H-NMR (DMSO-d$_6$): δ=1.82 (1H), 2.09 (1H), 2.17 (3H), 2.25 (2H), 2.32 (2H), 2.83-3.00 (2H), 3.12-3.25 (3H), 3.48 (2H), 3.56 (2H), 3.95 (3H), 7.06 (1H), 7.97 (1H), 8.18 (1H), 8.43 (1H), 8.74 (1H), 12.82 (1H) ppm.

Example 66

(RS)-4-[(6-Methoxy-1H-indazol-5-yl)amino]-N-(propan-2-yl)-5,6,7,8-tetrahydro[1]benzothieno[2,3-d]pyrimidine-7-carboxamide

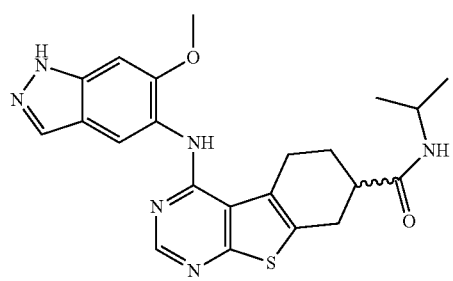

60 mg (194 µmol) (RS)-4-chloro-N-isopropyl-5,6,7,8-tetrahydro[1]benzothieno[2,3-d]pyrimidine-7-carboxamide (prepared according to intermediate example 2a) were transformed in analogy to example 1 using 6-methoxy-1H-indazol-5-amine to give after working up and purification 8.4 mg (9%) of the title compound.

$^1$H-NMR (DMSO-$d_6$): δ=1.08 (6H), 1.86 (1H), 2.17 (1H), 2.62 (1H), 2.93 (2H), 3.10 (1H), 3.25 (1H), 3.87 (1H), 3.97 (3H), 7.09 (1H), 7.83 (1H), 7.99 (1H), 8.22 (1H), 8.46 (1H), 8.78 (1H), 12.83 (1H) ppm.

Example 67

N-Ethyl-4-[(6-Methoxy-1H-indazol-5-yl)amino]-N-(propan-2-yl)-5,6,7,8-tetrahydro[1]benzothieno[2,3-d]pyrimidine-7-carboxamide

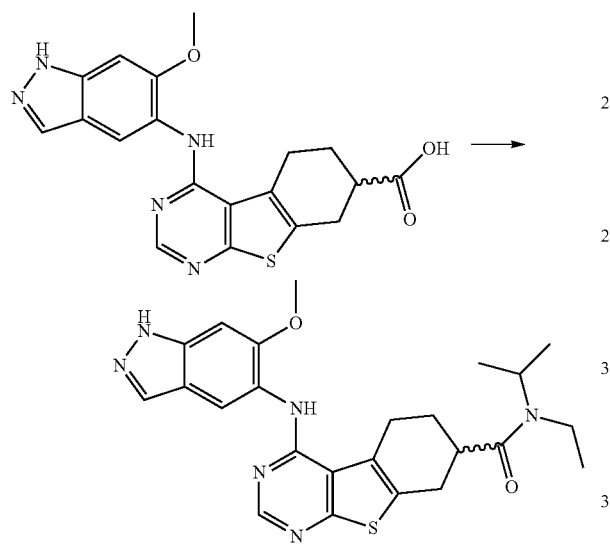

40 mg (101 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-ethylpropan-2-amine to give after working up and purification 7.5 mg (15%) of the title compound.

$^1$H-NMR (DMSO-$d_6$): δ=1.01-1.21 (9H), 1.85 (1H), 2.07 (1H), 2.82-3.02 (2H), 3.10-3.38 (4H), 3.96 (3H), 4.24 (1H), 4.53 (1H), 7.06 (1H), 7.97 (1H), 8.20 (1H), 8.43 (1H), 8.76 (1H), 12.82 (1H) ppm.

Example 68

4-[(6-Methoxy-1H-indazol-5-yl)amino]-N-methyl-N-propyl-5,6,7,8-tetrahydro[1]benzothieno[2,3-d]pyrimidine-7-carboxamide

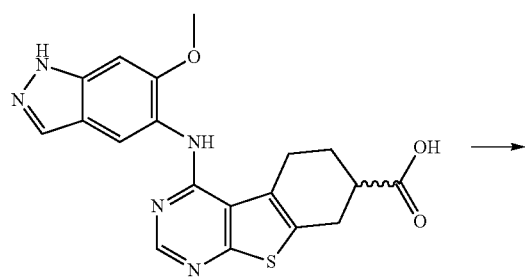

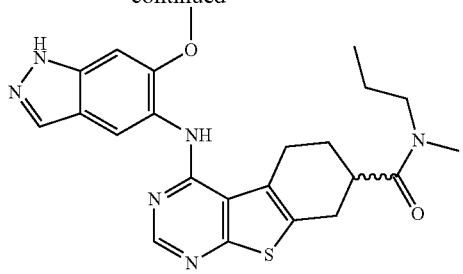

40 mg (101 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-methylpropan-1-amine to give after working up and purification 10.4 mg (22%) of the title compound.

$^1$H-NMR (DMSO-$d_6$): δ=0.76-0.89 (3H), 1.40-1.60 (2H), 1.82 (1H), 2.09 (1H), 2.89 (2H), 2.82+3.05 (3H), 3.06-3.43 (5H), 3.95 (3H), 7.06 (1H), 7.97 (1H), 8.19 (1H), 8.43 (1H), 8.75 (1H), 12.83 (1H) ppm.

Example 69

(RS)-4-{[6-(Propan-2-yloxy)-1H-indazol-5-yl]amino}-5,6,7,8-tetrahydro[1]benzothieno[2,3-d]pyrimidine-7-carboxylic acid

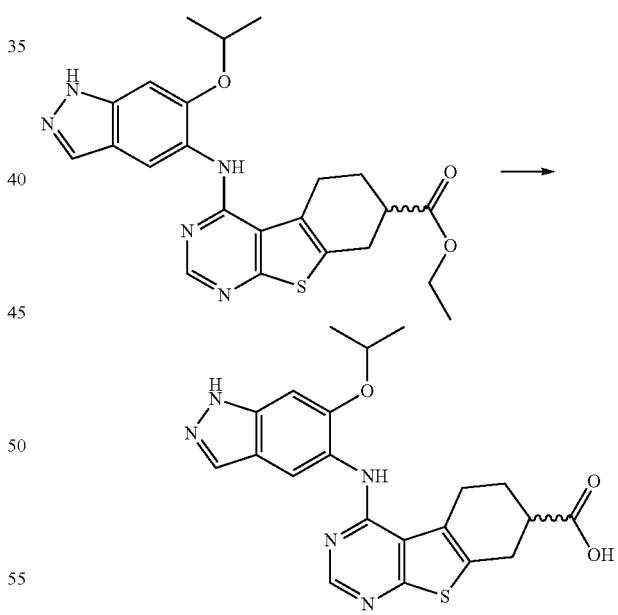

333 mg (737 µmol) ethyl 4-[(6-isopropoxy-1H-indazol-5-yl)amino]-5,6,7,8-tetrahydro[1]benzothieno[2,3-d]pyrimidine-7-carboxylate (prepared according to intermediate example 69a) were transformed in analogy to intermediate example 1a to give after working up and purification 313 mg (95%) of the title compound.

$^1$H-NMR (DMSO-$d_6$): δ=1.38 (6H), 1.94 (1H), 2.22 (1H), 2.79-3.24 (5H), 4.85 (1H), 7.08 (1H), 7.96 (1H), 8.32 (1H), 8.49 (1H), 9.03 (1H), 12.64 (1H) ppm.

Example 69a

Ethyl 4-[(6-isopropoxy-1H-indazol-5-yl)amino]-5,6,7,8-tetrahydro[1]benzothieno[2,3-d]pyrimidine-7-carboxylate

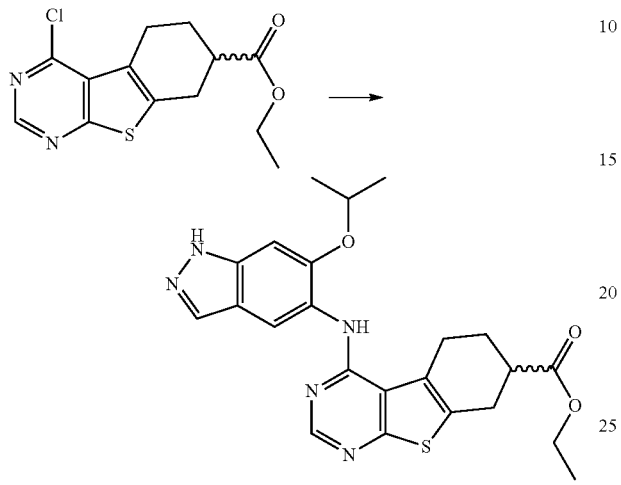

500 mg (1.69 mmol) (RS)-ethyl 4-chloro-5,6,7,8-tetrahydro[1]benzothieno[2,3-d]pyrimidine-7-carboxylate (prepared according to WO 2005/010008, example 14, steps 1 to 3) were transformed in analogy to example 1 using 6-isopropoxy-1H-indazol-5-amine (prepared according to intermediate example 71b) to give after working up and purification 370.6 mg (44%) of the title compound.

Example 69b

6-Isopropoxy-1H-indazol-5-amine

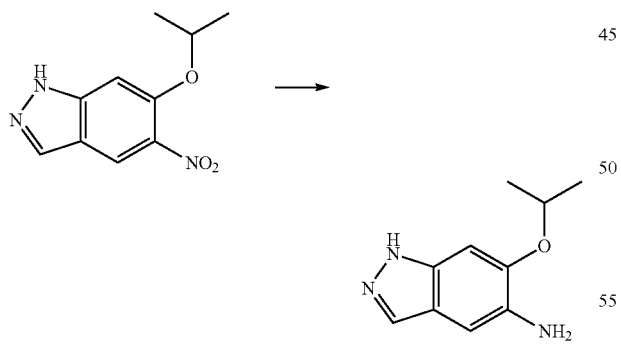

A mixture comprising 5.0 g (22.6 mmol) 6-isopropoxy-5-nitro-1H-indazole (purchased from Tractus chemicals, Unit 5, 3/F Harry Industrial Building; 4951 Au Pui Wan Street, Fo Tan; Shatin, New Territories; Hong Kong; Email: contact@tractuschem.com), 100 mL ethanol and 601 mg palladium on charcoal (10%) was heavily stirred under an atmosphere of hydrogen overnight. After filtration and removal of the solvent, the residue was washed with diethyl ether to give 3.64 g (80%) of the title compound.

Example 70

(RS)—N,N-Dimethyl-4-{[6-(propan-2-yloxy)-1H-indazol-5-yl]amino}-5,6,7,8-tetrahydro[1]benzothieno[2,3-d]pyrimidine-7-carboxamide

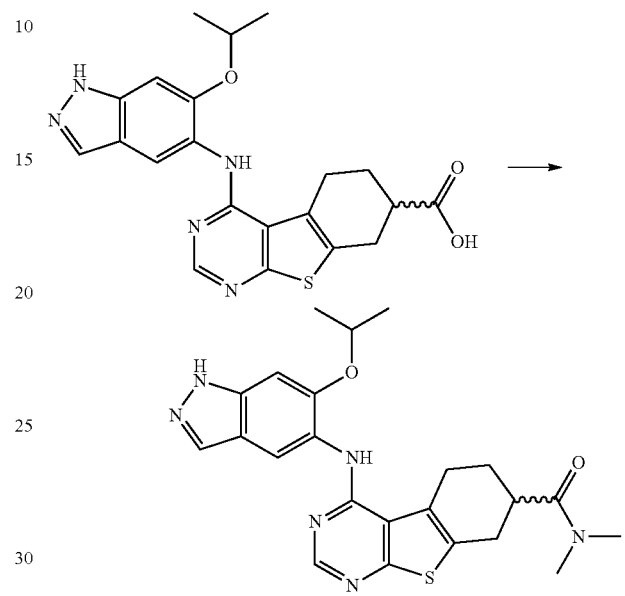

310 mg (732 μmol) (RS)-4-{[6-(Propan-2-yloxy)-1H-indazol-5-yl]amino}-5,6,7,8-tetrahydro[1]benzothieno[2,3-d]pyrimidine-7-carboxylic acid (prepared according to intermediate example 69) were transformed in analogy to intermediate example 2a using N-methylmethanamine to give after working up and purification 153.4 mg (46%) of the title compound.

$^{1}$H-NMR (DMSO-$d_6$): δ=1.38 (6H), 1.85 (1H), 2.06 (1H), 2.85 (3H), 2.91 (2H), 3.07 (3H), 3.14-3.31 (3H), 4.86 (1H), 7.09 (1H), 7.96 (1H), 8.35 (1H), 8.50 (1H), 9.04 (1H), 12.73 (1H) ppm.

Example 71

(RS)-(4-Methylpiperazin-1-yl)(4-{[6-(propan-2-yloxy)-1H-indazol-5-yl]amino}-5,6,7,8-tetrahydro[1]benzothieno[2,3-d]pyrimidin-7-yl)methanone

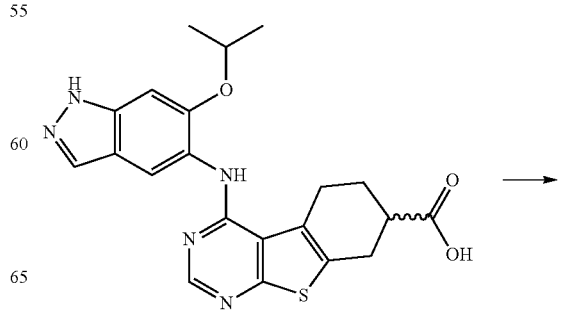

93

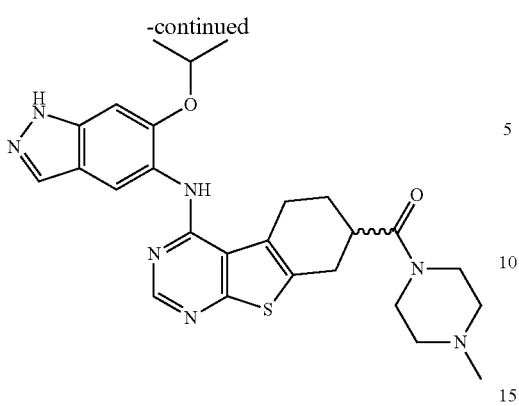

25 mg (59 µmol) (RS)-4-{[6-(Propan-2-yloxy)-1H-indazol-5-yl]amino}-5,6,7,8-tetrahydro[1]benzothieno[2,3-d]pyrimidine-7-carboxylic acid (prepared according to intermediate example 69) were transformed in analogy to intermediate example 2a using 1-methylpiperazine to give after working up and purification 18.8 mg (60%) of the title compound.

$^1$H-NMR (DMSO-d$_6$): δ=1.38 (6H), 1.87 (1H), 2.04 (1H), 2.16 (3H), 2.20-2.37 (4H), 2.90 (2H), 3.15-3.58 (7H), 4.86 (1H), 7.08 (1H), 7.96 (1H), 8.34 (1H), 8.50 (1H), 9.04 (1H), 12.75 (1H) ppm.

Example 72

(RS)—N-(Propan-2-yl)-4-{[6-(propan-2-yloxy)-1H-indazol-5-yl]amino}-5,6,7,8-tetrahydro[1]benzothieno[2,3-d]pyrimidine-7-carboxamide

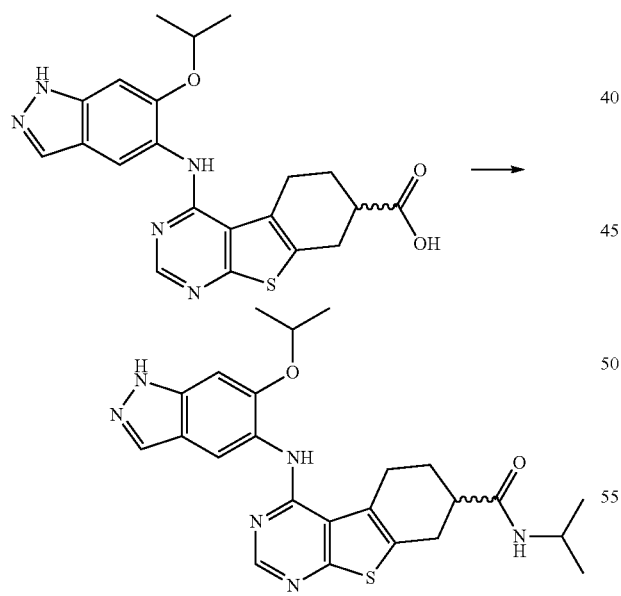

25 mg (59 µmol) (RS)-4-{[6-(Propan-2-yloxy)-1H-indazol-5-yl]amino}-5,6,7,8-tetrahydro[1]benzothieno[2,3-d]pyrimidine-7-carboxylic acid (prepared according to intermediate example 69) were transformed in analogy to intermediate example 2a using propan-2-amine to give after working up and purification 13.6 mg (47%) of the title compound.

94

$^1$H-NMR (DMSO-d$_6$): δ=1.05 (6H), 1.38 (6H), 1.89 (1H), 2.08 (1H), 2.61 (1H), 2.90 (2H), 3.12 (1H), 3.23 (1H), 3.84 (1H), 4.86 (1H), 7.09 (1H), 7.84 (1H), 7.96 (1H), 8.33 (1H), 8.50 (1H), 9.05 (1H), 12.75 (1H) ppm.

Example 73

(RS)-Methyl 4-(1H-indazol-5-ylamino)-5,6,7,8-tetrahydro[1]benzothieno[2,3-d]pyrimidine-7-carboxylate

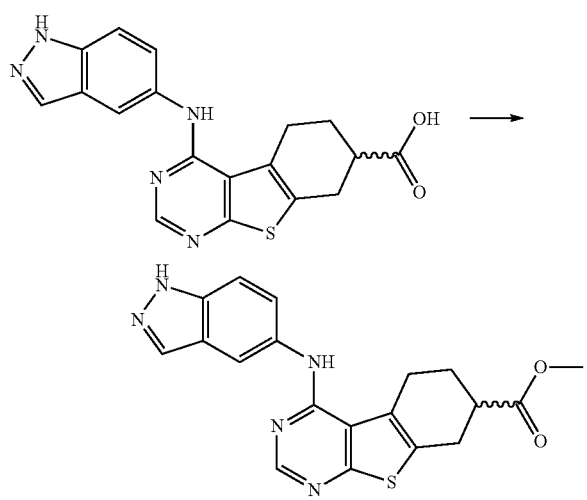

A mixture comprising 820 mg (2.04 mmol) (RS)-4-(1H-indazol-5-ylamino)-5,6,7,8-tetrahydro[1]benzothieno[2,3-d]pyrimidine-7-carboxylic acid (prepared according to example 2), 50 mL tetrahydrofuran and 711 µL N-ethyl-N-isopropylpropan-2-amine was cooled to 3° C. A solution of diazomethane in diethylether was added and the mixture stirred for 1 hour. The solvents were removed and the residue washed with diethylether and propan-2-ol to give 658 mg (85%) of the title compound.

$^1$H-NMR (DMSO-d$_6$): δ=1.91 (1H), 2.18 (1H), 2.89-3.25 (5H), 3.64 (3H), 7.45 (1H), 7.49 (1H), 7.95 (1H), 8.02 (1H), 8.17 (1H), 8.27 (1H), 13.01 (1H) ppm.

Example 74

(RS)-Propan-2-yl 4-(1H-indazol-5-ylamino)-5,6,7,8-tetrahydro[1]benzothieno[2,3-d]pyrimidine-7-carboxylate

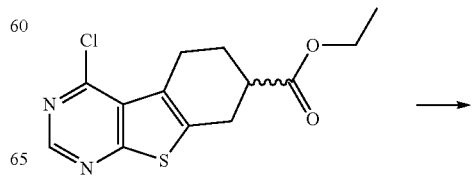

-continued

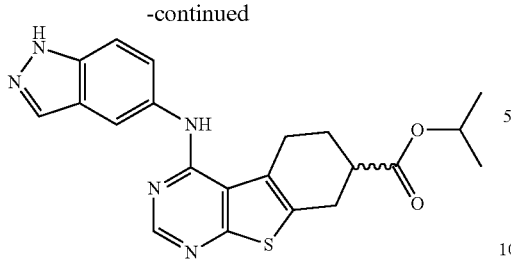

To a mixture of 1.22 g (4.10 mmol) ethyl 4-chloro-5,6,7,8-tetrahydro[1]benzothieno[2,3-d]pyrimidine-7-carboxylate (prepared according to WO 2005/010008, example 14, steps 1 to 3) and 628 mg 5-aminoindazole in 40 mL propan-2-ol were added 1.63 mL hydrogen chloride (4N in dioxane). The mixture was heated to reflux with stirring for 16 hours poured into water and extracted with dichloromethane. The organic layer was dried over sodiumsulphate. After filtration and removal of the solvent the residue was purified by chromatography to give 48.9 mg (3%) of the title compound.

$^1$H-NMR (DMSO-$d_6$): δ=1.18 (6H), 1.89 (1H), 2.16 (1H), 2.87 (1H), 2.98 (1H), 3.08 (1H), 3.19 (2H), 4.92 (1H), 7.44 (1H), 7.55 (1H), 7.92 (1H), 8.07 (1H), 8.40 (1H), 8.91 (1H) ppm.

Example 75

(RS)-4-(1H-Indazol-5-ylamino)-N-(2-methylphenyl)-5,6,7,8-tetrahydro[1]benzothieno[2,3-d]pyrimidine-7-carboxamide

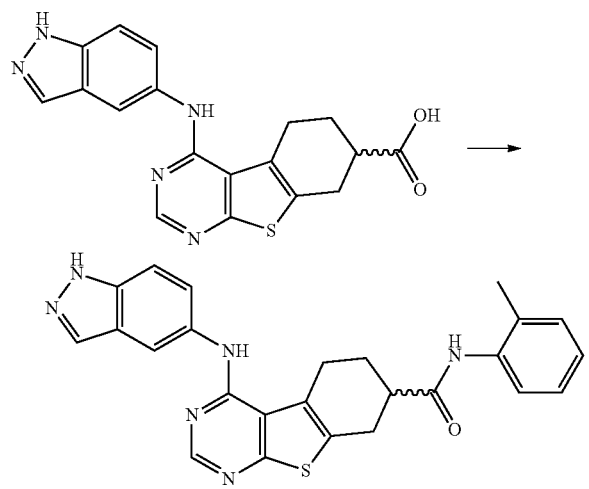

150 mg (410 μmol) (RS)-4-(1H-indazol-5-ylamino)-5,6,7,8-tetrahydro[1]benzothieno[2,3-d]pyrimidine-7-carboxylic acid (prepared according to example 2) were transformed in analogy to intermediate example 2a using o-toluidine to give after working up and purification 81 mg (43%) of the title compound.

$^1$H-NMR (DMSO-$d_6$): δ=1.92 (1H), 2.20 (3H), 2.22 (1H), 2.90-3.38 (5H), 7.06 (1H), 7.11 (1H), 7.19 (1H), 7.36 (1H), 7.43-7.54 (2H), 7.96 (1H), 8.03 (1H), 8.22 (1H), 8.29 (1H), 9.45 (1H), 13.00 (1H) ppm.

Example 76

(RS)-4-(1H-Indazol-5-ylamino)-N-(pyridin-3-ylmethyl)-5,6,7,8-tetrahydro[1]benzothieno[2,3-d]pyrimidine-7-carboxamide

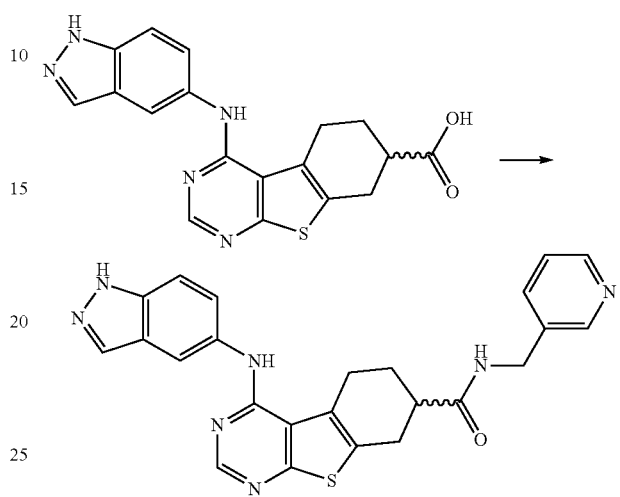

500 mg (1.37 mmol) (RS)-4-(1H-indazol-5-ylamino)-5,6,7,8-tetrahydro[1]benzothieno[2,3-d]pyrimidine-7-carboxylic acid (prepared according to example 2) were transformed in analogy to intermediate example 2a using 1-(pyridin-3-yl)methanamine to give after working up and purification 257 mg (38%) of the title compound as hydrochloride.

$^1$H-NMR (DMSO-$d_6$): δ=1.83 (1H), 2.15 (1H), 2.79 (1H), 2.91-3.31 (4H), 4.49 (2H), 7.45 (1H), 7.54 (1H), 7.93 (1H), 8.01 (1H), 8.06 (1H), 8.37 (1H), 8.45 (1H), 8.73 (1H), 8.80 (1H), 8.82 (1H), 8.96 (1H) ppm.

Example 77

(RS)—N-(4-Cyanophenyl)-4-(1H-indazol-5-ylamino)-5,6,7,8-tetrahydro[1]benzothieno[2,3-d]pyrimidine-7-carboxamide

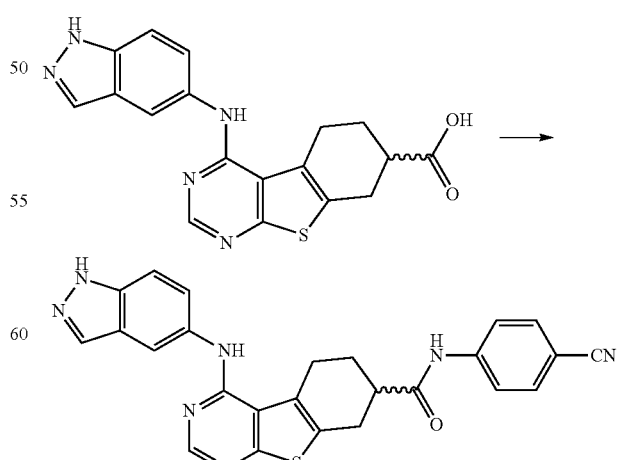

550 mg (1.51 mmol) (RS)-4-(1H-indazol-5-ylamino)-5,6,7,8-tetrahydro[1]benzothieno[2,3-d]pyrimidine-7-carboxylic acid (prepared according to example 2) were transformed in analogy to intermediate example 2a using 4-aminobenzonitrile to give after working up and purification 161 mg (23%) of the title compound.

$^1$H-NMR (DMSO-d$_6$): δ=1.91 (1H), 2.22 (1H), 2.89-3.21 (4H), 3.31 (1H), 7.44-7.53 (2H), 7.75 (2H), 7.81 (2H), 7.96 (1H), 8.02 (1H), 8.20 (1H), 8.29 (1H), 10.50 (1H), 12.98 (1H) ppm.

Example 78

(RS)-4-(1H-Indazol-5-ylamino)-N-(oxetan-3-yl)-5,6,7,8-tetrahydro[1]benzothieno[2,3-d]pyrimidine-7-carboxamide

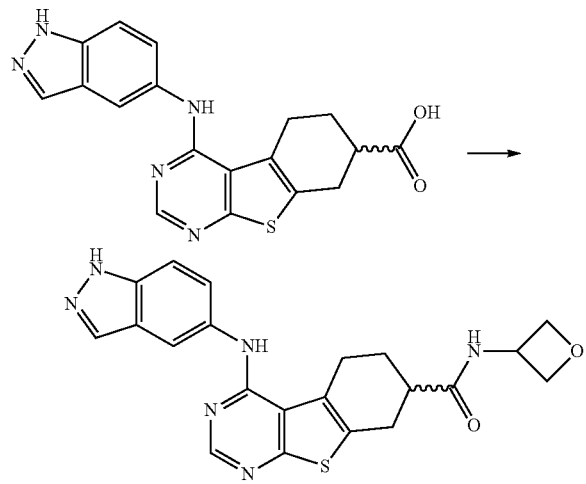

300 mg (821 μmol) (RS)-4-(1H-indazol-5-ylamino)-5,6,7,8-tetrahydro[1]benzothieno[2,3-d]pyrimidine-7-carboxylic acid (prepared according to example 2) were transformed in analogy to intermediate example 2a using oxetan-3-amine to give after working up and purification 31 mg (9%) of the title compound.

$^1$H-NMR (DMSO-d$_6$): δ=1.80 (1H), 2.08 (1H), 2.66 (1H), 2.92 (2H), 3.10 (1H), 3.24 (1H), 4.42 (2H), 4.70 (2H), 4.79 (1H), 7.43-7.52 (2H), 7.95 (1H), 8.02 (1H), 8.17 (1H), 8.27 (1H), 8.72 (1H), 12.97 (1H) ppm.

Example 79

(RS)—N-(3-Cyanophenyl)-4-(1H-indazol-5-ylamino)-5,6,7,8-tetrahydro[1]benzothieno[2,3-d]pyrimidine-7-carboxamide

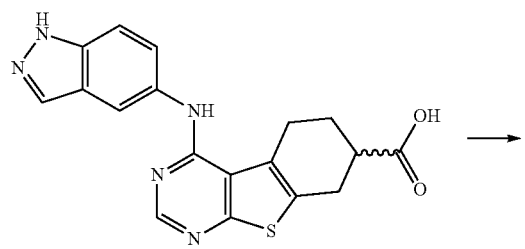

-continued

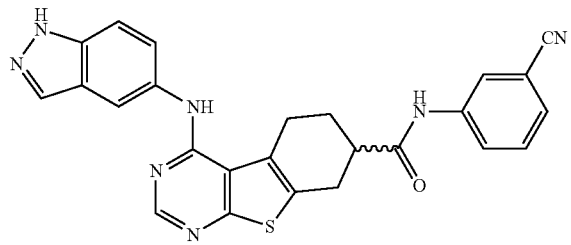

500 mg (1.37 mmol) (RS)-4-(1H-indazol-5-ylamino)-5,6,7,8-tetrahydro[1]benzothieno[2,3-d]pyrimidine-7-carboxylic acid (prepared according to example 2) were transformed in analogy to intermediate example 2a using 3-aminobenzonitrile to give after working up and purification 43 mg (7%) of the title compound.

$^1$H-NMR (DMSO-d$_6$): δ=1.91 (1H), 2.22 (1H), 2.90 (1H), 3.00-3.23 (3H), 3.32 (1H), 7.44-7.55 (4H), 7.82 (1H), 7.96 (1H), 8.02 (1H), 8.12 (1H), 8.20 (1H), 8.29 (1H), 10.41 (1H), 12.98 (1H) ppm.

Examples 80-169

The compounds of examples 80-169 listed in Table 2 were prepared and purified in analogy to intermediate example 2a.

The compound of example 80 was analyzed according to the equipment and conditions given below:

Instrument: Waters Acquity UPLCMS SQD;

Column: Acquity UPLC BEH C18 1.7 μm, 50×2.1 mm;

Eluent A: water+0.05 vol % formic acid (95%), eluent B: acetonitrile+0.05 vol % formic acid (95%);

Gradient: 0-1.6 min 1-99% B, 1.6-2.0 min 99% B; flow 0.8 mL/min;

Temperature: 60° C.;

Injection: 2 μL;

DAD scan: 210-400 nm; ELSD

The compounds of examples 81-169 were analyzed according to the equipment and conditions given below:

Instrument MS: Waters ZQ;

Instrument HPLC: Waters UPLC Acquity;

Column: Acquity BEH C18 (Waters), 50 mm×2.1 mm, 1.7 μm; Eluent A: H$_2$O+0.1 vol % formic acid, Eluent B: Acetonitrile (Lichrosolv Merck);

Gradient: 0.0 min 99% A—1.6 min 1% A—1.8 min 1% A—1.81 min 99% A—2.0 min 99% A;

Oven temperature: 60° C.; Flow: 0.800 ml/min;

UV-Detection PDA 210-400 nm

TABLE 2

Column header: A: Example B: Structure C: IUPAC Name D: Retention time [min] E: MS (ESIpos) m/z [M+H]+

| A | B | C | D | E |
|---|---|---|---|---|
| 80 | 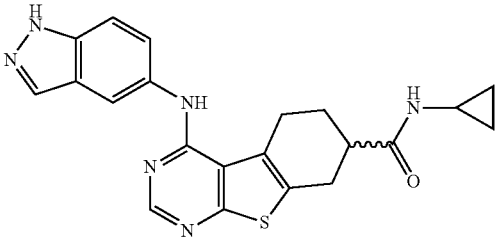 | (RS)-N-Cyclopropyl-4-(1H-indazol-5-ylamino)-5,6,7,8-tetrahydro[1]benzothieno[2,3-d]pyrimidine-7-carboxamide | 0.80 | 405 |
| 81 | 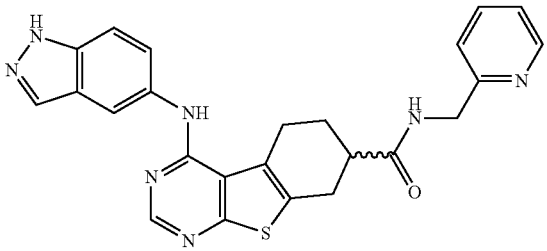 | (RS)-4-(1H-indazol-5-ylamino)-N-(pyridin-2-ylmethyl)-5,6,7,8-tetrahydro[1]benzothieno[2,3-d]pyrimidine-7-carboxamide | 0.70 | 456 |
| 82 | 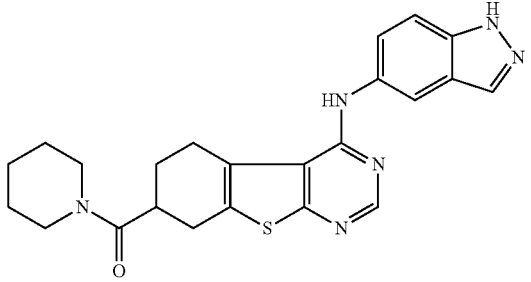 | (RS)-[4-(1H-indazol-5-ylamino)-5,6,7,8-tetrahydro[1]benzothieno[2,3-d]pyrimidin-7-yl](piperidin-1-yl)methanone | 0.99 | 433 |
| 83 | 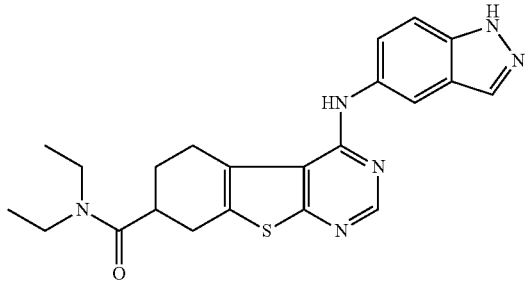 | (RS)-N,N-diethyl-4-(1H-indazol-5-ylamino)-5,6,7,8-tetrahydro[1]benzothieno[2,3-d]pyrimidine-7-carboxamide | 0.97 | 421 |
| 84 | 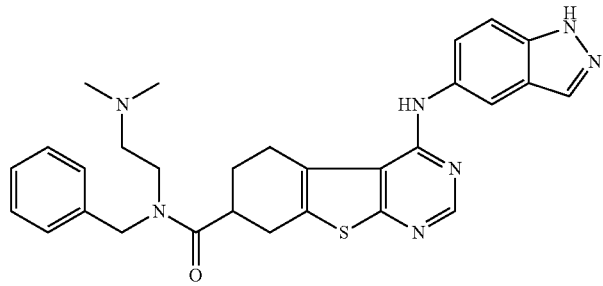 | (RS)-N-benzyl-N-[2-(dimethylamino)ethyl]-4-(1H-indazol-5-ylamino)-5,6,7,8-tetrahydro[1]benzothieno[2,3-d]pyrimidine-7-carboxamide | 0.77 | 526 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 85 | | (RS)-(4-hydroxypiperidin-1-yl)[4-(1H-indazol-5-ylamino)-5,6,7,8-tetrahydro[1]benzothieno[2,3-d]pyrimidin-7-yl]methanone | 0.75 | 449 |
| 86 | | (RS)-(4-benzylpiperazin-1-yl)[4-(1H-indazol-5-ylamino)-5,6,7,8-tetrahydro[1]benzothieno[2,3-d]pyrimidin-7-yl]methanone | 0.73 | 524 |
| 87 | | (RS)-[4-(1H-indazol-5-ylamino)-5,6,7,8-tetrahydro[1]benzothieno[2,3-d]pyrimidin-7-yl][4-(pyridin-2-yl)piperazin-1-yl]methanone | 0.72 | 511 |
| 88 | | (RS)-[3-(hydroxymethyl)piperidin-1-yl][4-(1H-indazol-5-ylamino)-5,6,7,8-tetrahydro[1]benzothieno[2,3-d]pyrimidin-7-yl]methanone | 0.83 | 463 |
| 89 | | (RS)-4-(1H-indazol-5-ylamino)-N-(1H-pyrazol-3-yl)-5,6,7,8-tetrahydro[1]benzothieno[2,3-d]pyrimidine-7-carboxamide | 0.89 | 431 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 90 | 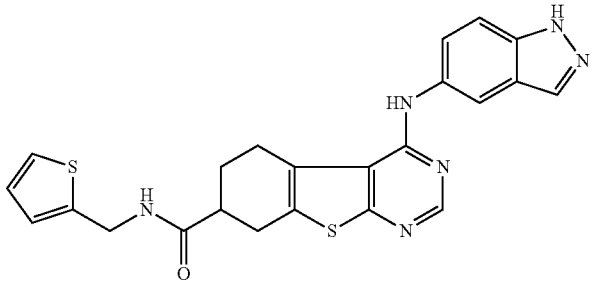 | (RS)-4-(1H-indazol-5-ylamino)-N-(thiophen-2-ylmethyl)-5,6,7,8-tetrahydro[1]benzothieno[2,3-d]pyrimidine-7-carboxamide | 0.97 | 461 |
| 91 | 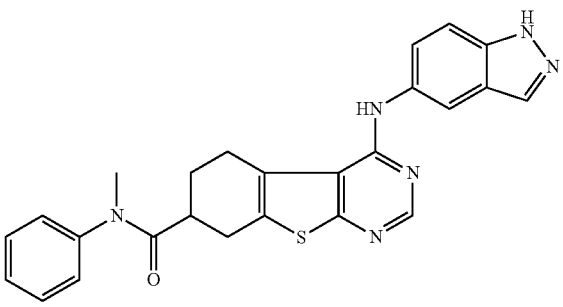 | (RS)-4-(1H-indazol-5-ylamino)-N-methyl-N-phenyl-5,6,7,8-tetrahydro[1]benzothieno[2,3-d]pyrimidine-7-carboxamide | 1.05 | 455 |
| 92 | 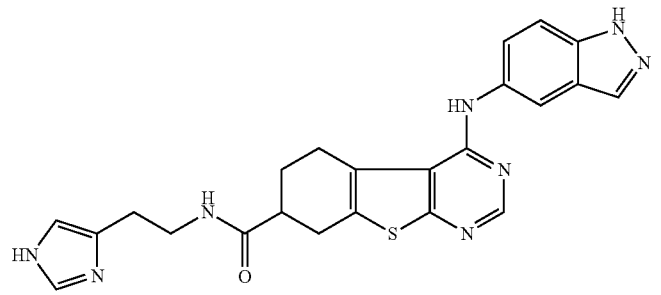 | (RS)-N-[2-(1H-imidazol-4-yl)ethyl]-4-(1H-indazol-5-ylamino)-5,6,7,8-tetrahydro[1]benzothieno[2,3-d]pyrimidine-7-carboxamide | 0.61 | 459 |
| 93 | 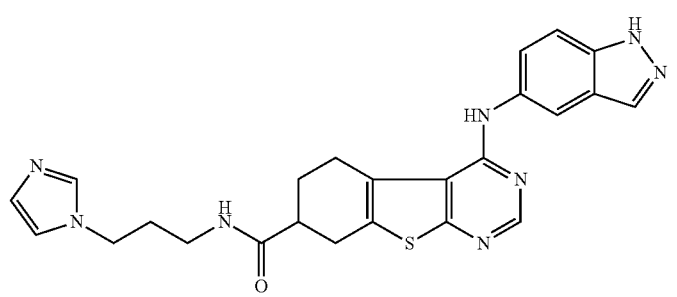 | (RS)-N-[3-(1H-imidazol-1-yl)propyl]-4-(1H-indazol-5-ylamino)-5,6,7,8-tetrahydro[1]benzothieno[2,3-d]pyrimidine-7-carboxamide | 0.62 | 473 |
| 94 | 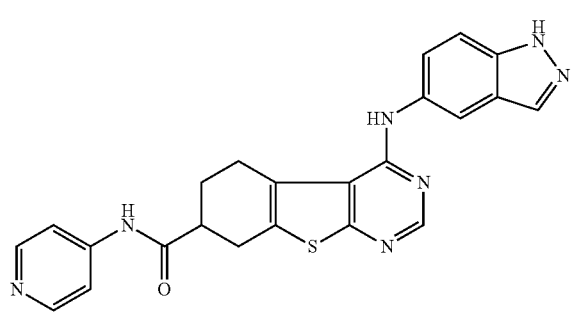 | (RS)-4-(1H-indazol-5-ylamino)-N-(pyridin-4-yl)-5,6,7,8-tetrahydro[1]benzothieno[2,3-d]pyrimidine-7-carboxamide | 0.69 | 442 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 95 | | (RS)-N-[2-(diethylamino)ethyl]-4-(1H-indazol-5-ylamino)-N-methyl-5,6,7,8-tetrahydro[1]benzothieno[2,3-d]pyrimidine-7-carboxamide | 0.67 | 478 |
| 96 | | (RS)-N-[3-(dimethylamino)propyl]-4-(1H-indazol-5-ylamino)-N-methyl-5,6,7,8-tetrahydro[1]benzothieno[2,3-d]pyrimidine-7-carboxamide | 0.64 | 464 |
| 97 | | (RS)-1-(4-{[4-(1H-indazol-5-ylamino)-5,6,7,8-tetrahydro[1]benzothieno[2,3-d]pyrimidin-7-yl]carbonyl}piperazin-1-yl)ethanone | 0.76 | 476 |
| 98 | | (RS)-4-(1H-indazol-5-ylamino)-N-[2-(pyrrolidin-1-yl)ethyl]-5,6,7,8-tetrahydro[1]benzothieno[2,3-d]pyrimidine-7-carboxamide | 0.63 | 462 |
| 99 | | (RS)-4-(1H-indazol-5-ylamino)-N-(pyridin-2-yl)-5,6,7,8-tetrahydro[1]benzothieno[2,3-d]pyrimidine-7-carboxamide | 0.90 | 442 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 100 | | (RS)-4-(1H-indazol-5-ylamino)-N-(pyridin-3-yl)-5,6,7,8-tetrahydro[1]benzothieno[2,3-d]pyrimidine-7-carboxamide | 0.73 | 442 |
| 101 | | (RS)-N-benzyl-4-(1H-indazol-5-ylamino)-N-methyl-5,6,7,8-tetrahydro[1]benzothieno[2,3-d]pyrimidine-7-carboxamide | 1.08 | 469 |
| 102 | | (RS)-N-tert-butyl-4-(1H-indazol-5-ylamino)-5,6,7,8-tetrahydro[1]benzothieno[2,3-d]pyrimidine-7-carboxamide | 1.00 | 421 |
| 103 | | (RS)-ethyl4-{[4-(1H-indazol-5-ylamino)-5,6,7,8-tetrahydro[1]benzothieno[2,3-d]pyrimidin-7-yl]carbonyl}piperazine-1-carboxylate | 0.94 | 506 |
| 104 | | (RS)-[4-(1H-indazol-5-ylamino)-5,6,7,8-tetrahydro[1]benzothieno[2,3-d]pyrimidin-7-yl](3-methylpiperidin-1-yl)methanone | 1.08 | 447 |

TABLE 2-continued

Column header: A: Example B: Structure C: IUPAC Name D: Retention time [min] E: MS (ESIpos) m/z [M+H]⁺

| A | B | C | D | E |
|---|---|---|---|---|
| 105 | 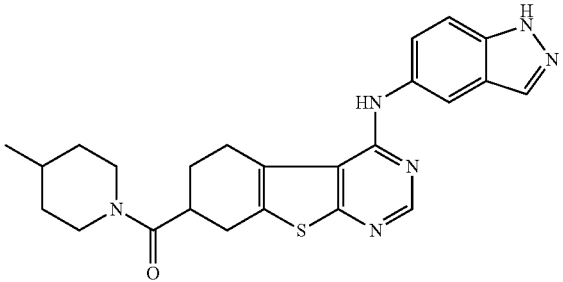 | (RS)-[4-(1H-indazol-5-ylamino)-5,6,7,8-tetrahydro[1]benzothieno[2,3-d]pyrimidin-7-yl](4-methylpiperidin-1-yl)methanone | 1.08 | 447 |
| 106 | 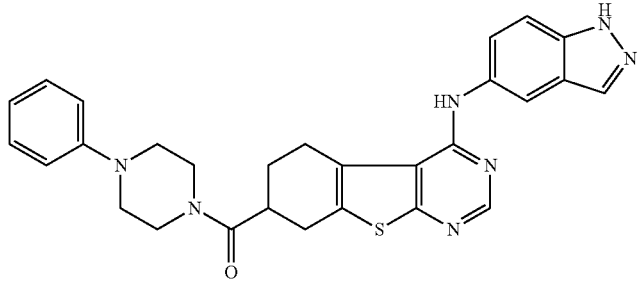 | (RS)-[4-(1H-indazol-5-ylamino)-5,6,7,8-tetrahydro[1]benzothieno[2,3-d]pyrimidin-7-yl](4-phenylpiperazin-1-yl)methanone | 1.10 | 510 |
| 107 | 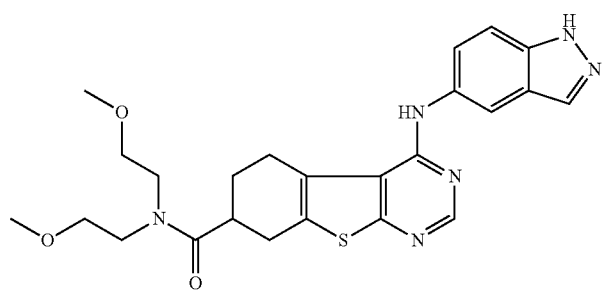 | (RS)-4-(1H-indazol-5-ylamino)-N,N-bis(2-methoxyethyl)-5,6,7,8-tetrahydro[1]benzothieno[2,3-d]pyrimidine-7-carboxamide | 0.91 | 481 |
| 108 | 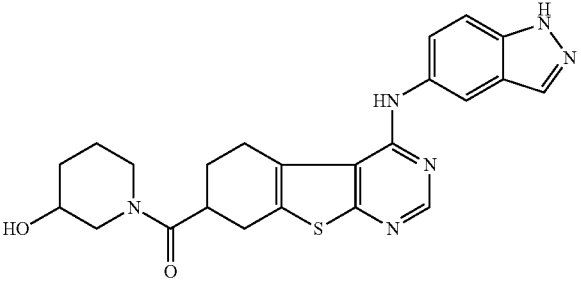 | (RS)-(3-hydroxypiperidin-1-yl)[4-(1H-indazol-5-ylamino)-5,6,7,8-tetrahydro[1]benzothieno[2,3-d]pyrimidin-7-yl]methanone | 0.79 | 449 |
| 109 | 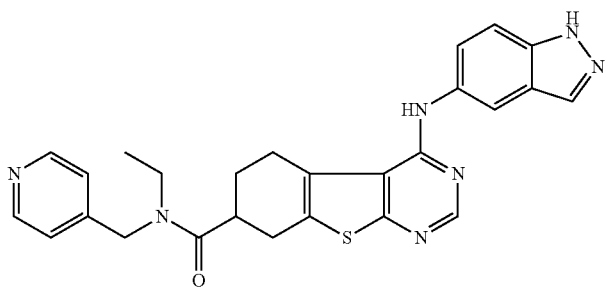 | (RS)-N-ethyl-4-(1H-indazol-5-ylamino)-N-(pyridin-4-ylmethyl)-5,6,7,8-tetrahydro[1]benzothieno[2,3-d]pyrimidine-7-carboxamide | 0.71 | 484 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 110 | | (R)S-[4-(1H-indazol-5-ylamino)-5,6,7,8-tetrahydro[1]benzothieno[2,3-d]pyrimidin-7-yl][4-(2-methylphenyl)piperazin-1-yl]methanone | 1.23 | 524 |
| 111 | | (RS)-[4-(1H-indazol-5-ylamino)-5,6,7,8-tetrahydro[1]benzothieno[2,3-d]pyrimidin-7-yl][4-(3-methylphenyl)piperazin-1-yl]methanone | 1.17 | 524 |
| 112 | | (RS)-[4-(1H-indazol-5-ylamino)-5,6,7,8-tetrahydro[1]benzothieno[2,3-d]pyrimidin-7-yl][4-(pyridin-4-yl)piperazin-1-yl]methanone | 0.67 | 511 |
| 113 | | (RS)-N-(2,2-dimethylpropyl)-4-(1H-indazol-5-ylamino)-5,6,7,8-tetrahydro[1]benzothieno[2,3-d]pyrimidine-7-carboxamide | 1.03 | 435 |
| 114 | | (RS)-[4-(1H-indazol-5-ylamino)-5,6,7,8-tetrahydro[1]benzothieno[2,3-d]pyrimidin-7-yl][4-(pyrazin-2-yl)piperazin-1-yl]methanone | 0.89 | 512 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 115 | 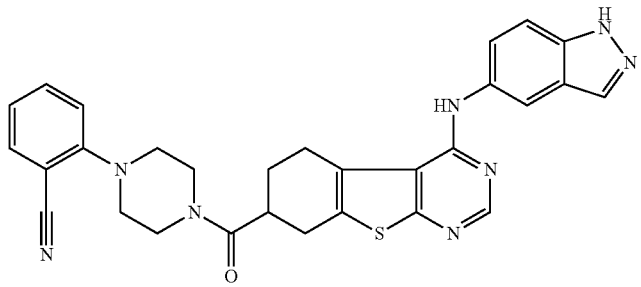 | (RS)-2-(4-{[4-(1H-indazol-5-ylamino)-5,6,7,8-tetrahydro[1]benzothieno[2,3-d]pyrimidin-7-yl]carbonyl}piperazin-1-yl)benzonitrile | 1.08 | 535 |
| 116 | 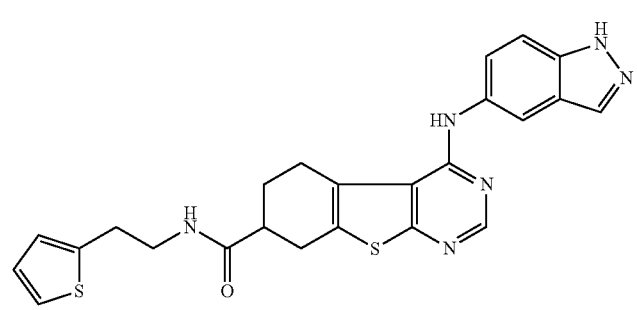 | (RS)-4-(1H-indazol-5-ylamino)-N-[2-(thiophen-2-yl)ethyl]-5,6,7,8-tetrahydro[1]benzothieno[2,3-d]pyrimidine-7-carboxamide | 1.00 | 475 |
| 117 | 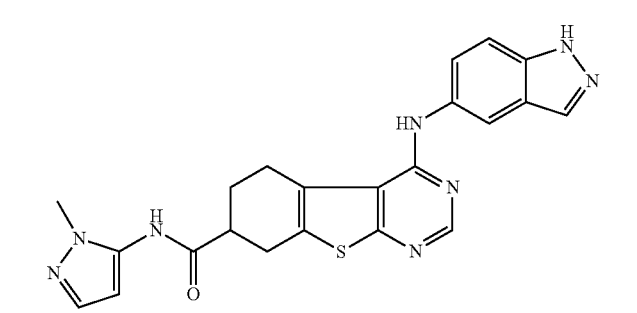 | (RS)-4-(1H-indazol-5-ylamino)-N-(1-methyl-1H-pyrazol-5-yl)-5,6,7,8-tetrahydro[1]benzothieno[2,3-d]pyrimidine-7-carboxamide | 0.81 | 445 |
| 118 | 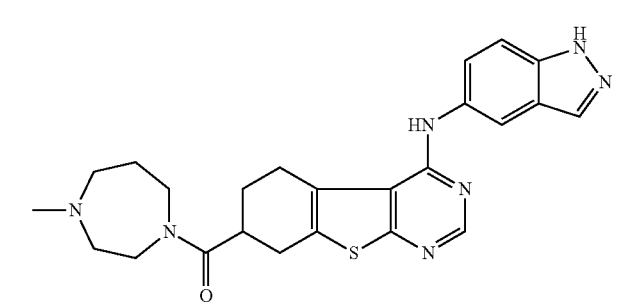 | (RS)-[4-(1H-indazol-5-ylamino)-5,6,7,8-tetrahydro[1]benzothieno[2,3-d]pyrimidin-7-yl](4-methyl-1,4-diazepan-1-yl)methanone | 0.62 | 462 |
| 119 | 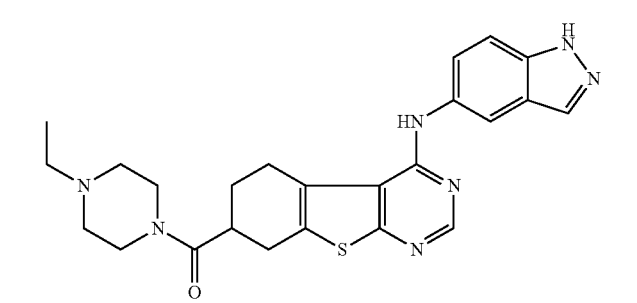 | (RS)-(4-ethylpiperazin-1-yl)[4-(1H-indazol-5-ylamino)-5,6,7,8-tetrahydro[1]benzothieno[2,3-d]pyrimidin-7-yl]methanone | 0.62 | 462 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 120 | | (RS)-N-[2-(dimethylamino)-2-oxoethyl]-4-(1H-indazol-5-ylamino)-N-methyl-5,6,7,8-tetrahydro[1]benzothieno[2,3-d]pyrimidine-7-carboxamide | 0.77 | 464 |
| 121 | | (RS)-4-(1H-indazol-5-ylamino)-N-(4-sulfamoylbenzyl)-5,6,7,8-tetrahydro[1]benzothieno[2,3-d]pyrimidine-7-carboxamide | 0.80 | 534 |
| 122 | | (RS)-N-(2-hydroxypropyl)-4-(1H-indazol-5-ylamino)-N-methyl-5,6,7,8-tetrahydro[1]benzothieno[2,3-d]pyrimidine-7-carboxamide | 0.78 | 437 |
| 123 | | (RS)-4-(1H-indazol-5-ylamino)-N-(tetrahydro-2H-pyran-4-yl)-5,6,7,8-tetrahydro[1]benzothieno[2,3-d]pyrimidine-7-carboxamide | 0.81 | 449 |
| 124 | | (RS)-N-(1-{[4-(1H-indazol-5-ylamino)-5,6,7,8-tetrahydro[1]benzothieno[2,3-d]pyrimidin-7-yl]carbonyl}pyrrolidin-3-yl)acetamide | 0.73 | 476 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 125 | | (RS)-4-(1H-indazol-5-ylamino)-N-[2-(2-oxoimidazolidin-1-yl)ethyl]-5,6,7,8-tetrahydro[1]benzothieno[2,3-d]pyrimidine-7-carboxamide | 0.71 | 477 |
| 126 | | (RS)-4-{[4-(1H-indazol-5-ylamino)-5,6,7,8-tetrahydro[1]benzothieno[2,3-d]pyrimidin-7-yl]carbonyl}-N,N-dimethylpiperazine-1-carboxamide | 0.83 | 505 |
| 127 | | (RS)-[4-(1H-indazol-5-ylamino)-5,6,7,8-tetrahydro[1]benzothieno[2,3-d]pyrimidin-7-yl](4-phenylpiperidin-1-yl)methanone | 1.19 | 509 |
| 128 | | (RS)-4-(1H-indazol-5-ylamino)-N-(pyridazin-4-yl)-5,6,7,8-tetrahydro[1]benzothieno[2,3-d]pyrimidine-7-carboxamide | 0.78 | 443 |
| 129 | | (RS)-{4-[2-(dimethylamino)ethyl]piperazin-1-yl}[4-(1H-indazol-5-ylamino)-5,6,7,8-tetrahydro[1]benzothieno[2,3-d]pyrimidin-7-yl]methanone | 0.63 | 505 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 130 | | (RS)-4-(1H-indazol-5-ylamino)-N-(2-methoxyethyl)-N-methyl-5,6,7,8-tetrahydro[1]benzothieno[2,3-d]pyrimidine-7-carboxamide | 0.86 | 437 |
| 131 | | (RS)-(4-cyclopentylpiperazin-1-yl)[4-(1H-indazol-5-ylamino)-5,6,7,8-tetrahydro[1]benzothieno[2,3-d]pyrimidin-7-yl]methanone | 0.68 | 502 |
| 132 | | (RS)-[4-(hydroxymethyl)piperidin-1-yl][4-(1H-indazol-5-ylamino)-5,6,7,8-tetrahydro[1]benzothieno[2,3-d]pyrimidin-7-yl]methanone | 0.80 | 463 |
| 133 | | (RS)-[4-(1H-indazol-5-ylamino)-5,6,7,8-tetrahydro[1]benzothieno[2,3-d]pyrimidin-7-yl][4-(2-methoxyethyl)piperazin-1-yl]methanone | 0.63 | 492 |
| 134 | | (RS)-(3-hydroxypyrrolidin-1-yl)[4-(1H-indazol-5-ylamino)-5,6,7,8-tetrahydro[1]benzothieno[2,3-d]pyrimidin-7-yl]methanone | 0.72 | 435 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 135 | 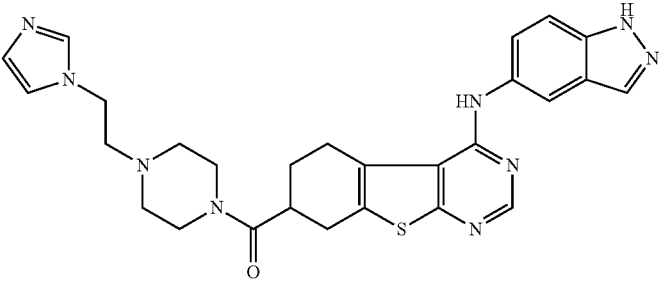 | (RS)-{4-[2-(1H-imidazol-2-yl)ethyl]piperazin-1-yl}[4-(1H-indazol-5-ylamino)-5,6,7,8-tetrahydro[1]benzothieno[2,3-d]pyrimidin-7-yl]methanone | 0.62 | 528 |
| 136 | 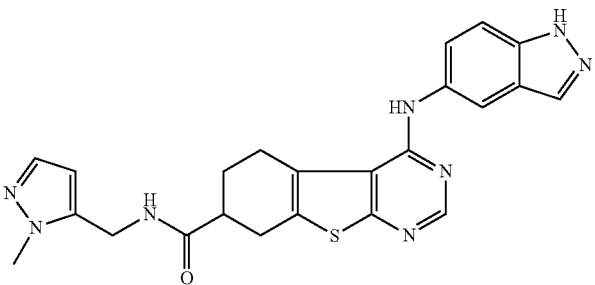 | (RS)-4-(1H-indazol-5-ylamino)-N-[(1-methyl-1H-pyrazol-5-yl)methyl]-5,6,7,8-tetrahydro[1]benzothieno[2,3-d]pyrimidine-7-carboxamide | 0.79 | 459 |
| 137 | 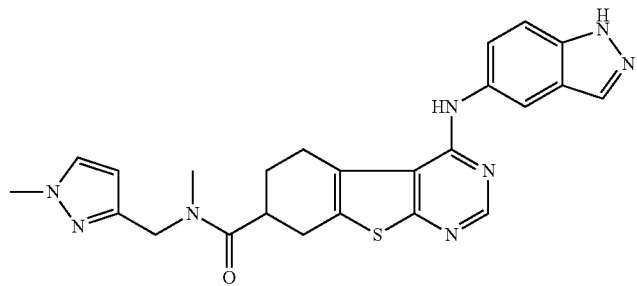 | (RS)-4-(1H-indazol-5-ylamino)-N-methyl-N-[(1-methyl-1H-pyrazol-3-yl)methyl]-5,6,7,8-tetrahydro[1]benzothieno[2,3-d]pyrimidine-7-carboxamide | 0.85 | 473 |
| 138 | 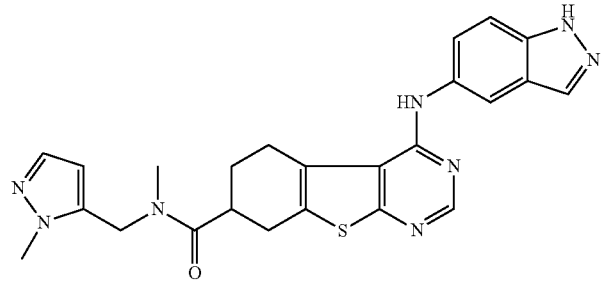 | (RS)-4-(1H-indazol-5-ylamino)-N-methyl-N-[(1-methyl-1H-pyrazol-5-yl)methyl]-5,6,7,8-tetrahydro[1]benzothieno[2,3-d]pyrimidine-7-carboxamide | 0.85 | 473 |
| 139 | 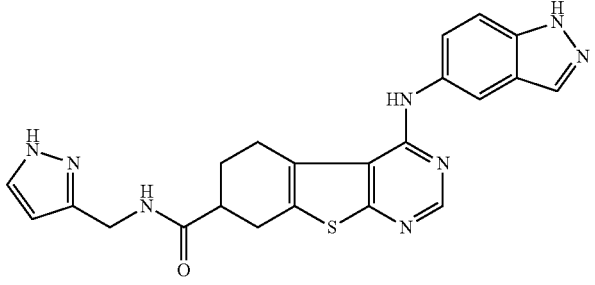 | (RS)-4-(1H-indazol-5-ylamino)-N-(1H-pyrazol-3-ylmethyl)-5,6,7,8-tetrahydro[1]benzothieno[2,3-d]pyrimidine-7-carboxamide | 0.75 | 445 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 140 | | (RS)-4-(1H-indazol-5-ylamino)-N-(1-methyl-1H-pyrazol-3-yl)-5,6,7,8-tetrahydro[1]benzothieno[2,3-d]pyrimidine-7-carboxamide | 0.83 | 445 |
| 141 | | (RS)-4-(4-{[4-(1H-indazol-5-ylamino)-5,6,7,8-tetrahydro[1]benzothieno[2,3-d]pyrimidin-7-yl]carbonyl}piperazin-1-yl)benzonitrile | 1.03 | 535 |
| 142 | | (RS)-[4-(1H-indazol-5-ylamino)-5,6,7,8-tetrahydro[1]benzothieno[2,3-d]pyrimidin-7-yl][4-(pyridin-4-ylmethyl)piperazin-1-yl]methanone | 0.66 | 525 |
| 143 | | (RS)-2-(4-{[4-(1H-indazol-5-ylamino)-5,6,7,8-tetrahydro[1]benzothieno[2,3-d]pyrimidin-7-yl]carbonyl}piperazin-1-yl)-N,N-dimethylacetamide | 0.63 | 519 |
| 144 | | (RS)-4-(1H-indazol-5-ylamino)-N-[2-(4-methylpiperazin-1-yl)ethyl]-5,6,7,8-tetrahydro[1]benzothieno[2,3-d]pyrimidine-7-carboxamide | 0.60 | 491 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 145 | | (RS)-N-(3-fluorobenzyl)-4-(1H-indazol-5-ylamino)-N-methyl-5,6,7,8-tetrahydro[1]benzothieno[2,3-d]pyrimidine-7-carboxamide | 1.09 | 487 |
| 146 | | (RS)-4-(1H-indazol-5-ylamino)-N-(1-methyl-1H-pyrazol-4-yl)-5,6,7,8-tetrahydro[1]benzothieno[2,3-d]pyrimidine-7-carboxamide | 0.80 | 445 |
| 147 | | (RS)-4-(1H-indazol-5-ylamino)-N-(1-phenylcyclopropyl)-5,6,7,8-tetrahydro[1]benzothieno[2,3-d]pyrimidine-7-carboxamide | 1.04 | 481 |
| 148 | | (RS)-4-(1H-indazol-5-ylamino)-N-[(5-methylpyrazin-2-yl)methyl]-5,6,7,8-tetrahydro[1]benzothieno[2,3-d]pyrimidine-7-carboxamide | 0.80 | 471 |
| 149 | | (RS)-4-(1H-indazol-5-ylamino)-N-(pyridazin-3-yl)-5,6,7,8-tetrahydro[1]benzothieno[2,3-d]pyrimidine-7-carboxamide | 0.84 | 443 |

TABLE 2-continued

Column header: A: Example B: Structure C: IUPAC Name D: Retention time [min] E: MS (ESIpos) m/z [M+H]⁺

| A | B | C | D | E |
|---|---|---|---|---|
| 150 | | (RS)-4-(1H-indazol-5-ylamino)-N-(pyrimidin-5-yl)-5,6,7,8-tetrahydro[1]benzothieno[2,3-d]pyrimidine-7-carboxamide | 0.81 | 443 |
| 151 | | (RS)-4-(1H-indazol-5-ylamino)-N-(thiophen-3-ylmethyl)-5,6,7,8-tetrahydro[1]benzothieno[2,3-d]pyrimidine-7-carboxamide | 0.96 | 461 |
| 152 | | (RS)-4-(1H-indazol-5-ylamino)-N-[(1-methyl-1H-imidazol-5-yl)methyl]-5,6,7,8-tetrahydro[1]benzothieno[2,3-d]pyrimidine-7-carboxamide | 0.61 | 459 |
| 153 | | (RS)-[4-(1H-indazol-5-ylamino)-5,6,7,8-tetrahydro[1]benzothieno[2,3-d]pyrimidin-7-yl][4-(3-methoxypropyl)piperazin-1-yl]methanone | 0.65 | 506 |
| 154 | | (RS)-[4-(1H-indazol-5-ylamino)-5,6,7,8-tetrahydro[1]benzothieno[2,3-d]pyrimidin-7-yl][4-(pyridin-2-ylmethyl)piperazin-1-yl]methanone | 0.67 | 525 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 155 | | (RS)-[4-(1H-indazol-5-ylamino)-5,6,7,8-tetrahydro[1]benzothieno[2,3-d]pyrimidin-7-yl][4-(pyridin-3-ylmethyl)piperazin-1-yl]methanone | 0.65 | 525 |
| 156 | | (RS)-[4-(1H-indazol-5-ylamino)-5,6,7,8-tetrahydro[1]benzothieno[2,3-d]pyrimidin-7-yl][4-(methylsulfonyl)piperazin-1-yl]methanone | 0.82 | 512 |
| 157 | | (RS)-4-(1H-indazol-5-ylamino)-N-methyl-N-[(1-methyl-1H-pyrazol-4-yl)methyl]-5,6,7,8-tetrahydro[1]benzothieno[2,3-d]pyrimidine-7-carboxamide | 0.83 | 473 |
| 158 | | (RS)-4-(1H-indazol-5-ylamino)-N-[(1-methyl-1H-pyrazol-4-yl)methyl]-5,6,7,8-tetrahydro[1]benzothieno[2,3-d]pyrimidine-7-carboxamide | 0.77 | 459 |
| 159 | | (RS)-(3-hydroxyazetidin-1-yl)[4-(1H-indazol-5-ylamino)-5,6,7,8-tetrahydro[1]benzothieno[2,3-d]pyrimidin-7-yl]methanone | 0.70 | 421 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 160 | | (RS)-methyl4-{[4-(1H-indazol-5-ylamino)-5,6,7,8-tetrahydro[1]benzothieno[2,3-d]pyrimidin-7-yl]carbonyl}piperazine-1-carboxylate | 0.86 | 492 |
| 161 | | (RS)-N-[2-(4-fluorophenyl)propan-2-yl]-4-(1H-indazol-5-ylamino)-5,6,7,8-tetrahydro[1]benzothieno[2,3-d]pyrimidine-7-carboxamide | 1.12 | 501 |
| 162 | | (RS)-4-(1H-indazol-5-ylamino)-N-methyl-N-(thiophen-3-ylmethyl)-5,6,7,8-tetrahydro[1]benzothieno[2,3-d]pyrimidine-7-carboxamide | 1.04 | 475 |
| 163 | | (RS)-4-(1H-indazol-5-ylamino)-N-methyl-N-[(1-methyl-1H-pyrrol-2-yl)methyl]-5,6,7,8-tetrahydro[1]benzothieno[2,3-d]pyrimidine-7-carboxamide | 1.02 | 472 |
| 164 | | (RS)-2-(4-{[4-(1H-indazol-5-ylamino)-5,6,7,8-tetrahydro[1]benzothieno[2,3-d]pyrimidin-7-yl]carbonyl}piperazin-1-yl)-N-methylacetamide | 0.63 | 505 |

TABLE 2-continued

Column header: A: Example B: Structure C: IUPAC Name D: Retention time [min] E: MS (ESIpos) m/z [M+H]+

| A | B | C | D | E |
|---|---|---|---|---|
| 165 | | (RS)-4-(1H-indazol-5-ylamino)-N-[(1-methyl-1H-imidazol-2-yl)methyl]-5,6,7,8-tetrahydro[1]benzothieno[2,3-d]pyrimidine-7-carboxamide | 0.62 | 459 |
| 166 | | (RS)-N-cyclopropyl-2-(4-{[4-(1H-indazol-5-ylamino)-5,6,7,8-tetrahydro[1]benzothieno[2,3-d]pyrimidin-7-yl]carbonyl}piperazin-1-yl)acetamide | 0.67 | 531 |
| 167 | | (RS)-4-(1H-indazol-5-ylamino)-N-methyl-N-[2-(pyrrolidin-1-yl)ethyl]-5,6,7,8-tetrahydro[1]benzothieno[2,3-d]pyrimidine-7-carboxamide | 0.65 | 476 |
| 168 | | (RS)-N-[2-(4-acetylpiperazin-1-yl)ethyl]-4-(1H-indazol-5-ylamino)-5,6,7,8-tetrahydro[1]benzothieno[2,3-d]pyrimidine-7-carboxamide | 0.61 | 519 |
| 169 | | (RS)-4-(1H-indazol-5-ylamino)-N-methyl-N-[2-(4-methylpiperidin-1-yl)ethyl]-5,6,7,8-tetrahydro[1]benzothieno[2,3-d]pyrimidine-7-carboxamide | 0.72 | 504 |

Example 170

(RS)—N-(2,2-Difluoroethyl)-4-[(6-methoxy-1H-indazol-5-yl)amino]-N-methyl-5,6,7,8-tetrahydro[1]benzothieno[2,3-d]pyrimidine-7-carboxamide

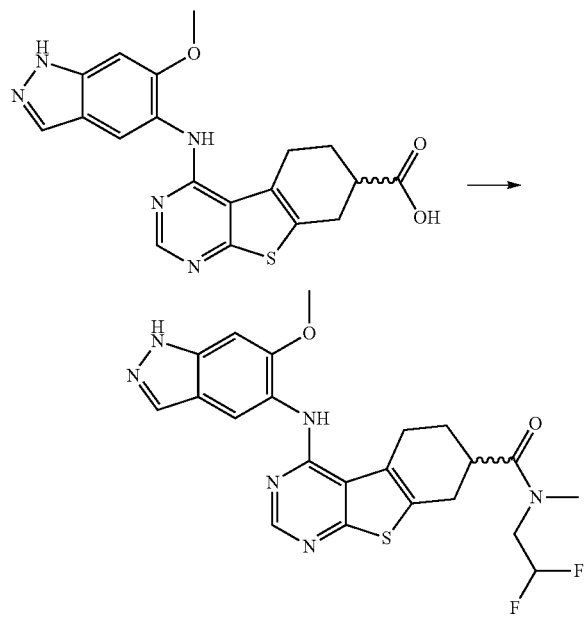

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2,2-difluoro-N-methylethanamine to give after working up and purification 12.5 mg (25%) of the title compound.

$^1$H-NMR (DMSO-$d_6$): δ=1.83 (1H), 2.12 (1H), 2.86-3.25 (8H), 3.61-4.03 (2H), 3.96 (3H), 5.95-6.41 (1H), 7.06 (1H), 7.97 (1H), 8.19 (1H), 8.44 (1H), 8.73-8.77 (1H), 12.81 (1H) ppm.

Example 171

(RS)—N-Ethyl-N-(2-hydroxyethyl)-4-[(6-methoxy-1H-indazol-5-yl)amino]-5,6,7,8-tetrahydro[1]benzothieno[2,3-d]pyrimidine-7-carboxamide

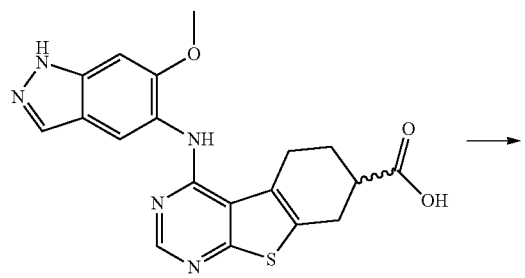

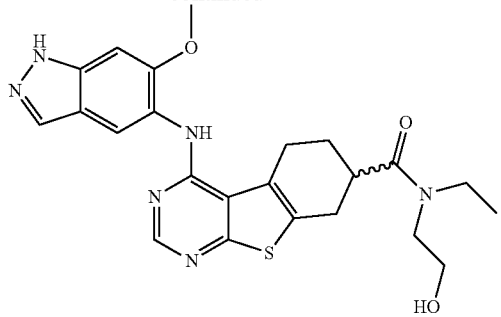

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2-(ethylamino)ethanol to give after working up and purification 12.4 mg (25%) of the title compound.

$^1$H-NMR (DMSO-$d_6$): δ=0.99-1.16 (3H), 1.83 (1H), 2.10 (1H), 2.84-3.00 (2H), 3.07-3.25 (4H), 3.31-3.54 (5H), 3.95 (3H), 4.64+4.80 (1H), 7.06 (1H), 7.97 (1H), 8.20 (1H), 8.43 (1H), 8.76 (1H), 12.81 (1H) ppm.

Example 172

(RS)—N-(2-Hydroxyethyl)-4-[(6-methoxy-1H-indazol-5-yl)amino]-N-methyl-5,6,7,8-tetrahydro[1]benzothieno[2,3-d]pyrimidine-7-carboxamide

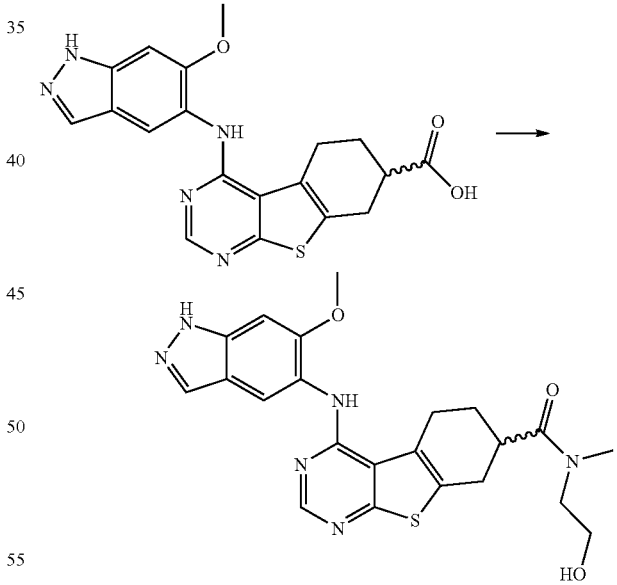

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2-(methylamino)ethanol to give after working up and purification 22.2 mg (46%) of the title compound.

$^1$H-NMR (DMSO-$d_6$): δ=1.81 (1H), 2.12 (1H), 2.85+3.11 (3H), 2.90 (2H), 3.13-3.58 (7H), 3.95 (3H), 4.72 (1H), 7.06 (1H), 7.97 (1H), 8.19 (1H), 8.43 (1H), 8.75 (1H), 12.83 (1H) ppm.

Example 173

(RS)—N—Isopropyl-4-[(6-methoxy-1H-indazol-5-yl)amino]-N-methyl-5,6,7,8-tetrahydro[1]benzothieno[2,3-d]pyrimidine-7-carboxamide

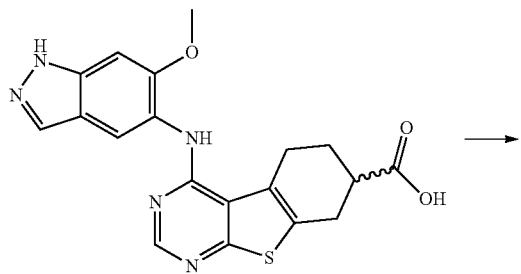

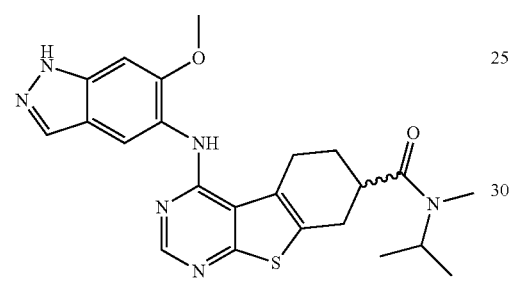

40 mg (101 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-methylpropan-2-amine to give after working up and purification 12.1 mg (25%) of the title compound.

¹H-NMR (DMSO-d₆): δ=1.03+1.16 (6H), 1.83 (1H), 2.09 (1H), 2.69+2.89 (3H), 2.82-3.01 (2H), 3.05-3.24 (3H), 3.96 (3H), 4.27+4.70 (1H), 7.06 (1H), 7.97 (1H), 8.19 (1H), 8.43 (1H), 8.73-8.78 (1H), 12.81 (1H) ppm.

Example 174

(RS)-1-({4-[(6-Methoxy-1H-indazol-5-yl)amino]-5,6,7,8-tetrahydro[1]benzothieno[2,3-d]pyrimidin-7-yl}carbonyl)piperidin-4-one

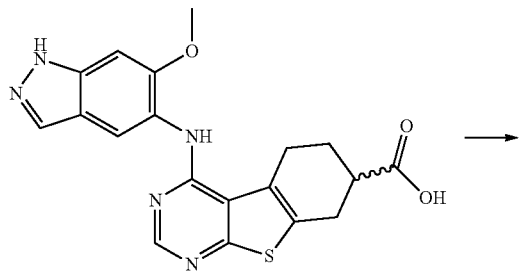

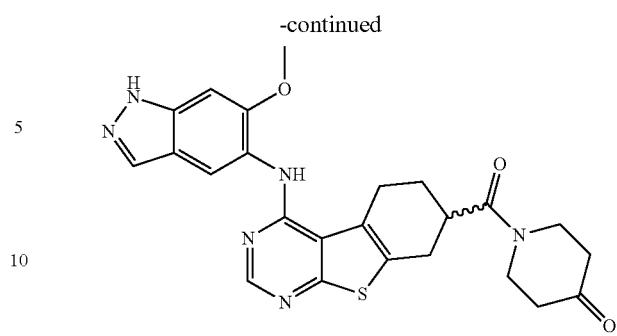

40 mg (101 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using piperidin-4-one to give after working up and purification 11.2 mg (22%) of the title compound.

¹H-NMR (DMSO-d₆): δ=1.85 (1H), 2.17 (1H), 2.36 (2H), 2.96 (2H), 3.13-3.46 (5H), 3.65-3.74 (1H), 3.77-3.91 (3H), 3.95 (3H), 7.06 (1H), 7.97 (1H), 8.20 (1H), 8.43 (1H), 8.74 (1H), 12.82 (1H) ppm.

Example 175

(RS)-{4-[(6-Methoxy-1H-indazol-5-yl)amino]-5,6,7,8-tetrahydro[1]benzothieno[2,3-d]pyrimidin-7-yl}(morpholin-4-yl)methanone

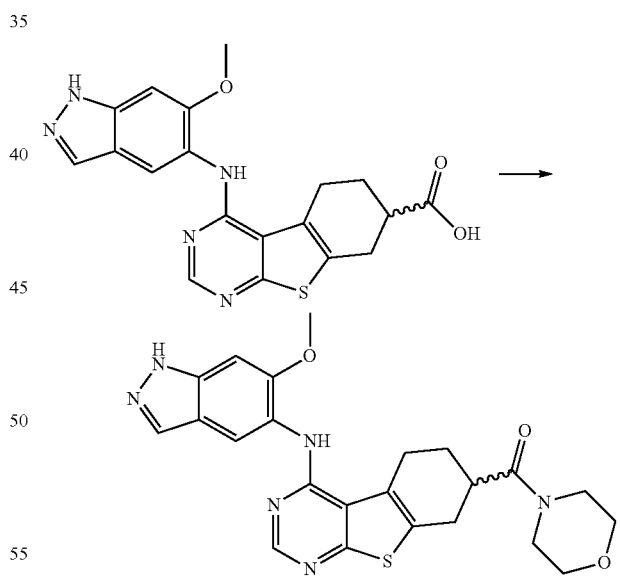

40 mg (101 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using morpholine to give after working up and purification 18.6 mg (38%) of the title compound.

¹H-NMR (DMSO-d₆): δ=1.83 (1H), 2.11 (1H), 2.82-3.01 (2H), 3.09-3.25 (3H), 3.43-3.64 (8H), 3.95 (3H), 7.05 (1H), 7.97 (1H), 8.18 (1H), 8.43 (1H), 8.73 (1H), 12.83 (1H) ppm.

Example 176

(RS)-{4-[(6-Methoxy-1H-indazol-5-yl)amino]-5,6,7,8-tetrahydro[1]benzothieno[2,3-d]pyrimidin-7-yl}(piperidin-1-yl)methanone

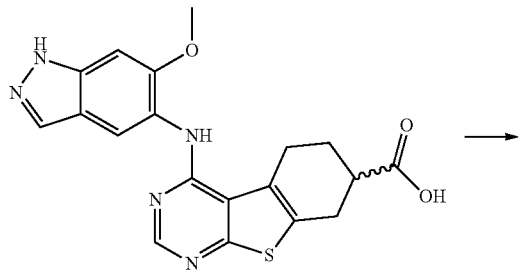

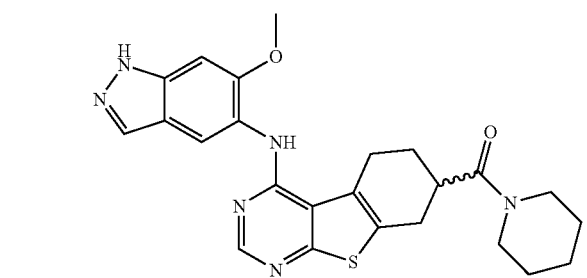

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using piperidine to give after working up and purification 15.4 mg (31%) of the title compound.

$^1$H-NMR (DMSO-d$_6$): δ=1.37-1.63 (6H), 1.81 (1H), 2.08 (1H), 2.79-3.03 (2H), 3.09-3.26 (3H), 3.45 (2H), 3.50 (2H), 3.95 (3H), 7.06 (1H), 7.97 (1H), 8.18 (1H), 8.42 (1H), 8.73 (1H), 12.83 (1H) ppm.

Example 177

(RS)-Azetidin-1-yl{4-[(6-methoxy-1H-indazol-5-yl)amino]-5,6,7,8-tetrahydro[1]benzothieno[2,3-d]pyrimidin-7-yl}methanone

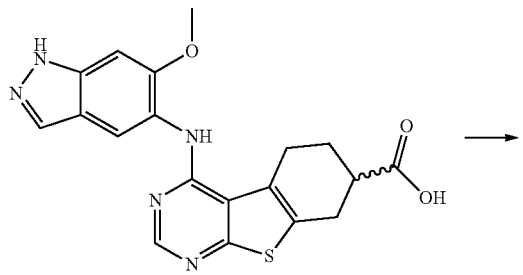

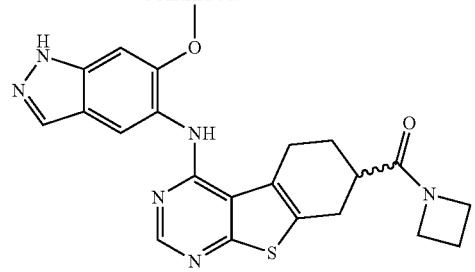

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using azetidine to give after working up and purification 12.5 mg (27%) of the title compound.

$^1$H-NMR (DMSO-d$_6$): δ=1.78 (1H), 2.05-2.28 (3H), 2.72 (1H), 2.86 (2H), 3.09 (1H), 3.22 (1H), 3.86 (2H), 3.95 (3H), 4.22 (2H), 7.06 (1H), 7.97 (1H), 8.19 (1H), 8.43 (1H), 8.74 (1H), 12.83 (1H) ppm.

Example 178

[(2R,5R)-2,5-Dimethylpyrrolidin-1-yl]{(7RS)-4-[(6-methoxy-1H-indazol-5-yl)amino]-5,6,7,8-tetrahydro[1]benzothieno[2,3-d]pyrimidin-7-yl}methanone

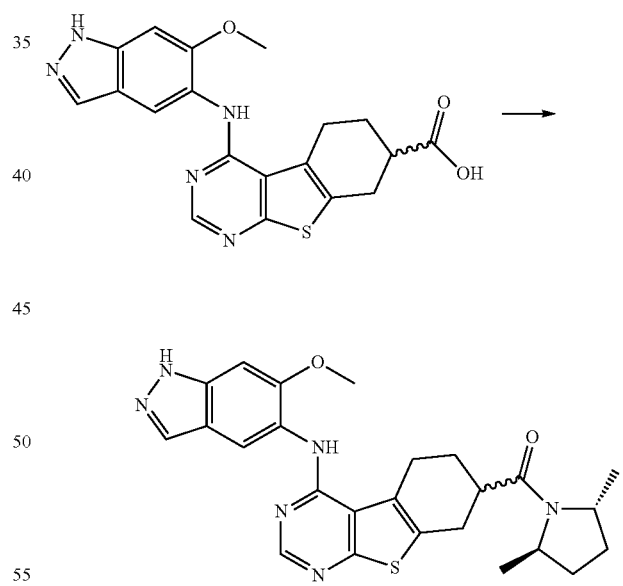

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using (2R,5R)-2,5-dimethylpyrrolidine to give after working up and purification 8.4 mg (17%) of the title compound.

$^1$H-NMR (DMSO-d$_6$): δ=0.99-1.17 (6H), 1.39-2.25 (7H), 2.75-3.26 (4H), 3.94+3.96 (3H), 4.05 (1H), 4.17 (1H), 7.06 (1H), 7.97 (1H), 8.20 (1H), 8.43 (1H), 8.71-8.81 (1H), 12.84 (1H) ppm.

Example 179

(RS)—N-Ethyl-4-[(6-methoxy-1H-indazol-5-yl)amino]-N-methyl-5,6,7,8-tetrahydro[1]benzothieno[2,3-d]pyrimidine-7-carboxamide

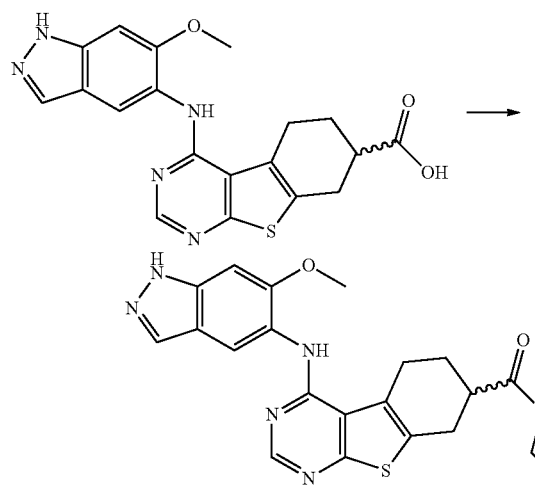

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-methylethanamine to give after working up and purification 7.5 mg (16%) of the title compound.

$^1$H-NMR (DMSO-d$_6$): δ=1.00+1.12 (3H), 1.81 (1H), 1.2.10 (1H), 2.82+3.05 (3H), 2.76-3.61 (7H), 3.95 (3H), 7.06 (1H), 7.97 (1H), 8.20 (1H), 8.43 (1H), 8.75 (1H), 12.66 (1H) ppm.

Example 180

(RS)-(3,3-Dimethylpyrrolidin-1-yl){4-[(6-methoxy-1H-indazol-5-yl)amino]-5,6,7,8-tetrahydro[1]benzothieno[2,3-d]pyrimidin-7-yl}methanone

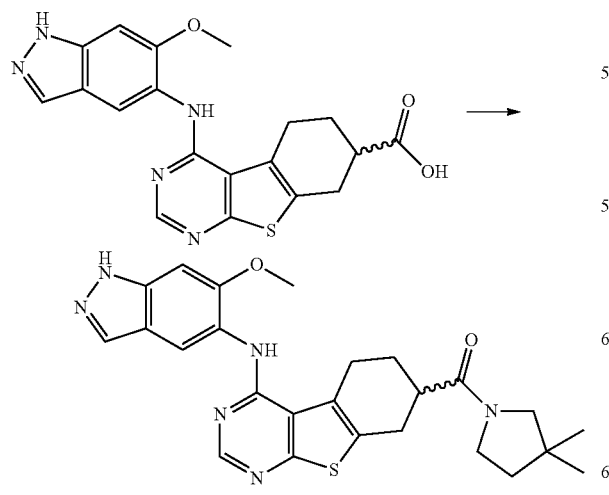

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 3,3-dimethylpyrrolidine to give after working up and purification 9.0 mg (18%) of the title compound.

$^1$H-NMR (DMSO-d$_6$): δ=1.03 (6H), 1.59 (1H), 1.70 (1H), 1.81 (1H), 2.13 (1H), 2.85-3.28 (7H), 3.39 (1H), 3.64 (1H), 3.95 (3H), 7.06 (1H), 7.97 (1H), 8.19 (1H), 8.43 (1H), 8.75 (1H), 12.84 (1H) ppm.

Example 181

(RS)—N—Cyclopropyl-4-[(6-methoxy-1H-indazol-5-yl)amino]-N-methyl-5,6,7,8-tetrahydro[1]benzothieno[2,3-d]pyrimidine-7-carboxamide

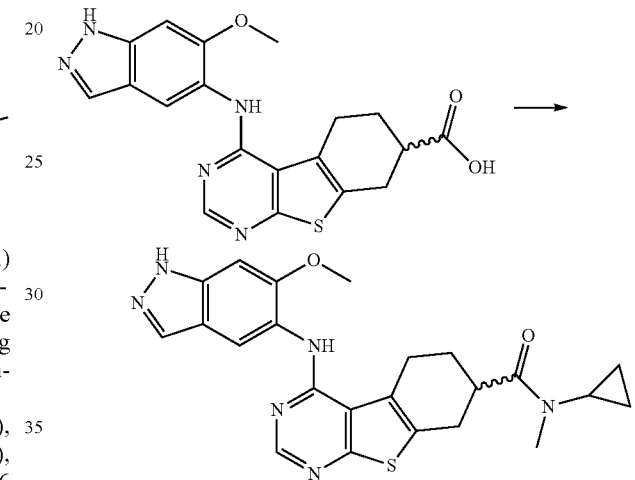

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using N-methylcyclopropanamine to give after working up and purification 22.2 mg (46%) of the title compound.

$^1$H-NMR (DMSO-d$_6$): δ=0.67-0.89 (4H), 1.80 (1H), 2.17 (1H), 2.82 (3H), 2.84-3.01 (3H), 3.12 (1H), 3.26 (1H), 3.51 (1H), 3.94 (3H), 7.06 (1H), 7.96 (1H), 8.20 (1H), 8.43 (1H), 8.73 (1H), 12.73 (1H) ppm.

Example 182

(RS)—N-(Cyclopropylmethyl)-4-[(6-methoxy-1H-indazol-5-yl)amino]-N-methyl-5,6,7,8-tetrahydro[1]benzothieno[2,3-d]pyrimidine-7-carboxamide

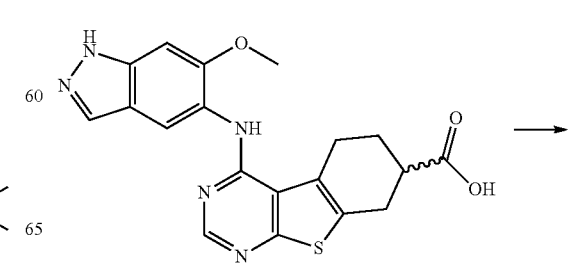

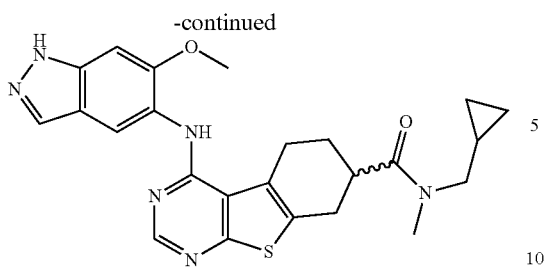

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 1-cyclopropyl-N-methylmethanamine to give after working up and purification 20.5 mg (42%) of the title compound.

$^1$H-NMR (DMSO-$d_6$): δ=0.17-0.31 (2H), 0.38-0.53 (2H), 0.96 (1H), 1.82 (1H), 2.11 (1H), 2.90 (3H), 3.07-3.36 (7H), 3.95 (3H), 7.06 (1H), 7.96 (1H), 8.19 (1H), 8.43 (1H), 8.75 (1H), 12.84 (1H) ppm.

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using pyrrolidine to give after working up and purification 13.3 mg (28%) of the title compound.

$^1$H-NMR (DMSO-$d_6$): δ=1.71-1.94 (5H), 2.15 (1H), 2.86-3.00 (3H), 3.06-3.25 (4H), 3.54 (2H), 3.95 (3H), 7.06 (1H), 7.97 (1H), 8.20 (1H), 8.43 (1H), 8.75 (1H), 12.75 (1H) ppm.

Example 183

(RS)-{4-[(6-Methoxy-1H-indazol-5-yl)amino]-5,6,7,8-tetrahydro[1]benzothieno[2,3-d]pyrimidin-7-yl}(pyrrolidin-1-yl)methanone

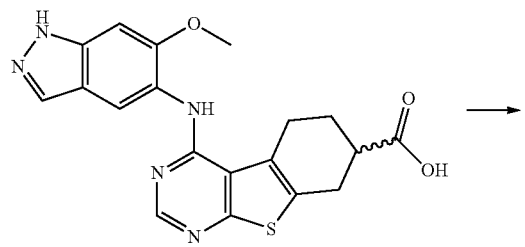

Examples 184-205

The compounds of examples 184-205 listed in Table 3 were prepared and purified in analogy to intermediate example 2a.

The compounds of examples 184-205 were analyzed according to the equipment and conditions given below:

Instrument MS: Waters ZQ;
Instrument HPLC: Waters UPLC Acquity;
Column: Acquity BEH C18 (Waters), 50 mm×2.1 mm, 1.7 μm; Eluent A: $H_2O$+0.1 vol % formic acid, Eluent B: Acetonitrile (Lichrosolv Merck);
Gradient:0.0 min 99% A—1.6 min 1% A—1.8 min 1% A—1.81 min 99% A—2.0 min 99% A;
Oven temperature: 60° C.; Flow: 0.800 ml/min;
UV-Detection PDA 210-400 nm

TABLE 3

Column header: A: Example B: Structure C: IUPAC Name D: Retention time [min] E: MS (ESIpos) m/z $[M+H]^+$

| A | B | C | D | E |
|---|---|---|---|---|
| 184 | | (RS)-2,5-dihydro-1H-pyrrol-1-yl[4-(1H-indazol-5-ylamino)-5,6,7,8-tetrahydro[1]benzothieno[2,3-d]pyrimidin-7-yl]methanone | 0.91 | 417 |
| 185 | | (RS)-2,6-dimethylmorpholin-4-yl[4-(1H-indazol-5-ylamino)-5,6,7,8-tetrahydro[1]benzothieno[2,3-d]pyrimidin-7-yl]methanone | 0.99 | 463 |

TABLE 3-continued

Column header: A: Example B: Structure C: IUPAC Name D: Retention time [min] E: MS (ESIpos) m/z [M+H]+

| A | B | C | D | E |
|---|---|---|---|---|
| 186 | | (RS)-[2-(hydroxymethyl)pyrrolidin-1-yl][4-(1H-indazol-5-ylamino)-5,6,7,8-tetrahydro[1]benzothieno[2,3-d]pyrimidin-7-yl]methanone | 0.84 | 449 |
| 187 | | (RS)-4-(1H-indazol-5-ylamino)-N-methyl-N-(2-methylpropyl)-5,6,7,8-tetrahydro[1]benzothieno[2,3-d]pyrimidine-7-carboxamide | 1.08 | 435 |
| 188 | | (RS)-(1,1-dioxidothiomorpholin-4-yl)[4-(1H-indazol-5-ylamino)-5,6,7,8-tetrahydro[1]benzothieno[2,3-d]pyrimidin-7-yl]methanone | 0.84 | 483 |
| 189 | | (RS)-4-(1H-indazol-5-ylamino)-N-methyl-N-[2-(methylamino)-2-oxoethyl]-5,6,7,8-tetrahydro[1]benzothieno[2,3-d]pyrimidine-7-carboxamide | 0.75 | 450 |
| 190 | | (RS)-N-(2-cyanoethyl)-N-ethyl-4-(1H-indazol-5-ylamino)-5,6,7,8-tetrahydro[1]benzothieno[2,3-d]pyrimidine-7-carboxamide | 0.91 | 446 |

TABLE 3-continued

Column header: A: Example B: Structure C: IUPAC Name D: Retention time [min] E: MS (ESIpos) m/z [M+H]⁺

| A | B | C | D | E |
|---|---|---|---|---|
| 191 | | (RS)-[4-(cyclopropylmethyl)piperazin-1-yl][4-(1H-indazol-5-ylamino)-5,6,7,8-tetrahydro[1]benzothieno[2,3-d]pyrimidin-7-yl]methanone | 0.69 | 488 |
| 192 | | (RS)-[4-(1H-indazol-5-ylamino)-5,6,7,8-tetrahydro[1]benzothieno[2,3-d]pyrimidin-7-yl](octahydro-2H-pyrido[1,2-a]pyrazin-2-yl)methanone | 0.68 | 488 |
| 193 | | (RS)-N-(4-hydroxybutyl)-4-(1H-indazol-5-ylamino)-N-methyl-5,6,7,8-tetrahydro[1]benzothieno[2,3-d]pyrimidine-7-carboxamide | 0.83 | 451 |
| 194 | | (RS)-[4-hydroxy-4-(trifluoromethyl)piperidin-1-yl][4-(1H-indazol-5-ylamino)-5,6,7,8-tetrahydro[1]benzothieno[2,3-d]pyrimidin-7-yl]methanone | 0.96 | 517 |
| 195 | | (RS)-[4-(1H-indazol-5-ylamino)-5,6,7,8-tetrahydro[1]benzothieno[2,3-d]pyrimidin-7-yl](5-methyl-2,5-d]azabicyclo[2.2.1]hept-2-yl)methanone | 0.63 | 460 |

TABLE 3-continued

Column header: A: Example B: Structure C: IUPAC Name D: Retention time [min] E: MS (ESIpos) m/z [M+H]+

| A | B | C | D | E |
|---|---|---|---|---|
| 196 | | (RS)-1-{[4-(1H-indazol-5-ylamino)-5,6,7,8-tetrahydro[1]benzothieno[2,3-d]pyrimidin-7-yl]carbonyl}piperidine-3-carbonitrile | 0.91 | 458 |
| 197 | | (RS)-[3-(2-hydroxyethyl)-4-methylpiperazin-1-yl][4-(1H-indazol-5-ylamino)-5,6,7,8-tetrahydro[1]benzothieno[2,3-d]pyrimidin-7-yl]methanone | 0.63 | 492 |
| 198 | | (RS)-N-(1-{[4-(1H-indazol-5-ylamino)-5,6,7,8-tetrahydro[1]benzothieno[2,3-d]pyrimidin-7-yl]carbonyl}pyrrolidin-3-yl)-N-methylacetamide | 0.81 | 490 |
| 199 | | (RS)-(4,4-difluoropiperidin-1-yl)[4-(1H-indazol-5-ylamino)-5,6,7,8-tetrahydro[1]benzothieno[2,3-d]pyrimidin-7-yl]methanone | 1.03 | 469 |
| 200 | | (RS)-[4-(1H-indazol-5-ylamino)-5,6,7,8-tetrahydro[1]benzothieno[2,3-d]pyrimidin-7-yl][3-(piperidin-1-yl)azetidin-1-yl]methanone | 0.65 | 488 |

TABLE 3-continued

Column header: A: Example B: Structure C: IUPAC Name D: Retention time [min] E: MS (ESIpos) m/z [M+H]+

| A | B | C | D | E |
|---|---|---|---|---|
| 201 | | (RS)-2-(4-{[4-(1H-indazol-5-ylamino)-5,6,7,8-tetrahydro[1]benzothieno[2,3-d]pyrimidin-7-yl]carbonyl}piperazin-1-yl)-1-(pyrrolidin-1-yl)ethanone | 0.69 | 545 |
| 202 | | (RS)-N-(3-hydroxypropyl)-4-(1H-indazol-5-ylamino)-N-methyl-5,6,7,8-tetrahydro[1]benzothieno[2,3-d]pyrimidine-7-carboxamide | 0.80 | 437 |
| 203 | | (RS)-hexahydrocyclopenta[c]pyrrol-2(1H)-yl[4-(1H-indazol-5-ylamino)-5,6,7,8-tetrahydro[1]benzothieno[2,3-d]pyrimidin-7-yl]methanone | 1.11 | 459 |
| 204 | | (RS)-[4-(1H-indazol-5-ylamino)-5,6,7,8-tetrahydro[1]benzothieno[2,3-d]pyrimidin-7-yl][2-(methoxymethyl)pyrrolidin-1-yl]methanone | 0.98 | 463 |
| 205 | | (RS)-[3-(dimethylamino)pyrrolidin-1-yl][4-(1H-indazol-5-ylamino)-5,6,7,8-tetrahydro[1]benzothieno[2,3-d]pyrimidin-7-yl]methanone|[3-(dimethylamino)pyrrolidin-1-yl][4-(1H-indazol-5-ylamino)-5,6,7,8-tetrahydro[1]benzothieno[2,3-d]pyrimidin-7-yl]methanone | 0.63 | 462 |

Example 206

(RS)-2-Oxa-6-azaspiro[3.3]hept-6-yl(4-{[6-(propan-2-yloxy)-1H-indazol-5-yl]amino}-5,6,7,8-tetrahydro[1]benzothieno[2,3-d]pyrimidin-7-yl)methanone

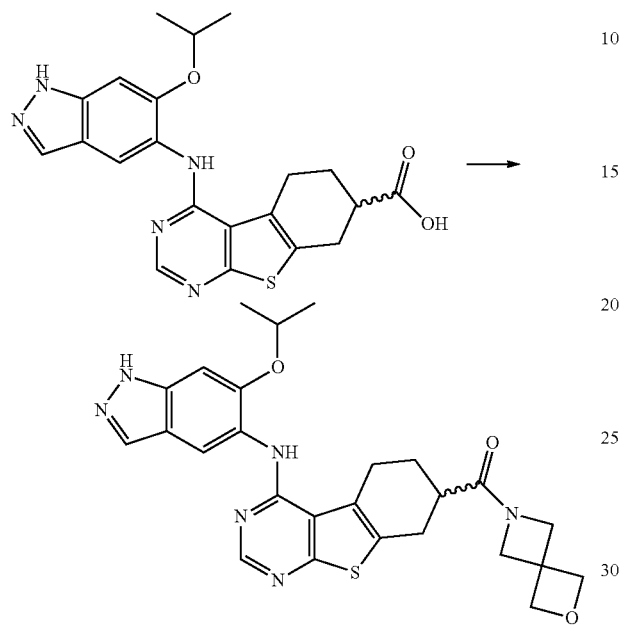

150 mg (354 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 2-oxa-6-azaspiro[3.3]heptane ethanedioate (2:1) to give after working up and purification 78 mg (42%) of the title compound.

$^1$H-NMR (DMSO-d6): δ=1.40 (6H), 1.84 (1H), 2.06 (1H), 2.69-2.96 (3H), 3.17 (1H), 3.25-3.42 (1H), 4.05 (2H), 4.41 (2H), 4.68 (4H), 4.88 (1H), 7.11 (1H), 7.99 (1H), 8.36 (1H), 8.52 (1H), 9.06 (1H), 12.77 (1H) ppm.

Example 207

(RS)—N-(2-Hydroxyethyl)-N-(2-methoxyethyl)-4-[(6-methoxy-1H-indazol-5-yl)amino]-5,6,7,8-tetrahydro[1]benzothieno[2,3-d]pyrimidine-7-carboxamide

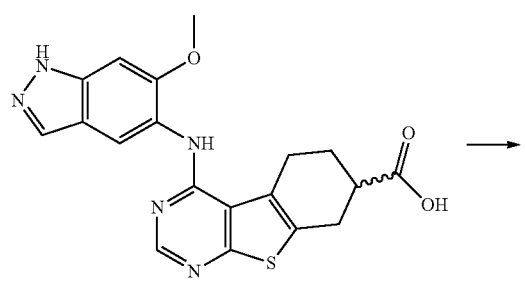

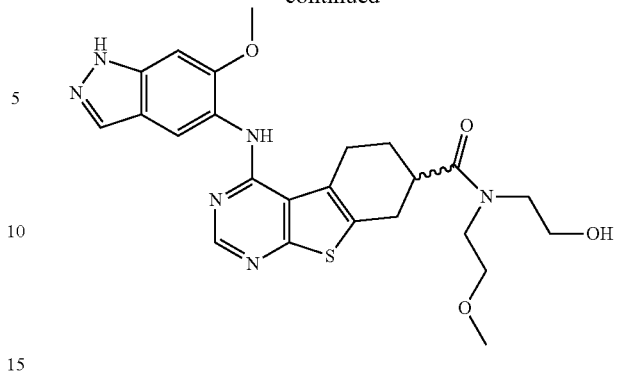

51 mg (129 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2-[(2-methoxyethyl)amino]ethanol to give after working up and purification 29.9 mg (44%) of the title compound.

$^1$H-NMR (DMSO-d6): δ=1.84 (1H), 2.12 (1H), 2.84-2.99 (2H), 3.16-3.64 (15H), 3.98 (3H), 7.09 (1H), 7.99 (1H), 8.22 (1H), 8.46 (1H), 8.78 (1H), 12.85 (1H) ppm.

Example 208

(RS)-1-[(4-{[6-(Propan-2-yloxy)-1H-indazol-5-yl]amino}-5,6,7,8-tetrahydro[1]benzothieno[2,3-d]pyrimidin-7-yl)carbonyl]azetidine-3-carbonitrile

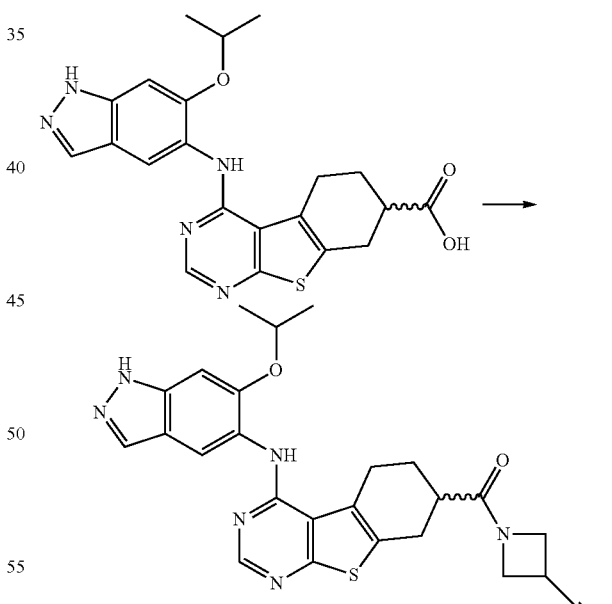

250 mg (590 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using azetidine-3-carbonitrile to give after working up and purification 185 mg (64%) of the title compound.

$^1$H-NMR (DMSO-d6): δ=1.41 (6H), 1.84 (1H), 2.10 (1H), 2.76-3.02 (3H), 3.12-3.35 (2H), 3.81 (1H), 4.04 (1H), 4.18 (1H), 4.42-4.59 (2H), 4.89 (1H), 7.11 (1H), 7.99 (1H), 8.35 (1H), 8.52 (1H), 9.06 (1H), 12.74 (1H) ppm.

Example 209

(RS)-{4-[(6-Ethoxy-1H-indazol-5-yl)amino]-5,6,7,8-tetrahydro[1]benzothieno[2,3-d]pyrimidin-7-yl}(piperidin-1-yl)methanone

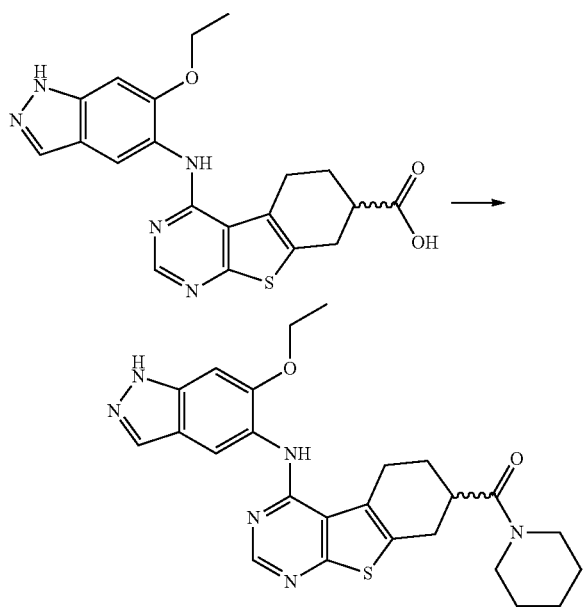

50 mg (122 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using piperidine to give after working up and purification 17.0 mg (30%) of the title compound.

¹H-NMR (DMSO-d6): δ=1.39-1.67 (6H), 1.47 (3H), 1.86 (1H), 2.05 (1H), 2.81-3.01 (2H), 3.14-3.57 (7H), 4.21 (2H), 7.06 (1H), 7.99 (1H), 8.37 (1H), 8.52 (1H), 9.02 (1H), 12.82 (1H) ppm.

Example 210

(RS)-4-[(6-Ethoxy-1H-indazol-5-yl)amino]-5,6,7,8-tetrahydro[1]benzothieno[2,3-d]pyrimidine-7-carboxylic acid

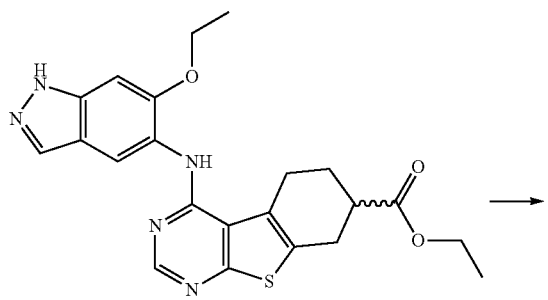

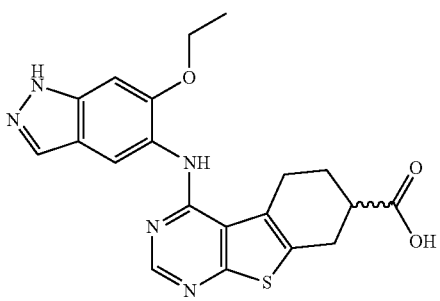

1.18 g (2.70 mmol) (RS)-ethyl 4-[(6-ethoxy-1H-indazol-5-yl)amino]-5,6,7,8-tetrahydro[1]benzothieno[2,3-d]pyrimidine-7-carboxylate (prepared according to intermediate example 210a) were transformed in analogy to intermediate example 1a to give after working up and purification 650 mg (57%) of the title compound.

¹H-NMR (DMSO-d6): δ=1.47 (3H), 1.85 (1H), 2.19 (1H), 2.40 (1H), 2.87-3.00 (2H), 3.06 (1H), 3.19-3.29 (2H), 4.19 (2H), 7.05 (1H), 7.96 (1H), 8.36 (1H), 8.48 (1H), 9.03 (1H), 12.92 (1H) ppm.

Example 210a (RS)-Ethyl 4-[(6-ethoxy-1H-indazol-5-yl)amino]-5,6,7,8-tetrahydro[1]benzothieno[2,3-d]pyrimidine-7-carboxylate

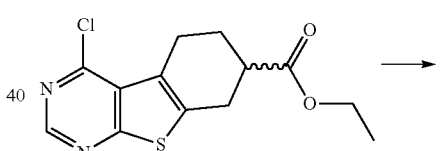

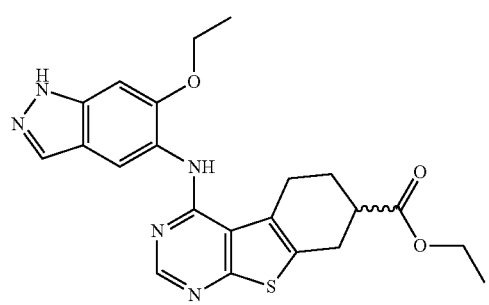

7.98 g (26.87 mmol) (RS)-ethyl 4-chloro-5,6,7,8-tetrahydro[1]benzothieno[2,3-d]pyrimidine-7-carboxylate (prepared according to WO 2005/010008, example 14, steps 1 to 3) were transformed in analogy to example 1 using 6-ethoxy-1H-indazol-5-amine (prepared according to intermediate example 210b) to give after working up and purification 5.22 g (43%) of the title compound.

Example 210b

6-Ethoxy-1H-indazol-5-amine

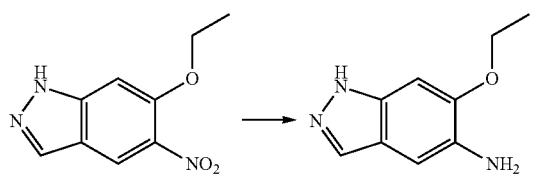

10.0 g (48.3 mmol) 6-ethoxy-5-nitro-1H-indazole (Supplier: Angene Chemicals, Hong Kong PO#2343258 Et 2374166) were transformed in analogy to intermediate example 69b to give after working up and purification 5.08 g (59%) of the title compound.

Example 211

(RS)-1-({4-[(6-Ethoxy-1H-indazol-5-yl)amino]-5,6,7,8-tetrahydro[1]benzothieno[2,3-d]pyrimidin-7-yl}carbonyl)piperidin-4-one

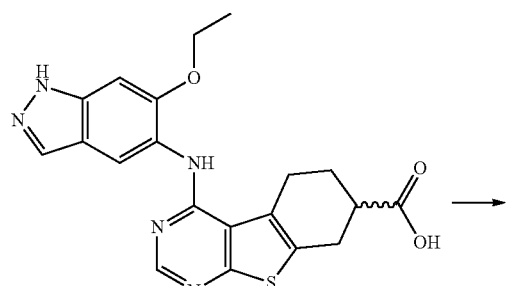

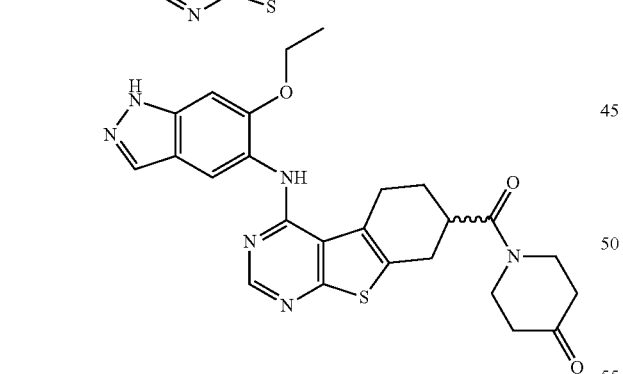

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using piperidin-4-one to give after working up and purification 30.0 mg (25%) of the title compound.

$^1$H-NMR (DMSO-d6): δ=1.47 (3H), 1.93 (1H), 2.12 (1H), 2.34-2.50 (4H), 2.72 (1H), 2.98 (2H), 3.21-3.30 (2H), 3.69-3.96 (4H), 4.21 (2H), 7.06 (1H), 7.99 (1H), 8.37 (1H), 8.53 (1H), 9.02 (1H), 12.84 (1H) ppm.

Example 212

(RS)-{4-[(6-Ethoxy-1H-indazol-5-yl)amino]-5,6,7,8-tetrahydro[1]benzothieno[2,3-d]pyrimidin-7-yl}(morpholin-4-yl)methanone

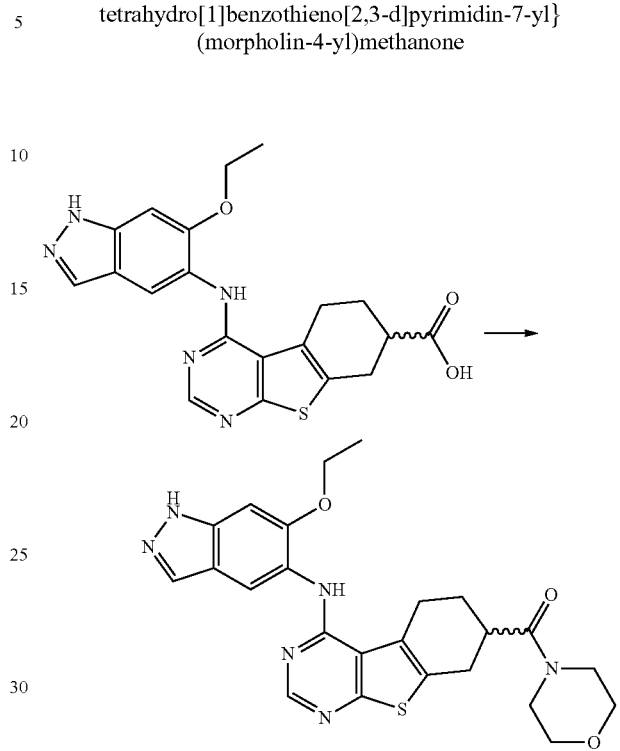

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using morpholine to give after working up and purification 57 mg (49%) of the title compound.

$^1$H-NMR (DMSO-d6): δ=1.47 (3H), 1.89 (1H), 2.07 (1H), 2.94 (2H), 3.12-3.29 (3H), 3.46-3.66 (8H), 4.21 (2H), 7.06 (1H), 7.99 (1H), 8.36 (1H), 8.52 (1H), 9.01 (1H), 12.83 (1H) ppm.

Example 213

(RS)-Piperidin-1-yl(4-{[6-(propan-2-yloxy)-1H-indazol-5-yl]amino}-5,6,7,8-tetrahydro[1]benzothieno[2,3-d]pyrimidin-7-yl)methanone

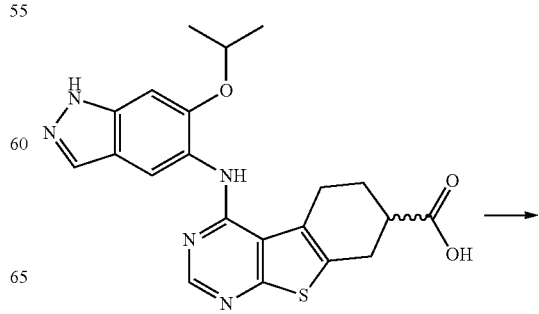

-continued

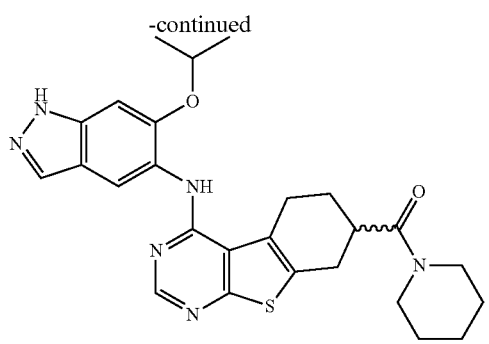

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using piperidine to give after working up and purification 48.3 mg (79%) of the title compound.

$^1$H-NMR (DMSO-d6): δ=1.37-1.66 (6H), 1.40 (6H), 1.88 (1H), 2.06 (1H), 2.84-3.02 (2H), 3.17-3.28 (3H), 3.38-3.59 (4H), 4.88 (1H), 7.10 (1H), 7.98 (1H), 8.36 (1H), 8.52 (1H), 9.07 (1H), 12.75 (1H) ppm.

Example 214

(RS)—N-ethyl-N-(2-hydroxyethyl)-4-{[6-(propan-2-yloxy)-1H-indazol-5-yl]amino}-5,6,7,8-tetrahydro[1]benzothieno[2,3-d]pyrimidine-7-carboxamide

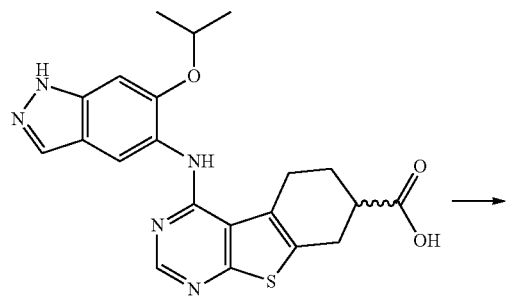

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 2-(ethylamino)ethanol to give after working up and purification 53.8 mg (88%) of the title compound.

$^1$H-NMR (DMSO-d6): δ=1.04+1.15 (3H), 1.40 (6H), 1.90 (1H), 2.06 (1H), 2.85-3.03 (2H), 3.07-3.56 (10H), 4.88 (1H), 7.11 (1H), 7.98 (1H), 8.36 (1H), 8.52 (1H), 9.07 (1H), 12.76 (1H) ppm.

Example 215

(RS)—N-Methyl-N-(propan-2-yl)-4-{[6-(propan-2-yloxy)-1H-indazol-5-yl]amino}-5,6,7,8-tetrahydro[1]benzothieno[2,3-d]pyrimidine-7-carboxamide

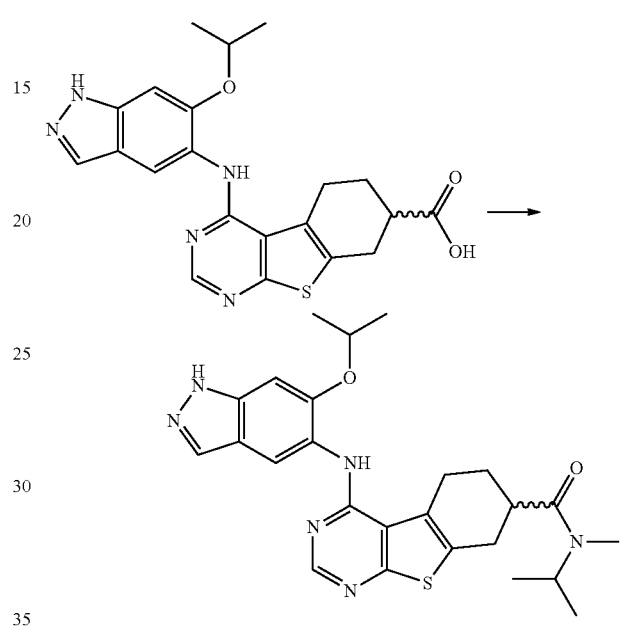

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using N-methylpropan-2-amine to give after working up and purification 44.7 mg (75%) of the title compound.

$^1$H-NMR (DMSO-d6): δ=1.05+1.17 (6H), 1.41 (6H), 1.90 (1H), 2.05 (1H), 2.70+2.90 (3H), 2.85-2.99 (2H), 3.06-3.29 (3H), 4.29+4.71 (1H), 4.88 (1H), 7.11 (1H), 7.98 (1H), 8.36 (1H), 8.52 (1H), 9.07 (1H), 12.76 (1H) ppm.

Example 216

(RS)—N-(2,2-Difluoroethyl)-N-methyl-4-{[6-(propan-2-yloxy)-1H-indazol-5-yl]amino}-5,6,7,8-tetrahydro[1]benzothieno[2,3-d]pyrimidine-7-carboxamide

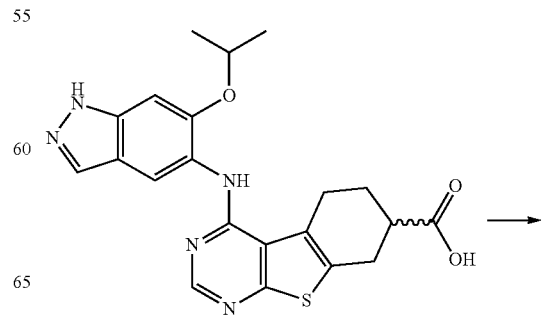

-continued

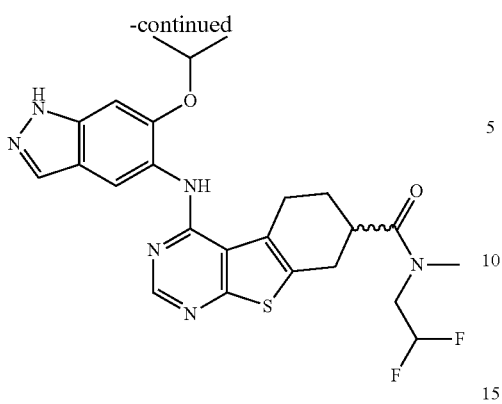

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 2,2-difluoro-N-methylethanamine to give after working up and purification 55.3 mg (89%) of the title compound.

$^1$H-NMR (DMSO-d6): δ=1.41 (6H), 1.90 (1H), 2.09 (1H), 2.86-3.02 (2H), 2.95+3.19 (3H), 3.23-3.30 (3H), 3.65-4.04 (2H), 4.89 (1H), 6.13+6.28 (1H), 7.11 (1H), 7.99 (1H), 8.36 (1H), 8.53 (1H), 9.07 (1H), 12.77 (1H) ppm.

Example 217

(RS)—N-Ethyl-N-methyl-4-{[6-(propan-2-yloxy)-1H-indazol-5-yl]amino}-5,6,7,8-tetrahydro[1]benzothieno[2,3-d]pyrimidine-7-carboxamide

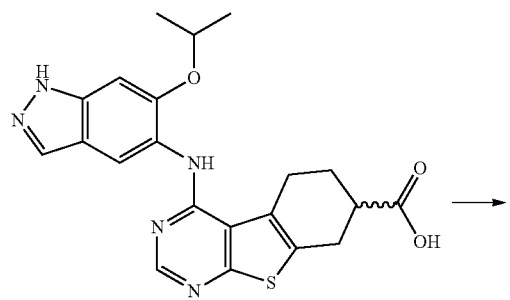

50 mg (118 µmol) (RS)-4-[(6-Isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using N-methylethanamine to give after working up and purification 34.7 mg (63%) of the title compound.

$^1$H-NMR (DMSO-d6): δ=1.03+1.15 (3H), 1.40 (6H), 1.88 (1H), 2.05 (1H), 2.84+3.07 (3H), 2.88-3.00 (2H), 3.11-3.48 (5H), 4.88 (1H), 7.10 (1H), 7.98 (1H), 8.35 (1H), 8.52 (1H), 9.06 (1H), 12.76 (1H) ppm.

Example 218

(RS)-Morpholin-4-yl(4-{[6-(propan-2-yloxy)-1H-indazol-5-yl]amino}-5,6,7,8-tetrahydro[1]benzothieno[2,3-d]pyrimidin-7-yl)methanone

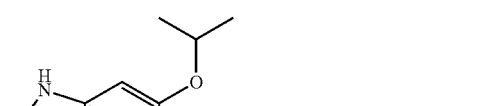
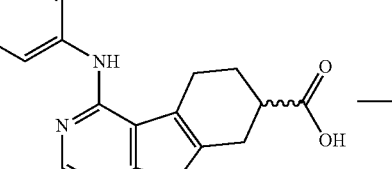
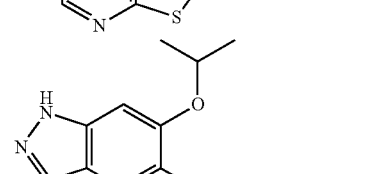

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using morpholine to give after working up and purification 25.9 mg (62%) of the title compound.

$^1$H-NMR (DMSO-d6): δ=1.40 (6H), 1.91 (1H), 2.07 (1H), 2.94 (2H), 3.16-3.28 (3H), 3.45-3.66 (8H), 4.88 (1H), 7.10 (1H), 7.98 (1H), 8.35 (1H), 8.52 (1H), 9.06 (1H), 12.75 (1H) ppm.

Example 219

(RS)-Azetidin-1-yl(4-{[6-(propan-2-yloxy)-1H-indazol-5-yl]amino}-5,6,7,8-tetrahydro[1]benzothieno[2,3-d]pyrimidin-7-yl)methanone

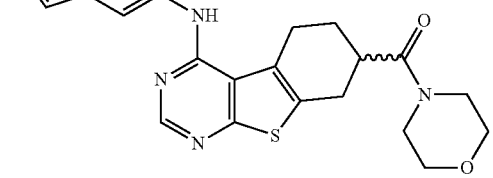
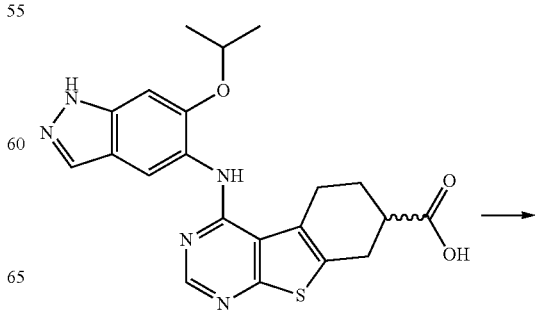

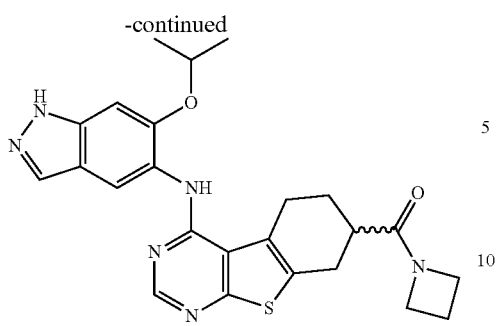

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using azetidine to give after working up and purification 38.1 mg (70%) of the title compound.

$^1$H-NMR (DMSO-d6): δ=1.41 (6H), 1.85 (1H), 2.07 (1H), 2.21 (2H), 2.77 (1H), 2.89 (2H), 3.16 (2H), 3.88 (2H), 4.23 (2H), 4.88 (1H), 7.10 (1H), 7.98 (1H), 8.34 (1H), 8.52 (1H), 9.06 (1H), 12.75 (1H) ppm.

Example 220

(RS)—N-(Cyclopropylmethyl)-N-methyl-4-{[6-(propan-2-yloxy)-1H-indazol-5-yl]amino}-5,6,7,8-tetrahydro[1]benzothieno[2,3-d]pyrimidine-7-carboxamide

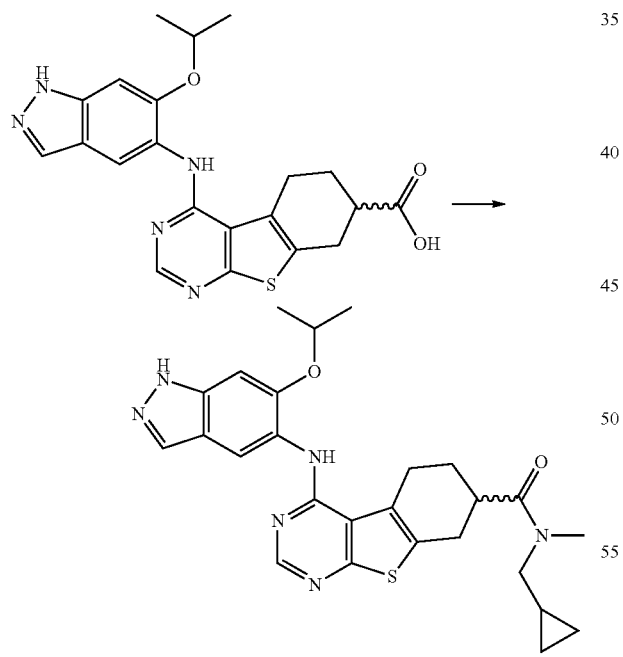

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 1-cyclopropyl-N-methylmethanamine to give after working up and purification 19.8 mg (32%) of the title compound.

$^1$H-NMR (DMSO-d6): δ=0.19-0.32 (2H), 0.41-0.54 (2H), 0.97 (1H), 1.41 (6H), 1.89 (1H), 2.07 (1H), 2.86-3.02 (2H), 2.92+3.14 (3H), 3.15-3.36 (5H), 4.88 (1H), 7.11 (1H), 7.98 (1H), 8.36 (1H), 8.52 (1H), 9.07 (1H), 12.75 (1H) ppm.

Example 221

(RS)-(4-{[6-(Propan-2-yloxy)-1H-indazol-5-yl]amino}-5,6,7,8-tetrahydro[1]benzothieno[2,3-d]pyrimidin-7-yl)(pyrrolidin-1-yl)methanone

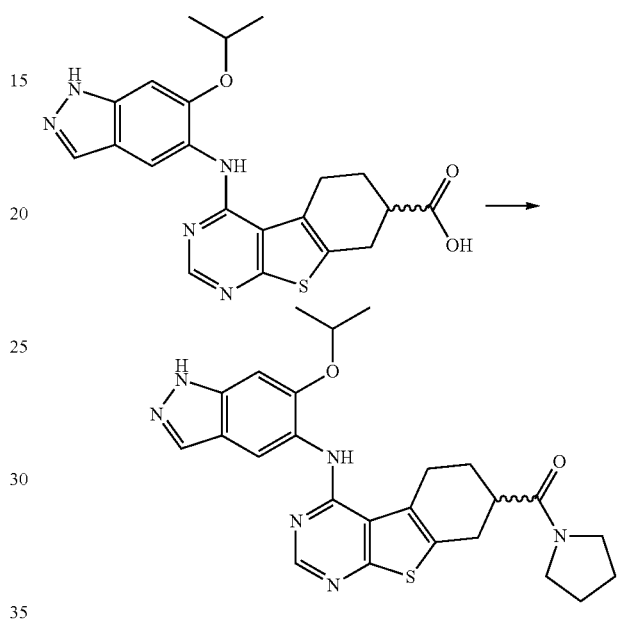

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using pyrrolidine to give after working up and purification 22.1 mg (37%) of the title compound.

$^1$H-NMR (DMSO-d6): δ=1.40 (6H), 1.74-1.98 (5H), 2.11 (1H), 2.86-3.08 (3H), 3.20 (1H), 3.12-3.38 (3H), 3.55 (2H), 4.88 (1H), 7.11 (1H), 7.99 (1H), 8.36 (1H), 8.52 (1H), 9.07 (1H), 12.78 (1H) ppm.

Example 222

(RS)-(1,1-Dioxido-1-thia-6-azaspiro[3.3]hept-6-yl)(4-{[6-(propan-2-yloxy)-1H-indazol-5-yl]amino}-5,6,7,8-tetrahydro[1]benzothieno[2,3-d]pyrimidin-7-yl)methanone

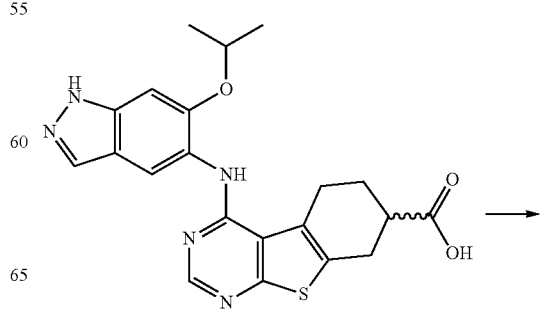

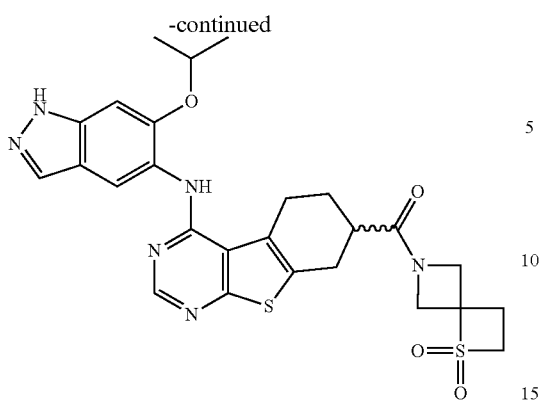

150 mg (354 μmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 1-thia-6-azaspiro[3.3]heptane 1,1-dioxide trifluoroacetate (1:1) to give after working up and purification 44.3 mg (22%) of the title compound.

$^{1}$H-NMR (DMSO-d6): δ=1.41 (6H), 1.86 (1H), 2.11 (1H), 2.43 (2H), 2.80-3.04 (3H), 3.12-3.27 (2H), 4.06-4.31 (4H), 4.54 (1H), 4.69 (1H), 4.89 (1H), 7.11 (1H), 7.99 (1H), 8.36 (1H), 8.53 (1H), 9.06 (1H), 12.74 (1H) ppm.

Example 223

(RS)-Azetidin-1-yl{4-[(6-ethoxy-1H-indazol-5-yl)amino]-5,6,7,8-tetrahydro[1]benzothieno[2,3-d]pyrimidin-7-yl}methanone

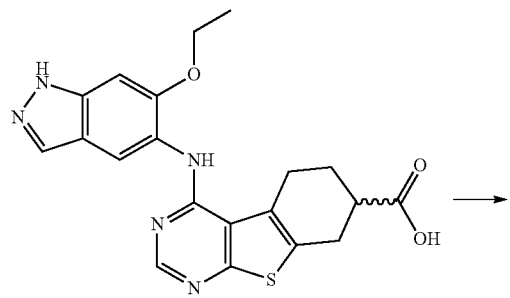

100 mg (244 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using azetidine to give after working up and purification 37.5 mg (34%) of the title compound.

$^{1}$H-NMR (DMSO-d6): δ=1.49 (3H), 1.89 (1H), 2.12 (1H), 2.24 (2H), 2.80 (1H), 2.93 (2H), 3.13-3.25 (3H), 3.33 (1H), 3.94 (2H), 4.26 (2H), 7.09 (1H), 7.96 (1H), 8.27 (1H), 8.49 (1H), 8.95 (1H), 12.50 (1H) ppm.

Example 224

(RS)-4-[(6-Ethoxy-1H-indazol-5-yl)amino]-N-isopropyl-N-methyl-5,6,7,8-tetrahydro[1]benzothieno[2,3-d]pyrimidine-7-carboxamide

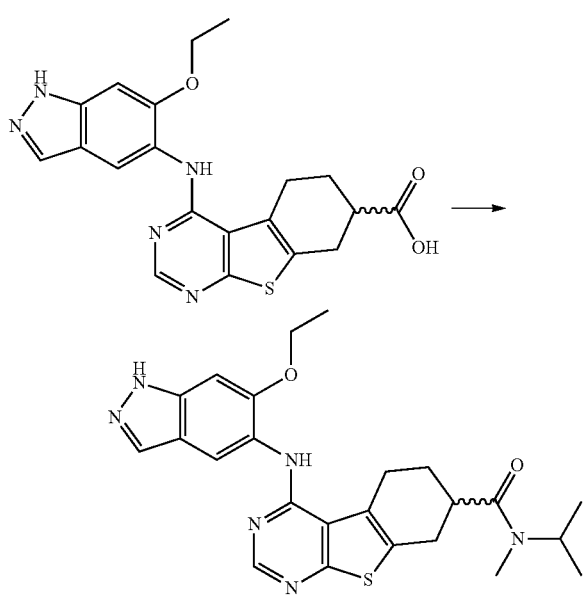

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-methylpropan-2-amine to give after working up and purification 17.0 mg (30%) of the title compound.

$^{1}$H-NMR (DMSO-d6): δ=1.05+1.17 (6H), 1.48 (3H), 1.74 (1H), 1.87 (1H), 2.05 (1H), 2.70+2.90 (3H), 2.84-3.00 (2H), 3.07-3.30 (2H), 4.22 (2H), 4.29+4.71 (1H), 7.06 (1H), 8.00 (1H), 8.37 (1H), 8.52 (1H), 9.02 (1H), 12.83 (1H) ppm.

Example 225

(RS)-4-[(6-Ethoxy-1H-indazol-5-yl)amino]-N-(2-hydroxyethyl)-N-methyl-5,6,7,8-tetrahydro[1]benzothieno[2,3-d]pyrimidine-7-carboxamide

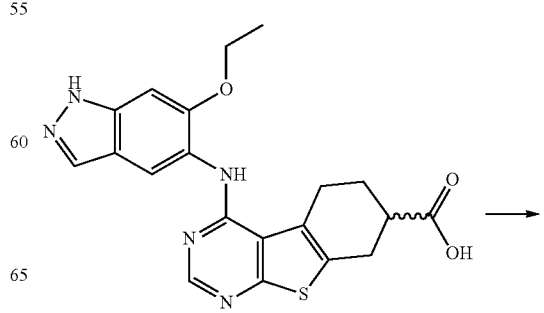

-continued

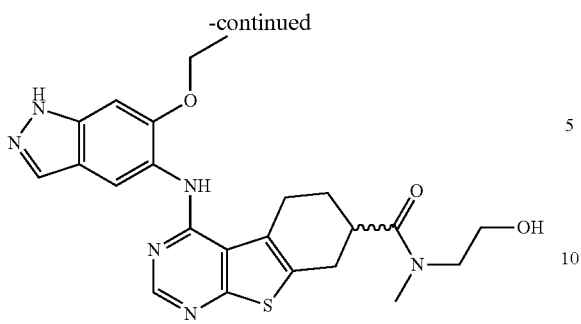

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2-(methylamino)ethanol to give after working up and purification 33.0 mg (29%) of the title compound.

$^1$H-NMR (DMSO-d6): δ=1.48 (3H), 1.87 (1H), 2.10 (1H), 2.87+3.13 (3H), 2.93 (2H), 3.06-3.20 (2H), 3.13-3.59 (5H), 4.22 (2H), 4.65+4.82 (1H), 7.06 (1H), 7.99 (1H), 8.37 (1H), 8.52 (1H), 9.02 (1H), 12.80 (1H) ppm.

Example 226

(RS)—N-(2,2-Difluoroethyl)-4-[(6-ethoxy-1H-indazol-5-yl)amino]-N-methyl-5,6,7,8-tetrahydro[1]benzothieno[2,3-d]pyrimidine-7-carboxamide

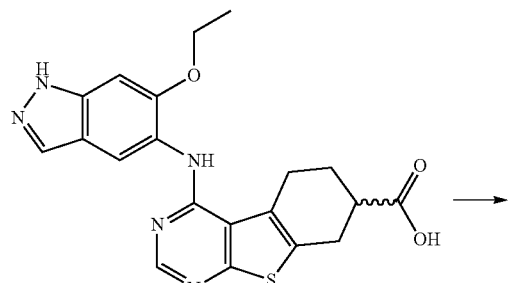

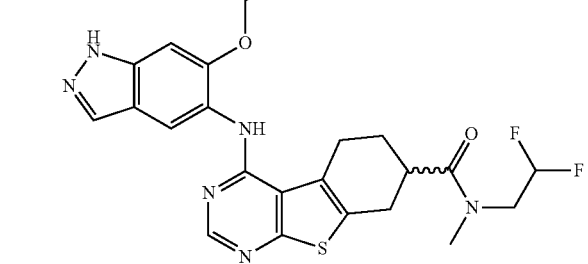

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2,2-difluoro-N-methylethanamine to give after working up and purification 12.0 mg (10%) of the title compound.

$^1$H-NMR (DMSO-d6): δ=1.48 (3H), 1.88 (1H), 2.09 (1H), 2.87-3.03 (2H), 2.95+3.19 (3H), 3.16-3.34 (3H), 3.64-4.03 (2H), 4.23 (2H), 6.13+6.27 (1H), 7.07 (1H), 7.99 (1H), 8.36 (1H), 8.53 (1H), 9.02 (1H), 12.80 (1H) ppm.

Example 227

[(2R,5R)-2,5-Dimethylpyrrolidin-1-yl]{(7RS)-4-[(6-isopropoxy-1H-indazol-5-yl)amino]-5,6,7,8-tetrahydro[1]benzothieno[2,3-d]pyrimidin-7-yl}methanone

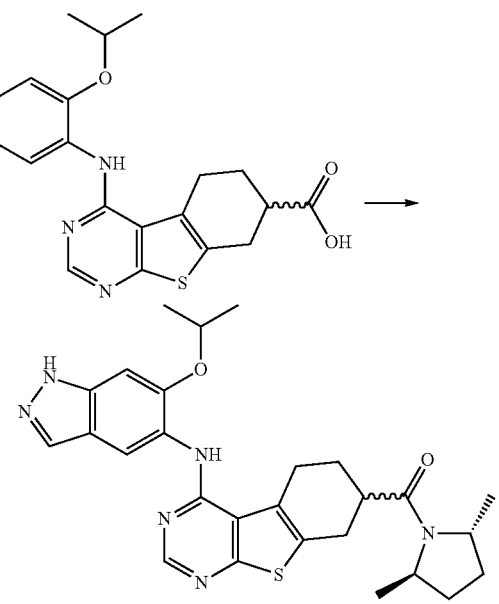

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using (2R,5R)-2,5-dimethylpyrrolidine to give after working up and purification 9.1 mg (15%) of the title compound.

$^1$H-NMR (DMSO-d6): δ=1.07-1.25 (6H), 1.40 (6H), 1.48 (1H), 1.58 (1H), 1.85-2.24 (4H), 2.82-3.11 (3H), 3.15-3.40 (2H), 3.95+4.08 (1H), 4.19 (1H), 4.88 (1H), 7.11 (1H), 7.98 (1H), 8.36 (1H), 8.53 (1H), 9.06 (1H), 12.75 (1H) ppm.

Example 228

(RS)-{4-[(6-Ethoxy-1H-indazol-5-yl)amino]-5,6,7,8-tetrahydro[1]benzothieno[2,3-d]pyrimidin-7-yl}(pyrrolidin-1-yl)methanone

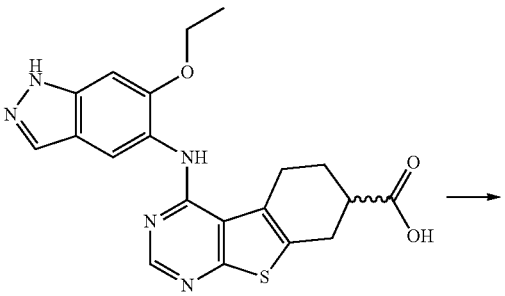

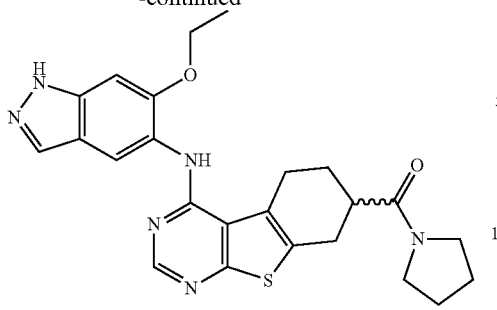

100 mg (244 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using pyrrolidine to give after working up and purification 21.0 mg (19%) of the title compound.

$^1$H-NMR (DMSO-d6): δ=1.47 (3H), 1.71-1.97 (5H), 2.12 (1H), 2.88-3.08 (3H), 3.13-3.38 (2H), 3.32-3.41 (2H), 3.55 (2H), 4.22 (2H), 7.06 (1H), 7.99 (1H), 8.36 (1H), 8.52 (1H), 9.01 (1H), 12.80 (1H) ppm.

Example 229

(RS)-4-[(6-Ethoxy-1H-indazol-5-yl)amino]-N-ethyl-N-methyl-5,6,7,8-tetrahydro[1]benzothieno[2,3-d]pyrimidine-7-carboxamide

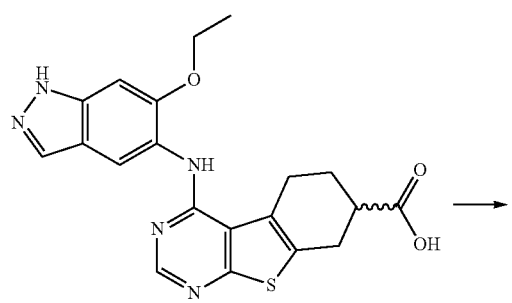

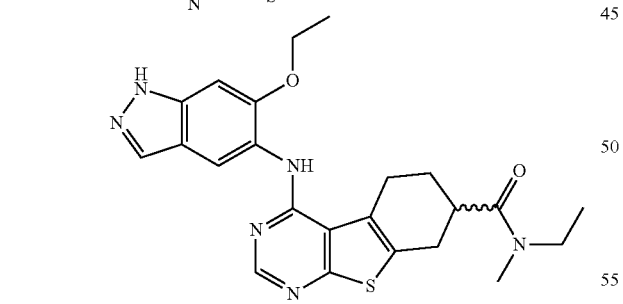

100 mg (244 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-methylethanamine to give after working up and purification 24.0 mg (22%) of the title compound.

$^1$H-NMR (DMSO-d6): δ=1.03+1.14 (3H), 1.48 (3H), 1.87 (1H), 2.06 (1H), 2.84+3.06 (3H), 2.93 (2H), 3.15 (1H), 3.22-3.50 (4H), 4.22 (2H), 7.07 (1H), 7.99 (1H), 8.37 (1H), 8.53 (1H), 9.02 (1H), 12.80 (1H) ppm.

Example 230

(RS)—N-(2-Hydroxyethyl)-4-[(6-isopropoxy-1H-indazol-5-yl)amino]-N-methyl-5,6,7,8-tetrahydro[1]benzothieno[2,3-d]pyrimidine-7-carboxamide

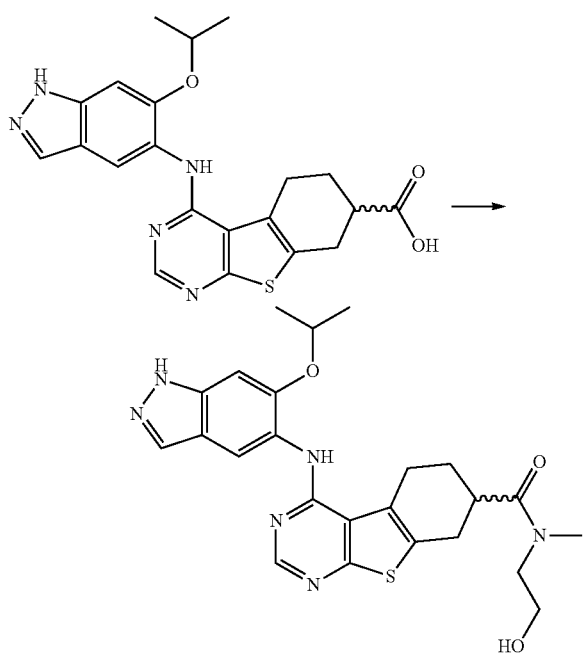

50 mg (118 μmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 2-(methylamino)ethanol to give after working up and purification 10.9 mg (18%) of the title compound.

$^1$H-NMR (DMSO-d6): δ=1.40 (6H), 1.88 (1H), 2.10 (1H), 2.87+3.13 (3H), 2.93 (2H), 3.15-3.57 (7H), 4.65+4.81 (1H), 4.89 (1H), 7.11 (1H), 7.99 (1H), 8.38 (1H), 8.53 (1H), 9.07 (1H), 12.76 (1H) ppm.

Example 231

(RS)-4-[(6-Ethoxy-1H-indazol-5-yl)amino]-N-ethyl-N-(2-hydroxyethyl)-5,6,7,8-tetrahydro[1]benzothieno[2,3-d]pyrimidine-7-carboxamide

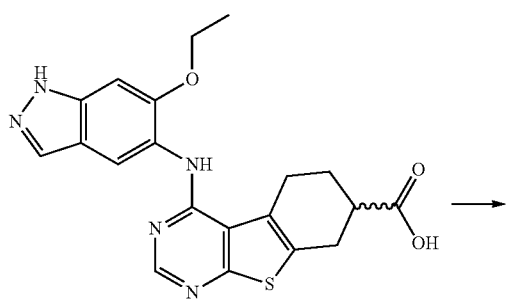

-continued

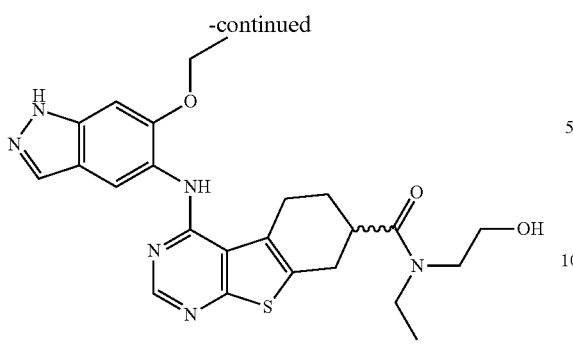

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2-(ethylamino)ethanol to give after working up and purification 55.0 mg (47%) of the title compound.

¹H-NMR (DMSO-d6): δ=1.04+1.15 (3H), 1.47 (3H), 1.89 (1H), 2.06 (1H), 2.85-3.03 (2H), 3.05-3.59 (9H), 4.22 (2H), 4.66+4.82 (1H), 7.06 (1H), 7.99 (1H), 8.36 (1H), 8.52 (1H), 9.02 (1H), 12.80 (1H) ppm.

Example 232

(RS)-1-({4-[(6-Ethoxy-1H-indazol-5-yl)amino]-5,6,7,8-tetrahydro[1]benzothieno[2,3-d]pyrimidin-7-yl}carbonyl)azetidine-3-carbonitrile

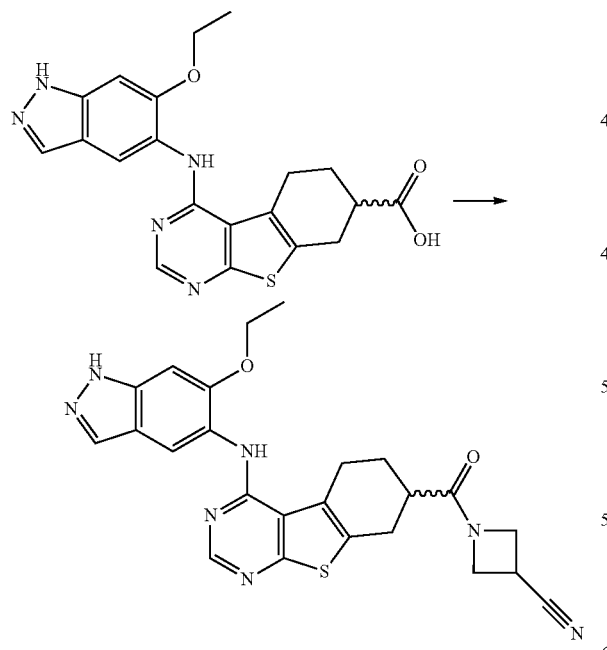

110 mg (269 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using azetidine-3-carbonitrile to give after working up and purification 6.0 mg (4%) of the title compound.

¹H-NMR (DMSO-d6): δ=1.49 (3H), 1.83 (1H), 2.09 (1H), 2.74-3.37 (5H), 3.82 (1H), 4.04 (1H), 4.12-4.28 (3H), 4.41-4.60 (2H), 7.07 (1H), 7.99 (1H), 8.35 (1H), 8.52 (1H), 9.01 (1H), 12.81 (1H) ppm.

Example 233

{(7RS)-4-[(6-Ethoxy-1H-indazol-5-yl)amino]-5,6,7,8-tetrahydro[1]benzothieno[2,3-d]pyrimidin-7-yl}[(3R)-3-hydroxypyrrolidin-1-yl]methanone

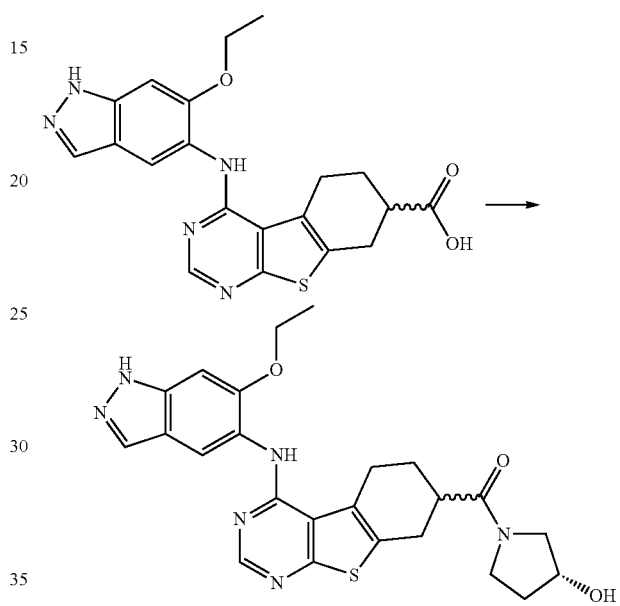

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (3S)-pyrrolidin-3-ol to give after working up and purification 11 mg (9%) of the title compound.

¹H-NMR (DMSO-d6): δ=1.48 (3H), 1.72-2.02 (3H), 2.11 (1H), 2.88-3.70 (9H), 4.18-4.37 (3H), 4.92+5.02 (1H), 7.07 (1H), 7.99 (1H), 8.37 (1H), 8.53 (1H), 9.02 (1H), 12.81 (1H) ppm.

Example 234

(RS)—N,N-Bis(2-hydroxyethyl)-4-[(6-methoxy-1H-indazol-5-yl)amino]-5,6,7,8-tetrahydro[1]benzothieno[2,3-d]pyrimidine-7-carboxamide

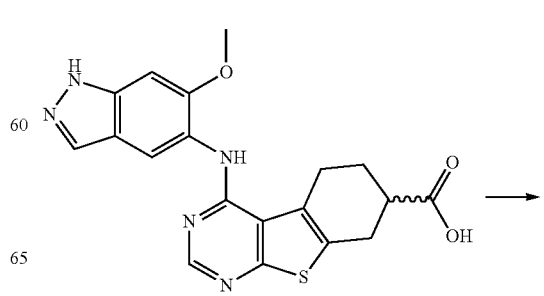

-continued

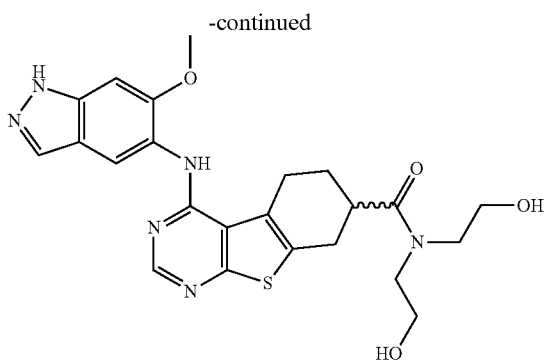

25 mg (63 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2,2'-iminodiethanol to give after working up and purification 6.5 mg (20%) of the title compound.

$^1$H-NMR (DMSO-d6): δ=1.85 (1H), 2.15 (1H), 2.87-3.01 (2H), 3.13-3.62 (11H), 3.98 (3H), 4.67 (1H), 4.83 (1H), 7.09 (1H), 7.99 (1H), 8.23 (1H), 8.46 (1H), 8.78 (1H), 12.82 (1H) ppm.

Example 235

(RS)—N—Cyclopropyl-4-[(6-ethoxy-1H-indazol-5-yl)amino]-N-methyl-5,6,7,8-tetrahydro[1]benzothieno[2,3-d]pyrimidine-7-carboxamide

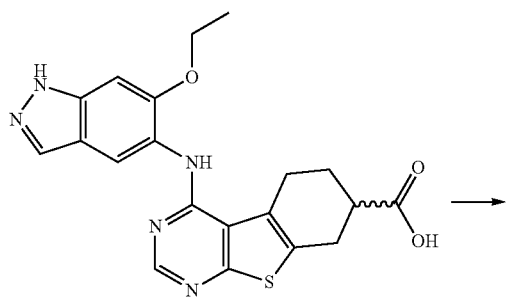

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-methylcyclopropanamine to give after working up and purification 17.0 mg (15%) of the title compound.

$^1$H-NMR (DMSO-d6): δ=0.73-0.94 (4H), 1.48 (3H), 1.85 (1H), 2.14 (1H), 2.81-3.01 (3H), 2.85 (3H), 3.15-3.41 (2H), 3.54 (1H), 4.22 (2H), 7.07 (1H), 8.00 (1H), 8.38 (1H), 8.53 (1H), 9.02 (1H), 12.82 (1H) ppm.

Example 236

(RS)-4-[(6-Ethoxy-1H-indazol-5-yl)amino]-N-ethyl-N-(propan-2-yl)-5,6,7,8-tetrahydro[1]benzothieno[2,3-d]pyrimidine-7-carboxamide

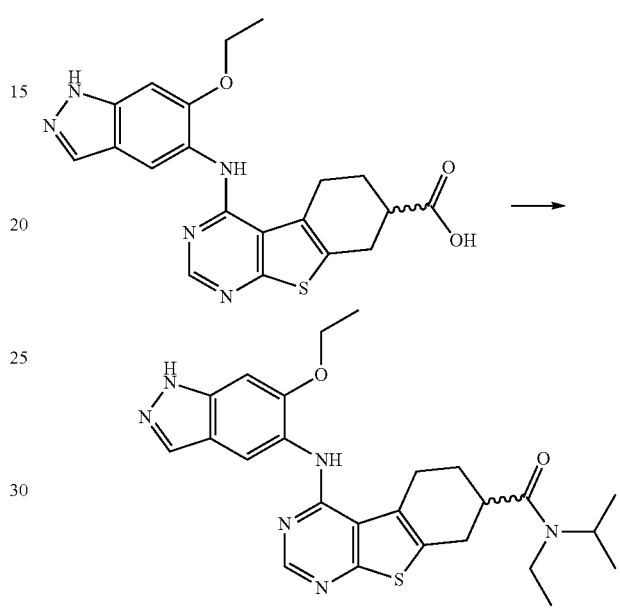

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-ethylpropan-2-amine to give after working up and purification 12.0 mg (10%) of the title compound.

$^1$H-NMR (DMSO-d6): δ=1.03-1.21 (9H), 1.48 (3H), 1.91 (1H), 2.03 (1H), 2.86-2.94 (1H), 2.91 (1H), 2.99 (1H), 3.14-3.37 (4H), 4.22 (2H), 4.26+4.54 (1H), 7.07 (1H), 7.99 (1H), 8.37 (1H), 8.53 (1H), 9.03 (1H), 12.81 (1H) ppm.

Example 237

(RS)-1-({4-[(6-Methoxy-1H-indazol-5-yl)amino]-5,6,7,8-tetrahydro[1]benzothieno[2,3-d]pyrimidin-7-yl}carbonyl)azetidine-3-carbonitrile

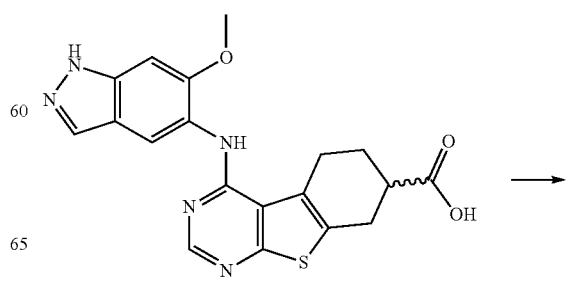

-continued

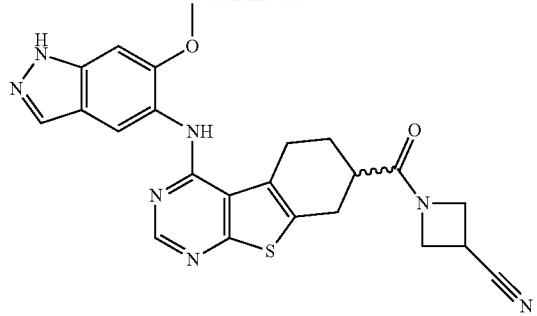

200 mg (506 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using azetidine-3-carbonitrile to give after working up and purification 140 mg (60%) of the title compound.

$^1$H-NMR (DMSO-d6): δ=1.81 (1H), 2.16 (1H), 2.70-3.39 (5H), 3.82 (1H), 3.98 (3H), 4.05 (1H), 4.19 (1H), 4.45-4.60 (2H), 7.09 (1H), 7.99 (1H), 8.21 (1H), 8.45 (1H), 8.76 (1H), 12.84 (1H) ppm.

Example 238

(RS)—N-tert-Butyl-4-[(6-ethoxy-1H-indazol-5-yl)amino]-N-methyl-5,6,7,8-tetrahydro[1]benzothieno[2,3-d]pyrimidine-7-carboxamide

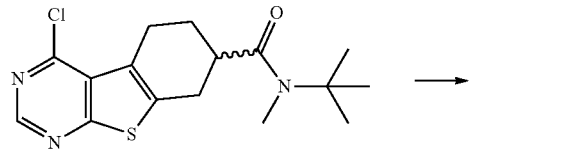

49 mg (145 µmol) (RS)—N-tert-butyl-4-chloro-N-methyl-5,6,7,8-tetrahydro[1]benzothieno[2,3-d]pyrimidine-7-carboxamide (prepared according to example 238a) were transformed in analogy to example 1 using 6-ethoxy-1H-indazol-5-amine to give after working up and purification 22 mg (32%) of the title compound.

$^1$H-NMR (DMSO-d6): δ=1.37 (9H), 1.48 (3H), 1.86 (1H), 2.07 (1H), 2.91 (2H), 2.98 (3H), 3.09-3.31 (3H), 4.23 (2H), 7.07 (1H), 7.99 (1H), 8.35 (1H), 8.52 (1H), 9.02 (1H), 12.80 (1H) ppm.

Example 238a (RS)—N-tert-butyl-4-chloro-N-methyl-5,6,7,8-tetrahydro[1]benzothieno[2,3-d]pyrimidine-7-carboxamide

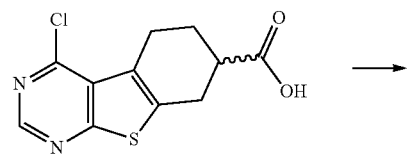

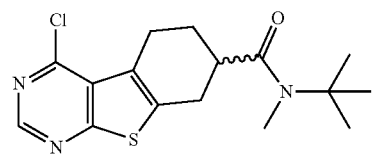

100 mg (372 µmol) (RS)-4-chloro-5,6,7,8-tetrahydro[1]benzothieno[2,3-d]pyrimidine-7-carboxylic acid (prepared according to intermediate example 1a) were transformed in analogy to intermediate example 2a using N,2-dimethylpropan-2-amine to give after working up and purification 50.1 mg (40%) of the title compound.

Example 239

(RS)-{4-[(6-Ethoxy-1H-indazol-5-yl)amino]-5,6,7,8-tetrahydro[1]benzothieno[2,3-d]pyrimidin-7-yl}(2-oxa-6-azaspiro[3.3]hept-6-yl)methanone

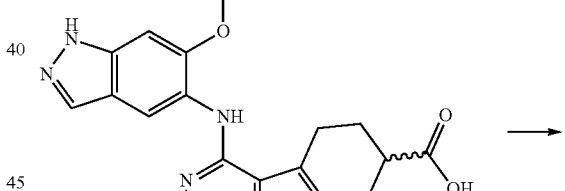
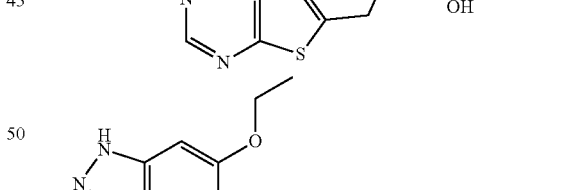
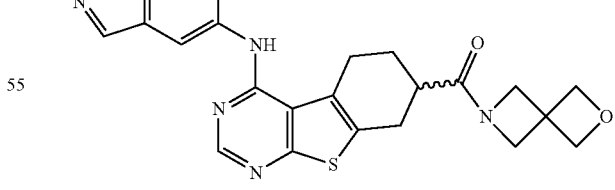
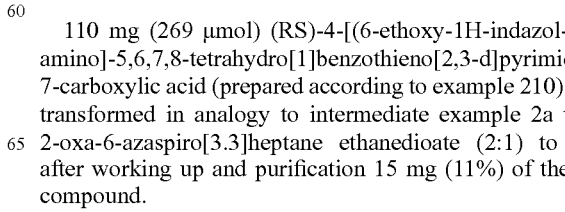

110 mg (269 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2-oxa-6-azaspiro[3.3]heptane ethanedioate (2:1) to give after working up and purification 15 mg (11%) of the title compound.

¹H-NMR (DMSO-d6): δ=1.47 (3H), 1.83 (1H), 2.06 (1H), 2.72-2.98 (3H), 3.09-3.40 (2H), 4.05 (2H), 4.21 (2H), 4.40 (2H), 4.68 (4H), 7.06 (1H), 7.99 (1H), 8.35 (1H), 8.52 (1H), 9.01 (1H), 12.83 (1H) ppm.

Example 240

(RS)—N-(Cyclopropylmethyl)-4-[(6-ethoxy-1H-indazol-5-yl)amino]-N-methyl-5,6,7,8-tetrahydro[1]benzothieno[2,3-d]pyrimidine-7-carboxamide

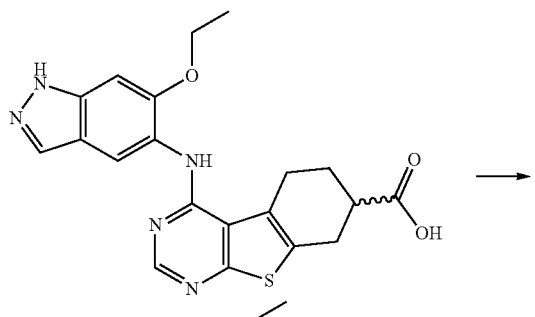

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 1-cyclopropyl-N-methylmethanamine to give after working up and purification 35 mg (30%) of the title compound.

¹H-NMR (DMSO-d6): δ=0.19-0.32 (2H), 0.47 (2H), 0.98 (1H), 1.48 (3H), 1.88 (1H), 2.06 (1H), 2.86-3.04 (3H), 2.93+3.14 (4H), 3.09-3.36 (3H), 4.22 (2H), 7.07 (1H), 7.99 (1H), 8.37 (1H), 8.52 (1H), 9.02 (1H), 12.80 (1H) ppm.

Example 241

(RS)-1-({4-[(6-Ethoxy-1H-indazol-5-yl)amino]-5,6,7,8-tetrahydro[1]benzothieno[2,3-d]pyrimidin-7-yl}carbonyl)piperidine-3-carbonitrile

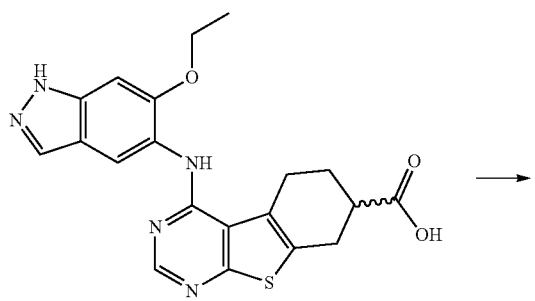

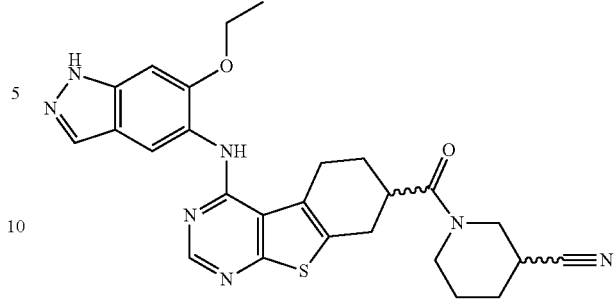

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (RS)-piperidine-3-carbonitrile to give after working up and purification 12 mg (10%) of the title compound.

¹H-NMR (DMSO-d6): δ=1.42-2.21 (7H), 1.49 (3H), 2.86-4.05 (9H), 4.23 (2H), 7.07 (1H), 7.99 (1H), 8.38 (1H), 8.53 (1H), 9.03 (1H), 12.81 (1H) ppm.

Example 242

(RS)—N-(2-Cyanoethyl)-4-[(6-ethoxy-1H-indazol-5-yl)amino]-N-ethyl-5,6,7,8-tetrahydro[1]benzothieno[2,3-d]pyrimidine-7-carboxamide

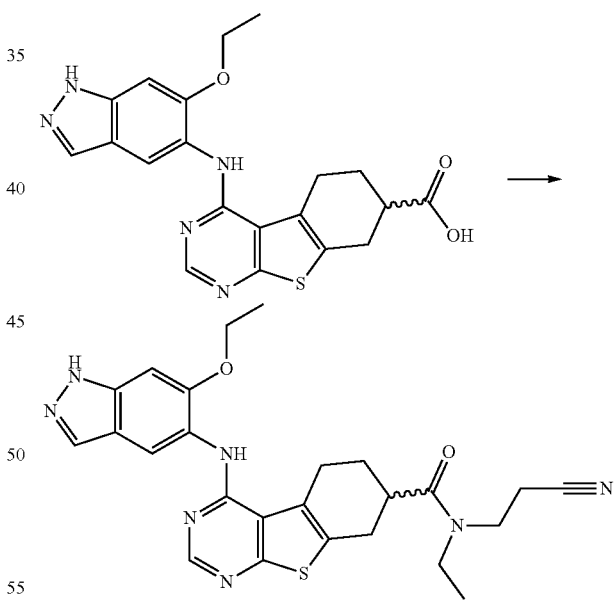

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 3-(ethylamino)propanenitrile to give after working up and purification 14 mg (11%) of the title compound.

¹H-NMR (DMSO-d6): δ=1.05+1.16 (3H), 1.48 (3H), 1.90 (1H), 2.08 (1H), 2.75+2.83 (2H), 2.89-3.02 (2H), 3.09-3.75 (7H), 4.22 (2H), 7.07 (1H), 7.99 (1H), 8.37 (1H), 8.53 (1H), 9.02 (1H), 12.81 (1H) ppm.

Example 243

[(3R,4R)-3,4-Dihydroxypyrrolidin-1-yl]{(7RS)-4-[(6-methoxy-1H-indazol-5-yl)amino]-5,6,7,8-tetrahydro[1]benzothieno[2,3-d]pyrimidin-7-yl}methanone

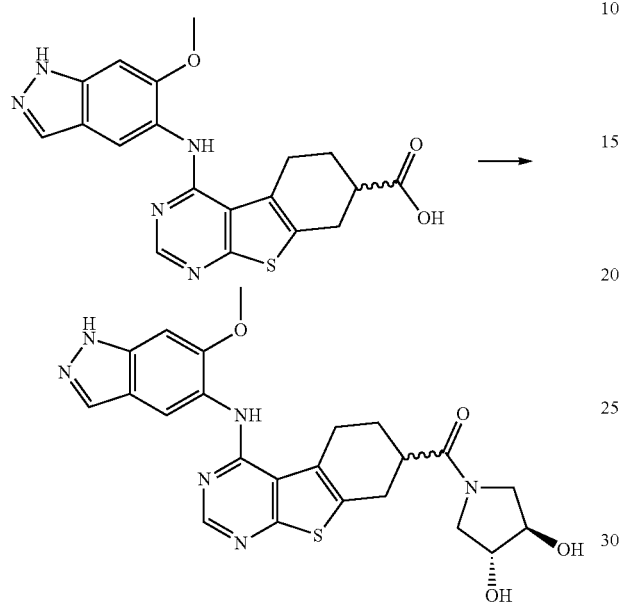

25 mg (63 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using (3R,4R)-pyrrolidine-3,4-diol to give after working up and purification 7.0 mg (22%) of the title compound.

¹H-NMR (DMSO-d6): δ=1.84 (1H), 2.17 (1H), 2.88-3.03 (3H), 3.13-3.37 (3H), 3.45 (2H), 3.74 (1H), 3.92 (1H), 3.98 (3H), 4.00 (1H), 5.15 (2H), 7.09 (1H), 7.99 (1H), 8.23 (1H), 8.46 (1H), 8.78 (1H), 12.84 (1H) ppm.

Example 244

[(3R,4R)-3,4-Dihydroxypyrrolidin-1-yl]{(7RS)-4-[(6-methoxy-1H-indazol-5-yl)amino]-5,6,7,8-tetrahydro[1]benzothieno[2,3-d]pyrimidin-7-yl}methanone

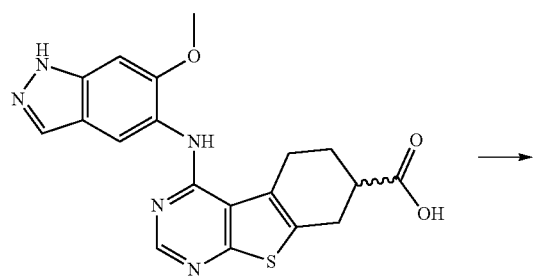

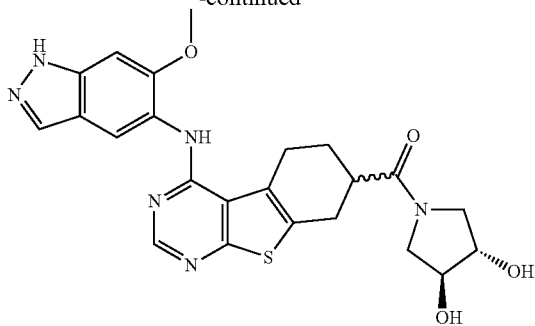

25 mg (63 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using (3S,4S)-pyrrolidine-3,4-diol to give after working up and purification 10.6 mg (33%) of the title compound.

¹H-NMR (DMSO-d6): δ=1.83 (1H), 2.16 (1H), 2.88-3.03 (3H), 3.11-3.51 (5H), 3.73 (1H), 3.92 (1H), 3.98 (3H), 4.00 (1H), 5.13 (2H), 7.09 (1H), 8.00 (1H), 8.23 (1H), 8.46 (1H), 8.78 (1H), 12.87 (1H) ppm.

Example 245

(RS)-4-[(6-Ethoxy-1H-indazol-5-yl)amino]-N-(2-methoxyethyl)-N-methyl-5,6,7,8-tetrahydro[1]benzothieno[2,3-d]pyrimidine-7-carboxamide

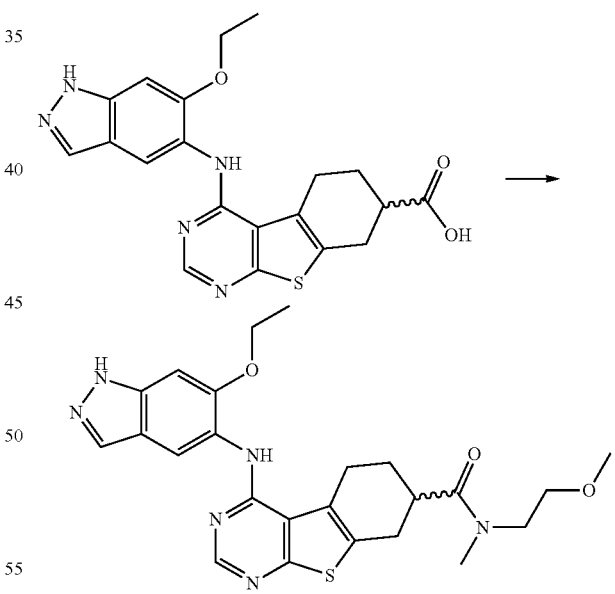

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2-methoxy-N-methylethanamine to give after working up and purification 20.0 mg (17%) of the title compound.

¹H-NMR (DMSO-d6): δ=1.48 (3H), 1.86 (1H), 2.09 (1H), 2.87+3.12 (3H), 2.84-2.99 (2H), 3.14-3.64 (10H), 4.23 (2H), 7.07 (1H), 7.99 (1H), 8.37 (1H), 8.53 (1H), 9.02 (1H), 12.80 (1H) ppm.

Example 246

{(7RS)-4-[(6-Ethoxy-1H-indazol-5-yl)amino]-5,6,7,8-tetrahydro[1]benzothieno[2,3-d]pyrimidin-7-yl}[(3S)-3-hydroxypyrrolidin-1-yl]methanone

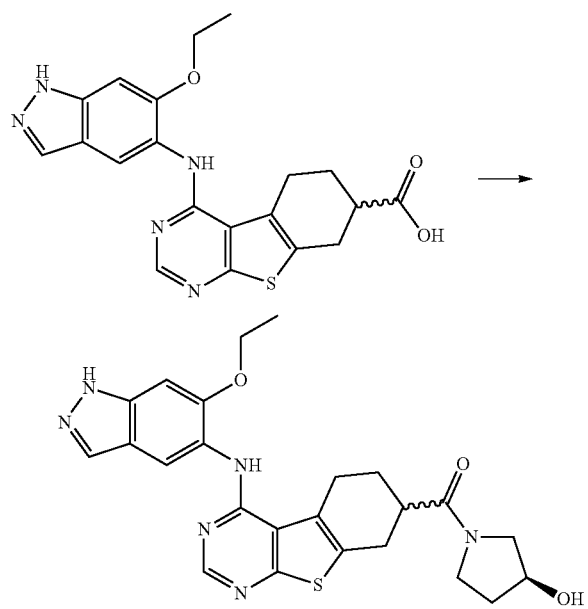

100 mg (244 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (3R)-pyrrolidin-3-ol to give after working up and purification 7.0 mg (6%) of the title compound.

$^1$H-NMR (DMSO-d6): δ=1.48 (3H), 1.72-2.02 (3H), 2.11 (1H), 2.86-3.09 (3H), 3.13-3.50 (5H), 3.64 (1H), 4.17-4.37 (3H), 4.92+5.02 (1H), 7.07 (1H), 7.99 (1H), 8.36 (1H), 8.52 (1H), 9.02 (1H), 12.80 (1H) ppm.

Example 247

(RS)-[4-(Cyclopropylmethyl)piperazin-1-yl]{4-[(6-ethoxy-1H-indazol-5-yl)amino]-5,6,7,8-tetrahydro[1]benzothieno[2,3-d]pyrimidin-7-yl}methanone

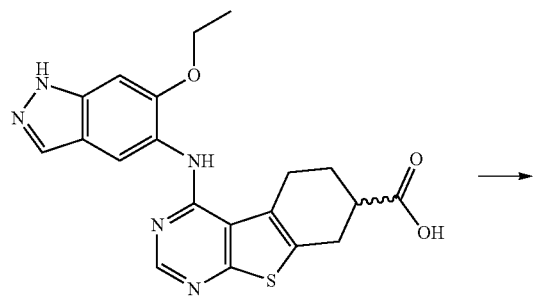

-continued

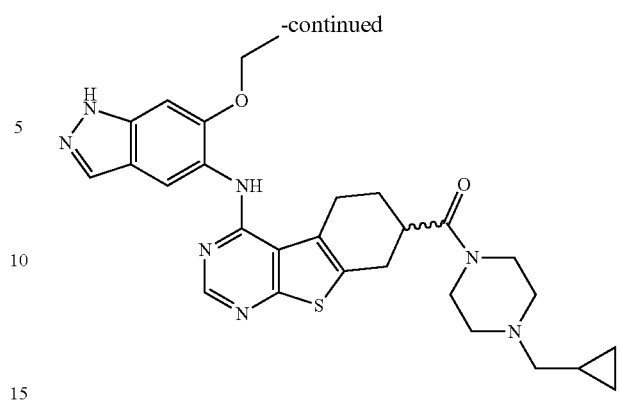

50 mg (122 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 1-(cyclopropylmethyl)piperazine to give after working up and purification 6.6 mg (10%) of the title compound.

$^1$H-NMR (DMSO-d6): δ=0.08 (2H), 0.46 (2H), 0.84 (1H), 1.48 (3H), 1.88 (1H), 2.07 (1H), 2.21 (2H), 2.35-2.53 (4H), 2.86-3.02 (2H), 3.15-3.37 (3H), 3.43-3.63 (4H), 4.22 (2H), 7.07 (1H), 7.99 (1H), 8.37 (1H), 8.52 (1H), 9.02 (1H), 12.80 (1H) ppm.

Example 248

(RS)-4-{[6-(Benzyloxy)-1H-indazol-5-yl]amino}-N,N-dimethyl-5,6,7,8-tetrahydro[1]benzothieno[2,3-d]pyrimidine-7-carboxamide

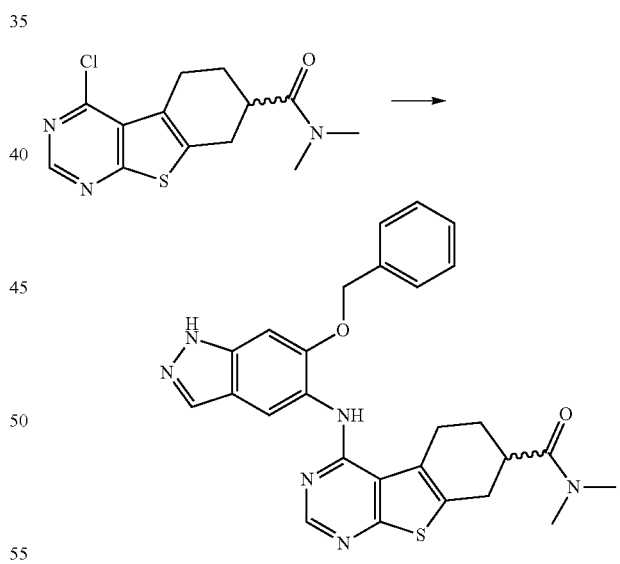

24.7 mg (83.4 µmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(benzyloxy)-1H-indazol-5-amine (prepared according to intermediate example 248b) to give after working up and purification 22 mg (53%) of the title compound.

$^1$H-NMR (DMSO-d6): δ=1.46 (2H), 2.65 (1H), 2.75-3.01 (4H), 2.88 (3H), 3.05 (3H), 5.25 (2H), 7.26 (1H), 7.37-7.49 (3H), 7.57 (2H), 8.01 (1H), 8.19 (1H), 8.50 (1H), 8.99 (1H), 12.87 (1H) ppm.

Example 248a (RS)-4-Chloro-N,N-dimethyl-5,6,7,8-tetrahydro[1]benzothieno[2,3-d]pyrimidine-7-carboxamide

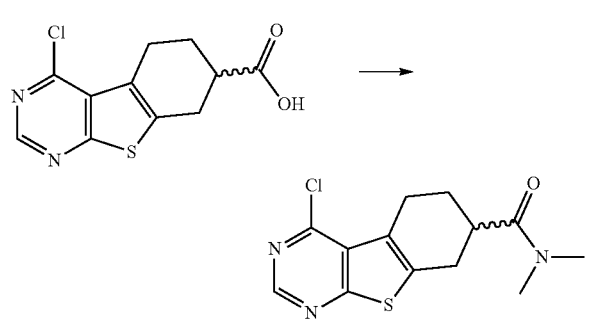

4.54 g (16.9 mmol) (RS)-4-chloro-5,6,7,8-tetrahydro[1]benzothieno[2,3-d]pyrimidine-7-carboxylic acid (prepared according to intermediate example 1a) were transformed in analogy to intermediate example 2a using N-methylmethanamine to give after working up and purification 3.44 g (65%) of the title compound.

Example 248b 6-(Benzyloxy)-1H-indazol-5-amine

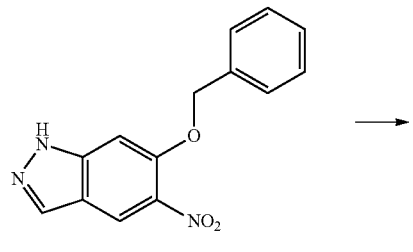

A mixture comprising 2.85 g (10.6 mmol) 6-(benzyloxy)-5-nitro-1H-indazole (prepared according to intermediate example 248c), 2.5 mL methylene chloride, 2.5 mL methanol and 14.3 g tin-(II)-chloride was stirred at 23° C. overnight. The solvents were removed and the residue purified by chromatography to give 2.34 g (92%) of the title compound.

Example 248c 6-(Benzyloxy)-5-nitro-1H-indazole

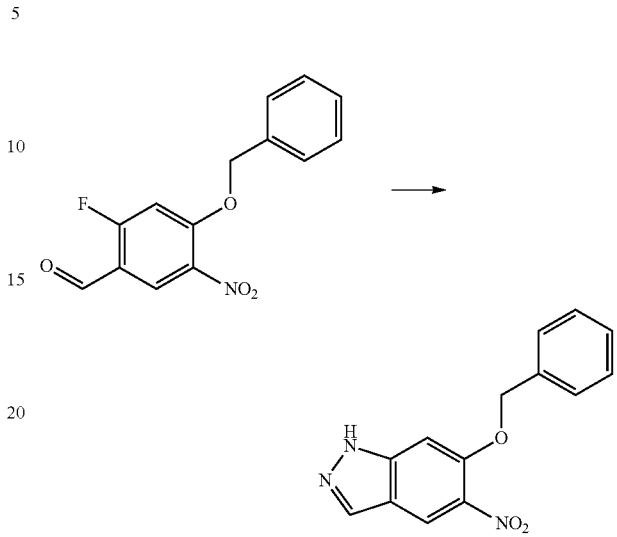

A mixture comprising 2.80 g (10.2 mmol) 4-(benzyloxy)-2-fluoro-5-nitrobenzaldehyde (prepared according to intermediate example 248d), 50 mL N,N-dimethylacetamide and 2.48 mL hydrazine hydrate was heated at 100° C. for 2 hours. The mixture was poured into water, the solid filtered, washed with hexane and dried to give 1.79 g (65%) of the title compound.

Example 248d 4-(Benzyloxy)-2-fluoro-5-nitrobenzaldehyde

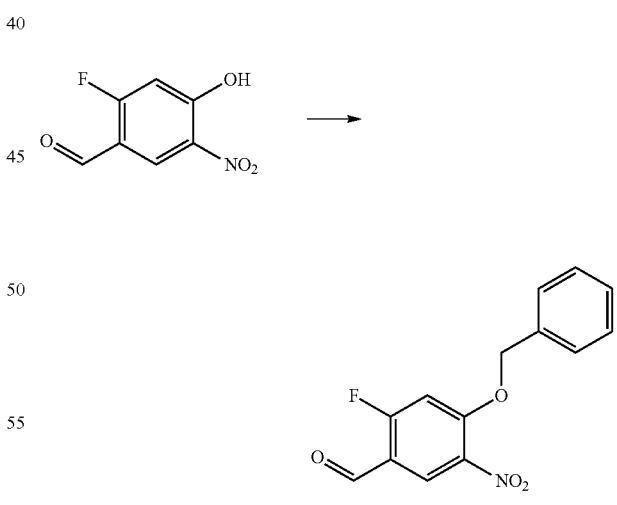

To a mixture comprising 1.00 g (5.40 mmol) 2-fluoro-4-hydroxy-5-nitrobenzaldehyde (prepared according to intermediate example 248e), 0.56 mL phenylmethanol, 1.7 g triphenylphosphane and 100 mL tetrahydrofuran were added at 3° C. 1.27 mL diisopropyl azodicarboxylate. The mixture was stirred at 23° C. overnight, concentrated and the residue was purified by chromatography to give 1.02 g (68%) of the title compound.

Example 248e

2-Fluoro-4-hydroxy-5-nitrobenzaldehyde

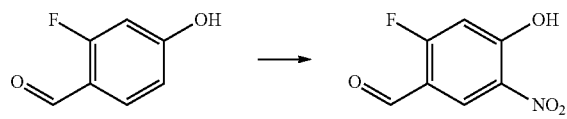 [SMILES: O=Cc1ccc(O)cc1F ; O=Cc1cc([N+](=O)[O-])c(O)cc1F]

A solution of 50.0 g (357 mmol) 2-fluoro-4-hydroxybenzaldehyde (CAS-No: 348-27-6) in 300 mL concentrated sulfuric acid was cooled to −15° C. A mixture comprising 22.5 mL nitric acid (65%) and 68.5 mL sulfuric acid was added slowly. After 1 hour the mixture was poured into ice-water. The precipitate was filtered, washed with water and hexan and dried to give 60.0 g (91%) of the title compound.

Example 249

(RS)—N,N-Dimethyl-4-{[6-(trifluoromethoxy)-1H-indazol-5-yl]amino}-5,6,7,8-tetrahydro[1]benzothieno[2,3-d]pyrimidine-7-carboxamide

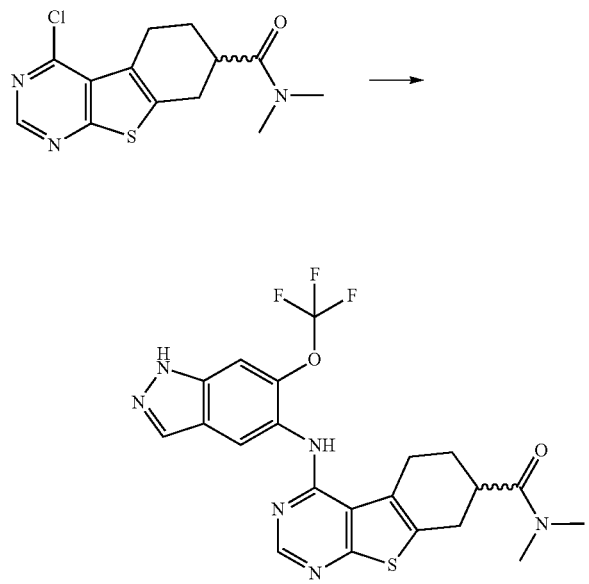 [SMILES: CN(C)C(=O)C1CCc2c(sc3ncnc(Cl)c23)C1 ; CCOc1cc2[nH]ncc2cc1Nc1ncnc2sc3c(c12)CCC(C(=O)N(C)C)C3]

100 mg (338 µmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(trifluoromethoxy)-1H-indazol-5-amine (prepared according to intermediate example 249a) to give after working up and purification 36 mg (23%) of the title compound.

$^1$H-NMR (DMSO-d6): δ=1.80 (1H), 2.07 (1H), 2.87 (3H), 2.88-3.00 (2H), 3.09 (3H), 3.11-3.27 (3H), 7.59 (1H), 8.16 (1H), 8.17 (1H), 8.21 (1H), 8.26 (1H), 13.24 (1H) ppm.

Example 249a 6-(Trifluoromethoxy)-1H-indazol-5-amine

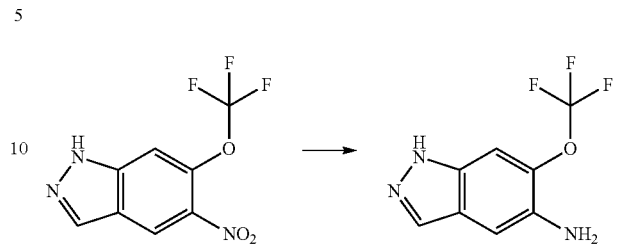

3.38 g (13.7 mmol) 5-nitro-6-(trifluoromethoxy)-1H-indazole (prepared according to intermediate example 249b) were transformed in analogy to intermediate example 69b to give after working up and purification 2.94 g (99%) of the title compound.

Example 249b

5-Nitro-6-(trifluoromethoxy)-1H-indazole (A) and N,N-dimethyl-5-nitro-1H-indazol-6-amine (B)

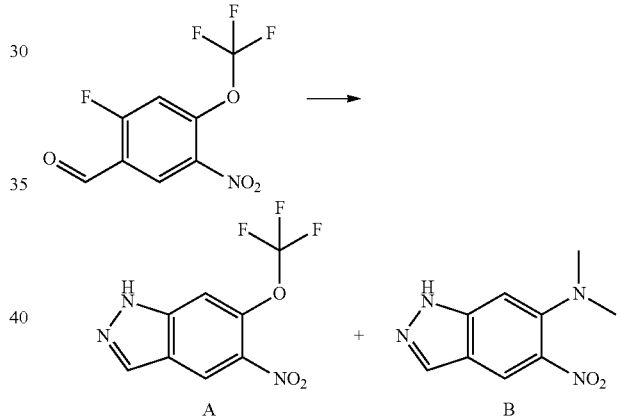

11.73 g (46.3 mmol) 2-fluoro-5-nitro-4-(trifluoromethoxy)benzaldehyde (prepared according to intermediate example 249c) were transformed in analogy to intermediate example 248c to give after working up and purification 3.44 g (30%) of the title compound A and 340 mg (4%) of the title compound B.

Example 249c

2-Fluoro-5-nitro-4-(trifluoromethoxy)benzaldehyde

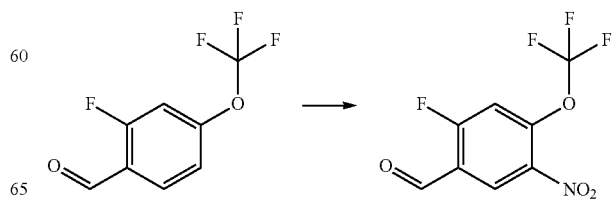

10.0 g (48.1 mmol) 2-fluoro-4-(trifluoromethoxy)benzaldehyde (JRD Fluorochemicals Ltd., United Kingdom) were transformed in analogy to intermediate example 248e to give after working up and purification 11.9 g (98%) of the title compound.

Example 250

(RS)-{4-[(6-Methoxy-1H-indazol-5-yl)amino]-5,6,7,8-tetrahydro[1]benzothieno[2,3-d]pyrimidin-7-yl}(2-oxa-6-azaspiro[3.3]hept-6-yl)methanone

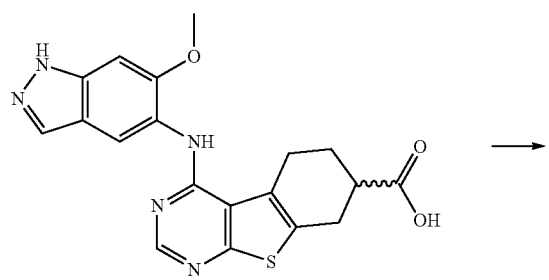

150 mg (379 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 2-oxa-6-azaspiro[3.3]heptane ethanedioate (2:1) to give after working up and purification 48.6 mg (27%) of the title compound.

$^1$H-NMR (DMSO-d6): δ=1.79 (1H), 2.12 (1H), 2.74 (1H), 2.82-2.94 (2H), 3.14 (1H), 3.25 (1H), 3.98 (3H), 4.06 (2H), 4.38-4.46 (2H), 4.64-4.73 (4H), 7.09 (1H), 7.99 (1H), 8.20 (1H), 8.45 (1H), 8.76 (1H), 12.84 (1H) ppm.

Example 251

(RS)-4-{[6-(Dimethylamino)-1H-indazol-5-yl]amino}-N,N-dimethyl-5,6,7,8-tetrahydro[1]benzothieno[2,3-d]pyrimidine-7-carboxamide

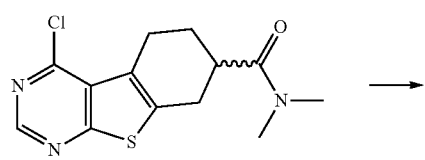

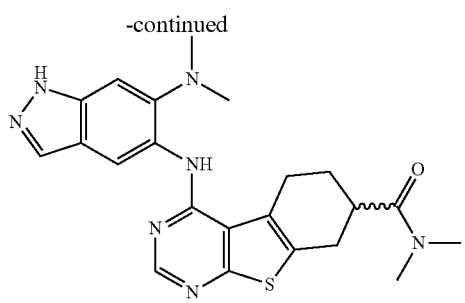

100 mg (338 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using $N^6,N^6$-dimethyl-1H-indazole-5,6-diamine (prepared according to intermediate example 251a) to give after working up and purification 10 mg (7%) of the title compound.

$^1$H-NMR (DMSO-d6): δ=1.85 (1H), 2.16 (1H), 2.72 (6H), 2.87 (3H), 2.91-2.97 (2H), 3.11 (3H), 3.16-3.29 (3H), 7.42 (1H), 8.03 (1H), 8.52 (1H), 8.99 (1H), 9.14 (1H), 12.87 (1H) ppm.

Example 251a $N^6,N^6$-Dimethyl-1H-indazole-5,6-diamine

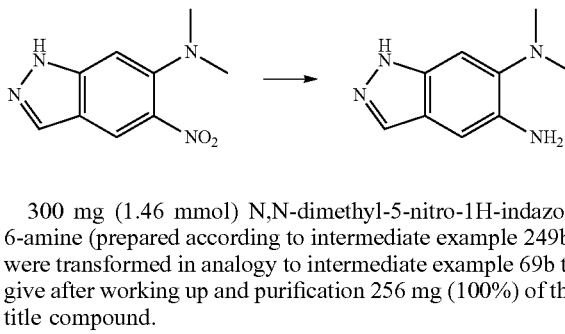

300 mg (1.46 mmol) N,N-dimethyl-5-nitro-1H-indazol-6-amine (prepared according to intermediate example 249b) were transformed in analogy to intermediate example 69b to give after working up and purification 256 mg (100%) of the title compound.

Example 252

(RS)-4-[(6-Ethoxy-1H-indazol-5-yl)amino]-N,N-bis(2-methoxyethyl)-5,6,7,8-tetrahydro[1]benzothieno[2,3-d]pyrimidine-7-carboxamide

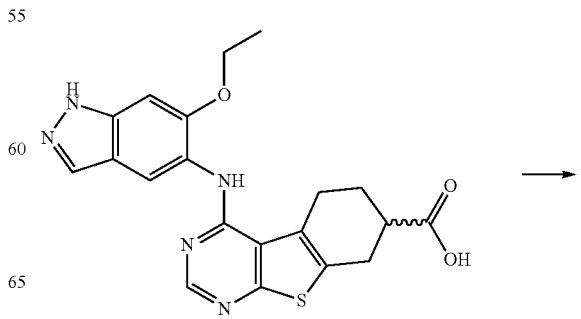

-continued

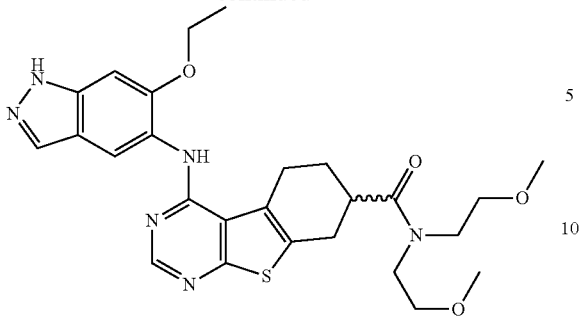

100 mg (244 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2-methoxy-N-(2-methoxyethyl)ethanamine to give after working up and purification 7.0 mg (5%) of the title compound.

$^1$H-NMR (DMSO-d6): δ=1.48 (3H), 1.89 (1H), 2.05 (1H), 2.92 (2H), 3.15-3.30 (3H), 3.25 (3H), 3.26 (3H), 3.39-3.56 (6H), 3.63 (2H), 4.22 (2H), 7.07 (1H), 7.99 (1H), 8.37 (1H), 8.53 (1H), 9.03 (1H), 12.83 (1H) ppm.

Example 253

(RS)-4-[(6-Ethoxy-1H-indazol-5-yl)amino]-N-methyl-N-propyl-5,6,7,8-tetrahydro[1]benzothieno[2,3-d]pyrimidine-7-carboxamide

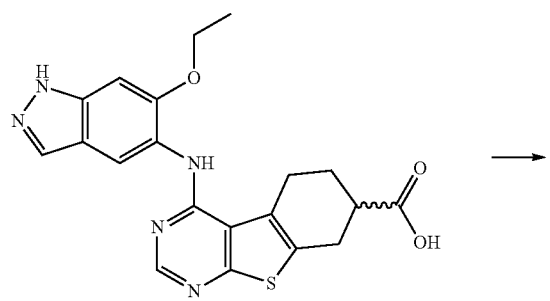

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-methylpropan-1-amine to give after working up and purification 25 mg (44%) of the title compound.

$^1$H-NMR (DMSO-d6): δ=0.79-0.92 (3H), 1.48 (3H), 1.55 (2H), 1.87 (1H), 2.06 (1H), 2.85+3.07 (3H), 2.88-3.01 (2H), 3.10-3.41 (5H), 4.22 (2H), 7.07 (1H), 7.99 (1H), 8.38 (1H), 8.53 (1H), 9.02 (1H), 12.83 (1H) ppm.

Example 254

(RS)-4-[(6-Ethoxy-1H-indazol-5-yl)amino]-N,N-dimethyl-5,6,7,8-tetrahydro[1]benzothieno[2,3-d]pyrimidine-7-carboxamide

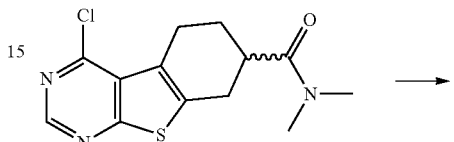

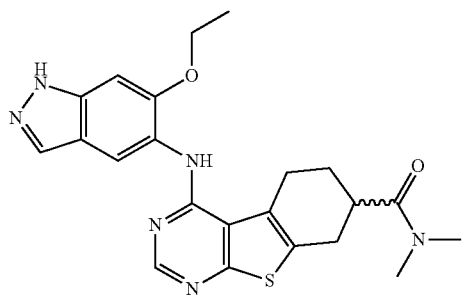

100 mg (338 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-ethoxy-1H-indazol-5-amine (prepared according to intermediate example 210b) to give after working up and purification 90.0 mg (61%) of the title compound.

$^1$H-NMR (DMSO-d6): δ=1.47 (3H), 1.85 (1H), 2.08 (1H), 2.87 (3H), 2.93 (2H), 3.09 (3H), 3.13-3.35 (3H), 4.22 (2H), 7.07 (1H), 8.00 (1H), 8.42 (1H), 8.53 (1H), 8.98 (1H), 12.69 (1H) ppm.

Example 255

(RS)-2,5-Dihydro-1H-pyrrol-1-yl{4-[(6-ethoxy-1H-indazol-5-yl)amino]-5,6,7,8-tetrahydro[1]benzothieno[2,3-d]pyrimidin-7-yl}methanone

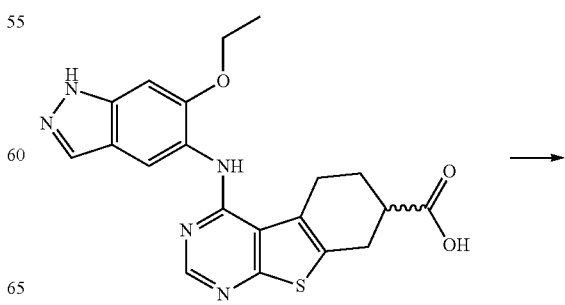

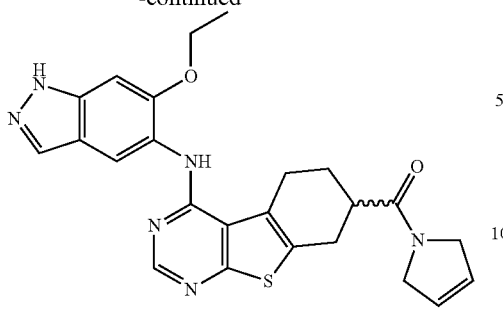

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 2,5-dihydro-1H-pyrrole to give after working up and purification 4.2 mg (7%) of the title compound.

¹H-NMR (DMSO-d6): δ=1.48 (3H), 1.89 (1H), 2.15 (1H), 2.92-3.06 (3H), 3.15-3.40 (2H), 4.12 (2H), 4.23 (2H), 4.41 (2H), 5.93 (2H), 7.07 (1H), 8.00 (1H), 8.37 (1H), 8.53 (1H), 9.02 (1H), 12.80 (1H) ppm.

Example 256

(RS)-4-{[6-(Benzyloxy)-1H-indazol-5-yl]amino}-N,N-dimethyl-5,6,7,8-tetrahydro[1]benzothieno[2,3-d]pyrimidine-7-carboxamide

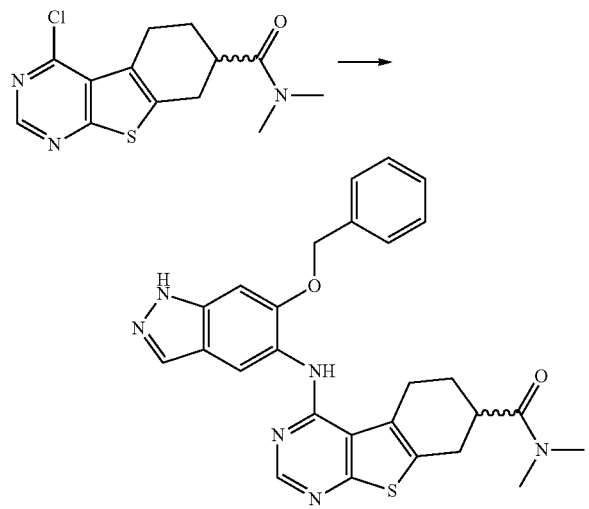

24.7 mg (83 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(benzyloxy)-1H-indazol-5-amine (prepared according to intermediate example 248b) to give after working up and purification 19.4 mg (47%) of the title compound.

¹H-NMR (DMSO-d6): δ=1.46 (2H), 2.59-2.73 (1H), 2.75-3.01 (4H), 2.88 (3H), 3.05 (3H), 5.25 (2H), 7.26 (1H), 7.37-7.49 (3H), 7.53-7.61 (2H), 8.01 (1H), 8.19 (1H), 8.50 (1H), 8.99 (1H), 12.87 (1H) ppm.

Example 257

(7RS)—N-[(2RS)-2,3-Dihydroxypropyl]-4-[(6-ethoxy-1H-indazol-5-yl)amino]-N-methyl-5,6,7,8-tetrahydro[1]benzothieno[2,3-d]pyrimidine-7-carboxamide

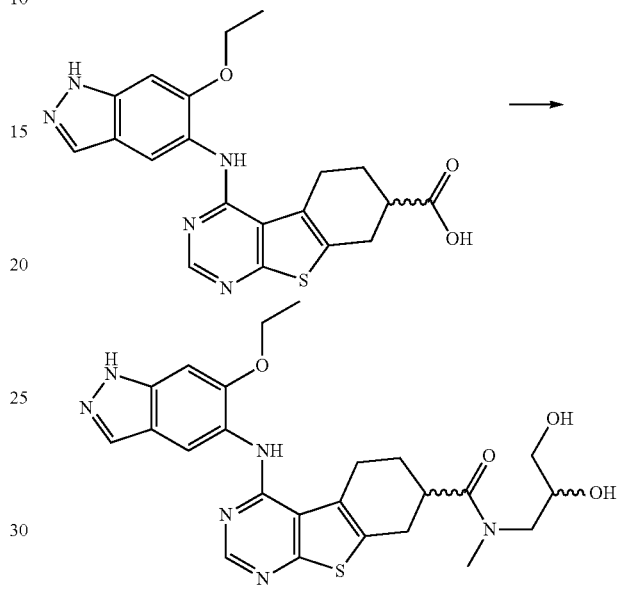

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (2RS)-3-(methylamino)propane-1,2-diol to give after working up and purification 20.8 mg (34%) of the title compound.

¹H-NMR (DMSO-d6): δ=1.48 (3H), 1.87 (1H), 2.10 (1H), 2.84-3.02 (4H), 3.10-3.56 (8H), 3.66 (1H), 4.22 (2H), 4.34-5.12 (2H), 7.07 (1H), 7.99 (1H), 8.37 (1H), 8.52 (1H), 9.02 (1H), 12.80 (1H) ppm.

Example 258

[(3RS)-3-(Dimethylamino)pyrrolidin-1-yl]{(7RS)-4-[(6-ethoxy-1H-indazol-5-yl)amino]-5,6,7,8-tetrahydro[1]benzothieno[2,3-d]pyrimidin-7-yl}methanone

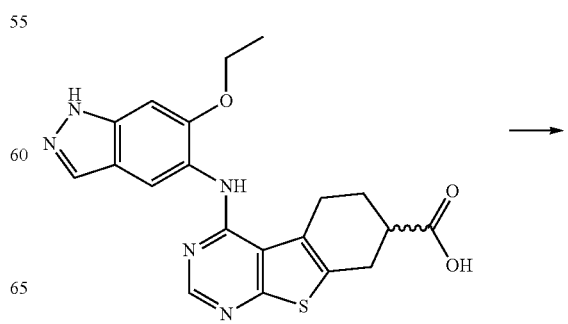

-continued

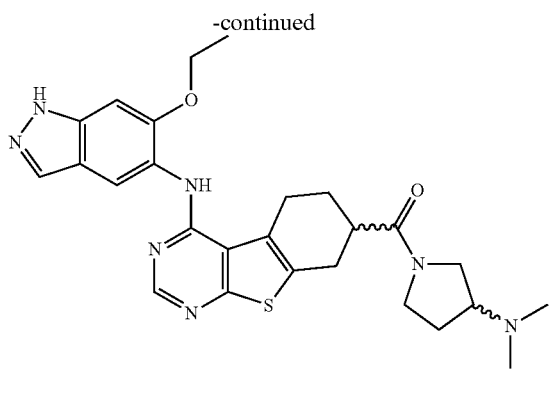

50 mg (122 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (3RS)—N,N-dimethylpyrrolidin-3-amine to give after working up and purification 6.8 mg (11%) of the title compound.

$^1$H-NMR (DMSO-d6): δ=1.48 (3H), 1.57-1.93 (2H), 1.96-2.22 (2H), 2.16 (6H), 2.43-2.69 (1H), 2.88-3.07 (3H), 3.13-3.30 (3H), 3.47-3.90 (3H), 4.22 (2H), 7.07 (1H), 8.00 (1H), 8.37 (1H), 8.53 (1H), 9.02 (1H), 12.83 (1H) ppm.

Example 259

(RS)-{4-[(6-Isopropoxy-1H-indazol-5-yl)amino]-5,6,7,8-tetrahydro[1]benzothieno[2,3-d]pyrimidin-7-yl}(1-oxa-6-azaspiro[3.3]hept-6-yl)methanone

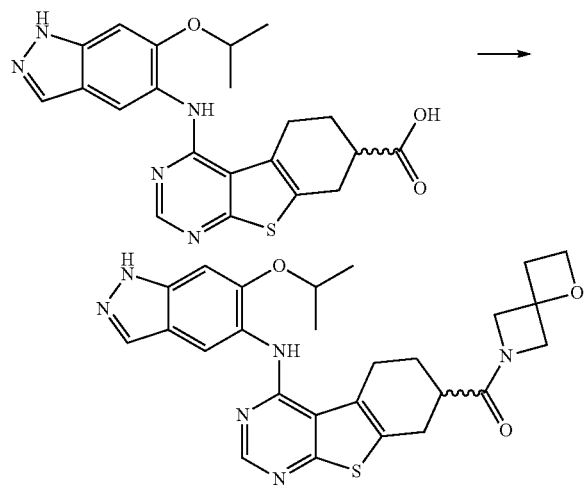

50 mg (118 µmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 1-oxa-6-azaspiro[3.3]heptane ethanedioate (1:1) to give after working up and purification 21.6 mg (34%) of the title compound.

$^1$H-NMR (DMSO-d6): δ=1.41 (6H), 1.85 (1H), 2.07 (1H), 2.76-2.98 (5H), 3.17 (1H), 3.29 (1H), 3.96 (1H), 4.13 (1H), 4.31-4.53 (4H), 4.88 (1H), 7.11 (1H), 7.98 (1H), 8.35 (1H), 8.52 (1H), 9.06 (1H), 12.75 (1H) ppm.

Example 260

(RS)-{4-[(6-Methoxy-1H-indazol-5-yl)amino]-5,6,7,8-tetrahydro[1]benzothieno[2,3-d]pyrimidin-7-yl}(1-oxa-6-azaspiro[3.3]hept-6-yl)methanone

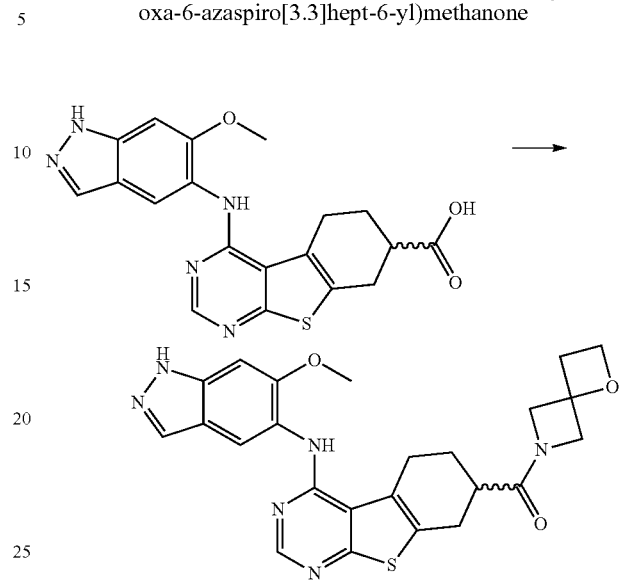

50 mg (126 µmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 1-oxa-6-azaspiro[3.3]heptane ethanedioate (1:1) to give after working up and purification 4.1 mg (7%) of the title compound.

$^1$H-NMR (DMSO-d6): δ=1.79 (1H), 2.13 (1H), 2.73-2.95 (5H), 3.12 (1H), 3.24 (1H), 3.96 (1H), 3.98 (3H), 4.14 (1H), 4.34-4.53 (4H), 7.08 (1H), 7.99 (1H), 8.20 (1H), 8.45 (1H), 8.77 (1H), 12.83 (1H) ppm.

Example 261

(RS)-5-Azaspiro[2.4]hept-5-yl{4-[(6-isopropoxy-1H-indazol-5-yl)amino]-5,6,7,8-tetrahydro[1]benzothieno[2,3-d]pyrimidin-7-yl}methanone

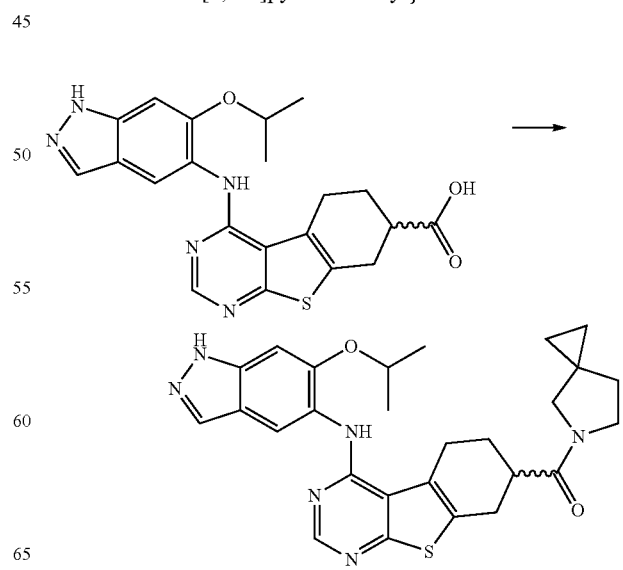

50 mg (118 μmol) (RS)-4-[(6-isopropoxy-1H-indazol-5-yl)amino]-5,6,7,8-tetrahydro[1]benzothieno[2,3-d]pyrimidine-7-carboxylic acid (prepared according to example 69) were transformed in analogy to intermediate example 2a using 5-azaspiro[2.4]heptane to give after working up and purification 26.0 mg (42%) of the title compound.

¹H-NMR (DMSO-d6): δ=0.50-0.67 (4H), 1.40 (6H), 1.67-1.98 (3H), 2.11 (1H), 2.86-3.08 (3H), 3.14-3.30 (3H), 3.49 (2H), 3.72 (1H), 4.89 (1H), 7.11 (1H), 7.99 (1H), 8.37 (1H), 8.53 (1H), 9.07 (1H), 12.77 (1H) ppm.

Example 262

{(7RS)-4-[(6-Methoxy-1H-indazol-5-yl)amino]-5,6,7,8-tetrahydro[1]benzothieno[2,3-d]pyrimidin-7-yl}[(1S,4S)-2-oxa-5-azabicyclo[2.2.1]hept-5-yl]methanone

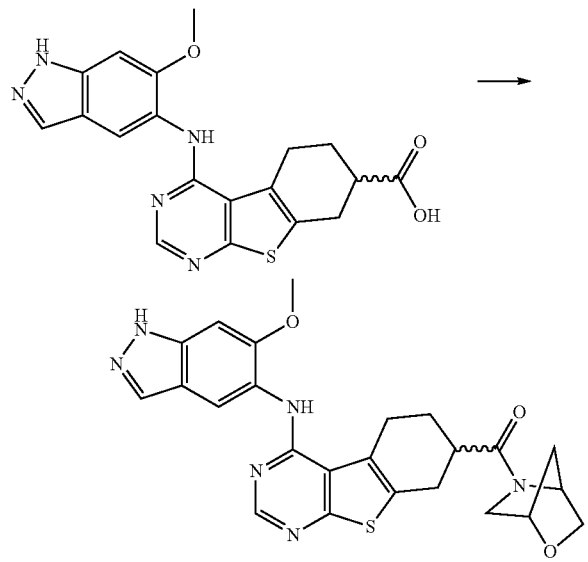

40 mg (101 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using (1S,4S)-2-oxa-5-azabicyclo[2.2.1]heptane to give after working up and purification 31.0 mg (61%) of the title compound.

¹H-NMR (DMSO-d6): δ=1.75-1.93 (3H), 2.16 (1H), 2.77-3.35 (6H), 3.51-3.80 (3H), 3.97+3.99 (3H), 4.61+4.67 (1H), 4.77+4.87 (1H), 7.09 (1H), 7.99 (1H), 8.18-8.25 (1H), 8.44-8.48 (1H), 8.74-8.81 (1H), 12.84 (1H) ppm.

Example 263

(RS)-(1,1-Dioxido-1-thia-6-azaspiro[3.3]hept-6-yl){4-[(6-ethoxy-1H-indazol-5-yl)amino]-5,6,7,8-tetrahydro[1]benzothieno[2,3-d]pyrimidin-7-yl}methanone

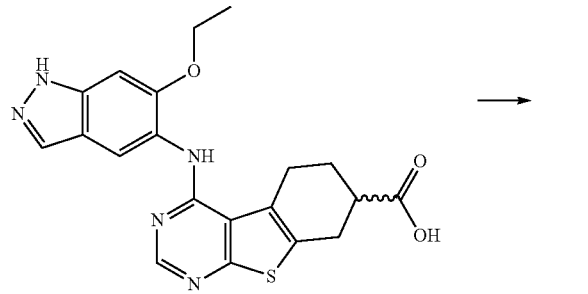

-continued

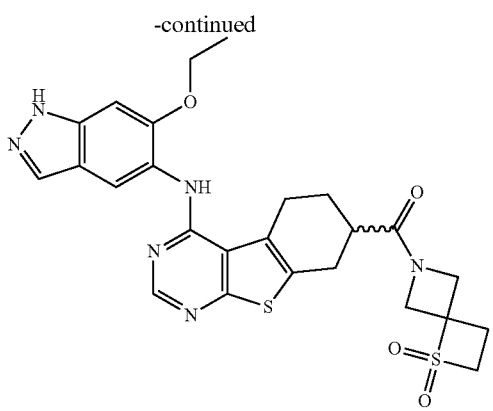

275 mg (672 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using 1-thia-6-azaspiro[3.3]heptane 1,1-dioxide trifluoroacetate (1:1) to give after working up and purification 78 mg (21%) of the title compound.

¹H-NMR (DMSO-d6): δ=1.46 (3H), 1.83 (1H), 2.08 (1H), 2.43 (2H), 2.75-3.43 (6H), 4.08-4.31 (5H), 4.48-4.76 (2H), 7.04 (1H), 7.99 (1H), 8.33 (1H), 8.52 (1H), 9.01 (1H), 12.82 (1H) ppm.

Example 264

(RS)-(1,1-Dioxido-1-thia-6-azaspiro[3.3]hept-6-yl){4-[(6-methoxy-1H-indazol-5-yl)amino]-5,6,7,8-tetrahydro[1]benzothieno[2,3-d]pyrimidin-7-yl}methanone

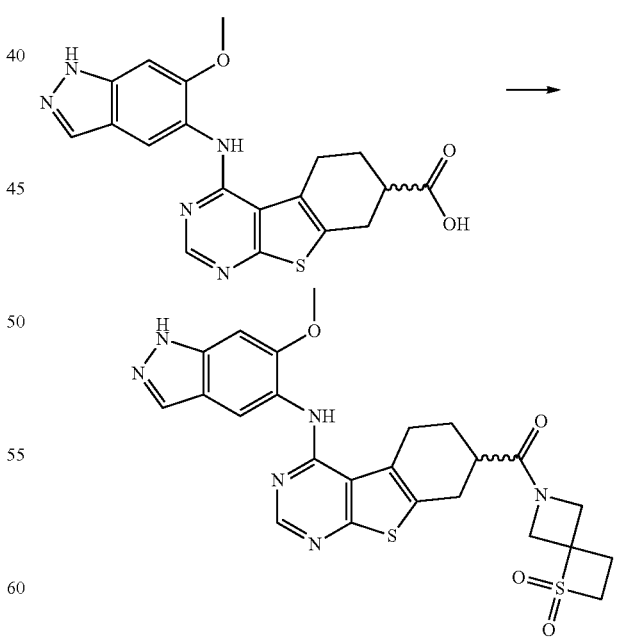

200 mg (506 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using 1-thia-6-azaspiro[3.3]heptane 1,1-dioxide trifluoroacetate (1:1) to give after working up and purification 54.3 mg (20%) of the title compound.

$^1$H-NMR (DMSO-d6): δ=1.81 (1H), 2.16 (1H), 2.43 (2H), 2.79-2.99 (3H), 3.08-3.26 (2H), 3.98 (3H), 4.12 (2H), 4.18 (1H), 4.28 (1H), 4.55 (1H), 4.70 (1H), 7.09 (1H), 7.99 (1H), 8.21 (1H), 8.46 (1H), 8.76 (1H), 12.84 (1H) ppm.

Example 265

(3RS)-1-({(7RS)-4-[(6-Ethoxy-1H-indazol-5-yl)amino]-5,6,7,8-tetrahydro[1]benzothieno[2,3-d]pyrimidin-7-yl}carbonyl)pyrrolidine-3-carbonitrile

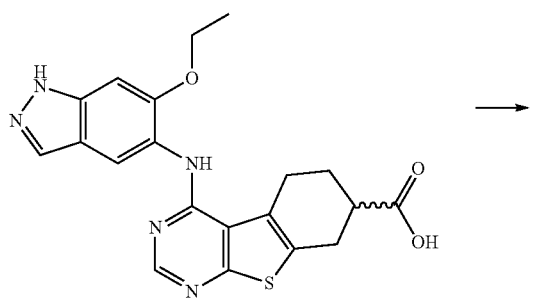

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (RS)-pyrrolidine-3-carbonitrile to give after working up and purification 17.0 mg (29%) of the title compound.

$^1$H-NMR (DMSO-d6): δ=1.48 (3H), 1.88 (1H), 2.06-2.45 (4H), 2.88-3.08 (3H), 3.15-3.98 (6H), 4.23 (2H), 7.07 (1H), 8.00 (1H), 8.36 (1H), 8.53 (1H), 9.02 (1H), 12.85 (1H) ppm.

Example 266

(RS)-4-{[6-(2-Chloroethoxy)-1H-indazol-5-yl]amino}-N,N-dimethyl-5,6,7,8-tetrahydro[1]benzothieno[2,3-d]pyrimidine-7-carboxamide

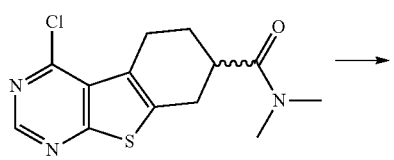

-continued

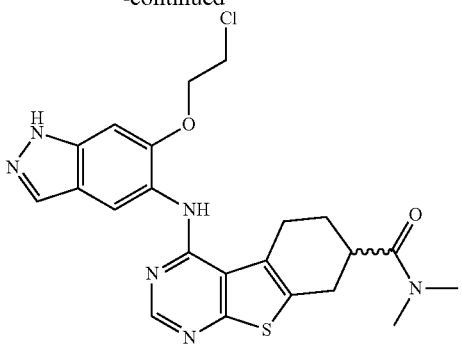

35 mg (118 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(2-chloroethoxy)-1H-indazol-5-amine (prepared according to intermediate example 266a) to give after working up and purification 4.9 mg (8%) of the title compound.

$^1$H-NMR (DMSO-d6): δ=1.82 (1H), 2.14 (1H), 2.87 (3H), 2.89-3.00 (2H), 3.09 (3H), 3.16 (1H), 3.23-3.38 (2H), 4.12 (2H), 4.47 (2H), 7.11 (1H), 8.01 (1H), 8.28 (1H), 8.52 (1H), 9.05 (1H), 12.86 (1H) ppm.

Example 266a 6-(2-Chloroethoxy)-1H-indazol-5-amine

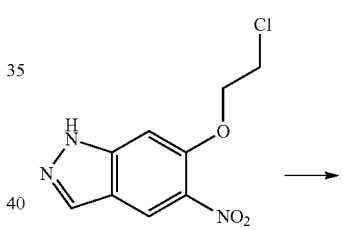

830 mg (3.44 mmol) 6-(2-chloroethoxy)-5-nitro-1H-indazole (prepared according to intermediate example 266b) were transformed in analogy to intermediate example 69b to give after working up and purification 724 mg (99%) of the title compound.

Example 266b 6-(2-Chloroethoxy)-5-nitro-1H-indazole

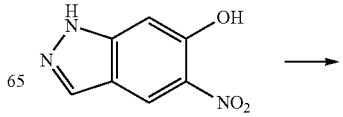

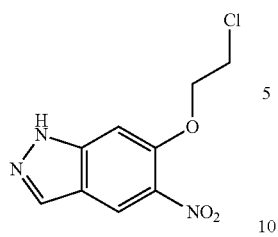

1.00 g (5.58 mmol) 5-nitro-1H-indazol-6-ol (prepared according to intermediate example 266c) were transformed in analogy to intermediate example 248d using 2-chloroethanol to give after working up and purification 937 mg (69%) of the title compound.

Example 266c

5-Nitro-1H-indazol-6-ol

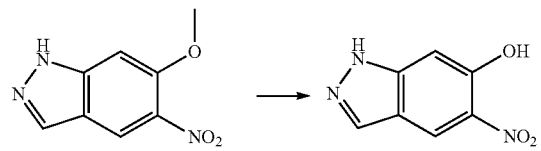

A mixture comprising 5.00 g (25.9 mmol) 6-methoxy-5-nitro-1H-indazole (CAS-No: 152626-75-0), 240 mL dichloromethane and 10.36 g aluminum trichloride was heated overnight. The mixture was cooled to 3° C. followed by careful addition of ice and water. Dichloromethane and methanol were added and the precipitate removed by filtration. The organic of the filtrate was separated and dried over sodium sulfate. After filtration and removal of the solvent the residue together with the previously removed precipitate was purified by chromatography to give 3.11 g (67%) of the title compound.

Example 267

(RS)-4-{[6-(3-Chloropropoxy)-1H-indazol-5-yl]amino}-N,N-dimethyl-5,6,7,8-tetrahydro[1]benzothieno[2,3-d]pyrimidine-7-carboxamide

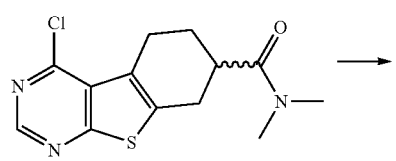

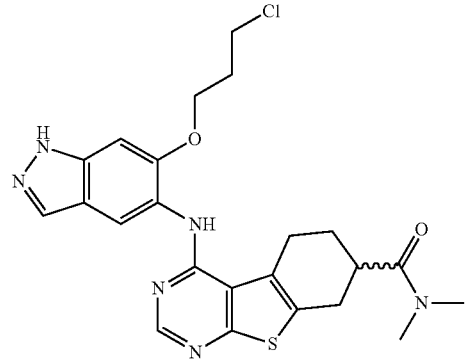

35 mg (118 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(3-chloropropoxy)-1H-indazol-5-amine (prepared according to intermediate example 267a) to give after working up and purification 27.9 mg (40%) of the title compound.

$^1$H-NMR (DMSO-d6): δ=1.82 (1H), 2.12 (1H), 2.29 (2H), 2.87 (3H), 2.89-2.98 (2H), 3.05-3.33 (3H), 3.10 (3H), 3.84 (2H), 4.27 (2H), 7.10 (1H), 8.01 (1H), 8.31 (1H), 8.51 (1H), 8.93 (1H), 12.77 (1H) ppm.

Example 267a 6-(3-Chloropropoxy)-1H-indazol-5-amine

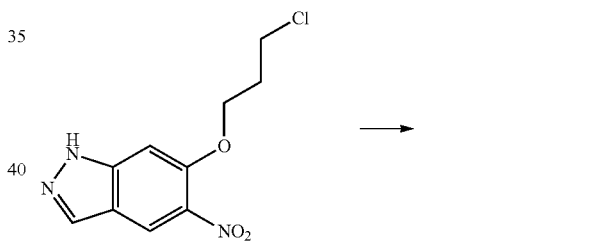

814 mg (3.18 mmol) 6-(3-chloropropoxy)-1H-indazol-5-amine (prepared according to intermediate example 267b) were transformed in analogy to intermediate example 69b to give after working up and purification 685 mg (95%) of the title compound.

Example 267b 6-(3-Chloropropoxy)-1H-indazol-5-amine

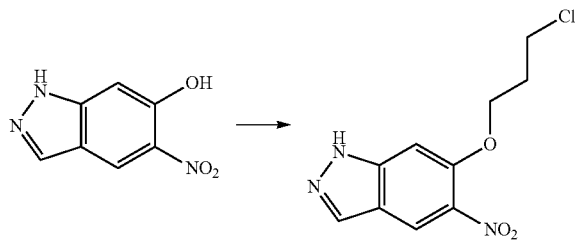 [SMILES: O=[N+]([O-])c1cc2cn[nH]c2cc1O ; O=[N+]([O-])c1cc2cn[nH]c2cc1OCCCCl]

1.00 g (5.58 mmol) 5-nitro-1H-indazol-6-ol (prepared according to intermediate example 266c) were transformed in analogy to intermediate example 248d using 3-chloropropan-1-ol to give after working up and purification 820 mg (57%) of the title compound.

Example 268

(RS)-tert-Butyl {2-[({4-[(6-ethoxy-1H-indazol-5-yl)amino]-5,6,7,8-tetrahydro[1]benzothieno[2,3-d]pyrimidin-7-yl}carbonyl)(methyl)amino]ethyl}carbamate

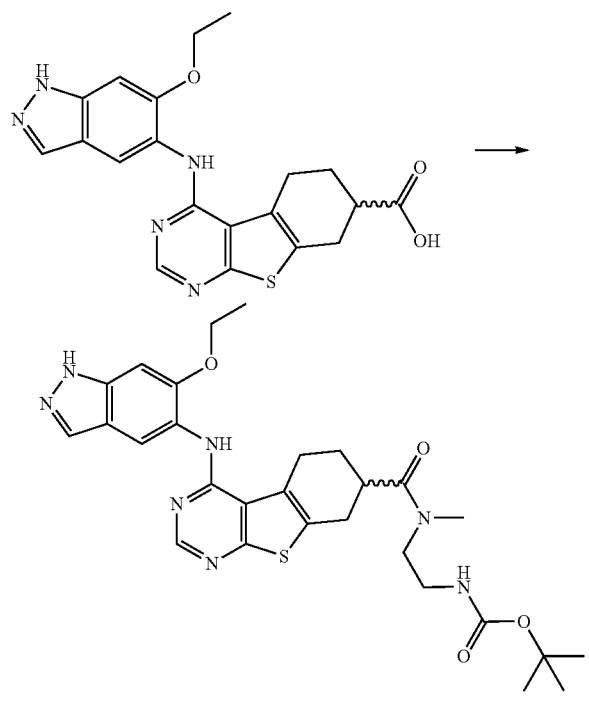

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using tert-butyl[2-(methylamino)ethyl]carbamate to give after working up and purification 41.0 mg (56%) of the title compound.

$^1$H-NMR (DMSO-d6): δ=1.29+1.38 (9H), 1.48 (3H), 1.85 (1H), 2.08 (1H), 2.84+3.09 (3H), 2.88-3.58 (9H), 4.22 (2H), 6.84+6.99 (1H), 7.07 (1H), 8.00 (1H), 8.37 (1H), 8.53 (1H), 9.02 (1H), 12.83 (1H) ppm.

Example 269

(RS)—N,N-Dimethyl-4-[(6-propoxy-1H-indazol-5-yl)amino]-5,6,7,8-tetrahydro[1]benzothieno[2,3-d]pyrimidine-7-carboxamide 117 mg (395 μmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-propoxy-1H-indazol-5-amine (prepared according to intermediate example 269a) to give after working up and purification 106 mg (60%) of the title compound.

$^1$H-NMR (DMSO-d6): δ=1.04 (3H), 1.78-1.91 (3H), 2.07 (1H), 2.87 (3H), 2.93 (2H), 3.09 (3H), 3.15-3.33 (3H), 4.12 (2H), 7.07 (1H), 8.00 (1H), 8.35 (1H), 8.52 (1H), 8.97 (1H), 12.82 (1H) ppm.

Example 269a

6-Propoxy-1H-indazol-5-amine 620 mg (2.83 mmol) 6-(allyloxy)-5-nitro-1H-indazole (prepared according to intermediate example 269a) were transformed in analogy to intermediate example 69b to give after working up and purification 520 mg (96%) of the title compound.

Example 269a 6-(Allyloxy)-5-nitro-1H-indazole

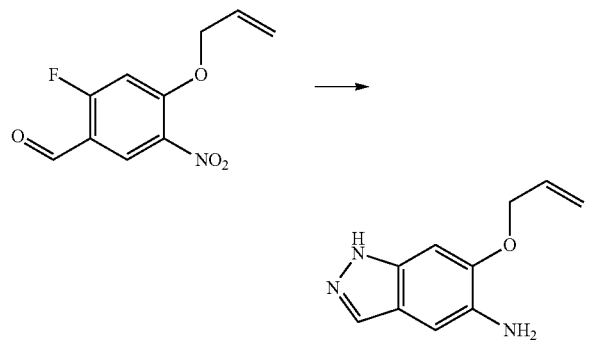

4.70 g (20.9 mmol) 4-(allyloxy)-2-fluoro-5-nitrobenzaldehyde (prepared according to intermediate example 269b) were transformed in analogy to intermediate example 248c to give after working up and purification 1.75 g (38%) of the title compound.

Example 269b 4-(Allyloxy)-2-fluoro-5-nitrobenzaldehyde

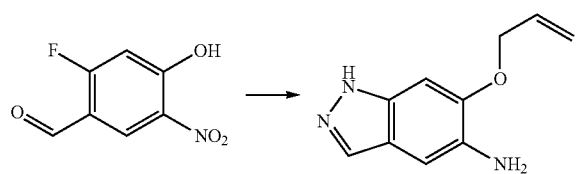

10.0 g (54.0 mmol) 2-fluoro-4-hydroxy-5-nitrobenzaldehyde (prepared according to intermediate example 248e) were transformed in analogy to intermediate example 248d using prop-2-en-1-ol to give after working up and purification 4.77 g (39%) of the title compound.

Example 270

{(7RS)-4-[(6-Ethoxy-1H-indazol-5-yl)amino]-5,6,7,8-tetrahydro[1]benzothieno[2,3-d]pyrimidin-7-yl}[(9aRS)-octahydro-2H-pyrido[1,2-a]pyrazin-2-yl]methanone

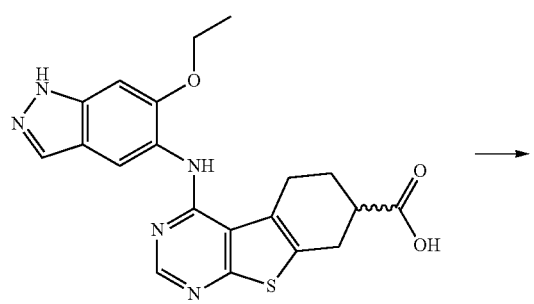

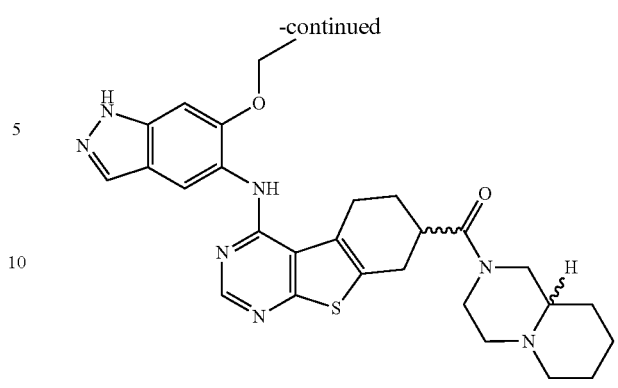

50 mg (122 µmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using (9aRS)-octahydro-2H-pyrido[1,2-a]pyrazine to give after working up and purification 8.5 mg (13%) of the title compound.

$^1$H-NMR (DMSO-d6): δ=1.03-1.33 (2H), 1.40-3.33 (21H), 3.88+3.99 (1H), 4.16-4.39 (3H), 7.06 (1H), 7.99 (1H), 8.33-8.41 (1H), 8.52 (1H), 8.99-9.06 (1H), 12.83 (1H) ppm.

Example 271

(RS)-5-({7-[(2-Ammonioethyl)(methyl)carbamoyl]-5,6,7,8-tetrahydro[1]benzothieno[2,3-d]pyrimidin-4-yl}amino)-6-ethoxy-1H-indazol-1-ium bis(trifluoroacetate)

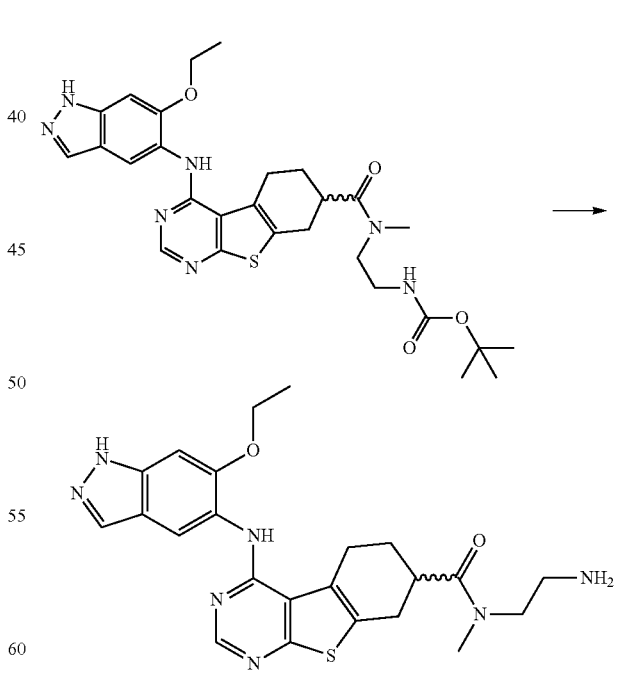

A solution of 33.0 mg (58 µmol) (RS)-tert-Butyl {2-[({4-[(6-ethoxy-1H-indazol-5-yl)amino]-5,6,7,8-tetrahydro[1]benzothieno[2,3-d]pyrimidin-7-yl}carbonyl)(methyl)amino]ethyl}carbamate (prepared according to example 268) in 2.0 mL trifluoroacetic acid was stirred at 23° C. for 1 hour. The solvent was removed and water was added. After lyophilization 42.6 mg (max 100%) of the title compound were obtained as salt with trifluoroacetic acid.

¹H-NMR (DMSO-d6): δ=1.48 (3H), 1.87 (1H), 2.16 (1H), 2.88+3.10 (3H), 2.91-3.06 (4H), 3.11-3.38 (3H), 3.46-3.69 (3H), 4.24 (2H), 7.08 (1H), 7.68 (2H), 7.77 (1H), 8.00 (1H), 8.36-8.41 (1H), 8.53 (1H), 9.02 (1H), 12.83 (1H) ppm.

Example 272

(RS)-(3-Hydroxyazetidin-1-yl){4-[(6-methoxy-1H-indazol-5-yl)amino]-5,6,7,8-tetrahydro[1]benzothieno[2,3-d]pyrimidin-7-yl}methanone

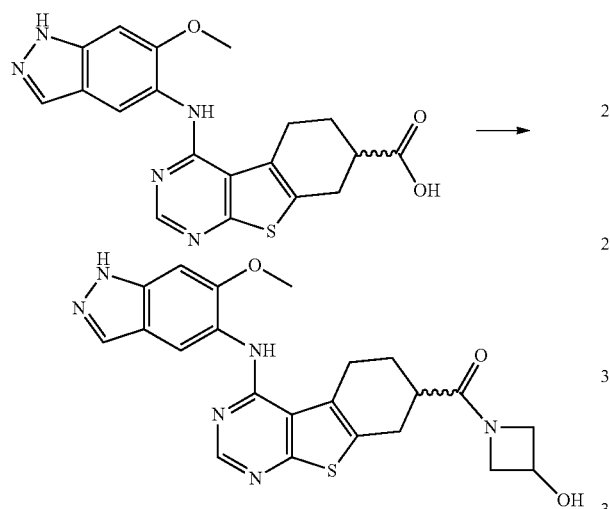

198 mg (500 μmol) (RS)-4-[(6-methoxy-1H-indazol-5-yl)amino]-5,6,7,8-tetrahydro[1]benzothieno[2,3-d]pyrimidine-7-carboxylic acid (prepared according to example 57) were transformed in analogy to intermediate example 2a using azetidin-3-ol to give after working up and purification 191 mg (80%) of the title compound.

¹H-NMR (DMSO-d6): δ=1.81 (1H), 2.13 (1H), 2.78 (1H), 2.84-2.96 (2H), 3.14 (1H), 3.25 (1H), 3.62 (1H), 3.98 (4H), 4.07 (1H), 4.39-4.52 (2H), 5.72 (1H), 7.08 (1H), 7.99 (1H), 8.21 (1H), 8.45 (1H), 8.76 (1H), 12.83 (1H) ppm.

Example 273

(RS)-4-[(6-Ethoxy-1H-indazol-5-yl)amino]-N-ethyl-N-(2-methoxyethyl)-5,6,7,8-tetrahydro[1]benzothieno[2,3-d]pyrimidine-7-carboxamide

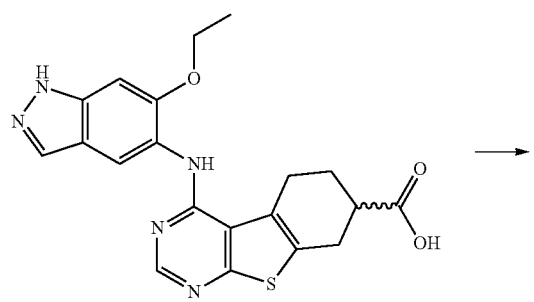

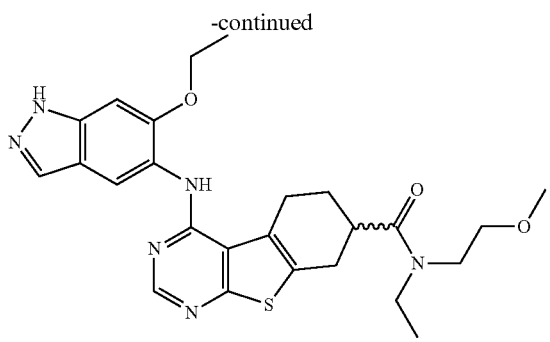

50 mg (122 μmol) (RS)-4-[(6-ethoxy-1H-indazol-5-yl)amino]-5,6,7,8-tetrahydro[1]benzothieno[2,3-d]pyrimidine-7-carboxylic acid (prepared according to example 210) were transformed in analogy to intermediate example 2a using N-ethyl-2-methoxyethanamine to give after working up and purification 6.0 mg (10%) of the title compound.

¹H-NMR (DMSO-d6): δ=1.04+1.14 (3H), 1.48 (3H), 1.89 (1H), 2.05 (1H), 2.86-3.60 (14H), 4.23 (2H), 7.07 (1H), 7.99 (1H), 8.37 (1H), 8.53 (1H), 9.03 (1H), 12.80 (1H) ppm.

Example 274

(RS)-5-Azaspiro[2.4]hept-5-yl{4-[(6-ethoxy-1H-indazol-5-yl)amino]-5,6,7,8-tetrahydro[1]benzothieno[2,3-d]pyrimidin-7-yl}methanone

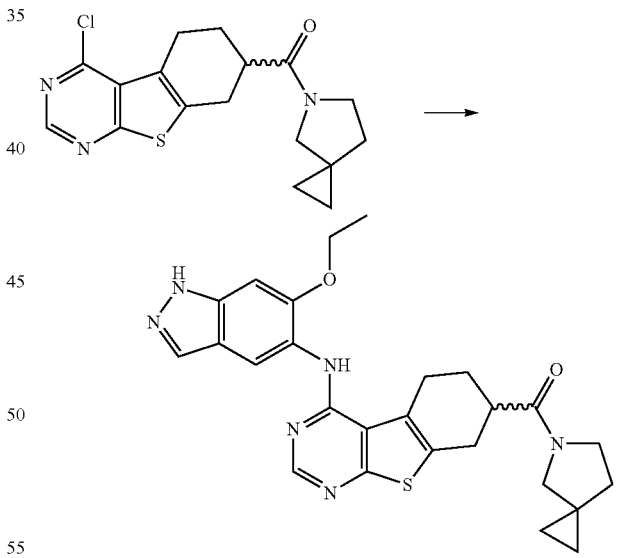

54.8 mg (158 μmol) (RS)-5-azaspiro[2.4]hept-5-yl(4-chloro-5,6,7,8-tetrahydro[1]benzothieno[2,3-d]pyrimidin-7-yl)methanone (prepared according to example 274a) were transformed in analogy to example 1 using 6-ethoxy-1H-indazol-5-amine to give after working up and purification 42.7 mg (55%) of the title compound.

¹H-NMR (DMSO-d6): δ=0.54-0.65 (4H), 1.47 (3H), 1.71-1.94 (3H), 2.11 (1H), 2.85-3.08 (3H), 3.14-3.37 (3H), 3.43-3.54 (3H), 4.22 (2H), 7.07 (1H), 8.00 (1H), 8.41 (1H), 8.53 (1H), 8.98 (1H), 12.74 (1H) ppm.

Example 274a (RS)-5-Azaspiro[2.4]hept-5-yl(4-chloro-5,6,7,8-tetrahydro[1]benzothieno[2,3-d]pyrimidin-7-yl)methanone

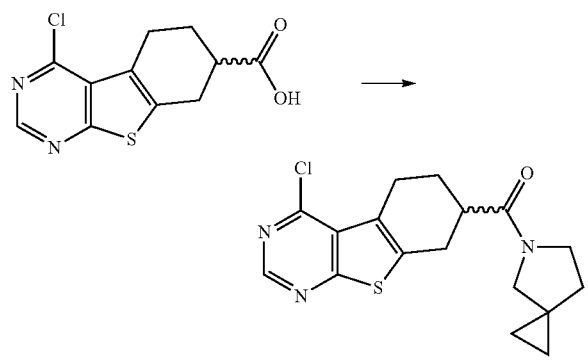

113 mg (421 µmol) (RS)-4-chloro-5,6,7,8-tetrahydro[1]benzothieno[2,3-d]pyrimidine-7-carboxylic acid (prepared according to intermediate example 1a) were transformed in analogy to intermediate example 2a using 5-azaspiro[2.4]heptane to give after working up and purification 61 mg (42%) of the title compound.

Example 275

(RS)-1-({4-[(6-Methoxy-1H-indazol-5-yl)amino]-5,6,7,8-tetrahydro[1]benzothieno[2,3-d]pyrimidin-7-yl}carbonyl)azetidin-3-yl dimethylcarbamate

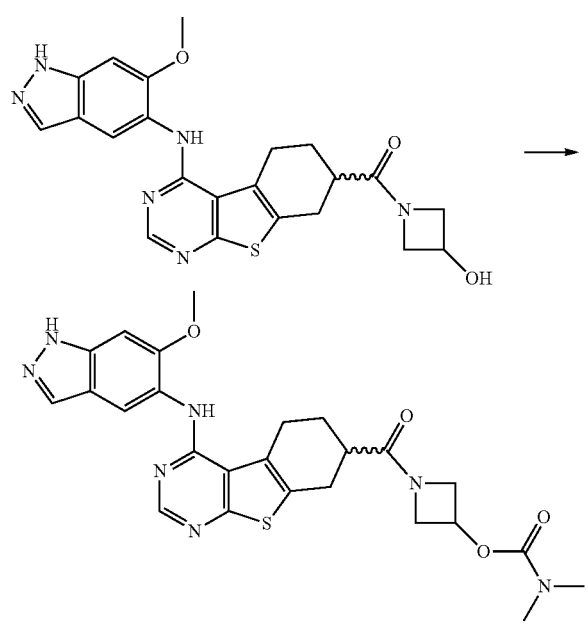

A mixture comprising 50 mg (111 µmol) (RS)-(3-Hydroxyazetidin-1-yl){4-[(6-methoxy-1H-indazol-5-yl)amino]-5,6,7,8-tetrahydro[1]benzothieno[2,3-d]pyrimidin-7-yl}methanone (prepared according to intermediate example 272), 1 mL tetrahydrofuran, 18.6 µL triethylamine and 33.7 µL dimethylcarbamic chloride added in three portions was heated at 140° C. for 3.5 hours under microwave irradiation. The crude product was purified by chromatography to give 11.8 mg (18%) of the title compound.

$^1$H-NMR (DMSO-d6): δ=1.81 (1H), 2.15 (1H), 2.77 (1H), 2.83-3.00 (3H), 3.16 (6H), 3.24 (2H), 3.62 (1H), 3.98 (1H), 4.02 (3H), 4.07 (1H), 4.40-4.52 (2H), 7.13 (1H), 8.41 (1H), 8.53 (1H), 8.66 (1H), 8.86 (1H) ppm.

Example 276

(RS)-4-{[6-(3-Azidopropoxy)-1H-indazol-5-yl]amino}-N,N-dimethyl-5,6,7,8-tetrahydro[1]benzothieno[2,3-d]pyrimidine-7-carboxamide

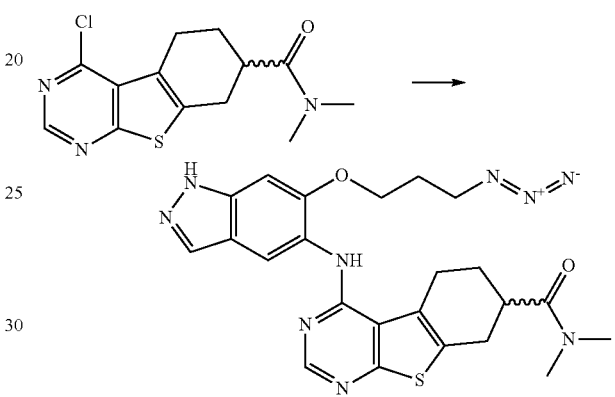

250 mg (845 µmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(3-azidopropoxy)-1H-indazol-5-amine (prepared according to intermediate example 276a) to give after working up and purification 260 mg (59%) of the title compound.

$^1$H-NMR (DMSO-d6): δ=1.82 (1H), 2.02-2.15 (3H), 2.87 (3H), 2.92 (2H), 3.10 (3H), 3.06-3.33 (3H), 3.56 (2H), 4.20 (2H), 7.08 (1H), 8.01 (1H), 8.35 (1H), 8.51 (1H), 8.89 (1H), 12.75 (1H) ppm.

Example 276a 6-(3-Azidopropoxy)-1H-indazol-5-amine

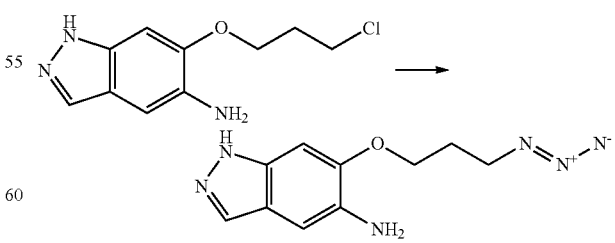

A mixture comprising 595 mg (2.64 mmol) 6-(3-chloropropoxy)-1H-indazol-5-amine (prepared according to intermediate example 267a), 8.0 mL N,N-dimethylformamide and 343 mg sodium azide was heated at 60° C. overnight.

Solid material was removed by filtration and the residue purified by chromatography to give 248 mg (41%) of the title compound.

Example 277

(RS)-4-{[6-(3-Aminopropoxy)-1H-indazol-5-yl]amino}-N, N-dimethyl-5,6,7,8-tetrahydro[1]benzothieno[2,3-d]pyrimidine-7-carboxamide

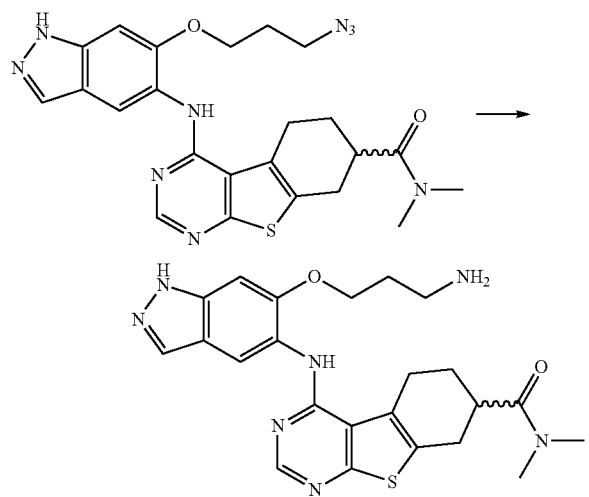

A mixture comprising 250 mg (509 µmol) (RS)-4-{[6-(3-Azidopropoxy)-1H-indazol-5-yl]amino}-N,N-dimethyl-5,6,7,8-tetrahydro[1]benzothieno[2,3-d]pyrimidine-7-carboxamide (prepared according to intermediate example 276), 10 mL tetrahydrofuran, 283 µL tributylphosphine was stirred at 23° C. for 2 hours. 1.09 mL aqueous ammonia (25%) was added and stirring continued overnight. The solvents were removed and the residue purified by crystallization to give 28.2 mg (12%) of the title compound.

¹H-NMR (DMSO-d6): δ=1.87 (1H), 1.97-2.20 (3H), 2.87 (3H), 2.90-2.99 (2H), 3.10 (3H), 3.13-3.33 (3H), 3.44 (1H), 4.20-4.30 (2H), 5.47 (1H), 7.09 (1H), 8.00 (1H), 8.26 (1H), 8.50 (1H), 8.91 (1H), 9.69 (2H), 12.89 (1H) ppm.

Example 278

(RS)-4-{[6-(4-Azidobutoxy)-1H-indazol-5-yl]amino}-N,N-dimethyl-5,6,7,8-tetrahydro[1]benzothieno[2,3-d]pyrimidine-7-carboxamide

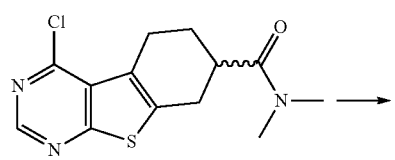

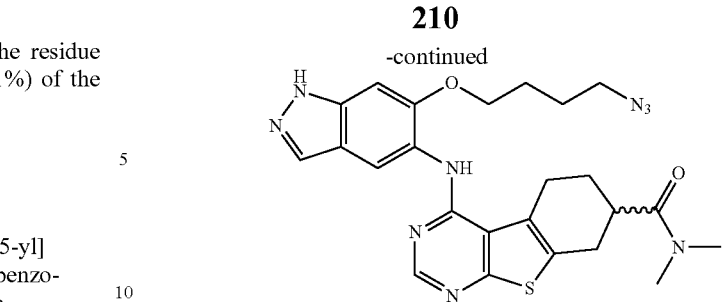

151 mg (512 µmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(4-azidobutoxy)-1H-indazol-5-amine (prepared according to intermediate example 278a) to give after working up and purification 57.2 mg (21%) of the title compound.

¹H-NMR (DMSO-d6): δ=1.71 (2H), 1.78-1.97 (3H), 2.10 (1H), 2.87 (3H), 2.90-2.97 (2H), 3.10 (3H), 3.13-3.29 (3H), 3.43 (2H), 4.18 (2H), 7.08 (1H), 7.99 (1H), 8.24 (1H), 8.49 (1H), 8.94 (1H), 12.82 (1H) ppm.

Example 278a 6-(4-Azidobutoxy)-1H-indazol-5-amine

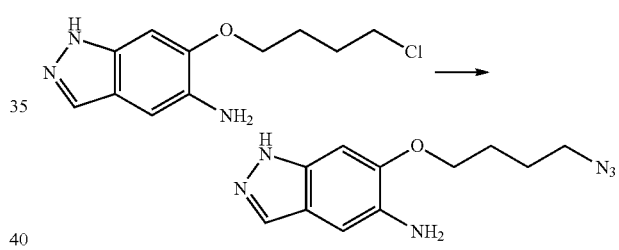

225 mg (939 µmol) 6-(4-chlorobutoxy)-1H-indazol-5-amine (prepared according to intermediate example 278b) were transformed in analogy to intermediate example 276a to give after working up and purification 126 mg (55%) of the title compound.

Example 278b 6-(4-Chlorobutoxy)-1H-indazol-5-amine

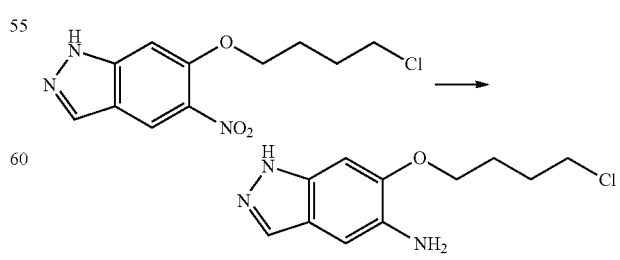

378 mg (1.40 mmol) (prepared according to intermediate example 278c) were transformed in analogy to intermediate example 69b to give after working up and purification 320 mg (95%) of the title compound.

Example 278c 6-(4-Chlorobutoxy)-5-nitro-1H-indazole

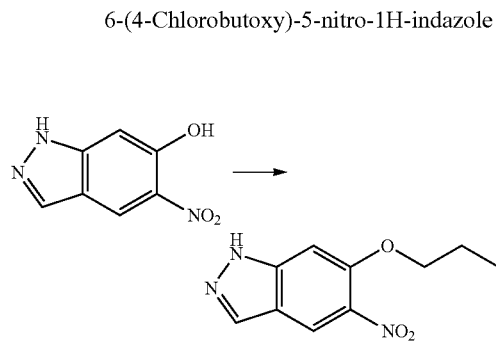

1.00 g (5.58 mmol) 5-nitro-1H-indazol-6-ol (prepared according to intermediate example 266c) were transformed in analogy to intermediate example 248d using 4-chlorobutan-1-ol to give after working up and purification 383 mg (25%) of the title compound.

Example 279

(RS)-4-{[6-(2-Azidoethoxy)-1H-indazol-5-yl]amino}-N,N-dimethyl-5,6,7,8-tetrahydro[1]benzothieno[2,3-d]pyrimidine-7-carboxamide

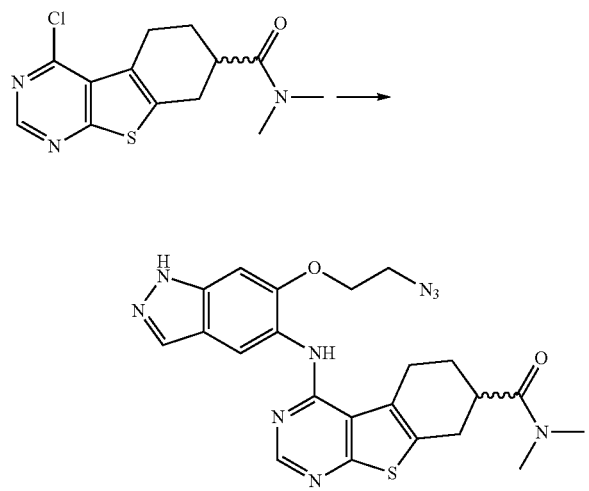

401 mg (1.36 mmol) (RS)-4-chloro-N,N-dimethyl-5,6,7,8-tetrahydro[1]benzothieno[2,3-d]pyrimidine-7-carboxamide (prepared according to intermediate example 248a) were transformed in analogy to example 1 using 6-(2-azidoethoxy)-1H-indazol-5-amine (prepared according to intermediate example 279a) to give after working up and purification 113.5 mg (18%) of the title compound.

$^1$H-NMR (DMSO-d6): δ=1.84 (1H), 2.15 (1H), 2.80-3.41 (5H), 2.87 (3H), 3.10 (3H), 3.85 (2H), 4.35 (2H), 7.13 (1H), 8.01 (1H), 8.21 (1H), 8.49 (1H), 8.93 (1H), 12.89 (1H) ppm.

Example 279a 6-(2-azidoethoxy)-1H-indazol-5-amine

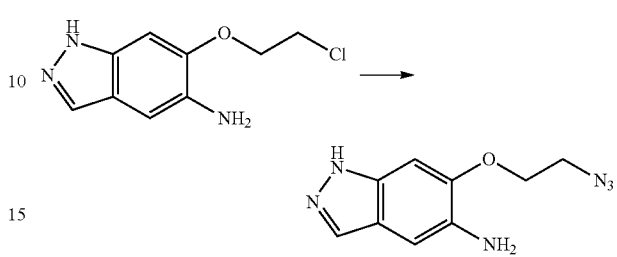

670 mg (3.17 mmol) 6-(2-chloroethoxy)-1H-indazol-5-amine (prepared according to intermediate example 266a) were transformed in analogy to intermediate example 276a to give after working up and purification 440 mg (64%) of the title compound.

Example 280

(RS)-(4-{[6-(3-Chloropropoxy)-1H-indazol-5-yl]amino}-5,6,7,8-tetrahydro[1]benzothieno[2,3-d]pyrimidin-7-yl)(4-methylpiperazin-1-yl)methanone

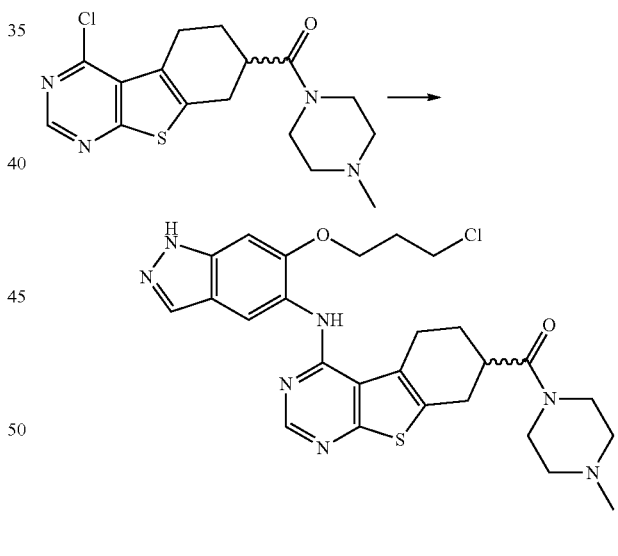

40 mg (114 μmol) (RS)-(4-chloro-5,6,7,8-tetrahydro[1]benzothieno[2,3-d]pyrimidin-7-yl)(4-methylpiperazin-1-yl)methanone (prepared according to intermediate example 280a) were transformed in analogy to example 1 using 6-(3-chloropropoxy)-1H-indazol-5-amine (prepared according to intermediate example 267a) to give after working up and purification 9.9 mg (15%) of the title compound.

$^1$H-NMR (DMSO-d6): δ=1.85 (1H), 2.10 (1H), 2.19 (3H), 2.22-2.39 (6H), 2.83-3.03 (2H), 3.12-3.28 (3H), 3.50 (2H), 3.57 (2H), 3.84 (2H), 4.27 (2H), 7.09 (1H), 7.99 (1H), 8.22 (1H), 8.49 (1H), 8.97 (1H), 12.82 (1H) ppm.

Example 280a (RS)-(4-chloro-5,6,7,8-tetrahydro[1]benzothieno[2,3-d]pyrimidin-7-yl)(4-methylpiperazin-1-yl)methanone

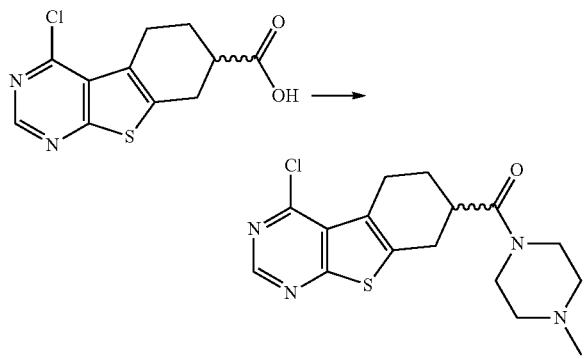

500 mg (1.86 mmol) (RS)-4-chloro-5,6,7,8-tetrahydro[1]benzothieno[2,3-d]pyrimidine-7-carboxylic acid (prepared according to intermediate example 1a) were transformed in analogy to intermediate example 2a using 1-methylpiperazine to give after working up and purification 204 mg (28%) of the title compound. Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC\equiv CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD& C Red No. 3, FD& C Red No. 20, FD& C Yellow No. 6, FD& C Blue No. 2, D& C Green No. 5, D& C Orange No. 5, D& C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption. Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

In a preferred embodiment, a compound of general formula (I) as defined herein is administered in combination with one or more inhibitors of the PI3K-AKT-mTOR pathway. Examples of inhibitors of the mammalian Target of Rapamycin (mTOR) are Afinitor, Votubia (everolimus).

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 µg/mL. The reaction was stopped by the addition of 5 µL of a solution of TR-FRET detection reagents (5 nM streptavidine-XL665 [Cisbio Bioassays, Codolet, France] and 1 nM anti-ribosomal protein 56 (pSer236)-antibody from Invitrogen [#44921G] and 1 nM LANCE EU-W1024 Labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software. Table 4 lists MKNK1 IC50 values of some compounds of the present invention.

TABLE 4

MKNK1 $IC_{50}$ values of compounds of the present invention

| Example | MKNK1 $IC_{50}$ [nM] |
|---------|----------------------|
| 1       | 5                    |
| 2       | 8                    |
| 4       | 8                    |
| 56      | 2                    |

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 3.3 mM=>final conc. in the 5 µL assay volume is 2 mM) and substrate (0.1 µM=>final conc. in the 5 µL assay volume is 0.06 µM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 µg/mL. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 Labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC50 values were calculated by a 4 parameter fit using an inhouse software. Table 5 lists MKNK1 high ATP IC50 values of some compounds of the present invention.

TABLE 5

MKNK1 high ATP $IC_{50}$ values of compounds of the present invention

| Example | MKNK1 $IC_{50}$ [nM] |
|---|---|
| 1 | 16 |
| 2 | 26 |
| 3 | 8 |
| 4 | 9 |
| 5 | 9 |
| 6 | 4 |
| 7 | 6 |
| 8 | 11 |
| 9 | 3 |
| 10 | 12 |
| 11 | 10 |
| 12 | 8 |
| 13 | 7 |
| 14 | 7 |
| 15 | 3 |
| 16 | 5 |
| 17 | 5 |
| 18 | 2 |
| 19 | 2 |
| 20 | 2 |
| 21 | 3 |
| 22 | 3 |
| 23 | 3 |
| 24 | 3 |
| 25 | 3 |
| 26 | 3 |
| 27 | 3 |
| 28 | 4 |
| 29 | 4 |
| 30 | 4 |
| 31 | 4 |
| 32 | 5 |
| 33 | 5 |
| 34 | 5 |
| 35 | 5 |
| 36 | 6 |
| 37 | 6 |
| 38 | 6 |
| 39 | 6 |
| 40 | 7 |
| 41 | 8 |
| 42 | 9 |
| 43 | 9 |
| 44 | 9 |
| 45 | 9 |
| 46 | 10 |
| 47 | 11 |
| 48 | 12 |
| 49 | 13 |
| 50 | 14 |
| 51 | 15 |
| 52 | 20 |
| 53 | 9 |
| 54 | 19 |
| 55 | 37 |

TABLE 5-continued

MKNK1 high ATP $IC_{50}$ values of compounds of the present invention

| Example | MKNK1 $IC_{50}$ [nM] |
|---|---|
| 56 | 2 |
| 57 | 7 |
| 58 | 0.7 |
| 59 | nd |
| 60 | 2180 |
| 61 | 1020 |
| 62 | 1420 |
| 63 | 10.2 |
| 64 | 0.8 |
| 65 | 0.5 |
| 66 | 1.6 |
| 67 | 0.7 |
| 68 | 0.7 |
| 69 | 3.9 |
| 70 | 0.4 |
| 71 | 0.5 |
| 72 | 0.6 |
| 73 | 8.9 |
| 74 | 27.6 |
| 75 | 2.7 |
| 76 | 5.1 |
| 77 | 19.7 |
| 78 | 15.6 |
| 79 | 10.5 |
| 80 | 9.1 |
| 81 | 2.4 |
| 82 | 14.6 |
| 83 | 14.7 |
| 84 | 5.5 |
| 85 | 11.7 |
| 86 | 14.9 |
| 87 | 20.6 |
| 88 | 9.9 |
| 89 | 24.1 |
| 90 | 16.4 |
| 91 | 6.6 |
| 92 | 9.8 |
| 93 | 9.9 |
| 94 | 23.4 |
| 95 | 20.6 |
| 96 | 16.3 |
| 97 | 20.3 |
| 98 | 8.1 |
| 99 | 27.7 |
| 100 | 7.5 |
| 101 | 4.7 |
| 102 | 14.9 |
| 103 | 16.4 |
| 104 | 7.4 |
| 105 | 16.8 |
| 106 | 14.5 |
| 107 | 8.1 |
| 108 | 12.0 |
| 109 | 8.0 |
| 110 | 132 |
| 111 | 24.7 |
| 112 | 9.4 |
| 113 | 20.4 |
| 114 | 12.5 |
| 115 | 15.3 |
| 116 | 5.8 |
| 117 | 11.2 |
| 118 | 13.2 |
| 119 | 15.9 |
| 120 | 8.3 |
| 121 | 4.0 |
| 122 | 11.2 |
| 123 | 11.3 |
| 124 | 8.0 |
| 125 | 10.5 |
| 126 | 14.8 |
| 127 | 10.7 |
| 128 | 15.0 |
| 129 | 7.7 |
| 130 | 9.5 |

TABLE 5-continued

MKNK1 high ATP IC$_{50}$ values of compounds of the present invention

| Example | MKNK1 IC$_{50}$ [nM] |
|---|---|
| 131 | 13.5 |
| 132 | 10.3 |
| 133 | 21.4 |
| 134 | 12.7 |
| 135 | 13.3 |
| 136 | 7.6 |
| 137 | 15.6 |
| 138 | 12.6 |
| 139 | 6.9 |
| 140 | 12.4 |
| 141 | 17.4 |
| 142 | 22.4 |
| 143 | 19.5 |
| 144 | 21.7 |
| 145 | 4.9 |
| 146 | 26.4 |
| 147 | 3.7 |
| 148 | 8.1 |
| 149 | 27.4 |
| 150 | 31.2 |
| 151 | 3.2 |
| 152 | 16.8 |
| 153 | 32.5 |
| 154 | 28.8 |
| 155 | 18.3 |
| 156 | 18.3 |
| 157 | 38.1 |
| 158 | 16.5 |
| 159 | 14.4 |
| 160 | 31.1 |
| 161 | 3.2 |
| 162 | 5.3 |
| 163 | 12.4 |
| 164 | 22.5 |
| 165 | 16.8 |
| 166 | 15.3 |
| 167 | 14.9 |
| 168 | 17.4 |
| 169 | 11.1 |
| 170 | 0.8 |
| 171 | 0.4 |
| 172 | 0.4 |
| 173 | 0.5 |
| 174 | 0.6 |
| 175 | 0.5 |
| 176 | 0.5 |
| 177 | 0.4 |
| 178 | 0.2 |
| 179 | 0.7 |
| 180 | 0.8 |
| 181 | 0.2 |
| 182 | 0.5 |
| 183 | 3.2 |
| 184 | 12.4 |
| 185 | nd |
| 186 | 40.6 |
| 187 | nd |
| 188 | 22.6 |
| 189 | nd |
| 190 | 6.0 |
| 191 | 7.3 |
| 192 | 15.1 |
| 193 | 16.8 |
| 194 | 12.0 |
| 195 | nd |
| 196 | 7.5 |
| 197 | 7.9 |
| 198 | 10.0 |
| 199 | nd |
| 200 | 8.6 |
| 201 | 18.1 |
| 202 | 15.0 |
| 203 | nd |
| 204 | 7.3 |
| 205 | 7.3 |
| 206 | 1.0 |
| 207 | 0.5 |
| 208 | 0.2 |
| 209 | 0.7 |
| 210 | 73.0 |
| 211 | 0.5 |
| 212 | 0.3 |
| 213 | 1.5 |
| 214 | 0.3 |
| 215 | 0.5 |
| 216 | 0.5 |
| 217 | 1.0 |
| 218 | 1.2 |
| 219 | 0.5 |
| 220 | 0.6 |
| 221 | 0.7 |
| 222 | 0.9 |
| 223 | 1.5 |
| 224 | 0.6 |
| 225 | 0.3 |
| 226 | 0.7 |
| 227 | 0.6 |
| 228 | 0.2 |
| 229 | 0.7 |
| 230 | 0.2 |
| 231 | 0.3 |
| 232 | 0.1 |
| 233 | 0.5 |
| 234 | 0.4 |
| 235 | 0.5 |
| 236 | 2.8 |
| 237 | 0.3 |
| 238 | 1.5 |
| 239 | 0.4 |
| 240 | 1.1 |
| 241 | 0.4 |
| 242 | 0.3 |
| 243 | 0.3 |
| 244 | 0.4 |
| 245 | 0.7 |
| 246 | 0.9 |
| 247 | 0.3 |
| 248 | 0.2 |
| 249 | 15 |
| 250 | 0.5 |
| 251 | 0.2 |
| 252 | 2.2 |
| 253 | 1.2 |
| 254 | 1.6 |
| 255 | 0.3 |
| 256 | 92 |
| 257 | 0.6 |
| 258 | 0.4 |
| 259 | 1.9 |
| 260 | 0.7 |
| 261 | 2.3 |
| 262 | 6.1 |
| 263 | 3.3 |
| 264 | 2.2 |
| 265 | 1.2 |
| 266 | 1.2 |
| 267 | 2.2 |
| 268 | 0.4 |
| 269 | 2.7 |
| 270 | 0.4 |
| 271 | 0.4 |
| 272 | 0.6 |
| 273 | 0.2 |
| 274 | 1.0 |
| 275 | 19.8 |
| 276 | 3.9 |
| Ref | 9.8 | nd: not yet determined

"Ref" means the compound N-[3-(dimethylamino)propyl]-4-[(4-fluoro-2-isopropoxyphenyl)amino]-5-methylthieno[2,3-d]pyrimidine-6-carboxamide which served as reference compound in the present invention and has been described in WO 2010/23181, WO 2011/104340 and US 2011/212103.

It was also observed that compounds derived from compounds of the present invention by substitution of the indazol-5-yl at the nitrogen at position 1 show a significant lower activity (higher $IC_{50}$ value) in the MKNK1 kinase high ATP assay.

MNK2 Kinase High ATP Assay

Mnk2-inhibitory activity at high ATP of compounds of the present invention after their preincubation with Mnk2 was quantified employing the TR-FRET-based Mnk2 high ATP assay as described in the following paragraphs.

A recombinant fusion protein of Glutathione-S-Transferase (GST, N-terminally) and human full-length Mnk2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Mnk2 in aqueous assay buffer [50 mM HEPES pH 7.5, 5 mM $MgCl_2$, 1.0 mM dithiothreitol, 0.005% (v/v) Nonidet-P40 (G-Biosciences, St. Louis, USA)] was added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (0.1 µM=>final conc. in the 5 µl assay volume is 0.06 µM) in assay buffer and the resulting mixture was incubated for a reaction time of 30 min at 22° C. The concentration of Mnk2 was adjusted depending of the activity of the enzyme lot and was chosen appropriate to have the assay in the linear range, typical concentrations were in the range of 0.0045 µg/mL. The reaction was stopped by the addition of 5 µl of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated by a 4 parameter fit using an inhouse software.

EGFR Kinase Assay

EGFR inhibitory activity of compounds of the present invention was quantified employing the TR-FRET based EGFR assay as described in the following paragraphs.

Epidermal Growth Factor Receptor (EGFR) affinity purified from human carcinoma A431 cells (Sigma-Aldrich, #E3641) was used as kinase. As substrate for the kinase reaction the biotinylated peptide biotin-Ahx-AEEEEYFEL-VAKKK (C-terminus in amid form) was used which can be purchased e.g. form the company Biosynthan GmbH (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of EGFR in aqueous assay [50 mM Hepes/HCl pH 7.0, 1 mM $MgCl_2$, 5 mM $MnCl_2$, 0.5 mM activated sodium ortho-vanadate, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration were in the range of 3 U/ml. The reaction was stopped by the addition of 5 µl of a solution of HTRF detection reagents (0.1 µM streptavidine-XL665 [Cis Biointernational] and 1 nM PT66-Tb-Chelate, an terbium-chelate labelled anti-phospho-tyrosine antibody from Cis Biointernational [instead of the PT66-Tb-chelate PT66-Eu-Cryptate from Perkin Elmer can also be used]) in an aqueous EDTA-solution (80 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated by a 4 parameter fit using an inhouse software. Compounds of the present invention, particularly compounds specifically disclosed within the Experimental Section showed weak or no significant inhibition of EGFR.

CDK2/CycE Kinase Assay

CDK2/CycE-inhibitory activity of compounds of the present invention was quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.25 µM=>final conc. in the 5 µL assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 µL of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

PDGFRβ Kinase Assay

PDGFRβ inhibitory activity of compounds of the present invention was quantified employing the PDGFRβ HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] was used. As substrate for the kinase reaction the biotinylated poly-Glu,Tyr (4:1) copolymer (#61GT0BLA) from Cis Biointernational (Marcoule, France) was used.

For the assay 50 nL of a 100 fold concentrated solution of the test compound in DMSO was pipetted into a black low volume 384 well microtiter plate (Greiner Bio-One, Frickenhausen, Germany), 2 µL of a solution of PDGFRβ in aqueous assay buffer [50 mM HEPES/NaOH pH 7.5, 10 mM $MgCl_2$, 2.5 mM dithiothreitol, 0.01% (v/v) Triton-X100 (Sigma)] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (2.27 µg/ml=>final conc. in the 5 µL assay volume is 1.36 µg/ml [~30 nM]) in assay buffer and the resulting mixture was incubated for a reaction time of 25 min at 22° C. The concentration of PDGFRβ in the assay was adjusted depending of the activity of the enzyme lot and was chosen appropriate to have the assay in the linear range, typical enzyme concentrations were in the range of about 125 pg/µL (final conc. in the 5 µL assay volume). The reaction was stopped by the addition of 5 µL of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

Fyn Kinase Assay

C-terminally His6-tagged human recombinant kinase domain of the human T-Fyn expressed in baculovirus infected insect cells (purchased from Invitrogen, P3042) was used as kinase. As substrate for the kinase reaction the biotinylated peptide biotin-KVEKIGEGTYGW (C-terminus in amid form) was used which can be purchased e.g. form the company Biosynthan GmbH (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of T-Fyn in aqueous assay buffer [25 mM Tris/HCl pH 7.2, 25 mM MgCl$_2$, 2 mM dithiothreitol, 0.1% (w/v) bovine serum albumin, 0.03% (v/v) Nonidet-P40 (Sigma)]. were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (2 µM=>final conc. in the 5 µL assay volume is 1.2 µM) in assay buffer and the resulting mixture was incubated for a reaction time of 60 min at 22° C. The concentration of Fyn was adjusted depending of the activity of the enzyme lot and was chosen appropriate to have the assay in the linear range, typical concentration was 0.13 nM. The reaction was stopped by the addition of 5 µL of a solution of HTRF detection reagents (0.2 µM streptavidine-XL [Cisbio Bioassays, Codolet, France) and 0.66 nM PT66-Eu-Chelate, an europium-chelate labelled anti-phospho-tyrosine antibody from Perkin Elmer [instead of the PT66-Eu-chelate PT66-Tb-Cryptate from Cisbio Bioassays can also be used]) in an aqueous EDTA-solution (125 mM EDTA, 0.2% (w/v) bovine serum albumin in 50 mM HEPES/NaOH pH 7.0).

The resulting mixture was incubated 1 h at 22° C. to allow the binding of the biotinylated phosphorylated peptide to the streptavidine-XL and the PT66-Eu-Chelate. Subsequently the amount of phosphorylated substrate was evaluated by measurement of the resonance energy transfer from the PT66-Eu-Chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

Flt4 Kinase Assay

Flt4 inhibitory activity of compounds of the present invention was quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] was used. As substrate for the kinase reaction the biotinylated peptide Biotin-Ahx-GGEEEEY-FELVKKKK (C-terminus in amide form, purchased from Biosyntan, Berlin-Buch, Germany) was used.

For the assay 50 nL of a 100 fold concentrated solution of the test compound in DMSO was pipetted into a black low volume 384 well microtiter plate (Greiner Bio-One, Frickenhausen, Germany), 2 µL of a solution of Flt4 in aqueous assay buffer [25 mM HEPES pH 7.5, 10 mM MgCl$_2$, 2 mM dithiothreitol, 0.01% (v/v) Triton-X100 (Sigma), 0.5 mM EGTA, and 5 mM β-phospho-glycerol] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 45 min at 22° C. The concentration of Flt4 in the assay was adjusted depending of the activity of the enzyme lot and was chosen appropriate to have the assay in the linear range, typical enzyme concentrations were in the range of about 120 pg/µL (final conc. in the 5 µL assay volume). The reaction was stopped by the addition of 5 µL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

TrkA Kinase Assay

TrkA inhibitory activity of compounds of the present invention was quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] was used. As substrate for the kinase reaction the biotinylated poly-Glu,Tyr (4:1) copolymer (#61GT0BLA) from Cis Biointernational (Marcoule, France) was used.

For the assay 50 nL of a 100 fold concentrated solution of the test compound in DMSO was pipetted into a black low volume 384 well microtiter plate (Greiner Bio-One, Frickenhausen, Germany), 2 µL of a solution of TrkA in aqueous assay buffer [8 mM MOPS/HCl pH 7.0, 10 mM MgCl$_2$, 1 mM dithiothreitol, 0.01% (v/v) NP-40 (Sigma), 0.2 mM EDTA] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (2.27 µg/ml=>final conc. in the 5 µL assay volume is 1.36 µg/ml [~30 nM]) in assay buffer and the resulting mixture was incubated for a reaction time of 60 min at 22° C. The concentration of TrkA in the assay was adjusted depending of the activity of the enzyme lot and was chosen appropriate to have the assay in the linear range, typical enzyme concentrations were in the range of about 20 pg/µL (final conc. in the 5 µL assay volume). The reaction was stopped by the addition of 5 µL of a solution of HTRF detection reagents (30 nM streptavidine-XL665 [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

Kinase Selectivity Profiling

Compounds of the present invention show a higher kinase inhibition selectivity than compounds disclosed in the patent applications WO 2010/023181 A1, WO 2011/104334 A1, WO 2011/104337 A1, WO 2011/104338 A1 and WO 2011/104340 A1 (Boehringer Ingelheim). This is demonstrated by a target profiling in which the selectivity of compounds against 221 kinases were tested by Merck Millipore in a service called KinaseProfiler.

The compounds were tested at a concentration of 1 µM using 221 kinases different from MKNK. Kinase activity is expressed as a percentage of the mean kinase activity in the positive control samples. The positive control value is considered to be 100%, and all test samples are measured in relation to this value. For example, a result of 40% means that, in comparison to the positive control sample, 40% kinase activity remains in the presence of the test compound. Expressed another way: the test compound inhibits the kinase activity by 60%.

Table 6 lists the fraction number of 221 investigated kinases with regard to their remaining activity in the presence of 1 µM of investigated compounds.

The compound described in example 10 is compared to the compound N-[3-(dimethylamino)propyl]-4-[(4-fluoro-2-isopropoxyphenyl)amino]-5-methylthieno[2,3-d]pyrimidine-6-carboxamide which served as reference compound (ref) and has been described in WO 2010/23181, WO 2011/104340 and US 2011/212103.

TABLE 6

Fraction number of 221 investigated kinases other than MKNK with regard to their remaining activity in the presence of the investigated compounds at a concentration of 1 µM.

| | Ref. compound | Compound of example 10 |
|---|---|---|
| Remaining activity ≥80% | 202/221 | 217/221 |
| Remaining activity >30% and <80% | 10/221 | 4/221 |
| Remaining activity ≤30% | 9/221 | 0/221 |

AlphaScreen SureFire eIF4E Ser209 Phosphorylation Assay

The AlphaScreen SureFire eIF4E Ser209 phoshorylation assay is used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 cells with 20% FCS stimulation

For the assay the AlphaScreen SureFire p-eIF4E Ser209 10K Assay Kit and the AlphaScreen ProteinA Kit (for 10K assay points) both from Perkin Elmer were used. On day one 50.000 A549 cells were plated in a 96-well plate in 100 µL per well in growth medium (DMEM/Hams' F12 with stable Glutamin, 10% FCS) and incubated at 37° C. After attachment of the cells, medium was changed to starving medium (DMEM, 0.1% FCS, without Glucose, with Glutamin, supplemented with 5 g/L Maltose). On day two, test compounds were serially diluted in 50 µL starving medium with a final DMSO concentration of 1% and were added to A549 cells in test plates at a final concentration range from as high 10 µM to as low 10 nM depending on the activities of the tested compounds. Treated cells were incubated at 37° C. for 2 h. 37 ul FCS was added to the wells (=final FCS concentration 20%) for 20 min. Then medium was removed and cells were lysed by adding 50 µL lysis buffer. Plates were then agitated on a plate shaker for 10 min. After 10 min lysis time, 4 µL of the lysate is transferred to a 384 well plate (Proxiplate from Perkin Elmer) and 5 µL Reaction Buffer plus Activation Buffer mix containing AlphaScreen Acceptor beads was added. Plates were sealed with TopSeal-A adhesive film, gently agitated on a plate shaker for 2 hours at room temperature. Afterwards 2 µL Dilution buffer with AlphaScreen Donor beads were added under subdued light and plates were sealed again with TopSeal-A adhesive film and covered with foil. Incubation takes place for further 2 h gently agitation at room temperature. Plates were then measured in an EnVision reader (Perkin Elmer) with the AlphaScreen program. Each data point (compound dilution) was measured as triplicate.

The IC50 values were determined by means of a 4-parameter fit using the company's own software.

Table 7 lists IC50 values of the EIF4e Alphascreen in A549 cells for some compounds of the present invention.

TABLE 7

IC50 values of the EIF4e phosphorylation (pEIF4e) in A549 cells for some compounds of the present invention

| Example | pEIF4e [nM] |
|---|---|
| 9 | 171 |
| 12 | 252 |
| 16 | 373 |
| 18 | 412 |
| 20 | 344 |
| 21 | 381 |
| 56 | 165 |
| 58 | 203 |
| 64 | 51 |
| 65 | 343 |
| 66 | 61 |
| 70 | 90 |
| 71 | 32 |
| 72 | 75 |
| 75 | 219 |
| Ref | 435 |

"Ref" means the compound N-[3-(dimethylamino)propyl]-4-[(4-fluoro-2-isopropoxyphenyl)amino]-5-methylthieno[2,3-d]pyrimidine-6-carboxamide which served as reference compound in the present invention and has been described in WO 2010/23181, WO 2011/104340 and US 2011/212103.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", *The Scientist* 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ #ACC 554), JJN-3 (human plasma cell leukemia cells obtained from DSMZ #ACC 541), Ramos (RA1) (human Burkitt's lymphoma cells obtained from ATCC #CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 µL of their respective growth medium supplemented with 10% fetal calf serum. After 24 hours, the cells of one plate (zero-point plate) are measured for viability. Therefore, 70 µL/well CTG solution (Promega Cell Titer Glo solution (catalog #G755B and G756B)) is added to zero-point plate. The plates are mixed for two minutes on orbital shaker to ensure cell lysis and incubated for ten minutes at room temperature in the dark to stabilize luminescence signal. The samples are read on a VICTOR 3 plate reader. In parallel, serially test compounds are diluted in growth medium, and 50 µL of 3× dilutions/well are pipetted into the test plates (final concentrations: 0 µM, as well as in the range of 0.001-30 µM). The final concentration of the solvent dimethyl sulfoxide is 0.3-0.4%. The cells are incubated for 3 days in the presence of test substances. 105 µL/well CTG solution (Promega Cell Titer Glo solution (catalog #G755B and G756B)) is added to the test wells. The plates are mixed for 2 minutes on an orbital shaker to ensure cell lysis and incubated for 10 min at room temperature in the dark to stabilize luminescence signal. The samples are read on a VICTOR 3 plate reader. The change of cell number, in percent, is calculated by normalization of the measured values to the extinction values of the zero-point plate (=0%) and the extinction of the untreated (0 µm) cells (=100%). The $IC_{50}$ values (inhibitory concentration at 50% of maximal effect) are determined by means of a 4 parameter fit using the company's own software.

Overview Cell Lines for Proliferation Assays

| Cell line | Origin | Cell number/well | Culture Medium |
|---|---|---|---|
| MOLM-13 (obtained from DSMZ # ACC 554) | human acute myeloid leukemia | 3000 | RPMI 1640 with stable Glutamin with 10% Fetal Bovine Serum |
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

In summary, the compounds of the present invention effectively and selectively inhibit MKNK1 and/or MKNK2 and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses are mediated by MKNK, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of formula (I):

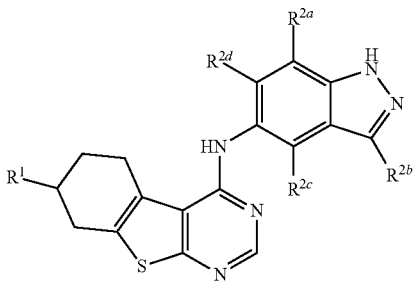

in which:
$R^1$ represents a group selected from:
—C(=O)O—$R^3$, —C(=O)N(H)$R^3$, and —C(=O)N$R^3R^4$;
$R^{2a}$ represents a hydrogen atom;
$R^{2b}$ represents a hydrogen atom;
$R^{2c}$ represents a hydrogen atom;
$R^{2d}$ represents a hydrogen atom or a group selected from: $C_1$-$C_3$-alkyl-, $C_1$-$C_3$-alkoxy-, halo-, —N(H)$R^5$, —N$R^5R^4$;
$R^3$ represents a hydrogen atom or a group selected from:
$C_1$-$C_6$-alkyl-, $C_2$-$C_6$-alkynyl-, $C_3$-$C_7$-cycloalkyl-, —(CH$_2$)$_q$—($C_3$-$C_7$-cycloalkyl), —(CH$_2$)$_q$—O—($C_3$-$C_7$-cycloalkyl),
3- to 10-membered heterocycloalkyl-, —(CH$_2$)$_q$-(3- to 10-membered heterocycloalkyl), —(CH$_2$)$_q$—O-(3- to 10-membered heterocyoalkyl),
aryl-, —(CH$_2$)$_q$-aryl, —(CH$_2$)$_q$—O-aryl, heteroaryl-, —(CH$_2$)$_q$-heteroaryl, —(CH$_2$)$_q$—O-heteroaryl;
said group being optionally substituted, one or more times, identically or differently, with a substituent selected from:
halo-, hydroxyl, oxo (=O), cyano-, $C_1$-$C_6$-alkyl-, $C_2$-$C_6$-alkynyl-,
halo-$C_1$-$C_6$-alkyl-, $C_1$-$C_6$-alkoxy-, —N(H)$R^5$, —N$R^5R^6$, —$R^4$—S(=O)$_2$—;
or
when two substituents are present ortho to each other on an aryl- or heteroaryl-ring, said two substituents together form a bridge:
*O(CH$_2$)$_p$O*, *NH(C(=O))NH*, wherein * represents the point of attachment to said aryl- or heteroaryl-ring;
$R^4$ represents a
$C_1$-$C_6$-alkyl-group
or
N$R^3R^4$ together
represent a 3- to 10-membered heterocycloalkyl group, which is optionally substituted, one or more times, identically or differently, with —CN, —OH, $C_1$-$C_6$-alkyl-, $R^6R^7$N—, $R^6R^7$N—$C_1$-$C_6$-alkyl- or —C(=O)N$R^6R^7$;
$R^5$ represents a hydrogen atom or a $C_1$-$C_6$-alkyl-group;
$R^6$ represents a hydrogen atom or a $C_1$-$C_6$-alkyl-group;
$R^7$ represents a hydrogen atom or a $C_1$-$C_6$-alkyl-group;
or
N$R^6R^7$ together represent a 3- to 10-membered heterocycloalkyl group;
p represents 1;
q represents an integer of 1, 2 or 3;

or a tautomer, an N-oxide, a hydrate, a solvate, or a salt thereof.
2. The compound of claim 1, wherein:
$R^1$ represents a group selected from:
—C(=O)O—$R^3$, —C(=O)N(H)$R^3$, and —C(=O)N$R^3R^4$;
$R^{2a}$ represents a hydrogen atom;
$R^{2b}$ represents a hydrogen atom;
$R^{2c}$ represents a hydrogen atom;
$R^{2c}$ represents a hydrogen atom or a group selected from: $C_1$-$C_3$-alkoxy-, halo-;
$R^3$ represents a hydrogen atom or a group selected from:
$C_1$-$C_6$-alkyl-, $C_2$-$C_6$-alkynyl-, $C_3$-$C_7$-cycloalkyl-, —(CH$_2$)$_q$—($C_3$-$C_7$-cycloalkyl),
3- to 10-membered heterocycloalkyl,
—(CH$_2$)$_q$-(3- to 10-membered heterocycloalkyl), aryl, —(CH$_2$)$_q$-aryl,
—(CH$_2$)$_q$—O-aryl, heteroaryl, —(CH$_2$)$_q$-heteroaryl, —(CH$_2$)$_q$—O-heteroaryl;
said group being optionally substituted, one or more times, identically or differently, with a substituent selected from:
halo-, hydroxy-, oxo-(O=), cyano-, $C_1$-$C_6$-alkyl-, $C_2$-$C_6$-alkynyl-, halo-$C_1$-$C_6$-alkyl-,
$C_1$-$C_6$-alkoxy-, —N(H)$R^5$, —N$R^5R^4$, S(=O)$_2$—;
or
when two substituents are present ortho to each other on an aryl- or heteroaryl-ring, said two substituents together form a bridge:
*O(CH$_2$)$_p$O*, *NH(C(=O))NH*, wherein * represent the point of attachment to said aryl- or heteroaryl-ring;
$R^4$ represents a $C_1$-$C_6$-alkyl-group;
or
N$R^3R^4$ together
represent a 3- to 10-membered heterocycloalkyl group;
which is optionally substituted, one or more times, identically or differently, with —CN, —OH, $C_1$-$C_6$-alkyl-, $R^6R^7$N—$C_1$-$C_6$-alkyl- or —C(=O)N$R^6R^7$;
$R^5$ represents a hydrogen atom or a $C_1$-$C_6$-alkyl-group;
$R^6$ represents a hydrogen atom or a $C_1$-$C_6$-alkyl-group;
$R^7$ represents a hydrogen atom or a $C_1$-$C_6$-alkyl-group;
or
N$R^6R^7$ together represent a 3- to 10-membered heterocycloalkyl group;
p represents 1;
q represents an integer of 1, 2 or 3;
or a stereoisomer, a tautomer, an N-oxide, a hydrate, a solvate, or a salt thereof.
3. The compound of claim 1, wherein:
$R^1$ represents a group selected from —C(=O)N(H)$R^3$, and —C(=O)N$R^3R^4$;
$R^{2a}$ represents a hydrogen atom;
$R^{2b}$ represents a hydrogen atom;
$R^{2c}$ represents a hydrogen atom;
and
$R^{2d}$ represents a hydrogen atom or a $C_1$-$C_3$-alkoxy-group;
$R^3$ represents a hydrogen atom or a group selected from
$C_1$-$C_6$-alkyl-, $C_3$-$C_7$-cycloalkyl-, —(CH$_2$)$_q$—($C_3$-$C_7$-cycloalkyl), aryl-, —(CH$_2$)$_q$-aryl, —(CH$_2$)$_q$—O-aryl, heteroaryl-, —(CH$_2$)$_q$-heteroaryl;
said group being optionally substituted, one or more times, identically or differently, with a substituent selected from:
halo-, hydroxy-, $C_1$-$C_6$-alkyl-, halo-$C_1$-$C_6$-alkyl-, $C_1$-$C_6$-alkoxy-,
—N$R^5R^4$, —S(=O)$_2$N(H)$R^5$;

or when two substituents are present ortho to each other on an aryl- or heteroaryl-ring, said two substituents together form a bridge:

*O(CH$_2$)$_p$O*, wherein * represent the point of attachment to said aryl- or heteroaryl-ring;

R$^4$ represents a group selected from: C$_1$-C$_6$-alkyl-, C$_2$-C$_6$-alkynyl-;

or

NR$^3$R$^4$ together represent a 3- to 10-membered heterocycloalkyl-group; which is optionally substituted, one or more times, identically or differently, with —CN, halo-, hydroxy-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-;

R$^5$ represents a hydrogen atom, a C$_1$-C$_6$-alkyl- or C$_3$-C$_7$-cycloalkyl-group;

p represents an integer of 1;

q represents an integer of 1 or 2;

or a stereoisomer, a tautomer, an N-oxide, a hydrate, a solvate, or a salt thereof.

4. A compound of claim 1, wherein:

R$^1$ represents a —C(=O)O—R$^3$ group;

R$^{2a}$ represents a hydrogen atom;

R$^{2b}$ represents a hydrogen atom;

R$^{2c}$ represents a hydrogen atom;

R$^{2d}$ represents a hydrogen atom or a group selected from C$_1$-C$_3$-alkoxy-, halo-;

R$^3$ represents a hydrogen atom or a C$_1$-C$_6$-alkyl-group;

or a stereoisomer, a tautomer, an N-oxide, a hydrate, a solvate, or a salt thereof.

5. The compound of claim 1, wherein:

or a stereoisomer, a tautomer, an N-oxide, a hydrate, a solvate, or a salt thereof.

6. The compound of claim 1, which is selected from the group consisting of:

Ethyl 4-(1H-indazol-5-ylamino)-5,6,7,8-tetrahydro[1]benzothieno[2,3-d]pyrimidine-7-carboxylate, 4-(1H-Indazol-5-ylamino)-5,6,7,8-tetrahydro[1]benzothieno[2,3-d]pyrimidine-7-carboxylic acid, 4-(1H-Indazol-5-ylamino)-5,6,7,8-tetrahydro[1]benzothieno[2,3-d]pyrimidine-7-carboxamide, 4-(1H-Indazol-5-ylamino)-N-[3-(methylsulfonyl)propyl]-5,6,7,8-tetrahydro[1]benzothieno[2,3-d]pyrimidine-7-carboxamide, 4-(1H-Indazol-5-ylamino)-N-phenyl-5,6,7,8-tetrahydro[1]benzothieno[2,3-d]pyrimidine-7-carboxamide, 4-(1H-Indazol-5-ylamino)-N-isopropyl-5,6,7,8-tetrahydro[1]benzothieno[2,3-d]pyrimidine-7-carboxamide, N-(Cyclopropylmethyl)-4-(1H-indazol-5-ylamino)-5,6,7,8-tetrahydro[1]benzothieno[2,3-d]pyrimidine-7-carboxamide,

[4-(1H-Indazol-5-ylamino)-5,6,7,8-tetrahydro[1]benzothieno[2,3-d]pyrimidin-7-yl]4-methylpiperazin-1-yl)methanone, 4-(1H-indazol-5-ylamino)-N-[3-(trifluoromethyl)benzyl]-5,6,7,8-tetrahydro[1]benzothieno[2,3-d]pyrimidine-7-carboxamide, 4-(1H-indazol-5-ylamino)-N,N-dimethyl-5,6,7,8-tetrahydro[1]benzothieno[2,3-d]pyrimidine-7-carboxamide, 4-(1H-indazol-5-ylamino)-N-methyl-5,6,7,8-tetrahydro[1]benzothieno[2,3-d]pyrimidine-7-carboxamide, 4-(1H-indazol-5-ylamino)-N-(2-methoxyphenyl)-5,6,7,8-tetrahydro[1]benzothieno[2,3-d]pyrimidine-7-carboxamide, 4-(1H-indazol-5-ylamino)-N-(3-methoxyphenyl)-5,6,7,8-tetrahydro[1]benzothieno[2,3-d]pyrimidine-7-carboxamide, 4-(1H-indazol-5-ylamino)-N-(4-methoxyphenyl)-5,6,7,8-tetrahydro[1]benzothieno[2,3-d]pyrimidine-7-carboxamide, 4-(1H-indazol-5-ylamino)-N-(2-methylphenyl)-5,6,7,8-tetrahydro[1]benzothieno[2,3-d]pyrimidine-7-carboxamide, 4-(1H-indazol-5-ylamino)-N-(3-methylphenyl)-5,6,7,8-tetrahydro[1]benzothieno[2,3-d]pyrimidine-7-carboxamide, 4-(1H-indazol-5-ylamino)-N-(4-methylphenyl)-5,6,7,8-tetrahydro[1]benzothieno[2,3-d]pyrimidine-7-carboxamide, N-(3-Fluorobenzyl)-4-(1H-indazol-5-ylamino)-5,6,7,8-tetrahydro[1]benzothieno-[2,3-d]pyrimidine-7-carboxamide, 4-(1H-indazol-5-ylamino)-N-(3-methoxybenzyl)-5,6,7,8-tetrahydro[1]benzothieno[2,3-d]pyrimidine-7-carboxamide, 4-(1H-indazol-5-ylamino)-N-(3-methylbenzyl)-5,6,7,8-tetrahydro[1]benzothieno[2,3-d]pyrimidine-7-carboxamide, N-Benzyl-4-(1H-indazol-5-ylamino)-5,6,7,8-tetrahydro[1]benzothieno[2,3-d]pyrimidine-7-carboxamide, 4-(1H-Indazol-5-ylamino)-N-(2-methoxybenzyl)-5,6,7,8-tetrahydro[1]benzothieno[2,3-d]pyrimidine-7-carboxamide, N-(1,3-Benzodioxol-5-ylmethyl)-4-(1H-indazol-5-ylamino)-5,6,7,8-tetrahydro[1]benzothieno[2,3-d]pyrimidine-7-carboxamide, N-(4-Fluorobenzyl)-4-(1H-indazol-5-ylamino)-5,6,7,8-tetrahydro[1]benzothieno[2,3-d]pyrimidine-7-carboxamide, 4-(1H-Indazol-5-ylamino)-N-[2-(4-methoxyphenyl)ethyl]-5,6,7,8-tetrahydro[1]benzothieno[2,3-d]pyrimidine-7-carboxamide, 4-(1H-Indazol-5-ylamino)-N-methyl-N-(pyridin-4-ylmethyl)-5,6,7,8-tetrahydro[1]benzothieno[2,3-d]pyrimidine-7-carboxamide, 4-(1H-Indazol-5-ylamino)-N-(4-methylbenzyl)-5,6,7,8-tetrahydro[1]benzothieno[2,3-d]pyrimidine-7-carboxamide, 4-(1H-Indazol-5-ylamino)-N-[4-(trifluoromethyl)benzyl]-5,6,7,8-tetrahydro[1]benzothieno[2,3-d]pyrimidine-7-carboxamide, 4-(1H-Indazol-5-ylamino)-N-(pyridin-4-ylmethyl)-5,6,7,8-tetrahydro[1]benzothieno[2,3-d]pyrimidine-7-carboxamide, 4-(1H-Indazol-5-ylamino)-N-(4-methoxybenzyl)-5,6,7,8-tetrahydro[1]benzothieno[2,3-d]pyrimidine-7-carboxamide, 4-(1H-Indazol-5-ylamino)-N-(2-phenoxyethyl)-5,6,7,8-tetrahydro[1]benzothieno[2,3-d]pyrimidine-7-carboxamide, 4-(1H-Indazol-5-ylamino)-N-(pyridin-3-ylmethyl)-5,6,7,8-tetrahydro[1]benzothieno[2,3-d]pyrimidine-7-carboxamide, 4-(1H-Indazol-5-ylamino)-N-(2,2,2-trifluoroethyl)-5,6,7,8-tetrahydro[1]benzothieno[2,3-d]pyrimidine-7-carboxamide, N-[4-(Dimethylamino)benzyl]-4-(1H-indazol-5-ylamino)-5,6,7,8-tetrahydro[1]benzothieno[2,3-d]pyrimidine-7-carboxamide,
4-(1H-Indazol-5-ylamino)-N-methyl-N-(prop-2-yn-1-yl)-5,6,7,8-tetrahydro[1]benzothieno[2,3-d]pyrimidine-7-carboxamide,
4-(1H-Indazol-5-ylamino)-N-[2-(pyridin-4-yl)ethyl]-5,6,7,8-tetrahydro[1]benzothieno[2,3-d]pyrimidine-7-carboxamide,
4-(1H-Indazol-5-ylamino)-N-(2-phenylethyl)-5,6,7,8-tetrahydro[1]benzothieno[2,3-d]pyrimidine-7-carboxamide,
N-[2-(Dimethylamino)ethyl]-4-(1H-indazol-5-ylamino)-5,6,7,8-tetrahydro[1]benzothieno[2,3-d]pyrimidine-7-carboxamide,
4-(1H-Indazol-5-ylamino)-N-(2-methylpropyl)-5,6,7,8-tetrahydro[1]benzothieno[2,3-d]pyrimidine-7-carboxamide,
N-[3-(Dimethylamino)propyl]-4-(1H-indazol-5-ylamino)-5,6,7,8-tetrahydro[1]benzothieno[2,3-d]pyrimidine-7-carboxamide,
N-(2-Hydroxyethyl)-4-(1H-indazol-5-ylamino)-N-methyl-5,6,7,8-tetrahydro[1]benzothieno[2,3-d]pyrimidine-7-carboxamide,
4-(1H-Indazol-5-ylamino)-N-[2-(morpholin-4-yl)ethyl]-5,6,7,8-tetrahydro[1]benzothieno[2,3-d]pyrimidine-7-carboxamide,
Azetidin-1-yl[4-(1H-indazol-5-ylamino)-5,6,7,8-tetrahydro[1]benzothieno[2,3-d]pyrimidin-7-yl]methanone,
N-Cyclopropyl-4-(1H-indazol-5-ylamino)-5,6,7,8-tetrahydro[1]benzothieno[2,3-d]pyrimidine-7-carboxamide,
N-[2-(Dimethylamino)ethyl]-4-(1H-indazol-5-ylamino)-N-methyl-5,6,7,8-tetrahydro[1]benzothieno[2,3-d]pyrimidine-7-carboxamide,
N-Ethyl-4-(1H-indazol-5-ylamino)-5,6,7,8-tetrahydro[1]benzothieno[2,3-d]pyrimidine-7-carboxamide,
[4-(1H-Indazol-5-ylamino)-5,6,7,8-tetrahydro[1]benzothieno[2,3-d]pyrimidin-7-yl](morpholin-4-yl)methanone,
4-(1H-Indazol-5-ylamino)-N-(3-methoxypropyl)-5,6,7,8-tetrahydro[1]benzothieno[2,3-d]pyrimidine-7-carboxamide,
4-(1H-Indazol-5-ylamino)-N-[3-(2-oxopyrrolidin-1-yl)propyl]-5,6,7,8-tetrahydro[1]benzothieno[2,3-d]pyrimidine-7-carboxamide,
4-(1H-Indazol-5-ylamino)-N-(2-methoxyethyl)-5,6,7,8-tetrahydro[1]benzothieno[2,3-d]pyrimidine-7-carboxamide,
[4-(1H-Indazol-5-ylamino)-5,6,7,8-tetrahydro[1]benzothieno[2,3-d]pyrimidin-7-yl](pyrrolidin-1-yl)methanone,
[4-(1H-Indazol-5-ylamino)-5,6,7,8-tetrahydro[1]benzothieno[2,3-d]pyrimidin-7-yl][4-(pyrrolidin-1-ylcarbonyl)piperazin-1-yl]methanone,
Ethyl 4-[(6-chloro-1H-indazol-5-yl)amino]-5,6,7,8-tetrahydro[1]benzothieno[2,3-d]pyrimidine-7-carboxylate,
Ethyl 4-[(6-fluoro-1H-indazol-5-yl)amino]-5,6,7,8-tetrahydro[1]benzothieno[2,3-d]pyrimidine-7-carboxylate,
4-[(6-Fluoro-1H-indazol-5-yl)amino]-5,6,7,8-tetrahydro[1]benzothieno[2,3-d]pyrimidine-7-carboxylic acid,
Ethyl 4-[(6-methoxy-1H-indazol-5-yl)amino]-5,6,7,8-tetrahydro[1]benzothieno[2,3-d]pyrimidine-7-carboxylate,
4-[(6-Methoxy-1H-indazol-5-yl)amino]-5,6,7,8-tetrahydro[1]benzothieno[2,3-d]pyrimidine-7-carboxylic acid,
N-Ethyl-4-[(6-methoxy-1H-indazol-5-yl)amino]-5,6,7,8-tetrahydro[1]benzothieno[2,3-d]pyrimidine-7-carboxamide,
N-Isopropyl-4-[(6-methoxy-1H-indazol-5-yl)amino]-5,6,7,8-tetrahydro[1]benzothieno[2,3-d]pyrimidine-7-carboxamide,
(RS)-4-[(6-fluoro-1H-indazol-5-yl)amino]-N-(propan-2-yl)-5,6,7,8-tetrahydro[1]benzothieno[2,3-d]pyrimidine-7-carboxamide,
(RS)-4-[(6-methoxy-1H-indazol-5-yl)amino]-N,N-dimethyl-5,6,7,8-tetrahydro[1]benzothieno[2,3-d]pyrimidine-7-carboxamide,
(RS)-{4-[(6-methoxy-1H-indazol-5-yl)amino]-5,6,7,8-tetrahydro[1]benzothieno[2,3-d]pyrimidin-7-yl}(4-methylpiperazin-1-yl)methanone,
(RS)-4-[(6-methoxy-1H-indazol-5-yl)amino]-N-(propan-2-yl)-5,6,7,8-tetrahydro[1]benzothieno[2,3-d]pyrimidine-7-carboxamide,
N-ethyl-4-[(6-methoxy-1H-indazol-5-yl)amino]-N-(propan-2-yl)-5,6,7,8-tetrahydro[1]benzothieno[2,3-d]pyrimidine-7-carboxamide,
4-[(6-methoxy-1H-indazol-5-yl)amino]-N-methyl-N-propyl-5,6,7,8-tetrahydro[1]benzothieno[2,3-d]pyrimidine-7-carboxamide,
(RS)-4-{[6-(propan-2-yloxy)-1H-indazol-5-yl]amino}-5,6,7,8-tetrahydro[1]benzothieno[2,3-d]pyrimidine-7-carboxylicacid,
(RS)-N,N-dimethyl-4-{[6-(propan-2-yloxy)-1H-indazol-5-yl]amino}-5,6,7,8-tetrahydro[1]benzothieno[2,3-d]pyrimidine-7-carboxamide,
(RS)-(4-methylpiperazin-1-yl)(4-{[6-(propan-2-yloxy)-1H-indazol-5-yl]amino}-5,6,7,8-tetrahydro[1]benzothieno[2,3-d]pyrimidin-7-yl)methanone,
(RS)-N-(propan-2-yl)-4-{[6-(propan-2-yloxy)-1H-indazol-5-yl]amino}-5,6,7,8-tetrahydro[1]benzothieno[2,3-d]pyrimidine-7-carboxamide,
(RS)-methyl4-(1H-indazol-5-ylamino)-5,6,7,8-tetrahydro[1]benzothieno[2,3-d]pyrimidine-7-carboxylate,
(RS)-propan-2-yl4-(1H-indazol-5-ylamino)-5,6,7,8-tetrahydro[1]benzothieno[2,3-d]pyrimidine-7-carboxylate,
(RS)-4-(1H-indazol-5-ylamino)-N-(2-methylphenyl)-5,6,7,8-tetrahydro[1]benzothieno[2, 3-d]pyrimidine-7-carboxamide,
(RS)-4-(1H-indazol-5-ylamino)-N-(pyridin-3-ylmethyl)-5,6,7,8-tetrahydro[1]benzothieno[2, 3-d]pyrimidine-7-carboxamidehydrochloride(1:1),
(RS)-N-(4-cyanophenyl)-4-(1H-indazol-5-ylamino)-5,6,7,8-tetrahydro[1]benzothieno[2,3-d]pyrimidine-7-carboxamide,
(RS)-4-(1H-indazol-5-ylamino)-N-(oxetan-3-yl)-5,6,7,8-tetrahydro[1]benzothieno[2, 3-d]pyrimidine-7-carboxamide,
(RS)-N-(3-cyanophenyl)-4-(1H-indazol-5-ylamino)-5,6,7,8-tetrahydro[1]benzothieno[2,3-d]pyrimidine-7-carboxamide,
(RS)-N-cyclopropyl-4-(1H-indazol-5-ylamino)-5,6,7,8-tetrahydro[1]benzothieno[2, 3-d]pyrimidine-7-carboxamide,
(RS)-4-(1H-indazol-5-ylamino)-N-(pyridin-2-ylmethyl)-5,6,7,8-tetrahydro[1]benzothieno[2, 3-d]pyrimidine-7-carboxamide,
(RS)-[4-(1H-indazol-5-ylamino)-5,6,7,8-tetrahydro[1]benzothieno[2,3-d]pyrimidin-7-yl](piperidin-1-yl)methanone,
(RS)-N,N-diethyl-4-(1H-indazol-5-ylamino)-5,6,7,8-tetrahydro[1]benzothieno[2,3-d]pyrimidine-7-carboxamide, (RS)-(4-hydroxypiperidin-1-yl)[4-(1H-indazol-5-ylamino)-5,6,7,8-tetrahydro[1]benzothieno[2,3-d]pyrimidin-7-yl]methanone, (RS)-[3-(hydroxymethyl)piperidin-1-yl][4-(1H-indazol-5-ylamino)-5,6,7,8-tetrahydro[1]benzothieno[2,3-d]pyrimidin-7-yl]methanone, (RS)-4-(1H-indazol-5-ylamino)-N-(1H-pyrazol-3-yl)-5,6,7,8-tetrahydro[1]benzothieno[2,3-d]pyrimidine-7-carboxamide, (RS)-4-(1H-indazol-5-ylamino)-N-(thiophen-2-ylmethyl)-5,6,7,8-tetrahydro[1]benzothieno[2,3-d]pyrimidine-7-carboxamide, (RS)-4-(1H-indazol-5-ylamino)-N-methyl-N-phenyl-5,6,7,8-tetrahydro[1]benzothieno[2,3-d]pyrimidine-7-carboxamide, (RS)-N-[2-(1H-imidazol-4-yl)ethyl]-4-(1H-indazol-5-ylamino)-5,6,7,8-tetrahydro[1]benzothieno[2,3-d]pyrimidine-7-carboxamide, (RS)-N-[3-(1H-imidazol-1-yl)propyl]-4-(1H-indazol-5-ylamino)-5,6,7,8-tetrahydro[1]benzothieno[2,3-d]pyrimidine-7-carboxamide, (RS)-4-(1H-indazol-5-ylamino)-N-(pyridin-4-yl)-5,6,7,8-tetrahydro[1]benzothieno[2,3-d]pyrimidine-7-carboxamide, (RS)-N-[2-(diethylamino)ethyl]-4-(1H-indazol-5-ylamino)-N-methyl-5,6,7,8-tetrahydro[1]benzothieno[2,3-d]pyrimidine-7-carboxamide, (RS)-N-[3-(dimethylamino)propyl]-4-(1H-indazol-5-ylamino)-N-methyl-5,6,7,8-tetrahydro[1]benzothieno[2,3-d]pyrimidine-7-carboxamide, (RS)-4-(1H-indazol-5-ylamino)-N-[2-(pyrrolidin-1-yl)ethyl]-5,6,7,8-tetrahydro[1]benzothieno[2,3-d]pyrimidine-7-carboxamide, (RS)-4-(1H-indazol-5-ylamino)-N-(pyridin-2-yl)-5,6,7,8-tetrahydro[1]benzothieno[2,3-d]pyrimidine-7-carboxamide, (RS)-4-(1H-indazol-5-ylamino)-N-(pyridin-3-yl)-5,6,7,8-tetrahydro[1]benzothieno[2,3-d]pyrimidine-7-carboxamide, (RS)-N-benzyl-4-(1H-indazol-5-ylamino)-N-methyl-5,6,7,8-tetrahydro[1]benzothieno[2,3-d]pyrimidine-7-carboxamide, (RS)-N-tert-butyl-4-(1H-indazol-5-ylamino)-5,6,7,8-tetrahydro[1]benzothieno[2,3-d]pyrimidine-7-carboxamide, (RS)-[4-(1H-indazol-5-ylamino)-5,6,7,8-tetrahydro[1]benzothieno[2,3-d]pyrimidin-7-yl](3-methylpiperidin-1-yl)methanone, (RS)-[4-(1H-indazol-5-ylamino)-5,6,7,8-tetrahydro[1]benzothieno[2,3-d]pyrimidin-7-yl](4-methylpiperidin-1-yl)methanone, (RS)-(3-hydroxypiperidin-1-yl)[4-(1H-indazol-5-ylamino)-5,6,7,8-tetrahydro[1]benzothieno[2,3-d]pyrimidin-7-yl]methanone, (RS)-N-ethyl-4-(1H-indazol-5-ylamino)-N-(pyridin-4-ylmethyl)-5,6,7,8-tetrahydro[1]benzothieno[2,3-d]pyrimidine-7-carboxamide, (RS)-[4-(1H-indazol-5-ylamino)-5,6,7,8-tetrahydro[1]benzothieno[2,3-d]pyrimidin-7-yl][4-(pyridin-4-yl)piperazin-1-yl]methanone, (RS)-N-(2,2-dimethylpropyl)-4-(1H-indazol-5-ylamino)-5,6,7,8-tetrahydro[1]benzothieno[2,3-d]pyrimidine-7-carboxamide, (RS)-4-(1H-indazol-5-ylamino)-N-[2-(thiophen-2-yl)ethyl]-5,6,7,8-tetrahydro[1]benzothieno[2,3-d]pyrimidine-7-carboxamide, (RS)-4-(1H-indazol-5-ylamino)-N-(1-methyl-1H-pyrazol-5-yl)-5,6,7,8-tetrahydro[1]benzothieno[2,3-d]pyrimidine-7-carboxamide, (RS)-[4-(1H-indazol-5-ylamino)-5,6,7,8-tetrahydro[1]benzothieno[2,3-d]pyrimidin-7-yl](4-methyl-1,4-diazepan-1-yl)methanone, (RS)-(4-ethylpiperazin-1-yl)[4-(1H-indazol-5-ylamino)-5,6,7,8-tetrahydro[1]benzothieno[2,3-d]pyrimidin-7-yl]methanone, (RS)-N-(2-hydroxypropyl)-4-(1H-indazol-5-ylamino)-N-methyl-5,6,7,8-tetrahydro[1]benzothieno[2,3-d]pyrimidine-7-carboxamide, (RS)-4-(1H-indazol-5-ylamino)-N-(tetrahydro-2H-pyran-4-yl)-5,6,7,8-tetrahydro[1]benzothieno[2,3-d]pyrimidine-7-carboxamide, (RS)-4-(1H-indazol-5-ylamino)-N-[2-(2-oxoimidazolidin-1-yl)ethyl]-5,6,7,8-tetrahydro[1]benzothieno[2,3-d]pyrimidine-7-carboxamide, (RS)-4-(1H-indazol-5-ylamino)-N-(pyridazin-4-yl)-5,6,7,8-tetrahydro[1]benzothieno[2,3-d]pyrimidine-7-carboxamide, (RS)—{4-[2-(dimethylamino)ethyl]piperazin-1-yl}[4-(1H-indazol-5-ylamino)-5,6,7,8-tetrahydro[1]benzothieno[2,3-d]pyrimidin-7-yl]methanone, (RS)-4-(1H-indazol-5-ylamino)-N-(2-methoxyethyl)-N-methyl-5,6,7,8-tetrahydro[1]benzothieno[2,3-d]pyrimidine-7-carboxamide, (RS)-(4-cyclopentylpiperazin-1-yl)[4-(1H-indazol-5-ylamino)-5,6,7,8-tetrahydro[1]benzothieno[2,3-d]pyrimidin-7-yl]methanone, (RS)-[4-(1H-indazol-5-ylamino)-5,6,7,8-tetrahydro[1]benzothieno[2,3-d]pyrimidin-7-yl][4-(2-methoxyethyl)piperazin-1-yl]methanone, (RS)-(3-hydroxypyrrolidin-1-yl)[4-(1H-indazol-5-ylamino)-5,6,7,8-tetrahydro[1]benzothieno[2,3-d]pyrimidin-7-yl]methanone, (RS)-4-(1H-indazol-5-ylamino)-N-[(1-methyl-1H-pyrazol-5-yl)methyl]-5,6,7,8-tetrahydro[1]benzothieno[2,3-d]pyrimidine-7-carboxamide, (RS)-4-(1H-indazol-5-ylamino)-N-methyl-N-[(1-methyl-1H-pyrazol-3-yl)methyl]-5,6,7,8-tetrahydro[1]benzothieno[2,3-d]pyrimidine-7-carboxamide, (RS)-4-(1H-indazol-5-ylamino)-N-methyl-N-[(1-methyl-1H-pyrazol-5-yl)methyl]-5,6,7,8-tetrahydro[1]benzothieno[2,3-d]pyrimidine-7-carboxamide, (RS)-4-(1H-indazol-5-ylamino)-N-(1H-pyrazol-3-ylmethyl)-5,6,7,8-tetrahydro[1]benzothieno[2,3-d]pyrimidine-7-carboxamide, (RS)-4-(1H-indazol-5-ylamino)-N-(1-methyl-1H-pyrazol-3-yl)-5,6,7,8-tetrahydro[1]benzothieno[2,3-d]pyrimidine-7-carboxamide, (RS)-2-(4-{[4-(1H-indazol-5-ylamino)-5,6,7,8-tetrahydro[1]benzothieno[2,3-d]pyrimidin-7-yl]carbonyl}piperazin-1-yl)-N,N-dimethylacetamide, (RS)-4-(1H-indazol-5-ylamino)-N-[2-(4-methylpiperazin-1-yl)ethyl]-5,6,7,8-tetrahydro[1]benzothieno[2,3-d]pyrimidine-7-carboxamide, (RS)-N-(3-fluorobenzyl)-4-(1H-indazol-5-ylamino)-N-methyl-5,6,7,8-tetrahydro[1]benzothieno[2,3-d]pyrimidine-7-carboxamide, (RS)-4-(1H-indazol-5-ylamino)-N-(1-methyl-1H-pyrazol-4-yl)-5,6,7,8-tetrahydro[1]benzothieno[2,3-d]pyrimidine-7-carboxamide, (RS)-4-(1H-indazol-5-ylamino)-N-[(5-methylpyrazin-2-yl)methyl]-5,6,7,8-tetrahydro[1]benzothieno[2,3-d]pyrimidine-7-carboxamide, (RS)-4-(1H-indazol-5-ylamino)-N-(pyridazin-3-yl)-5,6, 7,8-tetrahydro[1]benzothieno[2,3-d]pyrimidine-7-carboxamide, (RS)-4-(1H-indazol-5-ylamino)-N-(pyrimidin-5-yl)-5,6, 7,8-tetrahydro[1]benzothieno[2,3-d]pyrimidine-7-carboxamide, (RS)-4-(1H-indazol-5-ylamino)-N-(thiophen-3-ylmethyl)-5,6,7,8-tetrahydro[1]benzothieno[2,3-d]pyrimidine-7-carboxamide, (RS)-4-(1H-indazol-5-ylamino)-N-[(1-methyl-1H-imidazol-5-yl)methyl]-5,6,7,8-tetrahydro[1]benzothieno[2, 3-d]pyrimidine-7-carboxamide, (RS)-[4-(1H-indazol-5-ylamino)-5,6,7,8-tetrahydro[1] benzothieno[2,3-d]pyrimidin-7-yl][4-(3-methoxypropyl)piperazin-1-yl]methanone, (RS)-[4-(1H-indazol-5-ylamino)-5,6,7,8-tetrahydro[1] benzothieno[2,3-d]pyrimidin-7-yl][4-(methyl sulfonyl) piperazin-1-yl]methanone, (RS)-4-(1H-indazol-5-ylamino)-N-methyl-N-[(1-methyl-1H-pyrazol-4-yl)methyl]-5,6,7,8-tetrahydro[1]benzothieno[2,3-d]pyrimidine-7-carboxamide, (RS)-4-(1H-indazol-5-ylamino)-N-[(1-methyl-1H-pyrazol-4-yl)methyl]-5,6,7,8-tetrahydro[1]benzothieno[2, 3-d]pyrimidine-7-carboxamide, (RS)-N-[2-(4-fluorophenyl)propan-2-yl]-4-(1H-indazol-5-ylamino)-5,6,7,8-tetrahydro[1]benzothieno[2,3-d] pyrimidine-7-carboxamide, (RS)-4-(1H-indazol-5-ylamino)-N-methyl-N-(thiophen-3-ylmethyl)-5,6,7,8-tetrahydro[1]benzothieno[2,3-d] pyrimidine-7-carboxamide, (RS)-4-(1H-indazol-5-ylamino)-N-methyl-N-[(1-methyl-1H-pyrrol-2-yl)methyl]-5,6,7,8-tetrahydro[1]benzothieno[2,3-d]pyrimidine-7-carboxamide, (RS)-2-(4-{[4-(1H-indazol-5-ylamino)-5,6,7,8-tetrahydro [1]benzothieno[2,3-d]pyrimidin-7-yl] carbonyl}piperazin-1-yl)-N-methylacetamide, (RS)-4-(1H-indazol-5-ylamino)-N-[(1-methyl-1H-imidazol-2-yl)methyl]-5,6,7,8-tetrahydro[1]benzothieno[2, 3-d]pyrimidine-7-carboxamide, (RS)-4-(1H-indazol-5-ylamino)-N-methyl-N-[2-(pyrrolidin-1-yl)ethyl]-5,6,7,8-tetrahydro[1]benzothieno[2,3-d]pyrimidine-7-carboxamide, (RS)-4-(1H-indazol-5-ylamino)-N-methyl-N-[2-(4-methylpiperidin-1-yl)ethyl]-5,6,7,8-tetrahydro[1]benzothieno[2,3-d]pyrimidine-7-carboxamide, (RS)-N-(2,2-difluoroethyl)-4-[(6-methoxy-1H-indazol-5-yl)amino]-N-methyl-5,6,7,8-tetrahydro[1]benzothieno [2,3-d]pyrimidine-7-carboxamide, (RS)-N-ethyl-N-(2-hydroxyethyl)-4-[(6-methoxy-1H-indazol-5-yl)amino]-5,6,7,8-tetrahydro[1]benzothieno[2, 3-d]pyrimidine-7-carboxamide, (RS)-N-(2-hydroxyethyl)-4-[(6-methoxy-1H-indazol-5-yl)amino]-N-methyl-5,6,7,8-tetrahydro[1]benzothieno [2,3-d]pyrimidine-7-carboxamide, (RS)-N-isopropyl-4-[(6-methoxy-1H-indazol-5-yl) amino]-N-methyl-5,6,7,8-tetrahydro[1]benzothieno[2, 3-d]pyrimidine-7-carboxamide, (RS)-1-({4-[(6-methoxy-1H-indazol-5-yl)amino]-5,6,7, 8-tetrahydro[1]benzothieno[2,3-d]pyrimidin-7-yl}carbonyl)piperidin-4-one, (RS)-{4-[(6-methoxy-1H-indazol-5-yl)amino]-5,6,7,8-tetrahydro[1]benzothieno[2,3-d]pyrimidin-7-yl}(morpholin-4-yl)methanone, (RS)-{4-[(6-methoxy-1H-indazol-5-yl)amino]-5,6,7,8-tetrahydro[1]benzothieno[2,3-d]pyrimidin-7-yl}(piperidin-1-yl)methanone, (RS)-azetidin-1-yl{4-[(6-methoxy-1H-indazol-5-yl) amino]-5,6,7,8-tetrahydro[1]benzothieno[2,3-d]pyrimidin-7-yl}methanone,

[(2R,5R)-2, 5-dimethylpyrrolidin-1-yl]{(7RS)-4-[(6-methoxy-1H-indazol-5-yl)amino]-5,6,7,8-tetrahydro [1]benzothieno[2,3-d]pyrimidin-7-yl}methanone, (RS)-N-ethyl-4-[(6-methoxy-1H-indazol-5-yl)amino]-N-methyl-5,6,7,8-tetrahydro[1]benzothieno[2,3-d]pyrimidine-7-carboxamide, (RS)-(3,3-dimethylpyrrolidin-1-yl){4-[(6-methoxy-1H-indazol-5-yl)amino]-5,6,7,8-tetrahydro[1]benzothieno [2,3-d]pyrimidin-7-yl}methanone, (RS)-N-cyclopropyl-4-[(6-methoxy-1H-indazol-5-yl) amino]-N-methyl-5,6,7,8-tetrahydro[1]benzothieno[2, 3-d]pyrimidine-7-carboxamide, (RS)-N-(cyclopropylmethyl)-4-[(6-methoxy-1H-indazol-5-yl)amino]-N-methyl-5,6,7,8-tetrahydro[1]benzothieno[2,3-d]pyrimidine-7-carboxamide, (RS)-{4-[(6-methoxy-1H-indazol-5-yl)amino]-5,6,7,8-tetrahydro[1]benzothieno[2,3-d]pyrimidin-7-yl}(pyrrolidin-1-yl)methanone, (RS)-2,6-dimethylmorpholin-4-yl[4-(1H-indazol-5-ylamino)-5,6,7,8-tetrahydro[1]benzothieno[2,3-d]pyrimidin-7-yl]methanone, (RS)-4-(1H-indazol-5-ylamino)-N-methyl-N-(2-methylpropyl)-5,6,7,8-tetrahydro[1]benzothieno[2,3-d]pyrimidine-7-carboxamide, (RS)-(1,1-dioxidothiomorpholin-4-yl)[4-(1H-indazol-5-ylamino)-5,6,7,8-tetrahydro[1]benzothieno[2,3-d]pyrimidin-7-yl]methanone, (RS)-4-(1H-indazol-5-ylamino)-N-methyl-N-[2-(methylamino)-2-oxoethyl]-5,6,7,8-tetrahydro[1]benzothieno [2,3-d]pyrimidine-7-carboxamide, (RS)-N-(2-cyanoethyl)-N-ethyl-4-(1H-indazol-5-ylamino)-5,6,7,8-tetrahydro[1]benzothieno[2,3-d]pyrimidine-7-carboxamide, (RS)-N-(4-hydroxybutyl)-4-(1H-indazol-5-ylamino)-N-methyl-5,6,7,8-tetrahydro[1]benzothieno[2,3-d]pyrimidine-7-carboxamide, (RS)-[4-hydroxy-4-(trifluoromethyl)piperidin-1-yl][4-(1H-indazol-5-ylamino)-5,6,7,8-tetrahydro[1]benzothieno[2,3-d]pyrimidin-7-yl]methanone, (RS)-[4-(1H-indazol-5-ylamino)-5,6,7,8-tetrahydro[1] benzothieno[2,3-d]pyrimidin-7-yl](5-methyl-2, 5-diazabicyclo[2.2.1]hept-2-yl)methanone, (RS)-1-{[4-(1H-indazol-5-ylamino)-5,6,7,8-tetrahydro[1] benzothieno[2,3-d]pyrimidin-7-yl] carbonyl}piperidine-3-carbonitrile, (RS)-(4,4-difluoropiperidin-1-yl)[4-(1H-indazol-5-ylamino)-5,6,7,8-tetrahydro[1]benzothieno[2,3-d]pyrimidin-7-yl]methanone, (RS)-2-(4-{[4-(1H-indazol-5-ylamino)-5,6,7,8-tetrahydro [1]benzothieno[2,3-d]pyrimidin-7-yl] carbonyl}piperazin-1-yl)-1-(pyrrolidin-1-yl)ethanone, (RS)-N-(3-hydroxypropyl)-4-(1H-indazol-5-ylamino)-N-methyl-5,6,7,8-tetrahydro[1]benzothieno[2,3-d]pyrimidine-7-carboxamide, (RS)-[3-(dimethylamino)pyrrolidin-1-yl][4-(1H-indazol-5-ylamino)-5,6,7,8-tetrahydro[1]benzothieno[2,3-d] pyrimidin-7-yl]methanone[3-(dimethylamino)pyrrolidin-1-yl][4-(1H-indazol-5-ylamino)-5,6,7,8-tetrahydro [1]benzothieno[2,3-d]pyrimidin-7-yl]methanone, (RS)-2-oxa-6-azaspiro[3.3]hept-6-yl(4-{[6-(propan-2-yloxy)-1H-indazol-5-yl]amino}-5,6,7,8-tetrahydro[1] benzothieno[2,3-d]pyrimidin-7-yl)methanone, (RS)-1-[(4-{[6-(propan-2-yloxy)-1H-indazol-5-yl]
amino}-5,6,7,8-tetrahydro[1]benzothieno[2,3-d]py-
rimidin-7-yl)carbonyl]azetidine-3-carbonitrile, (RS)-{4-[(6-ethoxy-1H-indazol-5-yl)amino]-5,6,7,8-tet-
rahydro[1]benzothieno[2,3-d]pyrimidin-7-yl}(piperi-
din-1-yl)methanone, (RS)-4-[(6-ethoxy-1H-indazol-5-yl)amino]-5,6,7,8-tetra-
hydro[1]benzothieno[2,3-d]pyrimidine-7-carboxylic
acid, (RS)-1-({4-[(6-ethoxy-1H-indazol-5-yl)amino]-5,6,7,8-
tetrahydro[1]benzothieno[2,3-d]pyrimidin-7-
yl}carbonyl)piperidin-4-one, (RS)-{4-[(6-ethoxy-1H-indazol-5-yl)amino]-5,6,7,8-tet-
rahydro[1]benzothieno[2,3-d]pyrimidin-7-yl}(mor-
pholin-4-yl)methanone, (RS)-piperidin-1-yl(4-{[6-(propan-2-yloxy)-1H-indazol-
5-yl]amino}-5,6,7,8-tetrahydro[1]benzothieno[2,3-d]
pyrimidin-7-yl)methanone, (RS)-N-ethyl-N-(2-hydroxyethyl)-4-{[6-(propan-2-
yloxy)-1H-indazol-5-yl]amino}-5,6,7,8-tetrahydro[1]
benzothieno[2,3-d]pyrimidine-7-carboxamide, (RS)-N-methyl-N-(propan-2-yl)-4-{[6-(propan-2-yloxy)-
1H-indazol-5-yl]amino}-5,6,7,8-tetrahydro[1]benzoth-
ieno[2,3-d]pyrimidine-7-carboxamide, (RS)-N-(2,2-difluoroethyl)-N-methyl-4-{[6-(propan-2-
yloxy)-1H-indazol-5-yl]amino}-5,6,7,8-tetrahydro[1]
benzothieno[2,3-d]pyrimidine-7-carboxamide, (RS)-N-ethyl-N-methyl-4-{[6-(propan-2-yloxy)-1H-in-
dazol-5-yl]amino}-5,6,7,8-tetrahydro[1]benzothieno
[2,3-d]pyrimidine-7-carboxamide, (RS)-morpholin-4-yl(4-{[6-(propan-2-yloxy)-1H-inda-
zol-5-yl]amino}-5,6,7,8-tetrahydro[1]benzothieno[2,3-
d]pyrimidin-7-yl)methanone, (RS)-azetidin-1-yl(4-{[6-(propan-2-yloxy)-1H-indazol-
5-yl]amino}-5,6,7,8-tetrahydro[1]benzothieno[2,3-d]
pyrimidin-7-yl)methanone, (RS)-N-(cyclopropylmethyl)-N-methyl-4-{[6-(propan-2-
yloxy)-1H-indazol-5-yl]amino}-5,6,7,8-tetrahydro[1]
benzothieno[2,3-d]pyrimidine-7-carboxamide, (RS)-(4-{[6-(propan-2-yloxy)-1H-indazol-5-yl]amino}-
5,6,7,8-tetrahydro[1]benzothieno[2,3-d]pyrimidin-7-
yl)(pyrrolidin-1-yl)methanone, (RS)-(1, 1-dioxido-1-thia-6-azaspiro[3.3]hept-6-yl)(4-
{[6-(propan-2-yloxy)-1H-indazol-5-yl]amino}-5,6,7,
8-tetrahydro[1]benzothieno[2,3-d]pyrimidin-7-yl)
methanone, (RS)-azetidin-1-yl {4-[(6-ethoxy-1H-indazol-5-yl)
amino]-5,6,7,8-tetrahydro[1]benzothieno[2,3-d]py-
rimidin-7-yl}methanone, (RS)-4-[(6-ethoxy-1H-indazol-5-yl)amino]-N-isopropyl-
N-methyl-5,6,7,8-tetrahydro[1]benzothieno[2,3-d]py-
rimidine-7-carboxamide, (RS)-4-[(6-ethoxy-1H-indazol-5-yl)amino]-N-(2-hy-
droxyethyl)-N-methyl-5,6,7,8-tetrahydro[1]benzoth-
ieno[2,3-d]pyrimidine-7-carboxamide, (RS)-N-(2,2-difluoroethyl)-4-[(6-ethoxy-1H-indazol-5-
yl)amino]-N-methyl-5,6,7,8-tetrahydro[1]benzothieno
[2,3-d]pyrimidine-7-carboxamide,

[(2R,5R)-2, 5-dimethylpyrrolidin-1-yl]{(7RS)-4-[(6iso-
propoxy-1H-indazol-5-yl)amino]-5,6,7,8-tetrahydro[1]
benzothieno[2,3-d]pyrimidin-7-yl}methanone, (RS)-{4-[(6-ethoxy-1H-indazol-5-yl)amino]-5,6,7,8-tet-
rahydro[1]benzothieno[2,3-d]pyrimidin-7-yl}(pyrroli-
din-1-yl)methanone, (RS)-4-[(6-ethoxy-1H-indazol-5-yl)amino]-N-ethyl-N-
methyl-5,6,7,8-tetrahydro[1]benzothieno[2,3-d]py-
rimidine-7-carboxamide, (RS)-N-(2-hydroxyethyl)-4-[(6isopropoxy-1H-indazol-5-
yl)amino]-N-methyl-5,6,7,8-tetrahydro[1]benzothieno
[2,3-d]pyrimidine-7-carboxamide, (RS)-4-[(6-ethoxy-1H-indazol-5-yl)amino]-N-ethyl-N-
(2-hydroxyethyl)-5,6,7,8-tetrahydro[1]benzothieno[2,
3-d]pyrimidine-7-carboxamide, (RS)-1-({4-[(6-ethoxy-1H-indazol-5-yl)amino]-5,6,7,8-
tetrahydro[1]benzothieno[2,3-d]pyrimidin-7-
yl}carbonyl)azetidine-3-carbonitrile, {(7 RS)-4-[(6-ethoxy-1H-indazol-5-yl)amino]-5,6,7,8-
tetrahydro[1]benzothieno[2,3-d]pyrimidin-7-yl}[(3R)-
3-hydroxypyrrolidin-1-yl]methanone, (RS)-N-cyclopropyl-4-[(6-ethoxy-1H-indazol-5-yl)
amino]-N-methyl-5,6,7,8-tetrahydro[1]benzothieno[2,
3-d]pyrimidine-7-carboxamide, (RS)-4-[(6-ethoxy-1H-indazol-5-yl)amino]-N-ethyl-N-
(propan-2-yl)-5,6,7,8-tetrahydro[1]benzothieno[2,3-d]
pyrimidine-7-carboxamide, (RS)-1-({4-[(6-methoxy-1H-indazol-5-yl)amino]-5,6,7,
8-tetrahydro[1]benzothieno[2,3-d]pyrimidin-7-
yl}carbonyl)azetidine-3-carbonitrile, (RS)-N-tert-butyl-4-[(6-ethoxy-1H-indazol-5-yl)amino]-
N-methyl-5,6,7,8-tetrahydro[1]benzothieno[2,3-d]py-
rimidine-7-carboxamide, (RS)-{4-[(6-ethoxy-1H-indazol-5-yl)amino]-5,6,7,8-tet-
rahydro[1]benzothieno[2,3-d]pyrimidin-7-yl}(2-oxa-
6-azaspiro[3.3]hept-6-yl)methanone, (RS)-N-(cyclopropylmethyl)-4-[(6-ethoxy-1H-indazol-5-
yl)amino]-N-methyl-5,6,7,8-tetrahydro[1]benzothieno
[2,3-d]pyrimidine-7-carboxamide, (RS)-1-({4-[(6-ethoxy-1H-indazol-5-yl)amino]-5,6,7,8-
tetrahydro[1]benzothieno[2,3-d]pyrimidin-7-
yl}carbonyl)piperidine-3-carbonitrile, (RS)-N-(2-cyanoethyl)-4-[(6-ethoxy-1H-indazol-5-yl)
amino]-N-ethyl-5,6,7,8-tetrahydro[1]benzothieno[2,3-
d]pyrimidine-7-carboxamide,

[(3R,4R)-3,4-dihydroxypyrrolidin-1-yl]{(7RS)-4-[(6-
methoxy-1H-indazol-5-yl)amino]-5,6,7,8-tetrahydro
[1]benzothieno[2,3-d]pyrimidin-7-yl}methanone,

[(3R,4R)-3,4-dihydroxypyrrolidin-1-yl]{(7RS)-4-[(6-
methoxy-1H-indazol-5-yl)amino]-5,6,7,8-tetrahydro
[1]benzothieno[2,3-d]pyrimidin-7-yl}methanone, (RS)-4-[(6-ethoxy-1H-indazol-5-yl)amino]-N-(2-
methoxyethyl)-N-methyl-5,6,7,8-tetrahydro[1]benzo-
thieno[2,3-d]pyrimidine-7-carboxamide, {(7 RS)-4-[(6-ethoxy-1H-indazol-5-yl)amino]-5,6,7,8-
tetrahydro[1]benzothieno[2,3-d]pyrimidin-7-yl}[(3S)-
3-hydroxypyrrolidin-1-yl]methanone, (RS)-{4-[(6-methoxy-1H-indazol-5-yl)amino]-5,6,7,8-
tetrahydro[1]benzothieno[2,3-d]pyrimidin-7-yl}(2-
oxa-6-azaspiro[3.3]hept-6-yl)methanone, (RS)-4-{[6-(dimethylamino)-1H-indazol-5-yl]amino}-N,
N-dimethyl-5,6,7,8-tetrahydro[1]benzothieno[2,3-d]
pyrimidine-7-carboxamide, (RS)-4-[(6-ethoxy-1H-indazol-5-yl)amino]-N-methyl-N-
propyl-5,6,7,8-tetrahydro[1]benzothieno[2,3-d]pyrimi-
dine-7-carboxamide, (RS)-4-[(6-ethoxy-1H-indazol-5-yl)amino]-N,N-dim-
ethyl-5,6,7,8-tetrahydro[1]benzothieno[2,3-d]pyrimi-
dine-7-carboxamide, (7RS)-N-[(2RS)-2, 3-dihydroxypropyl]-4-[(6-ethoxy-1H-
indazol-5-yl)amino]-N-methyl-5,6,7,8-tetrahydro[1]
benzothieno[2,3-d]pyrimidine-7-carboxamide,

[(3RS)-3-(dimethylamino)pyrrolidin-1-yl]{(7RS)-4-[(6-
ethoxy-1H-indazol-5-yl)amino]-5,6,7,8-tetrahydro[1]
benzothieno[2,3-d]pyrimidin-7-yl}methanone, (RS)-{4-[(6-isopropoxy-1H-indazol-5-yl)amino]-5,6,7,8-tetrahydro[1]benzothieno[2,3-d]pyrimidin-7-yl}(1-oxa-6-azaspiro[3.3]hept-6-yl)methanone, (RS)-{4-[(6-methoxy-1H-indazol-5-yl)amino]-5,6,7,8-tetrahydro[1]benzothieno[2,3-d]pyrimidin-7-yl}(1-oxa-6-azaspiro[3.3]hept-6-yl)methanone, (RS)-5-azaspiro[2.4]hept-5-yl{4-[(6-isopropoxy-1H-indazol-5-yl)amino]-5,6,7,8-tetrahydro[1]benzothieno[2,3-d]pyrimidin-7-yl}methanone, {(7RS)-4-[(6-methoxy-1H-indazol-5-yl)amino]-5,6,7,8-tetrahydro[1]benzothieno[2,3-d]pyrimidin-7-yl}[(1S,4S)-2-oxa-5-azabicyclo[2.2.1]hept-5-yl]methanone, (RS)-(1,1-dioxido-1-thia-6-azaspiro[3.3]hept-6-yl){4-[(6-ethoxy-1H-indazol-5-yl)amino]-5,6,7,8-tetrahydro[1]benzothieno[2,3-d]pyrimidin-7-yl}methanone, (RS)-(1,1-dioxido-1-thia-6-azaspiro[3.3]hept-6-yl){4-[(6-methoxy-1H-indazol-5-yl)amino]-5,6,7,8-tetrahydro[1]benzothieno[2,3-d]pyrimidin-7-yl}methanone, (3RS)-1-({(7RS)-4-[(6-ethoxy-1H-indazol-5-yl)amino]-5,6,7,8-tetrahydro[1]benzothieno[2,3-d]pyrimidin-7-yl}carbonyl)pyrrolidine-3-carbonitrile, (RS)-N,N-dimethyl-4-[(6-propoxy-1H-indazol-5-yl)amino]-5,6,7,8-tetrahydro[1]benzothieno[2,3-d]pyrimidine-7-carboxamide, {(7RS)-4-[(6-ethoxy-1H-indazol-5-yl)amino]-5,6,7,8-tetrahydro[1]benzothieno[2,3-d]pyrimidin-7-yl}[(9aRS)-octahydro-2H-pyrido[1,2-a]pyrazin-2-yl]methanone, (RS)-5-({7-[(2-ammonioethyl)(methyl)carbamoyl]-5,6,7,8-tetrahydro[1]benzothieno[2,3-d]pyrimidin-4-yl}amino)-6-ethoxy-1H-indazol-1-ium bis(trifluoroacetate), (3-hydroxyazetidin-1-yl){4-[(6-methoxy-1H-indazol-5-yl)amino]-5,6,7,8-tetrahydro[1]benzothieno[2,3-d]pyrimidin-7-yl}methanone, (RS)-4-[(6-ethoxy-1H-indazol-5-yl)amino]-N-ethyl-N-(2-methoxyethyl)-5,6,7,8-tetrahydro[1]benzothieno[2,3-d]pyrimidine-7-carboxamide, (RS)-5-azaspiro[2.4]hept-5-yl{4-[(6-ethoxy-1H-indazol-5-yl)amino]-5,6,7,8-tetrahydro[1]benzothieno[2,3-d]pyrimidin-7-yl}methanone, or a stereoisomer, a tautomer, an N-oxide, a hydrate, a solvate, or a salt thereof.

7. A method of preparing a compound of formula (I) according to claim 1, comprising reacting an intermediate compound of formula (II):

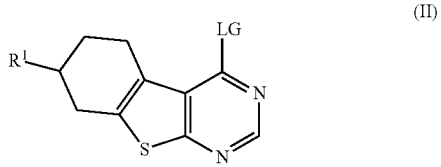

(II)

in which $R^1$ is as defined in claim 1, and LG represents a leaving group, with a compound of formula (III):

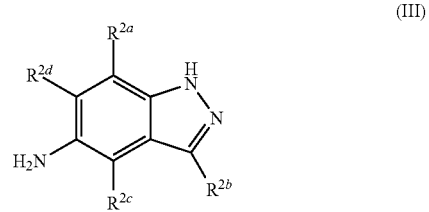

(III)

in which $R^{2a}$, $R^{2b}$, $R^{2c}$, and $R^{2d}$ are as defined in claim 1; thus providing a compound of formula (I):

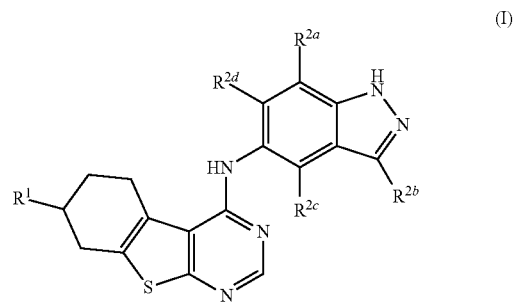

(I)

in which $R^1$, $R^{2a}$, $R^{2b}$, $R^{2c}$, and $R^{2d}$ are defined as in claim 1.

8. A pharmaceutical composition comprising a compound of formula (I), or a stereoisomer, a tautomer, an N-oxide, a hydrate, a solvate, or a pharmaceutically acceptable salt thereof, according to claim 1, and a pharmaceutically acceptable diluent or carrier.

9. A pharmaceutical combination comprising:
a compound of formula (I) according to claim 1, and
one or more second active ingredients selected from chemotherapeutic anti-cancer agents.

10. A method of treatment of rheumatoid arthritis comprising administering a pharmaceutically effective amount of a compound of claim 1 to a mammal in need thereof.

\* \* \* \* \*